United States Patent
Elgersma et al.

(10) Patent No.: US 11,419,944 B2
(45) Date of Patent: Aug. 23, 2022

(54) NON-LINEAR SELF-IMMOLATIVE LINKERS AND CONJUGATES THEREOF

(71) Applicant: Byondis B.V., Nijmegen (NL)

(72) Inventors: Ronald Christiaan Elgersma, Nijmegen (NL); Tijl Huijbregts, Nijmegen (NL); Rudy Gerardus Elisabeth Coumans, Nijmegen (NL)

(73) Assignee: Byondis B.V., Nijmegen (NL)

( * ) Notice: Subject to any disclaimer, the term of this patent is extended or adjusted under 35 U.S.C. 154(b) by 686 days.

(21) Appl. No.: 16/338,796

(22) PCT Filed: Oct. 11, 2017

(86) PCT No.: PCT/EP2017/075896
§ 371 (c)(1),
(2) Date: Apr. 2, 2019

(87) PCT Pub. No.: WO2018/069375
PCT Pub. Date: Apr. 19, 2018

(65) Prior Publication Data
US 2020/0297859 A1    Sep. 24, 2020

(30) Foreign Application Priority Data
Oct. 11, 2016 (EP) .................................... 16193337

(51) Int. Cl.
*A61K 47/68* (2017.01)
*A61K 31/4192* (2006.01)
*A61K 31/437* (2006.01)
*A61K 47/22* (2006.01)

(52) U.S. Cl.
CPC ...... *A61K 47/6803* (2017.08); *A61K 31/4192* (2013.01); *A61K 31/437* (2013.01); *A61K 47/22* (2013.01)

(58) Field of Classification Search
CPC combination set(s) only.
See application file for complete search history.

(56) References Cited

U.S. PATENT DOCUMENTS

2014/0363454 A1    12/2014   Jackson et al.

FOREIGN PATENT DOCUMENTS

| WO | WO 2010/062171 | 6/2010 |
|---|---|---|
| WO | WO 2011/133039 | 10/2011 |
| WO | WO 2012/171020 | 12/2012 |
| WO | WO 2013/067597 | 5/2013 |
| WO | WO 2014/100762 | 6/2014 |

(Continued)

OTHER PUBLICATIONS

Lyon et al., "Reducing hydrophobicity of homogeneous antibody-drug conjugates improves pharmacokinetics and therapeutic index," Nature Biotechnology, 33:7, pp. 733-736 (Year: 2015).*

(Continued)

*Primary Examiner* — Joanne Hama
(74) *Attorney, Agent, or Firm* — Buscher Patent PLLC

(57) ABSTRACT

The present invention relates to linker-drug compounds (LDs) and antibody-drug conjugates (ADCs) comprising a non-linear self-immolative linker, which is cleavable or transformable under appropriate conditions and which reduces the hydrophobicity of the antibody-drug conjugate.

20 Claims, 9 Drawing Sheets

(56) References Cited

FOREIGN PATENT DOCUMENTS

| WO | WO 2014/124316 | 8/2014 | | |
|---|---|---|---|---|
| WO | WO 2015/057699 | 4/2015 | | |
| WO | WO 2015/110935 | 7/2015 | | |
| WO | WO 2015/123679 | 8/2015 | | |
| WO | WO 2015/177360 | 11/2015 | | |
| WO | WO-2015177360 A1 | * 11/2015 | ........... | A61K 31/475 |

OTHER PUBLICATIONS

B.-Q. Shen et al. in Nature Biotechnology, vol. 30, No. 2, 2012, pp. 184-189.
Kabat, E.A. et al., Sequences of Proteins of Immunological Interest, 5th Ed. Public Health Service, National Institutes of Health, Bethesda, MD., NIH publication No. 91-3242, pp. 662, 680, 689 (1991).
Edelman, G.M. et al., Proc. Natl. Acad. Sci. USA, 63, 78-85 (1969).
Fan et al. Breast Cancer Res. 2012; 14: R116 1-13.
Elgersma et al. Mol. Pharmaceutics, 2015; 12: 1813-1835.
Elduque et al. Bioconjugate Chern. 2013; 24: 832-839.
Kim et al. Organic Letters, 2007, 9 (22): 4419-4422.
Nair et al. Chem. Commun. 2015; 51: 2403-2406.
Brezsky et al. PNAS 2009; 106: 17864-17869.
W. Dokter et al., "Preclinical Profile of the HER2-Targeting ADC SYD983/SYD985: Introduction of a New Duocarmycin-Based Linker-Drug Platform," Molecular Cancer Therapeutics, vol. 13, No. 11 Nov. 1, 2014 pp. 2618-2629.

* cited by examiner

1. SYD980, vc-*seco*-DUBA, reference linker-drug
3. n = 0
4. n = 1
5. n = 2
6. n = 3
7.
8.
9.
10.

NON-LINEAR SELF-IMMOLATIVE LINKERS AND CONJUGATES THEREOF

FIELD OF THE INVENTION

The present invention relates to linker-drug compounds (LDs) and antibody-drug conjugates (ADCs) comprising a cleavable or transformable non-linear self-immolative linker.

BACKGROUND OF THE PRESENT INVENTION

Antibody-drug conjugates (ADCs) are an emerging class of targeted therapeutics, in which the specificity of antibodies and the potency of cytotoxic molecules are combined.

In addition to antibody and target selection, drugs and linkers have been the focus of ADC development. As a result thereof, antibodies have been conjugated to a variety of cytotoxic drugs via either cleavable or non-cleavable linkers.

Examples of ADCs already approved for the treatment of human patients are Mylotarg™ (gemtuzumab ozogamicin, Wyeth) comprising a humanized anti-CD33 antibody conjugated via a cleavable, acid-hydrolyzable linker to a calicheamicin, which was approved in 2000 by the US Food and Drug Administration (FDA) for the treatment of acute myeloid leukaemia; Adcetris™ (brentuximab vedotin, Seattle Genetics), an ADC comprising a chimeric antibody to CD30 conjugated via an enzyme-cleavable linker to monomethyl auristatin E (MMAE), which was approved in 2011 by the FDA for the treatment of Hodgkin's lymphoma and anaplastic large cell lymphoma; and Kadcyla™ (T-DM1, ado-trastuzumab emtansine or trastuzumab emtansine, Roche), an ADC in which a humanized anti-HER2 antibody is conjugated via a non-cleavable thioether linker to mertansine (a maytansine derivative, also known as DM1), which was approved by the FDA in February 2013 for the treatment of patients with HER2-positive metastatic breast cancer who received prior treatment with trastuzumab and a taxane.

Compared to ADCs with a chemically-cleavable linker, enzyme-cleavable linkers can achieve better control of the drug release. However, the increased associated hydrophobicity of some enzyme-cleavable linkers can lead to aggregation of the ADC, particularly with strongly hydrophobic drugs. In addition, ADCs that are more hydrophobic are cleared more quickly from circulation in animal models. This faster clearance suggests a pharmacokinetics (PK) liability for such ADCs.

As disclosed in WO2014/124316 (Novartis) and WO2015/177360 (Synthon Biopharmaceuticals), the hydrophobicity of an ADC can be decreased by conjugating (hydrophobic) linker-drugs to engineered cysteine residues at specific locations in the Fab and/or Fc parts of both the heavy and light chains of antibodies. When conjugated to these cysteine residues the linker-drug is shielded from the hydrophilic aqueous environment surrounding the antibody, rendering the ADC less hydrophobic.

Alternatively, the hydrophobicity of a linker-drug and the resulting ADC can be decreased by choosing an appropriate linker. For example, Seattle Genetics in WO2015/123679 used a linker comprising only hydrophilic amino acids to maintain a conjugate hydrophilicity similar to that of the unconjugated antibody. In an alternative approach water-soluble groups such as polyethylene glycol polymers have been included in linkers, e.g., between the drug and attachment site of an antibody as in WO2014/100762 (Bioalliance and Abgenomics) or in a parallel position as in WO2015/057699 (Seattle Genetics). A third approach to minimize the hydrophobicity has been to append drug-polymers to an antibody, where each polymer contains a large number of drugs as in WO2012/171020 (Mersana). However, appending large solubilizing groups increases manufacturing complexity of such conjugates.

In spite of the above-described approaches to reduce the hydrophobicity of linker-drugs and/or ADCs, there is a need for new strategies to reduce said hydrophobicity of ADCs with the aim to (further) reduce aggregation of the ADC and to overcome the associated PK liabilities.

BRIEF DESCRIPTION OF THE PRESENT INVENTION

The present invention relates to linker-drug compounds (LDs) and antibody-drug conjugates (ADCs) comprising a non-linear self-immolative linker, which is cleavable or transformable under appropriate conditions and which reduces the hydrophobicity of the antibody-drug conjugate.

In a first aspect, the present invention relates to a linker-drug compound of formula (I)

(I)

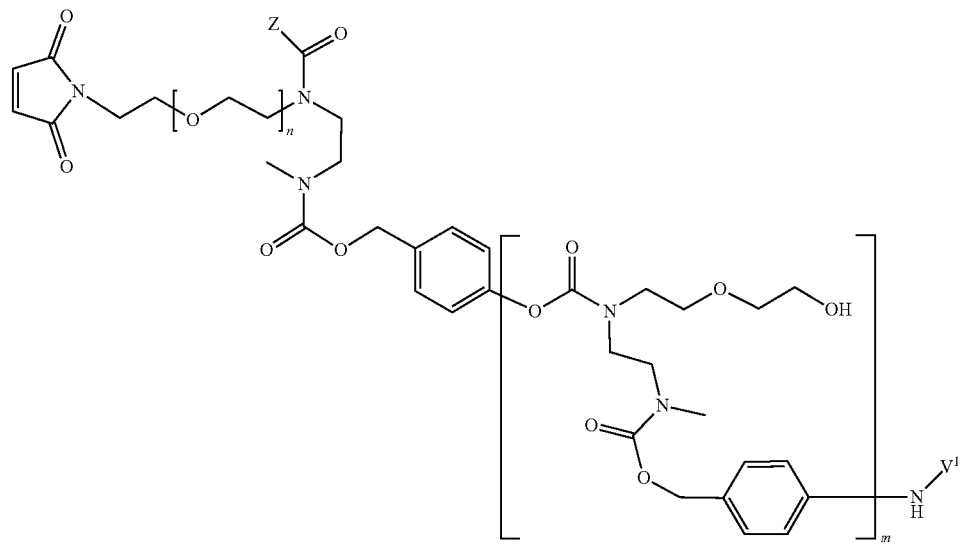

or a pharmaceutically acceptable salt, hydrate, or solvate thereof, wherein $V^1$ is a conditionally-cleavable or conditionally-transformable moiety, which can be cleaved or transformed by a chemical, photochemical, physical, biological, or enzymatic process;

Z is a cytotoxic drug comprising a phenolic hydroxyl group through which Z is attached to the linker, preferably, Z is a duocarmycin or a CBI dimer derivative, more preferably Z is a duocarmycin derivative;

n is 0, 1, 2, or 3; and m is 0 or 1.

In a second aspect, the present invention relates to an antibody-drug conjugate comprising the linker-drug compound of formula (I).

Other aspects of the present invention include pharmaceutical compositions of the linker-drug compound or the antibody-drug conjugate and their use as a medicament, particularly in the treatment of human solid tumours and haematological malignancies.

DETAILED DESCRIPTION OF THE PRESENT INVENTION

Figure 1:
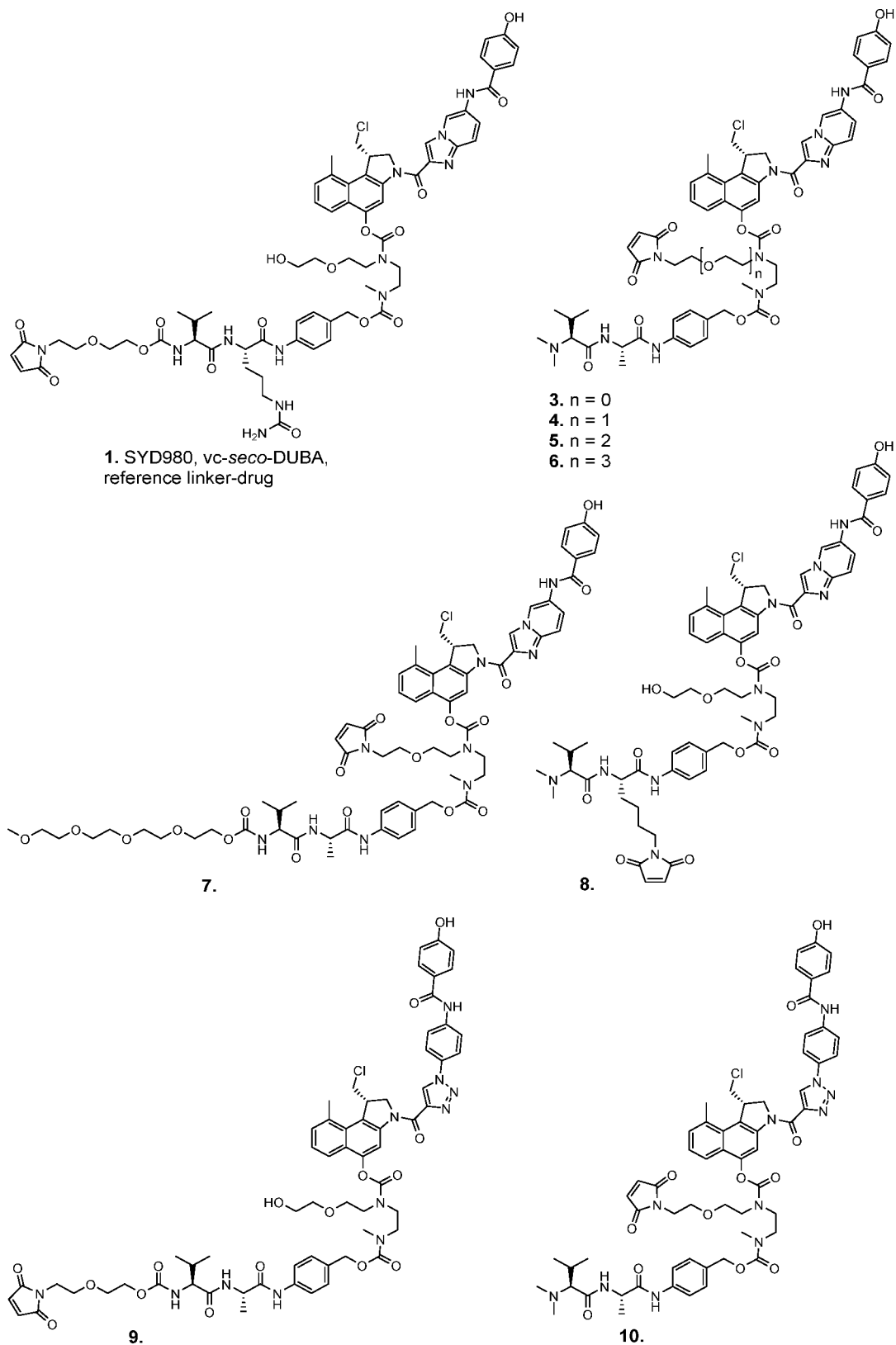
FIG. 1. Structural formulae of linker-drug compounds.
Figure 1:
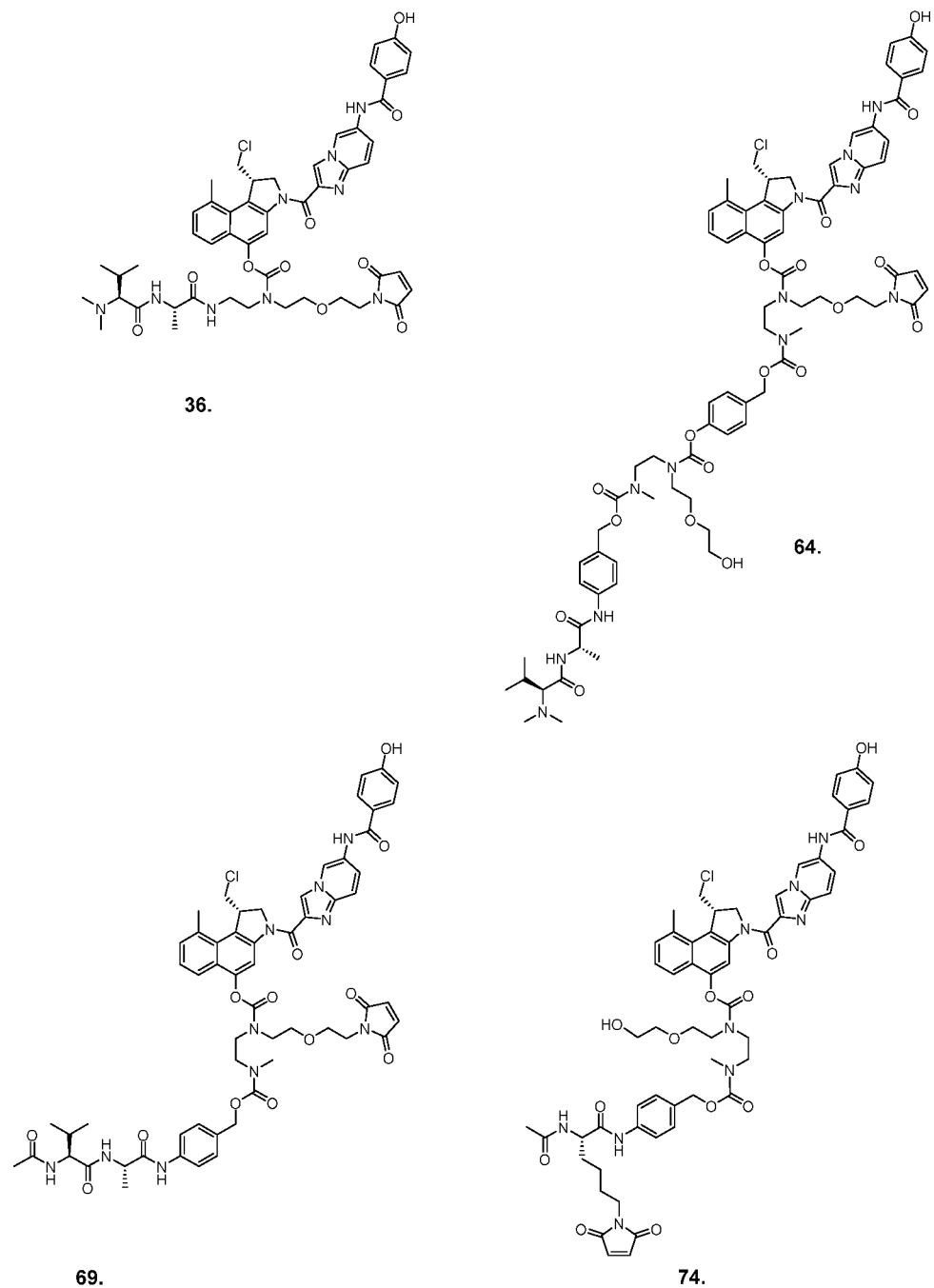

Antibody-drug conjugates (ADCs) are emerging as a new class of anticancer therapeutics that combine the efficacy of small-molecule therapeutics with the targeting ability of antibodies. By combining these two components into a single new molecular entity, highly cytotoxic small molecule drugs can be delivered to cancerous target tissues, thereby enhancing efficacy while reducing the potential systemic toxic side effects of the small molecule.

Antibodies have been conjugated to a variety of cytotoxic drugs, including small molecules that bind DNA (e.g. anthracyclines), alkylate or crosslink DNA (e.g. duocarmycins or CBI or pyrrolobenzodiazepine dimers, respectively), cause DNA strand breaks (e.g. calicheamicins) or disrupt microtubules (e.g. maytansinoids, auristatins and tubulysins).

Drugs can be attached to an antibody through specific compounds connecting the side chain of an antibody amino acid residue, e.g. the side chain of a cysteine or lysine residue, and the drug. This linking compound, i.e. linker, may be cleavable so that the release of the drug can be timed to occur at a predetermined location, e.g. inside a cancer cell lysosome, thus reducing the systemic toxic effects of the drug.

The present invention relates to a linker-drug compound, i.e. linker-drug, of formula (I) comprising a non-linear self-immolative linker

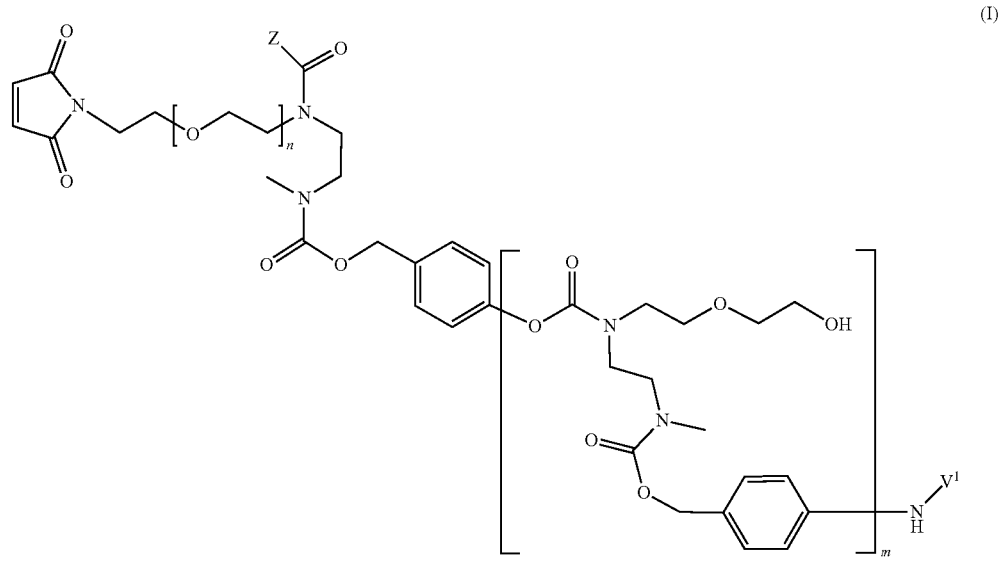

(I)

or a pharmaceutically acceptable salt, hydrate, or solvate thereof.

$V^1$ is a conditionally-cleavable or conditionally-transformable moiety.

Z is a cytotoxic drug comprising a phenolic hydroxyl group through which Z is attached to the linker.

Each m and n are independently 0 or a positive integer.

The maleimide moiety is used for conjugation of the linker-drug to an antibody or an antigen-binding fragment thereof.

A self-immolative linker may be defined as a bifunctional chemical or biochemical moiety which is capable of covalently linking together two spaced chemical moieties into a normally stable tripartite molecule. It can release one of the spaced chemical moieties, from the tripartite molecule by means of e.g. enzymatic cleavage; and following such enzymatic cleavage, can spontaneously cleave from the remainder of the molecule to release the other of the spaced chemical moieties. A linker is considered non-linear when the site for (enzymatic) cleavage is not in between the first chemical moiety and the attachment site of the second chemical moiety, as opposed to a linear linker.

The present invention is based, in part, on the discovery that certain combinations of linkers and cytotoxic drugs can be used to prepare ADCs, that have a hydrophobicity similar to that of the unconjugated (naked) antibody or antigen-binding fragment. By designing conjugates in order to obtain a hydrophobicity similar to that of the unconjugated antibody, certain desirable characteristics of the naked antibody, such as a favourable pharmacokinetic profile in vivo, including reduced clearance in vivo, and/or increased exposure of the target cell(s) may be maintained. Advantageously, such conjugates can be designed to have a hydrophobicity similar to that of the naked antibody without the need to include additional solubilizing groups, such as polyethylene glycol or other water-soluble polymers.

The non-linear self-immolative linker in the compound of formula (I) is designed to decrease the hydrophobicity of ADCs. The present inventors have found that by decreasing the number of atoms in the linker between the cytotoxic drug and the attachment site of the antibody, the hydrophobicity of the ADC decreases proportionally as well.

Without wishing to be bound by any theory, the present inventors think that through the arrangement in the linker of the invention, leading to a shorter distance between hydrophobic drug and antibody, the drug is shielded by the antibody from the hydrophilic aqueous environment surrounding the antibody, rendering the ADC less hydrophobic.

The linker allows efficient release of the cytotoxic drug at or in the target cells, sufficient to induce cytotoxicity or a cytostatic effect. Typically, the linkers are designed for efficient release of the drug once the conjugate has been internalised by the target cells.

$V^1$ is a conditionally-cleavable or conditionally-transformable moiety, which can be cleaved or transformed by a chemical, photochemical, physical, biological, or enzymatic process. In other words, it is designed to be transformed and/or cleaved by a chemical, photochemical, physical, biological, or enzymatic process upon being brought in or under a certain condition. This condition may for example be bringing a compound of the invention in an aqueous environment, which leads to hydrolysis of $V^1$, or bringing a compound of the invention in an environment that contains an enzyme that recognizes and cleaves $V^1$, or bringing a compound of the invention under reducing conditions, which leads to reduction and/or removal of $V^1$, or bringing a compound of the invention under oxidizing conditions, which leads to oxidation and/or removal of $V^1$, or bringing a compound of the invention in contact with radiation, e.g., UV light, which leads to transformation and/or cleavage, or bringing a compound of the invention in contact with heat, which leads to transformation and/or cleavage, or bringing a compound of the invention under reduced pressure, which leads to transformation, e.g., a retrocycloaddition, and/or cleavage, or bringing a compound of the invention under elevated or high pressure, which leads to transformation and/or cleavage. This condition may be met after administering a compound of this invention to a mammal, for example a human.

Preferably, $V^1$ is a conditionally-cleavable moiety. More preferably, $V^1$ is an enzyme-cleavable moiety.

Suitable recognition sites for release of the drug by cleavage are those that allow efficient separation of the drug from the linker. Preferably, the recognition site is a peptide cleavage site. Examples of peptide cleavage sites include those recognized by intracellular proteases, such as those present in lysosomes.

In one embodiment, $V^1$ is a peptide.

In a preferred embodiment, $V^1$ is a di-, tri- or tetra-peptide, i.e., a peptide composed of two, three or four amino acid residues, recognizable and cleavable by a proteolytic enzyme (protease), for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumour cells. Suitable peptides for include, without limitation, alanylphenylalanyllysine, valylleucyllysine, alanylleucyllysine, valylphenylalanyllysine, valyltryptophanyllysine, alanyltryptophanyllysine, alanylphenylalanylcitrulline, valylleucylcitrulline, alanylleucylcitrulline, valylphenylalanylcitrulline, valyltryptophanylcitrulline, alanyltryptophanylcitrulline, phenylalanyllysine, valyllysine, valylalanine, glycylphenylalanyllysine, alanyllysine, valylcitrulline, phenylalanylcitrulline, isoleucylcitrulline, tryptophanyllysine, tryptophanylcitrulline, phenylalanylarginine, phenylalanylalanine, alanylleucylalanylleucine, alanylarginylarginine, leucyllysine, and leucylcitrulline. Preferably, $V^1$ is selected from valylalanine, valyllysine, valylcitrulline, phenylalanyllysine, and alanylphenylalanyllysine. More preferably, $V^1$ is selected from valylcitrulline and valylalanine.

$V^1$ is attached to the non-linear linker through its C-terminal side, leaving the N-terminal side exposed. Optionally, the N-terminal side of $V^1$ is capped by an amine blocking group. Suitable examples of amine blocking groups include $C_1$-$C_6$ alkyl, $C_1$-$C_8$ acyl, (alkoxy)carbonyl (e.g., t-butoxycarbonyl known as Boc), (aryl alkoxy)carbonyl (e.g., benzyloxycarbonyl or carbobenzyloxy, known as Cbz) and 9-fluorenylmethyloxycarbonyl known as Fmoc).

In one embodiment, the N-terminal side of $V^1$ is capped by a water-soluble group, such as a linear polyethylene glycol (PEG) oligomer. Preferably, the linear PEG oligomer contains 1 to 20 ethylene glycol moieties, more preferably 3 to 10, even more preferably 5 to 7.

Z is a cytotoxic drug comprising a phenolic hydroxyl group through which Z is attached to the linker. Preferably, Z is a duocarmycin or a CBI dimer derivative. More preferably, Z is a duocarmycin derivative.

Duocarmycins, a class of structurally-related toxins first isolated from a culture broth of *Streptomyces* species, are members of a family of antitumour antibiotics that include duocarmycin A, duocarmycin SA, and CC-1065.

Duocarmycins bind to the minor groove of DNA and subsequently cause irreversible alkylation of DNA. This disrupts the nucleic acid architecture, which eventually leads to tumour cell death.

WO2010/062171 discloses a series of novel analogues of the DNA-alkylating agent CC-1065. These duocarmycin derivatives are suitable for use in accordance with the present invention. The chemical synthesis of a number of these drugs is described in Examples 1-22 of WO2010/062171.

CBI dimers (1,2,9,9a-tetrahydrocyclopropa[c]benz[e]indole-4-one dimers) are also part of the group of the highly toxic antibiotics originating from CC-1065, but whereas duocarmycins cause DNA alkylation, structurally-related CBI dimers cause interstrand DNA crosslinking, thereby leading to cell death.

In one embodiment of the present invention, Z is

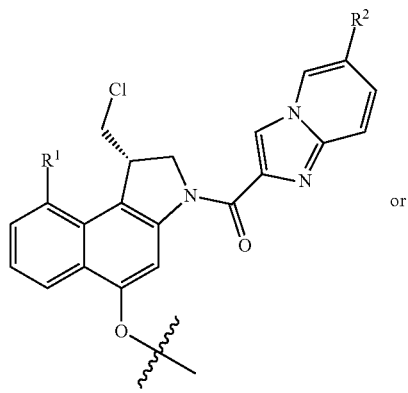

or

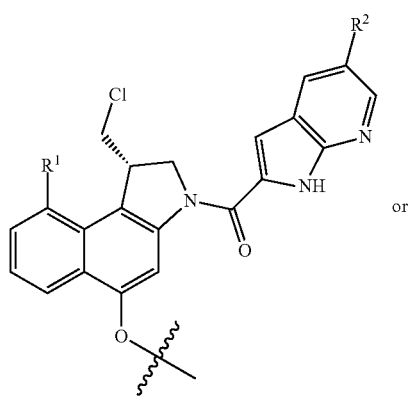

or

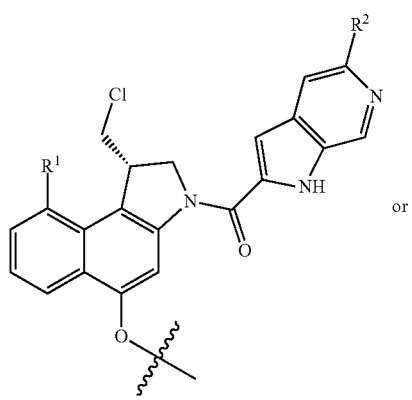

or

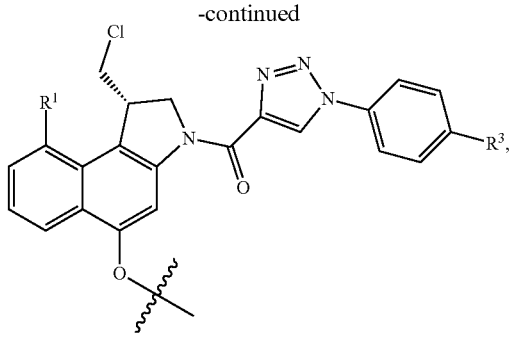

wherein $R^2$, and $R^3$ are independently selected from H, OH, SH, $NH_2$, $N_3$, $NO_2$, NO, $CF_3$, CN, $C(O)NH_2$, C(O)H, C(O)OH, halogen, $R^a$, $SR^a$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^a$, $NHR^a$, $N(R^a)R^b$, $^+N(R^a)(R^b)R^c$, $P(O)(OR^a)(OR^b)$, $OP(O)(OR^a)(OR^b)$, $SiR^aR^bR^c$, $C(O)R^a$, $C(O)OR^a$, $C(O)N(R^a)R^b$, $OC(O)R^a$, $OC(O)OR^a$, $OC(O)N(R^a)R^b$, $N(R^a)C(O)R^b$, $N(R^a)C(O)OR^b$, $N(R^a)C(O)N(R^b)R^c$, and a water-soluble group, wherein $R^a$, $R^b$, and $R^c$ are independently selected from H and optionally substituted $(CH_2CH_2O)_{aa}CH_2CH_2X^1R^{a1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, wherein aa is selected from 1 to 1000, $X^1$ is selected from O, S, and $NR^{b1}$, and $R^{b1}$ and $R^{a1}$ are independently selected from H and $C_{1-3}$ alkyl, one or more of the optional substituents in $R^a$, $R^b$, and/or $R^c$ optionally being a water-soluble group, two or more of $R^a$, $R^b$, and $R^c$ optionally being joined by one or more bonds to form one or more optionally substituted carbocycles and/or heterocycles.

The term "water-soluble group" refers to a functional group that is well solvated in aqueous environments and that imparts improved water solubility to the compound to which it is attached. Examples of water-soluble groups include, but are not limited to, polyalcohols, straight chain or cyclic saccharides, primary, secondary, tertiary, or quaternary amines and polyamines, sulfate groups, sulfonate groups, sulfinate groups, carboxylate groups, phosphate groups, phosphonate groups, phosphinate groups, ascorbate groups, glycols, including polyethylene glycols, and polyethers. Preferred water-soluble groups are primary, secondary, tertiary, and quaternary amines, carboxylates, phosphonates, phosphates, sulfonates, sulfates, $-(CH_2CH_2O)_{yy}CH_2CH_2X^2R^{yy}$, $-(CH_2CH_2O)_{yy}CH_2CH_2X^2-$, $-X^2(CH_2CH_2O)_{yy}CH_2CH_2-$, glycol, oligoethylene glycol, and polyethylene glycol, wherein yy is selected from 1 to 1000, $X^2$ is selected from O, S, and $NR^{zz}$, and $R^{zz}$ and $R^{yy}$ are independently selected from H and $C_{1-3}$ alkyl.

The term "substituted", when used as an adjective to "alkyl", "heteroalkyl", "cycloalkyl", "heterocycloalkyl", "aryl", "heteroaryl", or the like, indicates that said "alkyl", "heteroalkyl", "cycloalkyl", "heterocycloalkyl", "aryl", "heteroaryl", or similar group contains one or more substituents (introduced by substitution for hydrogen). Exemplary substituents include, but are not limited to, OH, =O, =S, $=NR^d$, $=N-OR^d$, SH, $NH_2$, $NO_2$, NO, $N_3$, $CF_3$, CN, OCN, SCN, NCO, NCS, $C(O)NH_2$, C(O)H, C(O)OH, halogen, $R^d$, $SR^d$, $S(O)R^d$, $S(O)OR^d$, $S(O)_2R^d$, $S(O)_2OR^d$, $OS(O)R^d$, $OS(O)OR^d$, $OS(O)_2R^d$, $OS(O)_2OR^d$, $S(O)N(R^d)R^e$, $OS(O)N(R^d)R^e$, $S(O)_2N(R^d)R^e$, $OS(O)_2N(R^d)R^e$, $OP(O)(OR^d)(OR^e)$, $P(O)(OR^d)(OR^e)$, $OR^d$, $NHR^d$, $N(R^d)R^e$, $^+N(R^d)(R^e)R^f$, $Si(R^d)(R^e)(R^f)$, $C(O)R^d$, $C(O)OR^d$, $C(O)N(R^d)R^e$, $OC(O)R^d$, $OC(O)OR^d$, $OC(O)N(R^d)R^e$, $N(R^d)C(O)R^e$, $N(R^d)C(O)OR^e$, $N(R^d)C(O)N(R^e)R^f$, a water-soluble group, and the thio derivatives of these substituents, and protonated, charged, and deprotonated forms of any of these substituents, wherein $R^d$, $R^e$, and $R^f$ are independently selected from H and optionally substituted —(CH$_2$CH$_2$O)$_{yy}$CH$_2$CH$_2$X$^2$R$_{yy}$, C$_{1-15}$ alkyl, C$_{1-15}$ heteroalkyl, C$_{3-15}$ cycloalkyl, C$_{1-15}$ heterocycloalkyl, C$_{5-15}$ aryl, or C$_{1-15}$ heteroaryl, or a combination thereof, wherein yy is selected from 1 to 1000, $X^2$ is independently selected from O, S, and NR$^{zz}$, and R$^{zz}$ and R$^{yy}$ are independently selected from H and C$_{1-3}$ alkyl, two or more of $R^d$, $R^e$, and $R^f$ optionally being joined by one or more bonds to form one or more optionally substituted carbocycles and/or heterocycles. When there is more than one substituent, each substituent is independently selected. Two or more substituents may be connected to each other by replacement of one or more hydrogen atoms on each of the substituents by one or more connecting bonds, which may be single, double, or triple bonds, or, if resonance structures are possible, the bond order of said bonds may be different in two or more of these resonance structures. Two substituents may thus be joined under formation of one or more rings.

When substituents may be "joined by one or more bonds to form one or more optionally substituted carbocycles and/or heterocycles", this means that the substituents may be connected to each other through replacement of one or more hydrogen atoms on each of the substituents by one or more connecting bonds.

The term "aryl" as used herein refers to a carbocyclic aromatic substituent comprising 5 to 24 ring carbon atoms, which may be charged or uncharged and which may consist of one ring or two or more rings fused together. Examples of aryl groups include, but are not limited to, phenyl, naphthyl, and anthracenyl.

The term "heteroaryl" as used herein refers to a heterocyclic aromatic substituent comprising 1 to 24 ring carbon atoms and at least one ring heteroatom, e.g., oxygen, nitrogen, sulfur, silicon, or phosphorus, wherein nitrogen and sulfur may optionally be oxidized and nitrogen may optionally be quaternized, which may consist of one ring or two or more rings fused together. Heteroatoms may be directly connected to each other. Examples of heteroaryl groups include, but are not limited to, pyridinyl, pyrimidyl, furanyl, pyrrolyl, triazolyl, pyrazolyl, pyrazinyl, oxazolyl, isoxazolyl, thiazolyl, imidazolyl, thienyl, indolyl, benzofuranyl, benzimidazolyl, benzothiazolyl, purinyl, indazolyl, benzotriazolyl, benzisoxazolyl, quinoxalinyl, isoquinolyl, and quinolyl. In one embodiment, a heteroaryl group comprises 1 to 4 heteroatoms. It should be noted that "C$_1$ heteroaryl group" denotes that there is only one carbon present in the ring system of the heteroaromatic group (carbon atoms in optional substituents are thus not counted). An example of such a heteroaromatic group is a tetrazolyl group.

"Aryl" and "heteroaryl" groups also encompass ring systems in which one or more non-aromatic rings are fused to an aryl or heteroaryl ring or ring system.

The term "alkyl" as used herein refers to a straight chain or branched, saturated or unsaturated hydrocarbyl substituent. Examples of alkyl groups include, but are not limited to, methyl, ethyl, propyl, butyl, pentyl, hexyl, octyl, decyl, isopropyl, sec-butyl, isobutyl, tert-butyl, isopentyl, 2-methylbutyl, vinyl, allyl, 1-butenyl, 2-butenyl, isobutylenyl, 1-pentenyl, 2-pentenyl, and 1-butynyl.

The term "heteroalkyl" as used herein refers to a straight chain or branched, saturated or unsaturated hydrocarbyl substituent in which at least one carbon atom is replaced by a heteroatom, e.g., by oxygen, nitrogen, sulfur, silicon, or phosphorus, wherein nitrogen and sulfur may optionally be oxidized and nitrogen may optionally be quaternized. Heteroatoms may be directly connected to each other. Examples include, but are not limited to, methoxy, ethoxy, propoxy, isopropoxy, n-butyloxy, tert-butyloxy, methyloxymethyl, ethyloxymethyl, methyloxyethyl, ethyloxyethyl, methylaminomethyl, dimethylaminomethyl, methylaminoethyl, dimethylaminoethyl, methylthiomethyl, ethylthiomethyl, ethylthioethyl, and methylthioethyl.

The term "cycloalkyl" as used herein refers to a saturated or unsaturated non-aromatic cyclic hydrocarbyl substituent, which may consist of one ring or two or more rings fused together. Examples include, but are not limited to, cyclopropyl, cyclobutyl, cyclopentyl, cyclopentenyl, cyclopentadienyl, cyclohexyl, cyclohexenyl, 1,3-cyclohexadienyl, decalinyl, and 1,4-cyclohexadienyl.

The term "heterocycloalkyl" as used herein refers to a saturated or unsaturated non-aromatic cyclic hydrocarbyl substituent, which may consist of one ring or two or more rings fused together, wherein at least one carbon in one of the rings is replaced by a heteroatom, e.g., by oxygen, nitrogen, sulfur, silicon, or phosphorus, wherein nitrogen and sulfur may optionally be oxidized and nitrogen may optionally be quaternized. Heteroatoms may be directly connected to each other. Examples include, but are not limited to, tetrahydrofuranyl, pyrrolidinyl, piperidinyl, 1,4-dioxanyl, decahydroquinolinyl, piperazinyl, oxazolidinyl, and morpholinyl. It should be noted that "C$_1$ heterocycloalkyl group" denotes that there is only one carbon present in the ring system of the heterocycloalkane (carbon atoms in optional substituents are thus not counted). An example of such a group is a dioxiranyl group.

The term "acyl" as used herein refers to a group having a straight, branched, or cyclic configuration or a combination thereof, attached to the parent structure through a carbonyl functionality. Such groups may be saturated or unsaturated, aliphatic or aromatic, and carbocyclic or heterocyclic. Examples of a C$_1$-C$_8$ acyl group include acetyl-, benzoyl-, nicotinoyl-, propionyl-, isobutyryl-, oxalyl-, and the like.

The number of carbon atoms that an "alkyl", "heteroalkyl", "cycloalkyl", "heterocycloalkyl", "aryl", "heteroaryl", "acyl", and the like, may contain is indicated by a designation preceding said terms, i.e., C$_{1-10}$ alkyl means that said alkyl may contain from one to ten carbons (carbon atoms in optional substituents attached to this alkyl are not counted).

The term "carbocycle" herein refers to a saturated or unsaturated cycloalkane or arene moiety, wherein the terms "cycloalkane" and "arene" are defined as parent moieties of the "cycloalkyl" and "aryl" substituents, respectively, as defined hereinabove.

The term "heterocycle" herein refers to a saturated or unsaturated heterocycloalkane or heteroarene moiety, wherein the terms "heterocycloalkane" and "heteroarene" are defined as parent moieties of the "heterocycloalkyl" and "heteroaryl" substituents, respectively, as defined hereinabove.

The extension "-ylene" as opposed to "-yl" in for example "alkylene" as opposed to "alkyl" indicates that said for example "alkylene" is a divalent (or multivalent) moiety connected to one or more other moieties via at least one or more double bonds or two or more single bonds, as opposed to being a monovalent group connected to one moiety via one single bond in said for example "alkyl". The term "alkylene" therefore refers to a straight chain or branched, saturated or unsaturated hydrocarbylene moiety; the term "heteroalkylene" as used herein refers to a straight chain or branched, saturated or unsaturated hydrocarbylene moiety in which at least one carbon is replaced by a heteroatom; the term "arylene" as used herein refers to a carbocyclic aromatic moiety, which may consist of one ring or two or more rings fused together; the term "heteroarylene" as used herein refers to a carbocyclic aromatic moiety, which may consist of one ring or two or more rings fused together, wherein at least one carbon in one of the rings is replaced by a heteroatom; the term "cycloalkylene" as used herein refers to a saturated or unsaturated non-aromatic cyclic hydrocarbylene moiety, which may consist of one ring or two or more rings fused together; the term "heterocycloalkylene" as used herein refers to a saturated or unsaturated non-aromatic cyclic hydrocarbylene moiety, which may consist of one ring or two or more rings fused together, wherein at least one carbon in one of the rings is replaced by a heteroatom. Exemplary divalent moieties include those examples given for the monovalent groups hereinabove in which one hydrogen atom is removed.

The prefix "poly" in "polyalkylene", "polyheteroalkylene", "polyarylene", "polyheteroarylene", "polycycloalkylene", "polyheterocycloalkylene", and the like, indicates that two or more of such "-ylene" moieties, e.g., alkylene moieties, are joined together to form a branched or unbranched multivalent moiety containing two or more attachment sites for adjacent moieties. Similarly, the prefix "oligo" in for example oligoethylene glycol indicates that two or more ethylene glycol moieties are joined together to form a branched or unbranched multivalent moiety. The difference between the prefixes "oligo" and "poly" is that the prefix "oligo" is most frequently used to denote a relatively small number of repeating units, while the prefix "poly" usually refers to a relatively large number of repeating units.

Each m and n are independently 0 or a positive integer. Preferably, n is 0, 1, 2, or 3, and m is 0 or 1. More preferably, n is 0, 1, 2, or 3, and m is 0.

In one embodiment, the invention relates to a linker-drug compound of formula (I) or a pharmaceutically acceptable salt, hydrate, or solvate thereof, wherein $V^1$ is a conditionally-cleavable or conditionally-transformable moiety, which can be cleaved or transformed by a chemical, photochemical, physical, biological, or enzymatic process;

Z is a cytotoxic drug comprising a phenolic hydroxyl group through which Z is attached to the linker, preferably, Z is a duocarmycin or a CBI dimer derivative, more preferably Z is a duocarmycin derivative;

n is 0, 1, 2, or 3; and m is 0 or 1.

In one embodiment, Z is

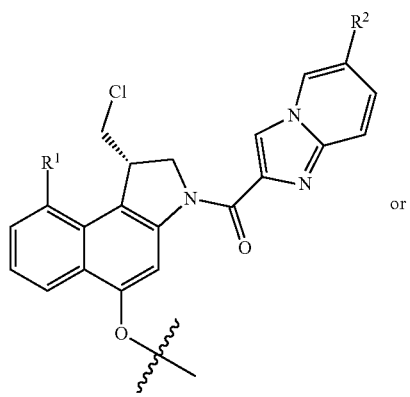

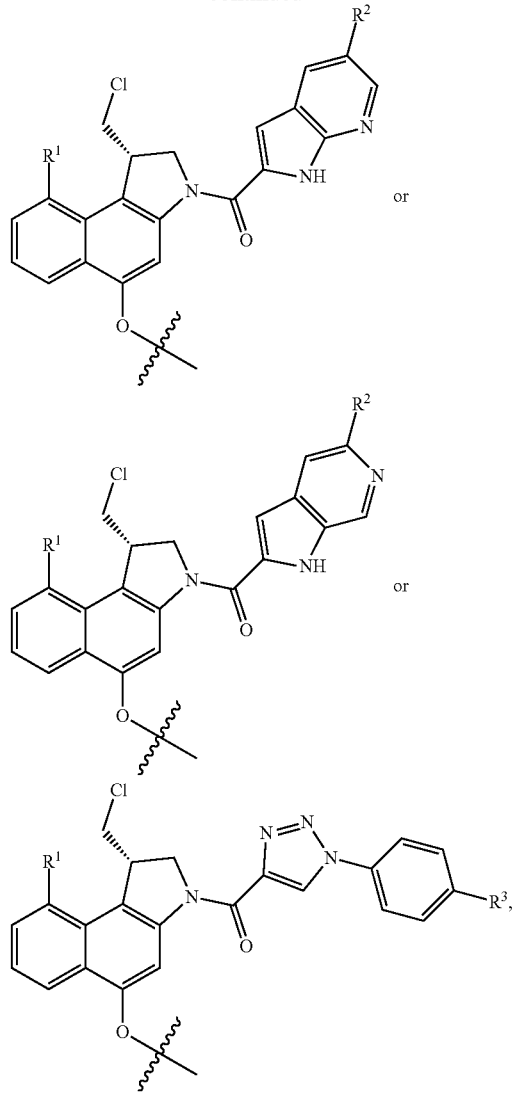

wherein $R^1$, $R^2$, and $R^3$ are independently selected from H, OH, SH, $NH_2$, $N_3$, $NO_2$, NO, $CF_3$, CN, $C(O)NH_2$, C(O)H, C(O)OH, halogen, $R^a$, $SR^a$, $S(O)R^a$, $S(O)_2R^a$, $S(O)OR^a$, $S(O)_2OR^a$, $OS(O)R^a$, $OS(O)_2R^a$, $OS(O)OR^a$, $OS(O)_2OR^a$, $OR^a$, $NHR^a$, $N(R^a)R^b$, $^+N(R^a)(R^b)R^c$, $P(O)(OR^a)(OR^b)$, $OP(O)(OR^a)(OR^b)$, $SiR^aR^bR^c$, $C(O)R^a$, $C(O)OR^a$, $C(O)N(R^a)R^b$, $OC(O)R^a$, $OC(O)OR^a$, $OC(O)N(R^a)R^b$, $N(R^a)C(O)R^b$, $N(R^a)C(O)OR^b$, $N(R^a)C(O)N(R^b)R^c$, and a water-soluble group, wherein $R^a$, $R^b$, and $R^c$ are independently selected from H and optionally substituted $(CH_2CH_2O)_{aa}CH_2CH_2X^1R^{a1}$, $C_{1-15}$ alkyl, $C_{1-15}$ heteroalkyl, $C_{3-15}$ cycloalkyl, $C_{1-15}$ heterocycloalkyl, $C_{5-15}$ aryl, or $C_{1-15}$ heteroaryl, wherein aa is selected from 1 to 1000, $X^1$ is selected from O, S, and $NR^{b1}$, and $R^{b1}$ and $R^{a1}$ are independently selected from H and $C_{1-3}$ alkyl, one or more of the optional substituents in $R^a$, $R^b$, and/or $R^c$ optionally being a water-soluble group, two or more of $R^a$, $R^b$, and $R^c$ optionally being joined by one or more bonds to form one or more optionally substituted carbocycles and/or heterocycles.

In one embodiment, Z is
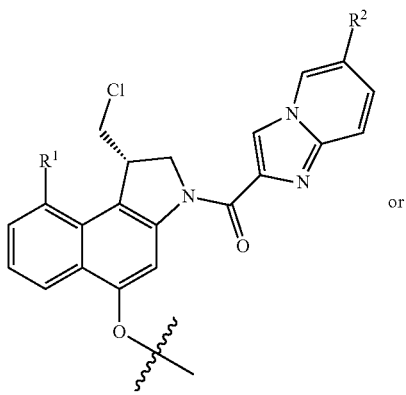
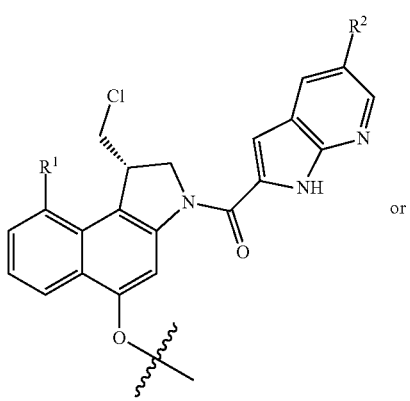
or
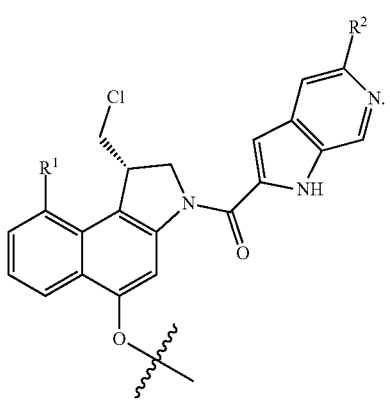
In a preferred embodiment, Z is
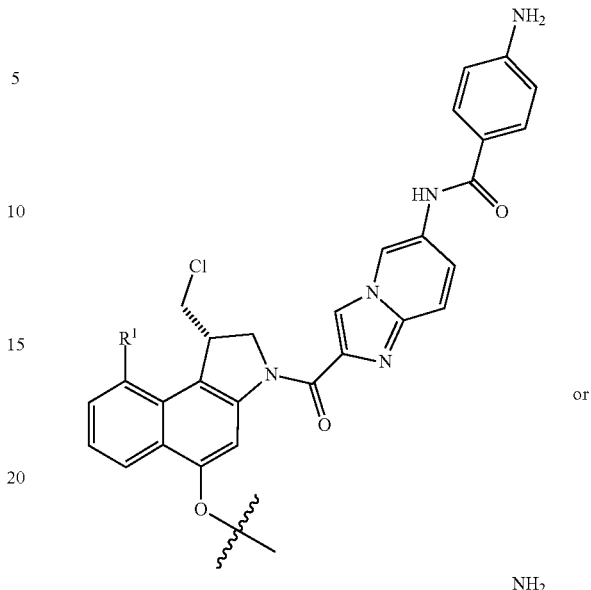
or
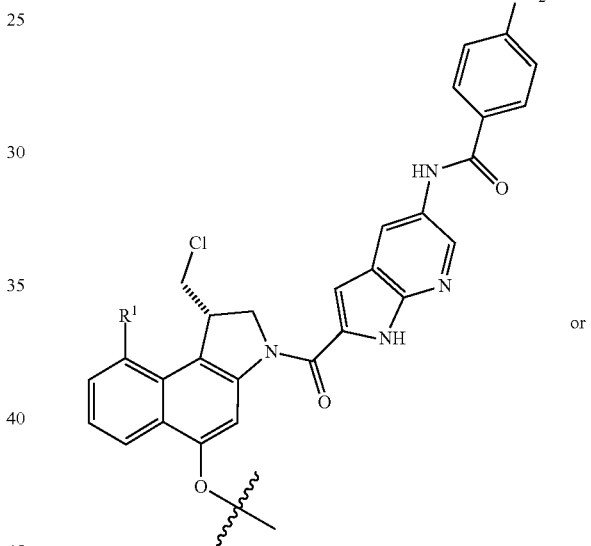
or
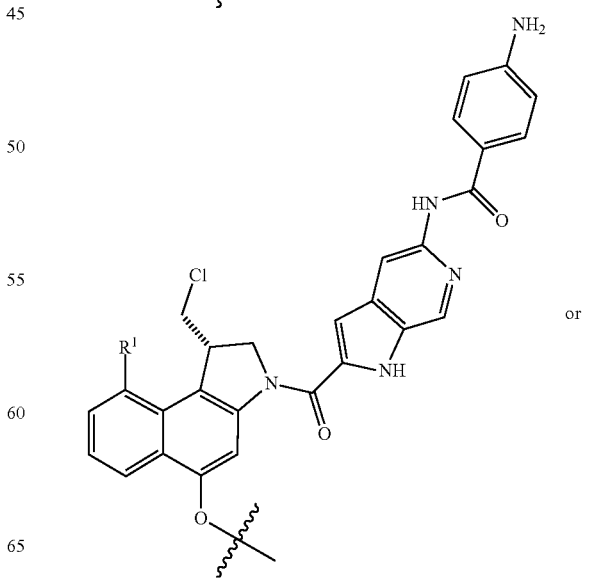
or

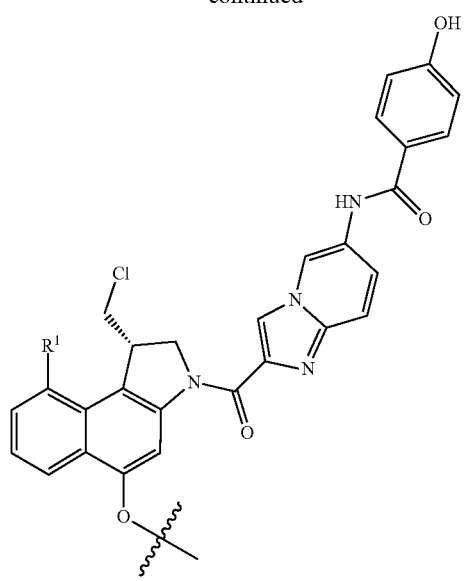
or
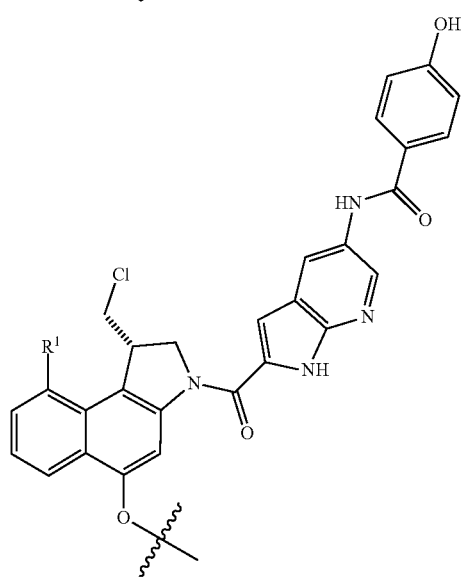
or
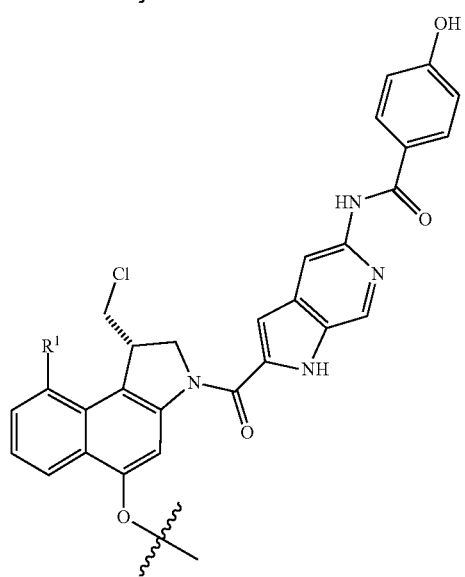
or
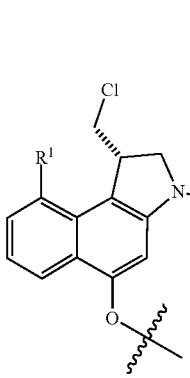
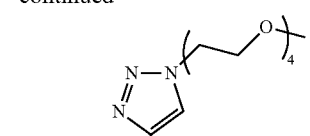
or
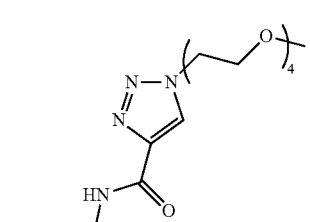
or
or
or 17
-continued
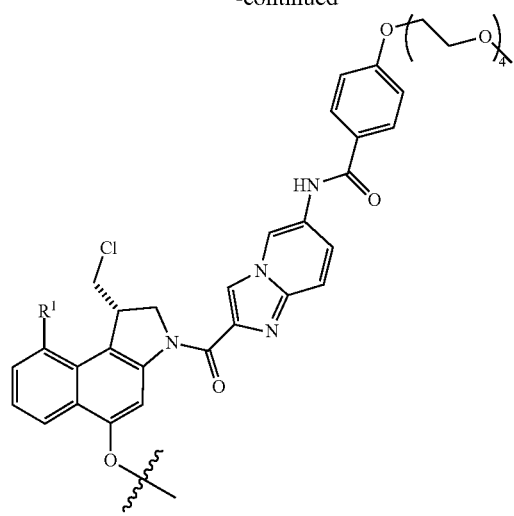
or
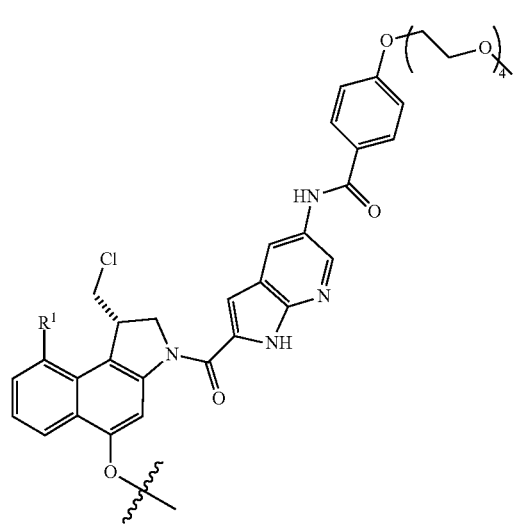
or
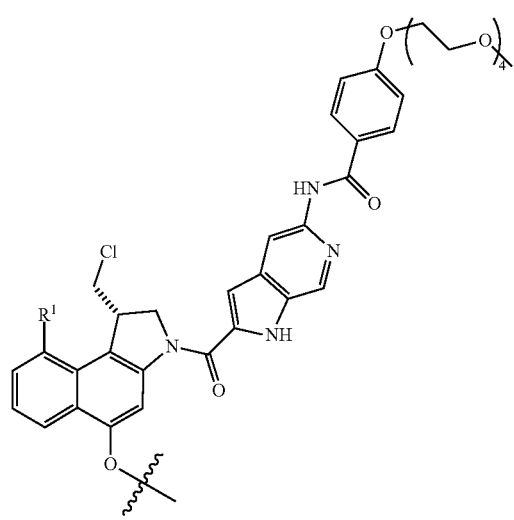
18
-continued
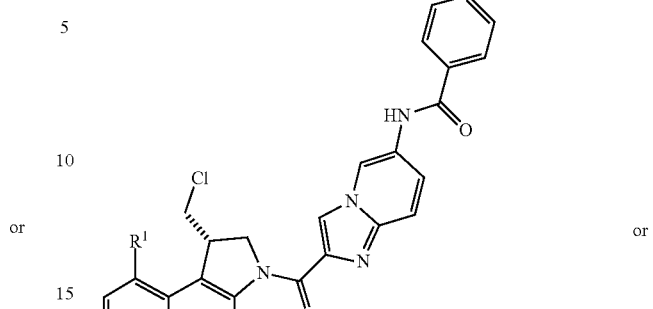
or
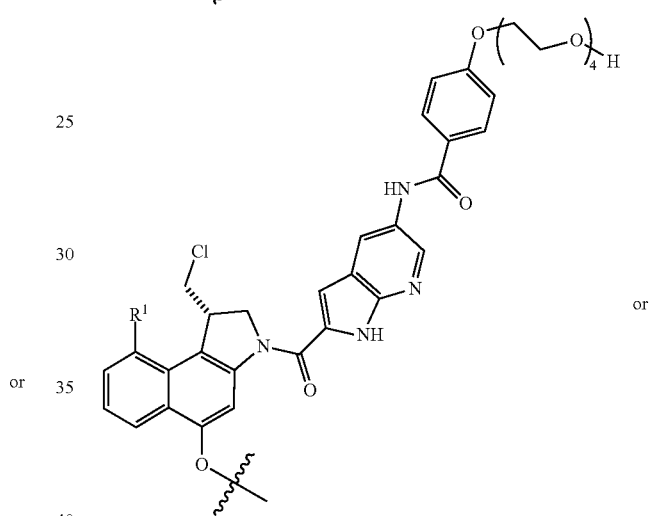
or
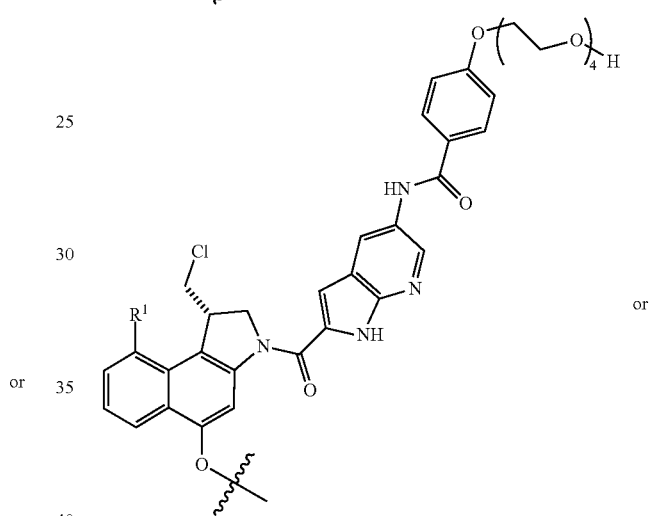
or
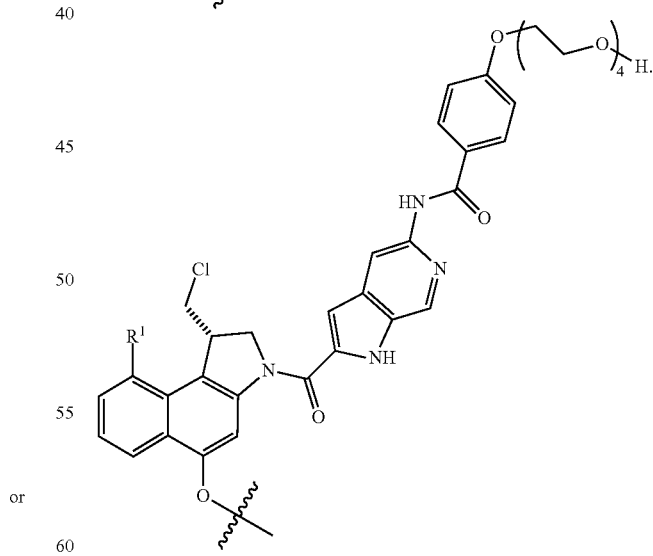
In one embodiment, $R^1$ is selected from H, methyl and methoxy. Preferably, $R^1$ is methyl.

19
In a more preferred embodiment, Z is
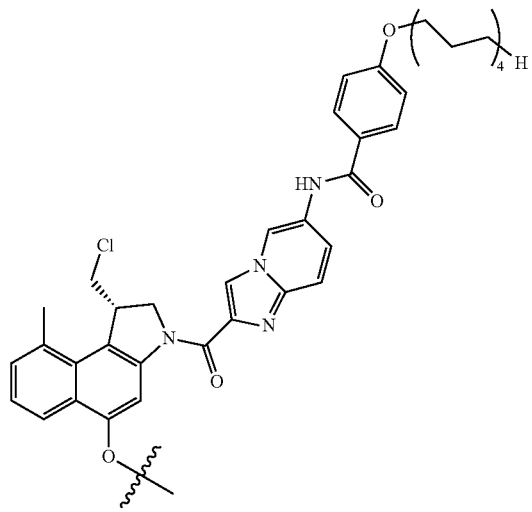
In a particularly preferred embodiment, Z is
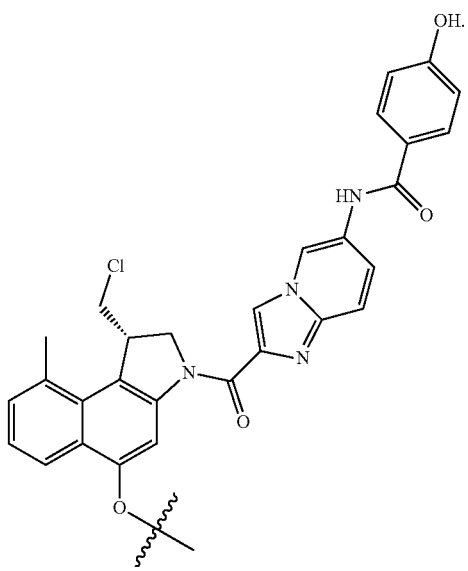 [SMILES: *Oc1cc2c(c3c(C)cccc13)[C@H](CCl)CN2C(=O)c1cn2cc(NC(=O)c3ccc(O)cc3)ccc2n1]
or
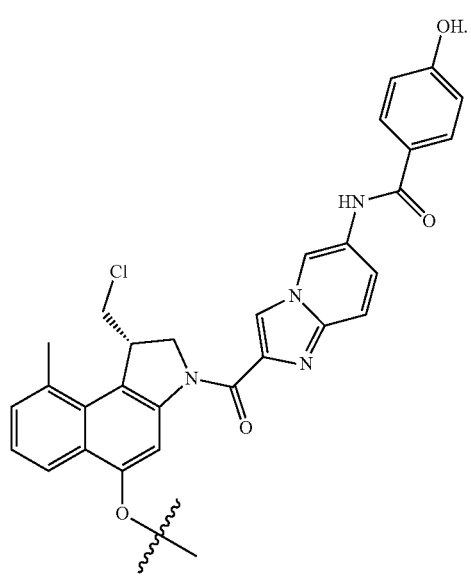
In another embodiment, Z is
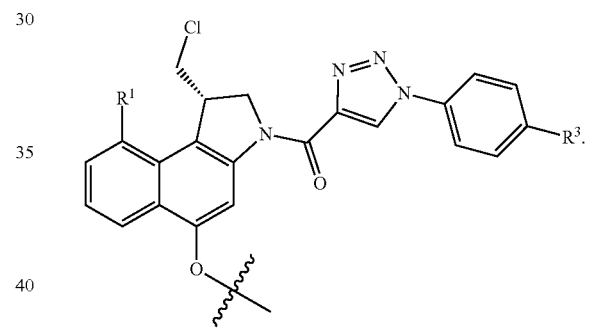
In a preferred embodiment, Z is
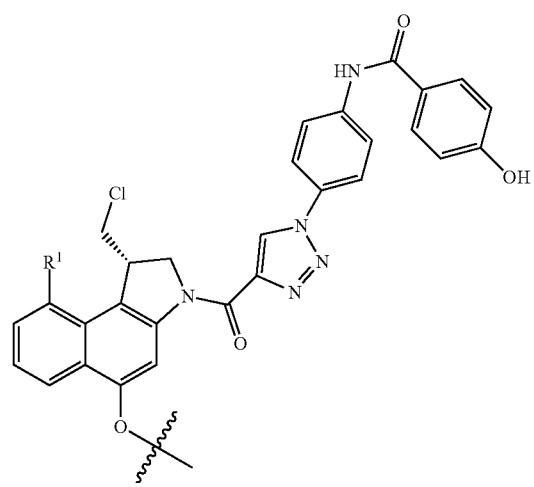 [SMILES: *Oc1cc2c(c3c(C)cccc13)[C@H](CCl)CN2C(=O)c1cn(-c2ccc(NC(=O)c3ccc(O)cc3)cc2)nn1]
or

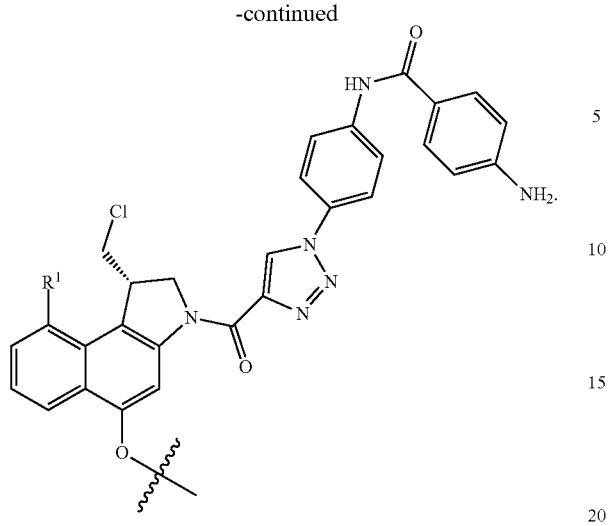
In one embodiment, $R^1$ is selected from H, methyl and methoxy. Preferably, $R^1$ is methyl.
In a more preferred embodiment, Z is
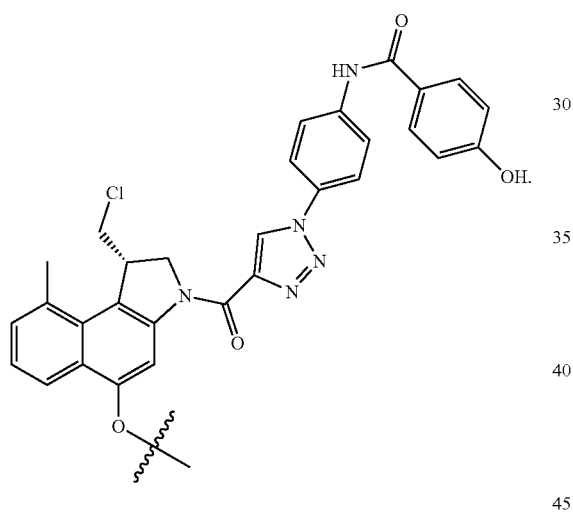
In one embodiment, the compound of formula (I) is represented by
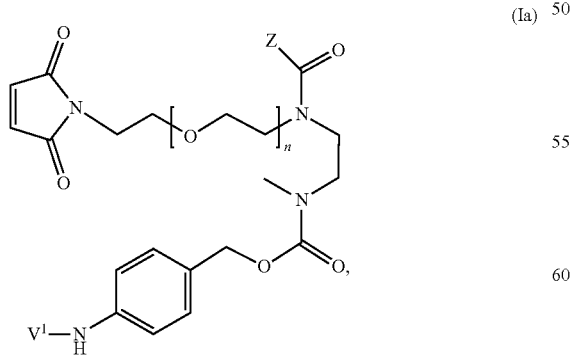
(Ia)
wherein $V^1$, Z and n are as defined in previous embodiments.
In a preferred embodiment, the compound of formula (Ia) is

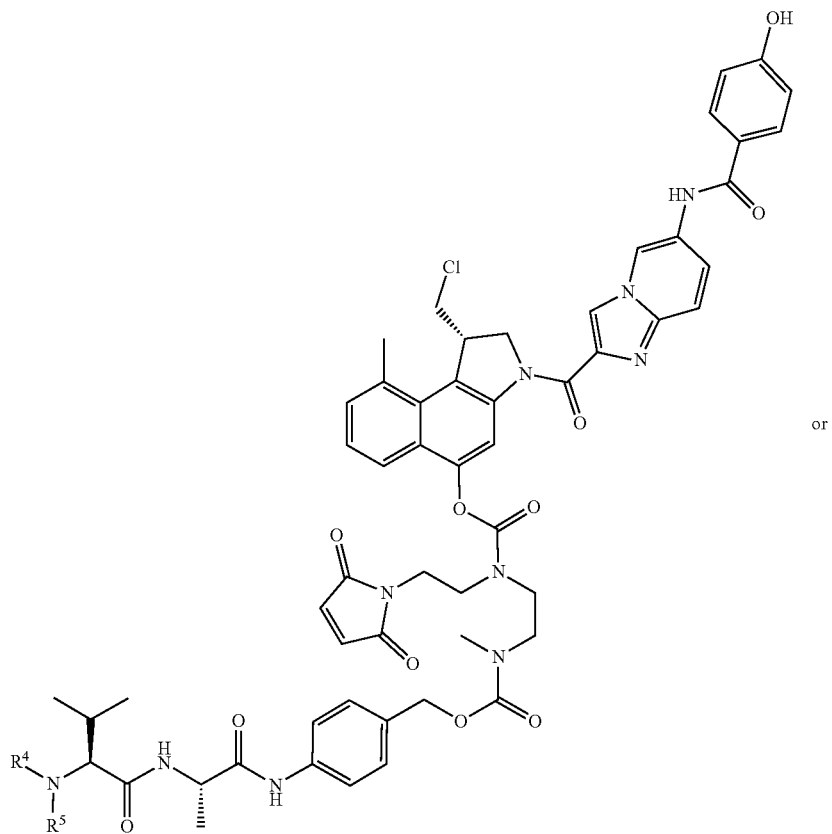
or
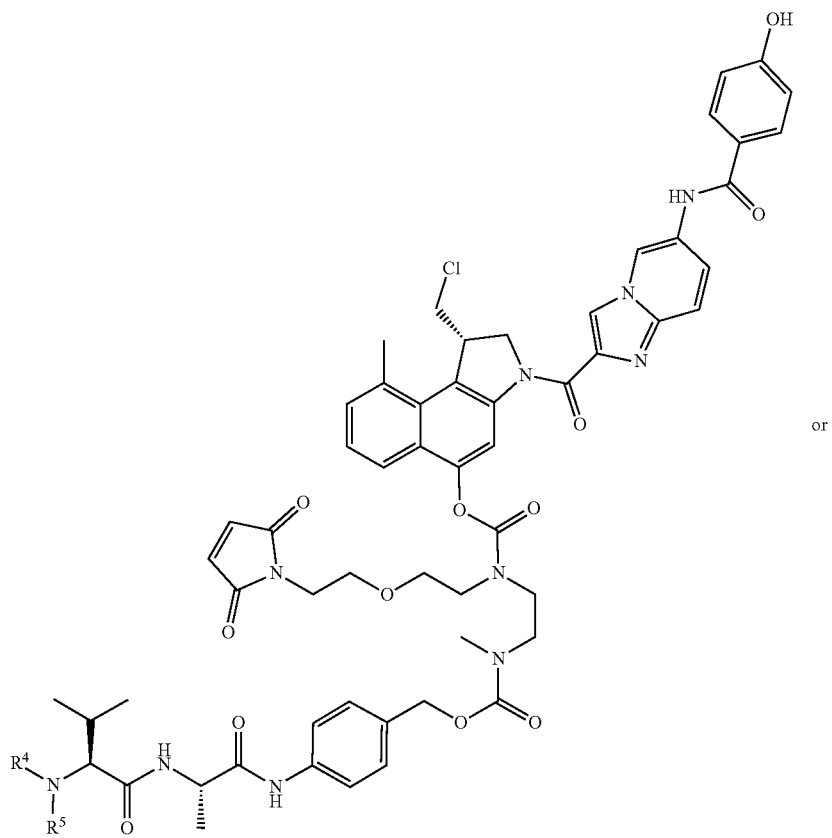
or

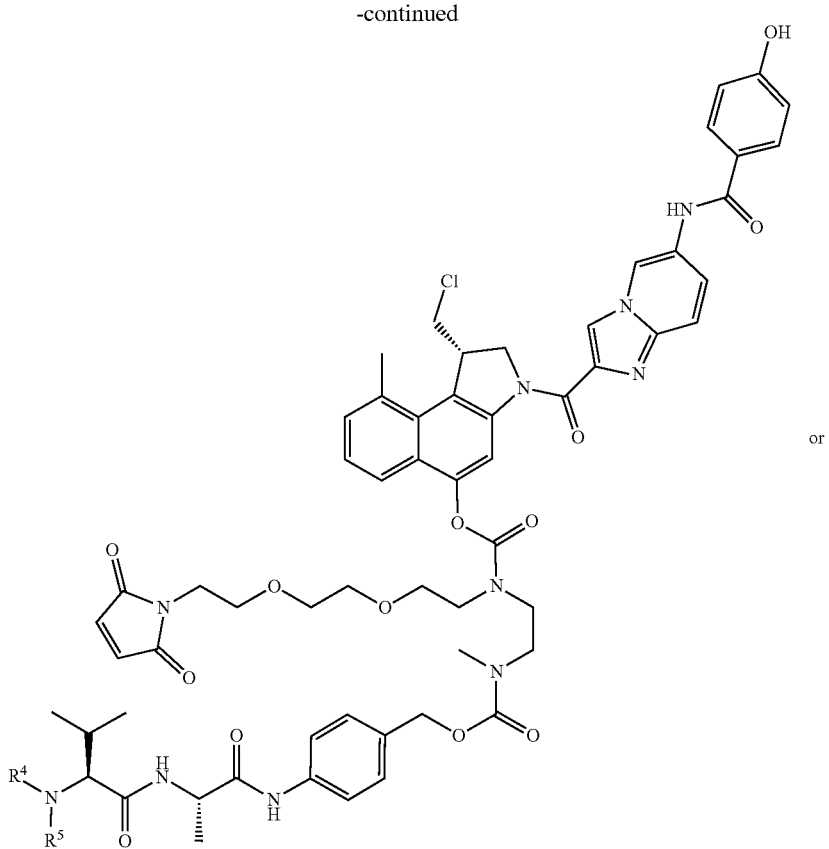
or
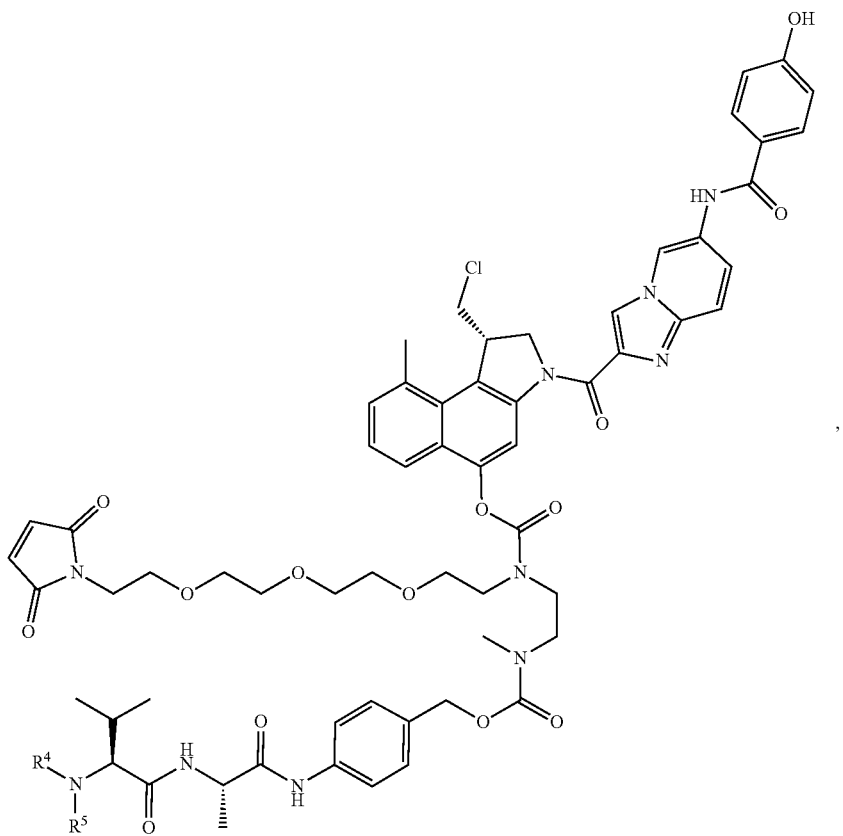

wherein R[4] and R[5] are independently H or an amine blocking group.
In a more preferred embodiment, the compound of formula (Ia) is
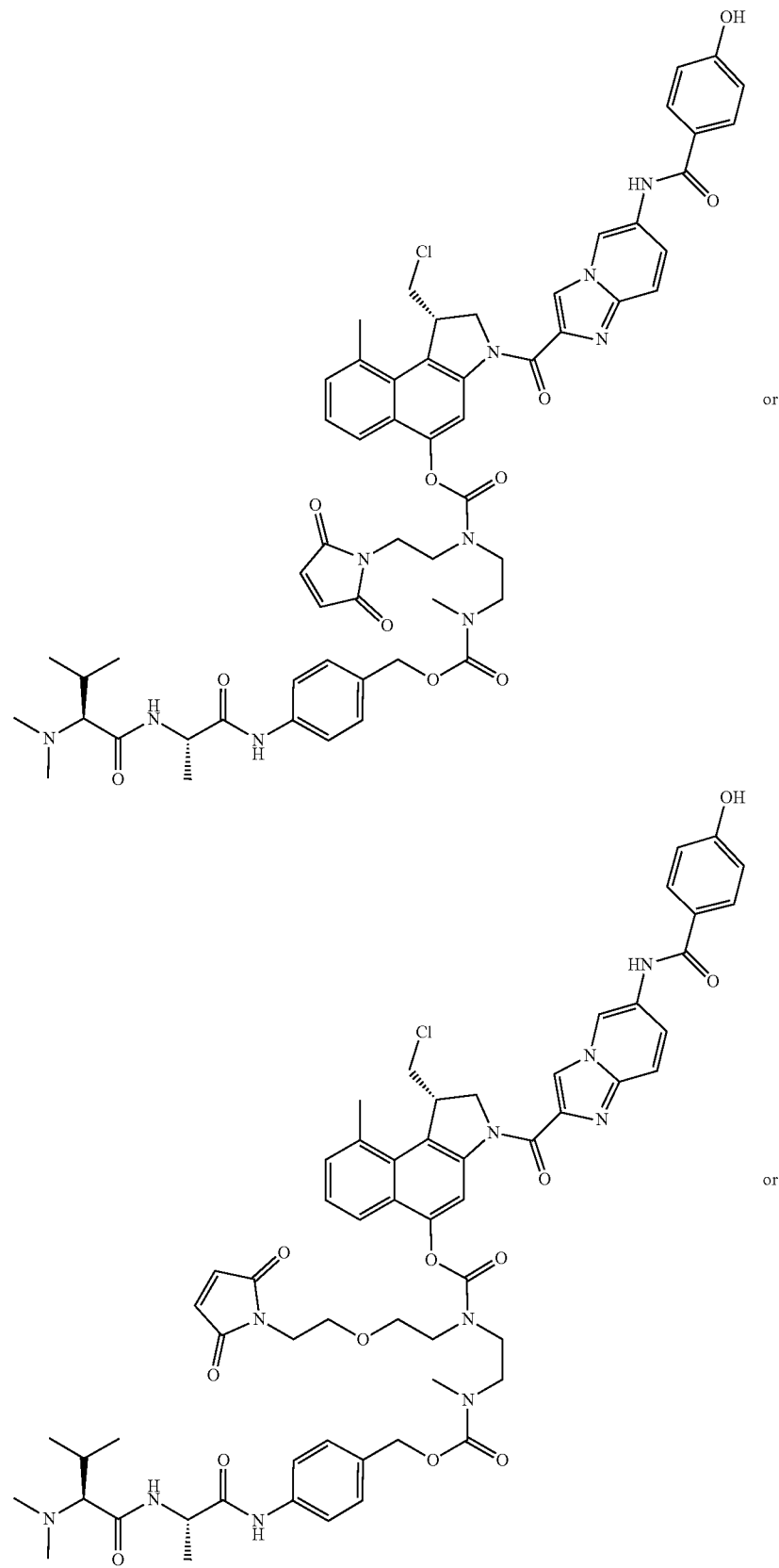
or

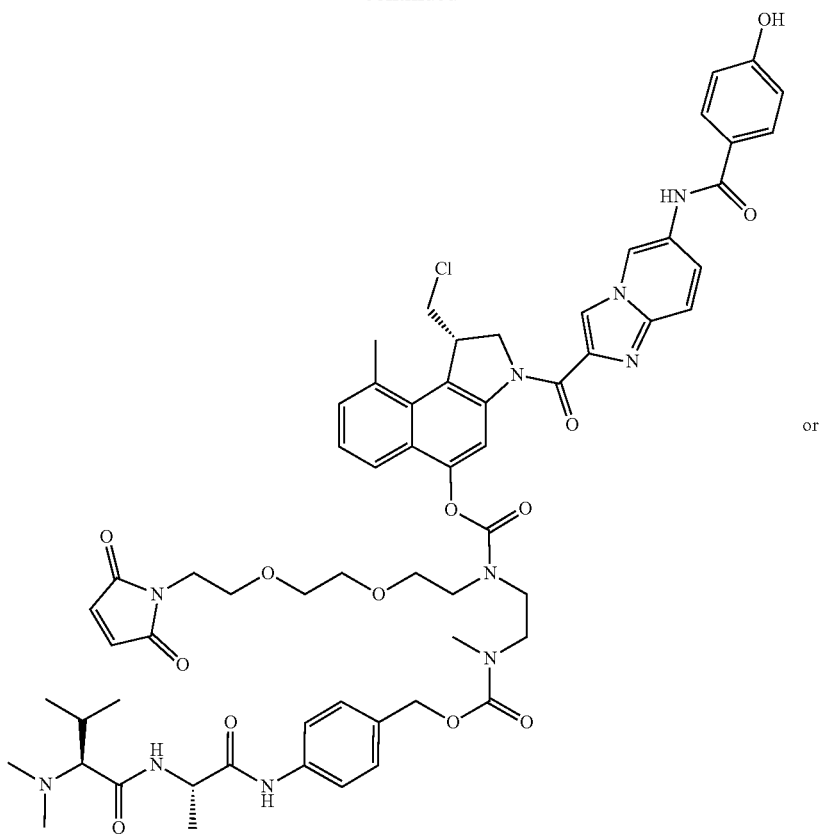
or
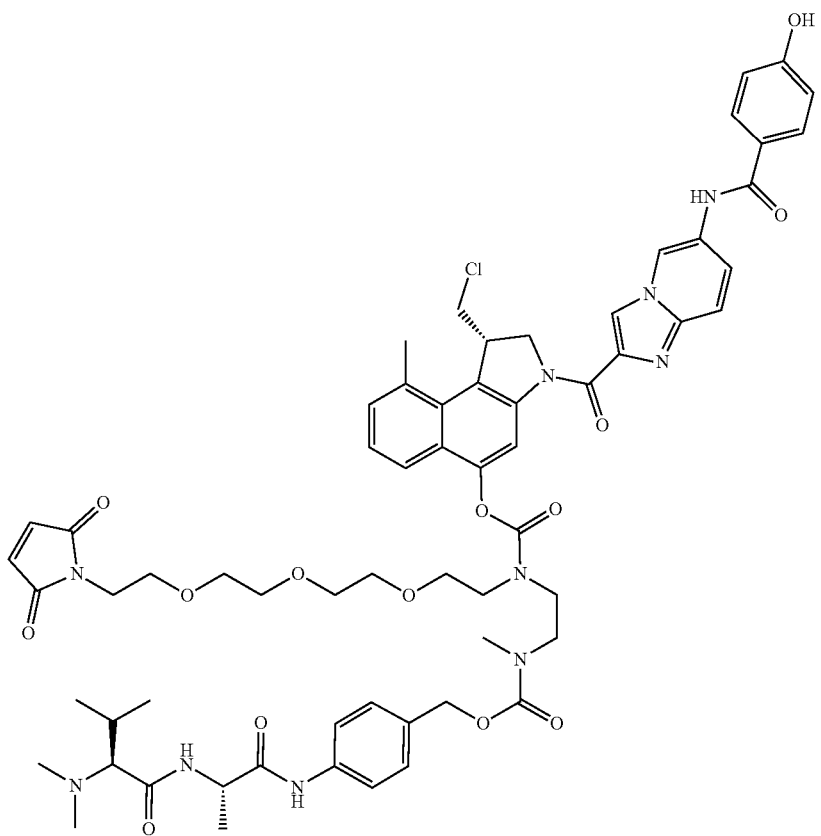

In another preferred embodiment, the compound of formula (Ia) is
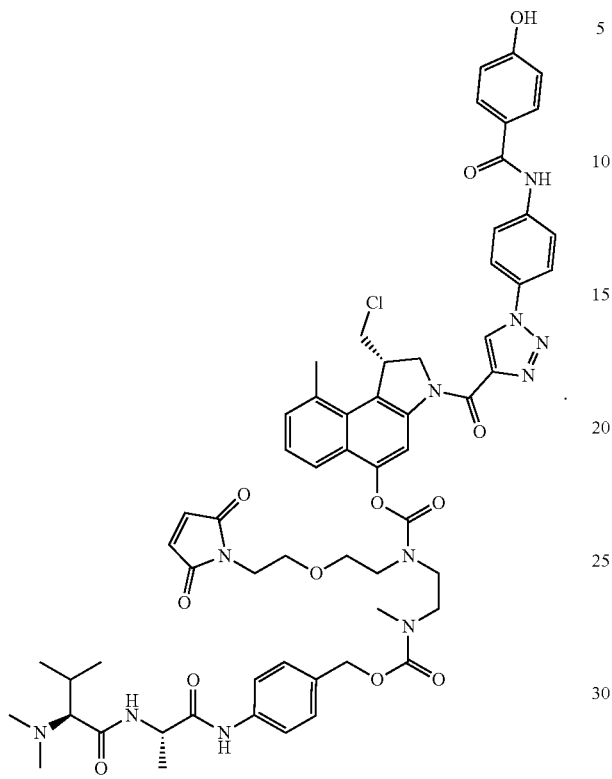
In a further preferred embodiment, the compound of formula (Ia) is
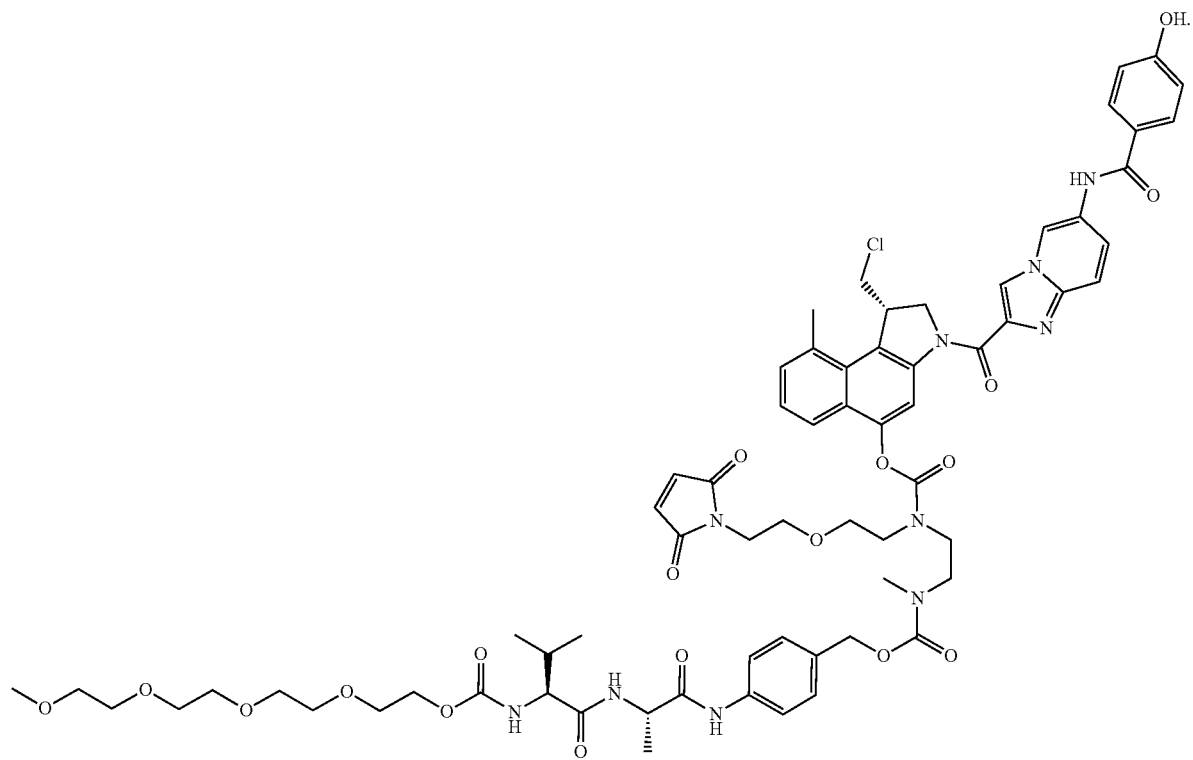 [SMILES: COCCOCCOCCOCCOC(=O)N[C@H](C(=O)N[C@@H](C)C(=O)Nc1ccc(COC(=O)N(C)CCN(CCOCCN2C(=O)C=CC2=O)C(=O)Oc2cc3c(c4c(C)cccc24)[C@H](CCl)CN3C(=O)c2cn3cc(NC(=O)c4ccc(O)cc4)ccc3n2)cc1)C(C)C]

In one embodiment, the compound of formula (I) is represented by
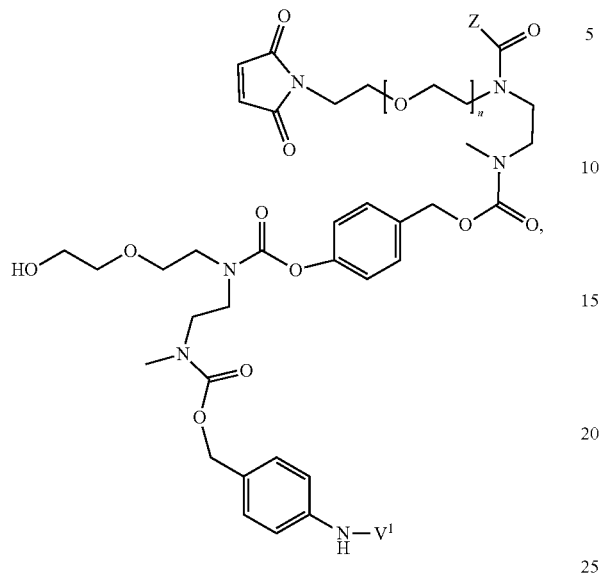
(Ib)
wherein $V^1$, Z and n are as defined in previous embodiments.
In a preferred embodiment, the compound of formula (Ib) is

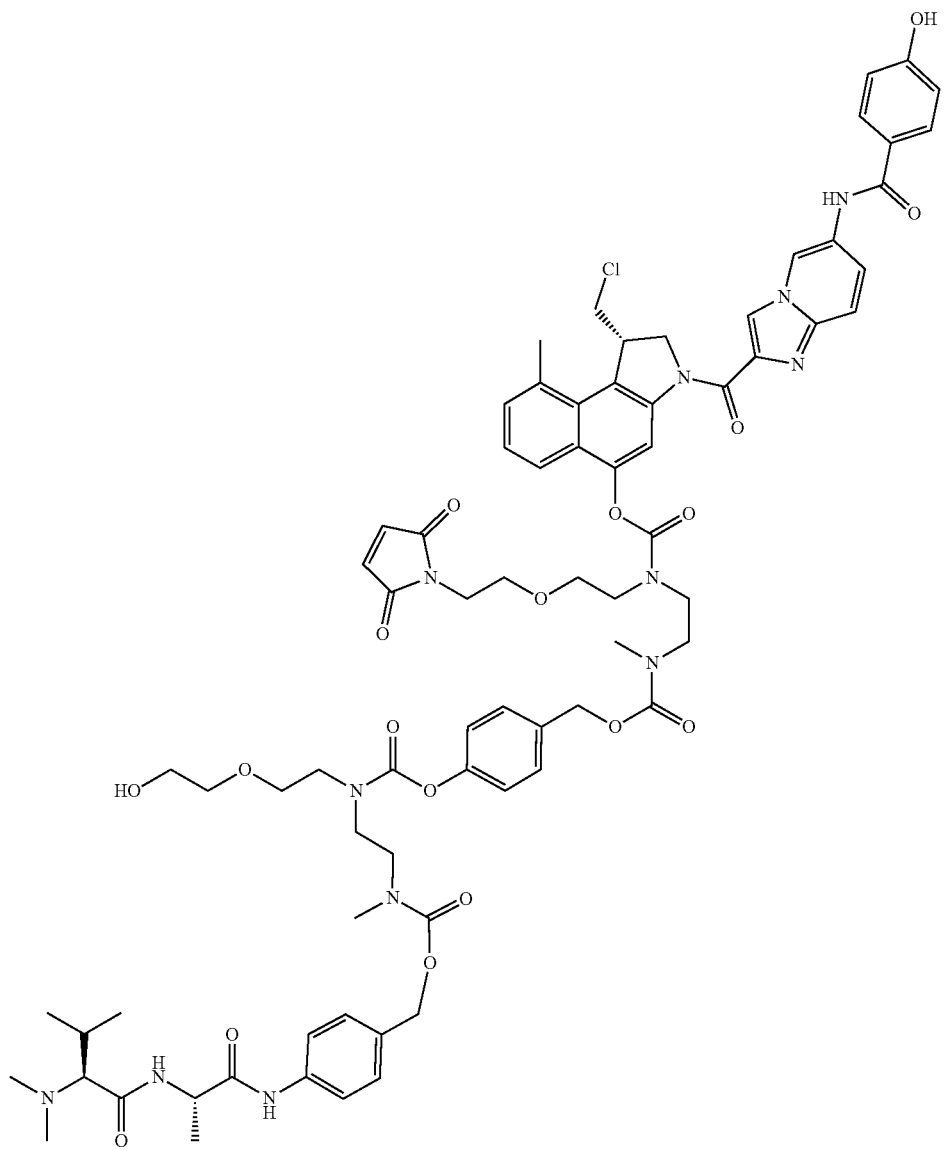 [SMILES: Cc1cccc2c(OC(=O)N(CCOCCN3C(=O)C=CC3=O)CCN(C)C(=O)OCc3ccc(OC(=O)N(CCOCCO)CCN(C)C(=O)OCc4ccc(NC(=O)[C@H](C)NC(=O)[C@H](C(C)C)N(C)C)cc4)cc3)cc3c(c12)[C@H](CCl)CN3C(=O)c1cn2cc(NC(=O)c3ccc(O)cc3)ccc2n1]

The present invention additionally relates to an antibody-drug conjugate (ADC) wherein a linker-drug compound according to the invention (formula I) is conjugated to an antibody or an antigen-binding fragment thereof through a cysteine present in the antibody or the antigen-binding fragment.

The average drug-to-antibody ratio (DAR) of the ADC, i.e. the average number of drugs conjugated to the antibody, typically ranges of from 1 to 6. As is well-known in the art, the DAR and drug load distribution can be determined, for example, by using hydrophobic interaction chromatography (HIC) or reversed phase high-performance liquid chromatography (RP-HPLC). HIC is particularly suitable for determining the average DAR. Preferably, the average DAR ranges of from 1 to 4, more preferably of from 1 to 3, most preferably of from 1.5 to 2.

The linker-drugs according to the present invention are designed such that the hydrophobicity of ADCs comprising such linker-drugs is more comparable to that of the naked antibodies or antigen-binding fragments thereof than is the case for the hydrophobicity of ADCs comprising linear linker-drugs. Control of the hydrophobicity can be used to manage pharmacokinetic parameters of the ADC.

ADC hydrophobicity can be determined by comparing the hydrophobicity of the conjugate to that of the unconjugated antibody or an antigen-binding fragment thereof, referred to as the relative hydrophobicity. In certain embodiments, the retention time of the conjugate is not more than three minutes longer than the retention time of the unconjugated antibody or antigen-binding fragment thereof, as determined by the method described in Tables 1A and 1B in the Examples. In certain other embodiments, the retention time of the conjugate is not more than two minutes longer than the retention time of the unconjugated antibody or antigen-binding fragment thereof, as determined by the method described in Tables 1A and 1B in the Examples. In certain other embodiments, the retention time of the conjugate is not more than one and a half minutes longer than the retention time of the unconjugated antibody or antigen-binding fragment thereof, as determined by the method described in Tables 1A and 1B in the Examples. In certain other embodiments, the retention time of the conjugate is not more than one minute longer than the retention time of the unconjugated antibody or antigen-binding fragment thereof, as determined by the method as described in Tables 1A and 1B.

The effects of the linker of the present invention on relative hydrophobicity will be more pronounced in embodiments wherein the drugs are more hydrophobic in nature.

In the context of the present invention, any antibody—particularly any antibody known to have therapeutic activity or any antibody known in the art of ADCs, or any antigen-binding fragment thereof, e.g. a F(ab')$_2$ or a Fab' fragment, a single chain (sc) antibody, a scFv, a single domain (sd) antibody, a diabody, or a minibody, can be used for (wild-type or site-specific) conjugation of a linker-drug claimed herein. Antibodies may be of any isotype such as IgG, IgA or IgM antibodies. Preferably, the antibody is an IgG antibody, more preferably an IgG$_1$ or IgG$_2$ antibody.

The antibody may be a monospecific (i.e. specific for one antigen; such antigen may be common between species or have related antigens between species) antibody or a bispecific (i.e. specific for two different antigens) antibody. In one embodiment of the present invention, the antibody is a monospecific antibody or an antigen-binding fragment thereof.

These antibodies may be produced recombinantly, synthetically, or by other suitable methods known in the art.

Preferably, the antibody binds to an antigen target that is expressed in or on the cell membrane (e.g., on the cell surface) of a tumour cell. More preferably, the ADC is internalised by the cell after binding of the antibody to the (antigen) target, after which the cytotoxic drug is released intracellularly.

In one embodiment, the antibody to be used in accordance with the present invention is a monospecific antibody (or an antigen-binding fragment thereof) against one of the targets selected from the group consisting of annexin A1, CA242 (cancer antigen 242), CD19, CD22, CD30 (tumour necrosis factor 8), CD33, CD37, CD38 (cyclic ADP ribose hydrolase), CD44, CD47 (integrin associated protein), CD56 (neural cell adhesion molecule), CD70, CD74, CD79, CD115 (colony stimulating factor 1 receptor), CD123 (interleukin-3 receptor), CD138 (Syndecan 1), CD203c (ENPP3), CD303, CD333, CEACAM, CLL-1 (C-type lectin-like molecule-1), c-MET (hepatocyte growth factor receptor), Cripto, DLL3, EGFR, EPCAM, EphA2, EphB3, ETBR (endothelin type B receptor), FAP, FcRL5 (Fc receptor-like protein 5, CD307), FGFR3, FOLR1 (folate receptor alpha), GCC (guanylyl cyclase C), GPNMB, HER2, HMW-MAA (high molecular weight melanoma-associated antigen), integrin, Lewis A like carbohydrate, Lewis Y (CD174), LIV1, mesothelin (MSLN), MN (CA9), MUC1, MUC16, NaPi2b, Nectin-4, PSMA, SLC44A4, STEAP-1, 5T4 antigen, Tag72, tissue factor (TF, thromboplastin, CD142), TF-Ag, TROP2 (tumour-associated calcium signal transducer 2), and VLA.

In another embodiment, the antibody to be used in accordance with the present invention is a bispecific antibody (or an antigen-binding fragment thereof) against a combination of two targets selected from the group listed above.

Examples of suitable antibodies include blinatumomab (CD19), epratuzumab (CD22), iratumumab and brentuximab (CD30), vadastuximab (CD33), tetulumab (CD37), isatuximab (CD38), bivatuzumab (CD44), lorvotuzumab (CD56), vorsetuzumab (CD70), milatuzumab (CD74), polatuzumab (CD79), rovalpituzumab (DLL3), futuximab (EGFR), oportuzumab (EPCAM), farletuzumab (FOLR1), glembatumumab (GPNMB), trastuzumab and pertuzumab (HER2), etaracizumab (integrin), anetumab (mesothelin), pankomab (MUC1), enfortumab (Nectin-4), and H8, A1, and A3 (5T4 antigen).

The antibody to be used in accordance with the present invention preferably is a monoclonal antibody (mAb) and can be a chimeric, humanized or human mAb. More preferably, in accordance with the present invention a humanized or human mAb is used, even more preferably a humanized or human IgG antibody, most preferably a humanized or human IgG1 mAb. Preferably, said antibody has κ (kappa) light chains, i.e., a humanized or human IgG$_1$-κ antibody.

In humanized antibodies, the antigen-binding complementarity determining regions (CDRs) in the variable regions of the heavy chain (HC) and light chain (LC) are derived from antibodies from a non-human species, commonly mouse, rat or rabbit. These non-human CDRs may be placed within a human framework of the variable regions (framework region FR1, FR2, FR3 and FR4) of the HC and LC. Selected amino acids in the human framework regions may be exchanged for the corresponding original non-human species amino acids to improve binding affinity, while retaining low immunogenicity. The thus humanized variable regions are combined with human constant regions. Alternatively, non-human variable regions including the non-human frameworks are combined with a human light chain constant region and a human heavy constant region. In this case, selected amino acids of the original non-human species framework regions are exchanged for their corresponding human amino acids to reduce immunogenicity, while retaining the antibody's binding affinity. In less preferred embodiments also amino acids located within the CDRs may be exchanged to reduce immunogenicity, without reducing affinity of the antibody. The amino acid sequence of these humanized antibodies can be numbered according to the Kabat numbering system (antibody variable regions and light chain constant region) and the Kabat Eu system (antibody heavy chain constant regions).

Antibodies and antigen-binding fragments thereof have been conjugated to a variety of cytotoxic drugs via either cleavable or non-cleavable linkers. Examples of linker-drugs known to the person skilled in the art include vc-seco-DUBA (i.e., SYD980), mc-vc-PAB-MMAE (also abbreviated as mc-vc-MMAE and vc-MMAE), mc-MMAF, and mc-vc-MMAF. These abbreviations are well-known to the skilled artisan (see also WO2015/177360). The linker-drug vc-seco-DUBA is disclosed in WO2011/133039 as compound 18b on p. 210, ll. 21-27.

The generic molecular structure of a vc-seco-DUBA ADC is depicted below.

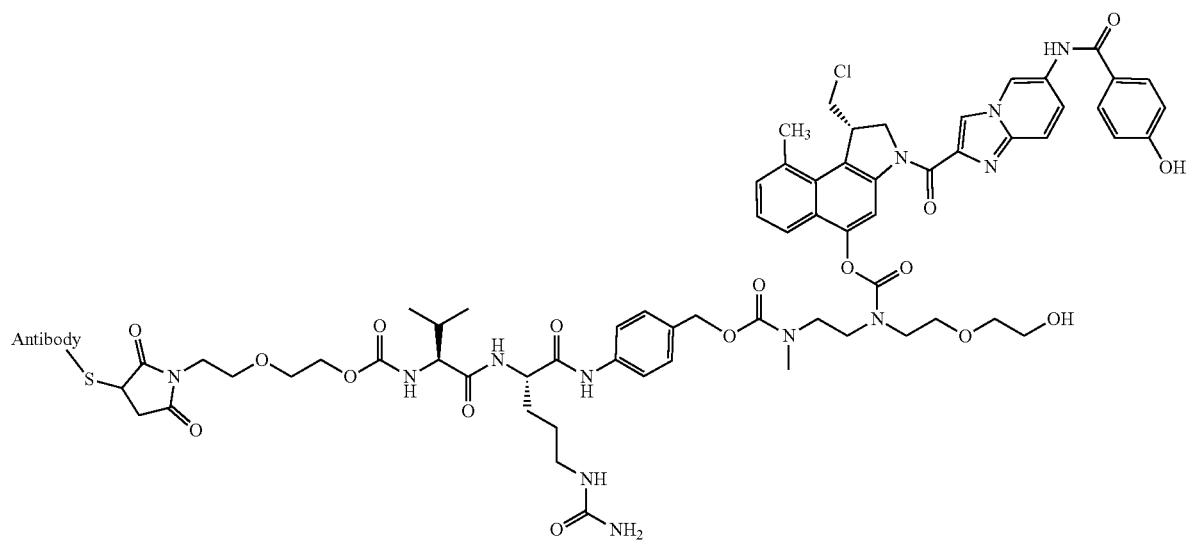

Molecular Structure of a Vc-Seco-DUBA ADC

The linker used in accordance with the present invention is a cleavable linker as opposed to e.g. the non-cleavable maleimidocaproyl (mc), and may comprise e.g. a cleavable dipeptide such as valinecitrulline (vc) or valinealanine (va).

Many of the linkers of the prior art are linear linkers, i.e. having the site for cleavage in between the drug and the attachment site of the antibody or antigen-binding fragment thereof. These linkers are defined by the present inventors as "endo-linkers". Attempts known in the art to improve the hydrophobicity of the linker-drug and thus the resulting ADC include attaching water-soluble groups such as polyethylene glycol polymers to linkers, either in between the drug and the antibody or antigen-binding fragment, or in a parallel position (as a side-group in the linker). However, appending solubilizing groups necessarily increases the complexity of the linker molecule and in case of large solubilizing groups even increases manufacturing complexity of the conjugates.

Surprisingly, the present inventors have found that the hydrophobicity of an ADC can be improved without the need of building in (bulky) water-soluble groups by using non-linear linkers, i.e., linkers not having the site for cleavage in between the drug and the antibody or antigen-binding fragment (defined by the present inventors as "exo-linkers"). Without wishing to be bound by any theory, the arrangement in the linker used in accordance with the invention may lead to a shorter distance between the hydrophobic drug and the antibody or antigen-binding fragment. As a result thereof the drug is shielded from the hydrophilic aqueous environment surrounding the antibody or antigen-binding fragment, thus rendering the ADC less hydrophobic.

This hydrophobicity lowering effect increases when the number of atoms between the antibody's (or antigen-binding fragment's) sulphur atom and the drug's oxygen atom is decreased as shown in Table A below.

For example, in the vc-seco-DUBA ADC there are 29 atoms between the antibody's S-atom and the drug's O-atom.

TABLE A

| Linker-drug in ADC* | Number of atoms | Relative hydrophobicity** | | | |
|---|---|---|---|---|---|
| | | PSMA | Trastuzumab | Rituximab | H8 |
| vc-seco-DUBA | 29 | 1.0 | 1.0 | 1.0 | 1.0 |
| LD6 | 16 | 0.9 | 0.8 | 0.8 | 0.8 |
| LD5 | 13 | 0.8 | 0.8 | 0.7 | 0.8 |
| LD4 | 10 | 0.7 | 0.7 | 0.6 | 0.7 |
| LD3 | 7 | 0.5 | 0.5 | 0.5 | 0.6 |

*wild-type ADCs; vc-seco-DUBA is a linear comparator linker-drug.
**The relative hydrophobicity is determined as described in Table 1A in the Examples.

In one embodiment, the present invention relates to an ADC wherein a linker-drug according to the invention is site-specifically conjugated to an antibody through an engineered cysteine.

In accordance with the present invention, the term "engineered cysteine" means replacing a non-cysteine amino acid in the HC or LC of an antibody by a cysteine, adding a cysteine in between existing amino acids or substituting a native interchain disulfide bond cysteine with a non-cysteine amino acid, e.g. serine, thus creating a free "engineered" cysteine in the other chain. As is known by the person skilled in the art, the cysteine-engineered antibody may be expressed in host cells by recombinant cloning methods or can be prepared by using conventional molecular cloning techniques or the HC or LC domain(s) of the antibody carrying the cysteine mutation(s) can be synthesized as such using known (peptide or DNA) synthesis equipment and procedures. Typically, procedures similar to those disclosed in WO2015/177360 are used.

Antibodies comprising engineered cysteines provide the opportunity to prepare site-specific ADCs, can provide conjugation positions that show good reactivity with the linker-drug, and at the same time have a reduced risk of forming additional disulfide bonds between antibodies (leading to aggregation) or disturbing the antibody structure. The introduction of a cysteine residue at a suitable position of the antibody allows control of the site of conjugation and the obtained site-specific conjugates are more homogeneous than the conjugates obtained via conventional methods, i.e. conjugation via wild-type interchain disulfide cysteines. Such conventional methods lead to a heterogeneous mixture of ADCs, which may require purification, e.g. to remove unconjugated antibody. Some individual constituents of a conventionally conjugated ADC mixture can have poor in vivo performance. The in vivo performance of ADCs in terms of efficacy, safety, and stability may be improved if the linker-drug of the ADCs is site-specifically conjugated via engineered cysteines according to B.-Q. Shen et al. in Nature Biotechnology, Vol. 30, Number 2, 2012, pages 184-189.

As shown in Table B below, the hydrophobicity lowering effect of the linker-drugs of the invention is also clearly visible in ADCs wherein the linker-drug is site-specifically conjugated at a position where the linker-drug is pointing outwards.

TABLE B

| Linker-drug in ADC | Number of atoms between drug and antibody | Relative hydrophobicity PSMA-HC120* |
|---|---|---|
| vc-seco-DUBA** | 29 | 1.0 |
| LD6 | 16 | 0.8 |
| LD5 | 13 | 0.7 |
| LD4 | 10 | 0.6 |
| LD3 | 7 | 0.5 |

*Engineered cysteine on position 120 in the heavy chain.
**vc-seco-DUBA is a linear comparator linker-drug.

The present inventors observed that the decrease in hydrophobicity is even more pronounced when the linker-drug is site-specifically conjugated at positions in the Fab or Fc cavity. This effect is shown in Table C for LC positions 40 and 41, and HC position 41. Relative hydrophobicity values were calculated using the hydrophobicity of wild-type conjugated PSMA-vc-seco-DUBA ADC as the reference value (first column showing the values for the site-specifically conjugated ADCs) or using the hydrophobicity of the respective site-specifically conjugated ADC (second column showing the values for the site-specifically conjugated ADCs). The reference values are indexed to 1.0.

TABLE C

| | | Relative hydrophobicity | | | | | | |
|---|---|---|---|---|---|---|---|---|
| Linker drug in ADC** | Number of atoms | PSMA | PSMA-LC40* | | PSMA-LC41* | | PSMA-HC41* | |
| vc-seco-DUBA | 29 | 1.0 | 0.9 | 1.0 | 0.6 | 1.0 | 0.6 | 1.0 |
| LD6 | 16 | 0.9 | 0.5 | 0.5 | 0.4 | 0.6 | 0.2 | 0.4 |
| LD5 | 13 | 0.8 | 0.4 | 0.4 | 0.3 | 0.4 | 0.2 | 0.3 |
| LD4 | 10 | 0.7 | 0.3 | 0.3 | 0.1 | 0.2 | 0.1 | 0.2 |
| LD3 | 7 | 0.5 | 0.3 | 0.3 | 0.1 | 0.1 | 0.1 | 0.1 |

*Engineered cysteine on position 40 in the light chain, 41 in the light chain and 41 in the heavy chain, respectively.
**vc-seco-DUBA is a linear comparator linker-drug.

In one embodiment, the present invention relates to an ADC wherein a linker-drug is site-specifically conjugated to an antibody through an engineered cysteine at one or more positions of said antibody selected from heavy chain 40, 41, 89 (Kabat numbering), 152, 153, 155, 171, 247, 297, 339, 375 and 376 (Eu numbering), and light chain 40, 41, 165 and 168 (Kabat numbering).

In the context of the present invention, Kabat numbering is used for indicating the amino acid positions of engineered cysteines in HC variable and LC variable and constant regions and Eu numbering is used for indicating the positions in the HC constant regions of the antibody.

The expression "Kabat numbering" refers to the numbering system used for heavy chain variable or light chain variable or constant domains of the compilation of antibodies in Kabat, E. A. et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, an FR or CDR of the variable domain. The Kabat numbering of residues may be determined for a given antibody by alignment at regions of homology of the sequence of the antibody with a "standard" Kabat numbered sequence.

The expression "Eu numbering" refers to the Eu index as in Kabat, E. A. et al., Sequences of Proteins of Immunological Interest, 5th Ed. Public Health Service, National Institutes of Health, Bethesda, Md., NIH publication no. 91-3242, pp. 662, 680, 689 (1991).

The "Eu index as in Kabat" refers to the residue numbering of the human IgG1 Eu antibody (Edelman, G. M. et al., Proc. Natl. Acad. Sci. USA, 63, 78-85 (1969)).

Heavy chain positions 40, 41 and 89 are located in the variable region and positions 152, 153, 155, 171, 247, 297, 339, 375 and 376 are located in the constant region of the antibody. Light chain positions 40 and 41 are located in the variable region and positions 165 and 168 are located in the constant region of the antibody.

Heavy chain positions 40, 41, 89, 152, 153, 155 and 171 and light chain positions 40, 41, 165 and 168 are located in the Fab part and heavy chain positions 247, 297, 339, 375 and 376 are located in the Fc part of the antibody.

The present inventors surprisingly have found that the site-specifically conjugated ADCs of the present invention show improved physicochemical, pharmacological and/or pharmacokinetic properties, as compared to conventional ADCs in which the linear linker-drug is conjugated through native (i.e., endogenous) interchain disulfide bond cysteines of the antibody.

Modification of the variable domains of an antibody, other than for humanization, is generally avoided as it can lead to partial or complete loss of antigen binding properties. However, specific amino acid residues in the framework regions of the heavy and light chain of the antibody are, when exchanged for a cysteine, both suitable for conjugation and do not lead to (significant) reduction of antigen binding after conjugation of a linker-drug. Moreover, conjugation to these positions in the Fab part also enables the use of antigen-binding fragments instead of fully intact antibodies. Conjugation in the Fab part is preferred over conjugation in the Fc part, as tumour-associated proteases in the tumour microenvironment can partially cleave the Fc constant domains under the hinge region. Such cleavage of the Fc constant domains would result in loss of Fc-conjugated linker-drugs, because these are not internalised by the cancer cell, which in turn could lead to a decreased activity of the ADC in vivo. (Fan et al. Breast Cancer Res. 2012; 14: R116 and Brersky et al. PNAS 2009; 106: 17864-17869).

Therefore, in a preferred embodiment, the present invention relates to an ADC wherein a linker-drug is site-specifically conjugated to an antibody through an engineered cysteine at one or more positions of said antibody selected from heavy chain positions 40, 41 and 89 and light chain positions 40 and 41.

In a more preferred embodiment, the present invention relates to an ADC wherein a linker-drug is site-specifically conjugated to an antibody through an engineered cysteine at one or more positions of said antibody selected from heavy chain position 41 and light chain positions 40 and 41.

In a particularly preferred embodiment, the present invention relates to an ADC wherein a linker-drug is site-specifically conjugated to an antibody through an engineered cysteine at heavy chain position 41.

As one representative example, the antibody to be used in accordance with the present invention is the anti-PSMA antibody having an engineered cysteine at position 41 of the heavy chain (i.e. PSMA-HC41) that is disclosed in WO2015/177360 as SYD1030 (the heavy chain comprises the amino acid sequence of SEQ ID NO:2 and the light chain comprises the amino acid sequence of SEQ ID NO:5).

As another representative example, the antibody to be used in accordance with the present invention is the anti-5T4 antigen antibody having an engineered cysteine at position 41 of the heavy chain that is disclosed in WO2015/177360 as H8-HC41 (the heavy chain comprises the amino acid sequence of SEQ ID NO:8 and the light chain comprises the amino acid sequence of SEQ ID NO:11).

ADCs in accordance with the present invention can be obtained according to methods and procedures that are well known to a person skilled in the art.

A suitable method for the non-site-specific (wild-type) conjugation of duocarmycin linker-drugs, i.e., conjugation to an endogenous interchain disulfide bond cysteine, is disclosed in Example 15 of WO2011/133039.

A suitable method for the non-site-specific (wild-type) conjugation of CBI dimer linker-drugs is disclosed in WO2015/110935.

The ADCs in accordance with the present invention have binding affinities similar to the naked antibodies, excellent in vitro toxicity, and good in vivo efficacy. Notably, it was found that the ADCs are generally less hydrophobic and less susceptible to cathepsin B cleavage and therefore likely also to other intra- or extracellular enzymes/proteases in the tumour mass (tumour microenvironment) than ADCs that are conjugated to linear linker-drug vc-seco-DUBA known from the prior art, but still show similar in vitro cytotoxicity.

Unexpectedly, ADCs in accordance with the present invention show improved in vivo efficacy in a tumour xenograft animal model as compared to ADCs that are conjugated to linear linker-drug vc-seco-DUBA.

In a particular embodiment, the present invention relates to an ADC of formula (II)

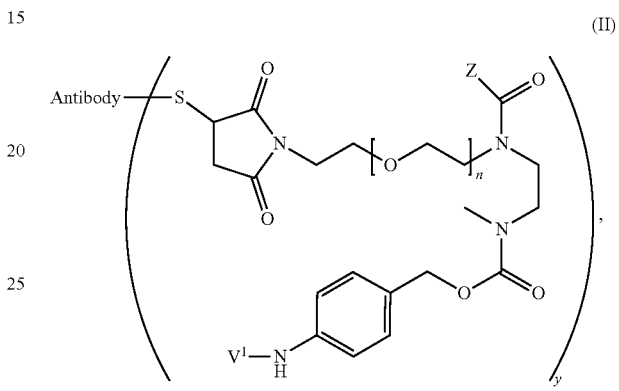

(II)

wherein "Antibody" is an antibody or an antigen-binding fragment thereof, either without or with at least one engineered cysteine as disclosed herein;

n is 0, 1, 2 or 3;

y represents an average DAR of from 1 to 6, preferably of from 1 to 4, more preferably of from 1 to 3, most preferably of from 1.5 to 2; and $V^1$ and Z are as defined in previous embodiments.

In a preferred embodiment, the present invention relates to an ADC of formula (III)

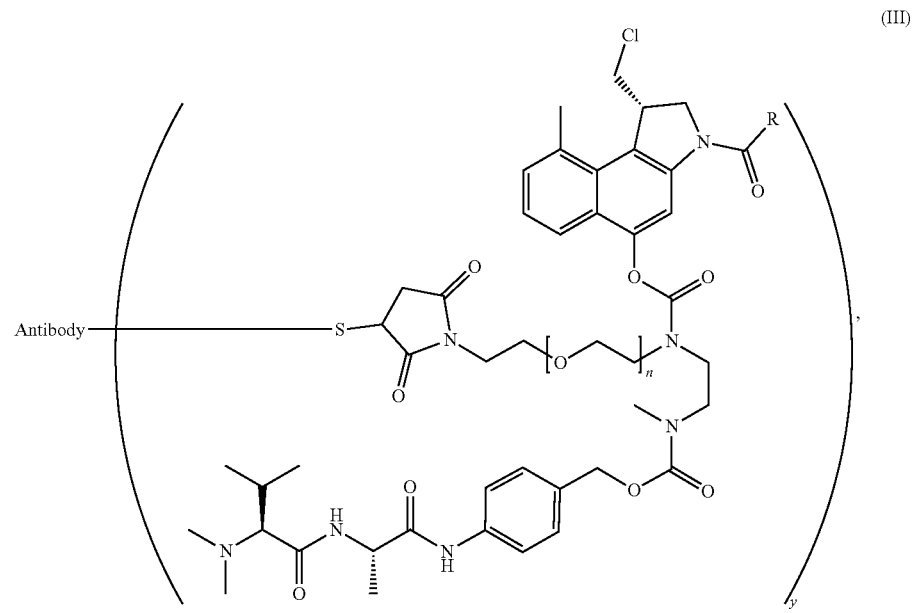

(III)

wherein "Antibody" is an antibody or an antigen-binding fragment thereof, either without or with at least one engineered cysteine as disclosed herein;
n is 0, 1, 2 or 3;
y represents an average DAR of from 1 to 6, preferably of from 1 to 4, more preferably of from 1 to 3, most preferably of from 1.5 to 2; and
R is selected from

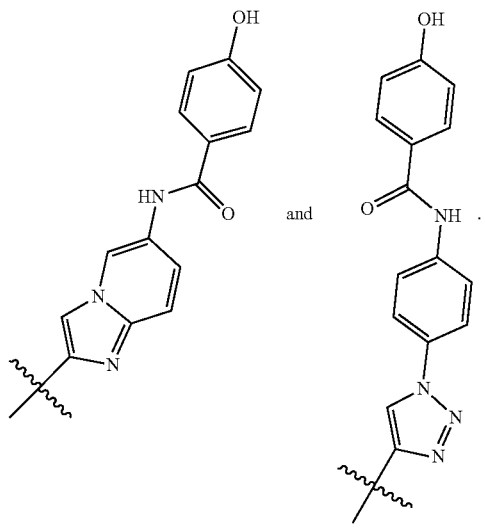 [SMILES: *c1cn2cc(NC(=O)c3ccc(O)cc3)ccc2n1 ; *c1cn(-c2ccc(NC(=O)c3ccc(O)cc3)cc2)nn1]

In a particularly preferred embodiment, the present invention relates to an ADC of formula (II) or (III) comprising an antibody with an engineered cysteine at one or more positions selected from heavy chain positions 40 and 41, and light chain positions 40 and 41. Preferably, said engineered cysteine is at heavy chain position 41 or light chain position 40 or 41, more preferably at heavy chain position 41.

The present invention further relates to a pharmaceutical composition comprising a linker-drug or an ADC as described hereinabove and one or more pharmaceutically acceptable excipients. Typical pharmaceutical formulations of therapeutic proteins such as monoclonal antibodies and (monoclonal) antibody-drug conjugates take the form of lyophilized cakes (lyophilized powders), which require (aqueous) dissolution (i.e., reconstitution) before intravenous infusion, or frozen (aqueous) solutions, which require thawing before use.

Typically, the pharmaceutical composition in accordance with the present invention is provided in the form of a lyophilized cake. Suitable pharmaceutically acceptable excipients for inclusion into the pharmaceutical composition (before freeze-drying) include buffer solutions (e.g. citrate, histidine or succinate containing salts in water), lyoprotectants (e.g. sucrose, trehalose), tonicity modifiers (e.g. sodium chloride), surfactants (e.g. polysorbate), and bulking agents (e.g. mannitol, glycine). Excipients used for freeze-dried protein formulations are selected for their ability to prevent protein denaturation during the freeze-drying process as well as during storage. As an example, the sterile, lyophilized powder single-use formulation of Kadcyla™ (Roche) contains—upon reconstitution with Bacteriostatic or Sterile Water for Injection (BWFI or SWFI)—20 mg/mL ado-trastuzumab emtansine, 0.02% w/v polysorbate 20, 10 mM sodium succinate, and 6% w/v sucrose with a pH of 5.0.

The present invention further relates to a linker-drug, an ADC or a pharmaceutical composition as described hereinabove for use as a medicament.

In one embodiment, the present invention relates to a linker-drug, an ADC or a pharmaceutical composition as described hereinabove for use in the treatment of human solid tumours and haematological malignancies.

In a first preferred embodiment, the present invention relates to a linker-drug, an ADC or a pharmaceutical composition as described hereinabove for use in the treatment of human solid tumours selected from the group consisting of breast cancer, brain cancer (e.g. glioblastoma), head and neck cancer, thyroid cancer, adrenal cancer, bone cancer, ocular cancer, oesophageal cancer, gastric cancer, small intestine cancer, colorectal cancer, urothelial cancer (e.g. bladder or renal cancer), ovarian cancer, uterine cancer, vaginal and cervical cancer, lung cancer (especially non-small cell lung cancer (NSCLC) and small-cell lung cancer (SCLC)), mesothelioma (especially malignant pleural mesothelioma), liver cancer, pancreatic cancer, skin cancer, testicular cancer, and prostate cancer.

In a second preferred embodiment, the present invention relates to a linker-drug, an ADC or a pharmaceutical composition as described hereinabove for use in the treatment of human solid tumours selected from the group consisting of breast cancer, gastric cancer, colorectal cancer, urothelial cancer (e.g. bladder cancer), ovarian cancer, uterine cancer, lung cancer (especially non-small cell lung cancer (NSCLC) and small-cell lung cancer (SCLC)), mesothelioma (especially malignant pleural mesothelioma), liver cancer, pancreatic cancer, and prostate cancer.

In a third preferred embodiment, the present invention relates to a linker-drug compound, an ADC or a pharmaceutical composition as described hereinabove for use in the treatment of human haematological malignancies, particularly leukaemia, more particularly leukaemia selected from the group consisting of acute lymphoblastic and myeloid leukaemia (ALL and AML, respectively).

The present invention further relates to the use of a sequentially or simultaneously administered combination of a linker-drug compound, an ADC or a pharmaceutical composition as described hereinabove with one or more other therapeutic agents, such as with a therapeutic antibody, a chemotherapeutic agent, and/or an ADC against a further cancer-related target for the treatment of human solid tumours and haematological malignancies as described hereinabove.

In one embodiment of the present invention, the therapeutic antibody is adecatumumab, alemtuzumab, amatuximab, bevacizumab, cetuximab, denosumab, etaracizumab, farletuzumab, gemtuzumab, labetuzumab, mapatumumab, minretumomab, nimotuzumab, nivolumab, oregovomab, panitumumab, pemtumomab, pertuzumab, ramucirumab, sibrotuzumab, trastuzumab or volociximab and the chemotherapeutic agent is i) an alkylating agent, particularly nitrogen mustards, such as mechlorethamine, chlorambucil, cyclophosphamide, ifosfamide and melphalan; nitrosoureas, such as streptozocin, carmustine and lomustine; alkyl sulfonates, such as busulfan; triazines, such as dacarbazine and temozolomide; ethylenimines, such as thiotepa and altretamine; or platinum drugs, such as cisplatin, carboplatin and oxaliplatin; ii) an anti-metabolite, particularly 5-fluorouracil, 6-mercaptopurine, capecitabine, cytarabine, floxuridine, fludarabine, gemcitabine, hydroxyurea, methotrexate or pemetrexed; iii) an anti-tumour antibiotic, particularly daunorubicin, doxorubicin, epirubicin, idarubicin, actinomycin D, bleomycin, mitomycin-C or mitoxantrone; iv) a topoisomerase inhibitor, particularly topoisomerase I inhibitors, such as topotecan and irinotecan; or topoisomerase II inhibitors, such as etoposide, teniposide and mitoxantrone; v) a mitotic inhibitor, particularly taxanes, such as paclitaxel, cabazitaxel and docetaxel; epothilones, such as ixabepilone; vinca alkaloids, such as vinblastine, vincristine and vinorelbine; or estramustine; vi) a signalling cascade inhibitor, particularly mTOR (mammalian target of rapamycin) inhibitors, such as temsirolimus and everolimus; or tyrosine kinase inhibitors, such as gefitinib, erlotinib, imatinib, pazopanib, ceritinib, crizotinib, lapatinib and afatinib; vii) a corticosteroid, particularly prednisone, methylprednisolone or dexamethasone; viii) a hormonal therapeutic agent, particularly androgen receptor modulating agents, such as bicalutamide, enzalutamide and abiraterone acetate; anti-oestrogens, such as tamoxifen; or aromatase inhibiting or steroid modifying agents, such as anastrozole, letrozole, fulvestrant and exemestane; ix) a PARP inhibitor, particularly olaparib; or x) another chemotherapy drug, particularly L-asparaginase or bortezomib. The person skilled in the art will have no difficulty in selecting suitable combination therapies for use in the treatment of human solid tumours and haematological malignancies as described hereinabove.

A therapeutically effective amount of the ADC in accordance with the present invention lies in the range of about 0.01 to about 15 mg/kg body weight, particularly in the range of about 0.1 to about 10 mg/kg body weight, more particularly in the range of about 0.3 to about 10 mg/kg body weight. This latter range corresponds roughly to a flat dose in the range of 20 to 800 mg of the linker-drug or ADC. The compound of the present invention may be administered weekly, bi-weekly, three-weekly, monthly or six-weekly. Suitable treatment regimens are depending upon the severity of the disease, the age of the patient, the compound being administered, and such other factors as would be considered by the treating physician.

EXAMPLES

Materials and Methods

Cysteine-engineered antibodies were obtained using the materials and procedures described in WO2015/177360. Reagents and buffers were procured from commercial suppliers.

HIC—For analytical HIC, 5-10 μL of sample (1 mg/ml) was injected onto a TSKgel Butyl-NPR column (4.6 mm ID×3.5 cm L, Tosoh Bioscience, cat. nr. 14947). The elution method consisted of a linear gradient from 100% Buffer A (25 mM sodium phosphate, 1.5 M ammonium sulphate, pH 6.95) to 100% of Buffer B (25 mM sodium phosphate, pH 6.95, 20% isopropanol) at 0.4 ml/min over 20 minutes. The column temperature was maintained at 25° C. A Waters Acquity H-Class ultra performance liquid chromatography (UPLC) system equipped with PDA-detector and Empower software was used. Absorbance was measured at 214 nm to quantify the average DAR and to determine the relative hydrophobicity of the various ADCs.

SEC—For analytical SEC, 5 μL of sample (1 mg/ml) was injected onto a TSKgel G3000SWXL column (5 μm, 7.8 mm ID×30 cm L, Tosoh Bioscience, cat. no. 08541) equipped with a TSKgel SWXL Guard column (7 μm, 6.0 mm ID×4.0 cm L, Tosoh Bioscience, cat. no. 08543). The elution method consisted of elution with 100% 50 mM sodium phosphate, 300 mM NaCl, pH 7.5 at 0.6 ml/min for 30 minutes. The column temperature was maintained at 25° C. A Waters Acquity H-Class UPLC system equipped with PDA-detector and Empower software was used. Absorbance was measured at 214 nm to quantify the amount of HMW species.

SHPC—Samples were prepared by mixing 70 μl ADC solution with 30 μl DMA. 50 μl of the samples was injected onto a shielded hydrophobic phase column (SUPELCOSIL LC-HISEP 5 μm, 4.6 mm ID×15 cm L, Supelco (Sigma-Aldrich), cat. no. 58935) mounted in a Waters Acquity H-Class UPLC system equipped with PDA-detector and Empower software. The elution method consisted of a linear gradient from 90% Buffer A (100 mM ammonium acetate, pH 4.0) and 10% of Buffer B (acetonitrile) to 32% Buffer A and 68% Buffer B at 1.0 ml/min over 10 minutes. The column temperature was maintained at 45° C. Absorbance was measured at 325 nm to quantify the amount of free linker-drug.

Synthesis of Exo-Linker-Drugs

The solvents used were Reagent grade or HPLC grade. NMR spectra were recorded on a Bruker AVANCE400 (400 MHz for $^1$H; 100 MHz for $^{13}$C). Chemical shifts are reported in ppm relative to tetramethylsilane as an internal standard.

The crude linker-drugs were purified by dissolving the linker-drugs in DMA and loading the solution onto a Waters SunFire™ Prep C18 OBD™ column (5 μm particle size, 50×150 mm) followed by elution with a flow rate of 117 ml/min using a linear gradient of 20% buffer A to 70% buffer A. Buffer A is acetonitrile. Buffer B is 0.1% TFA (m/m) in water. The purities were evaluated by UPLC using a Waters ACQUITY UPLC® BEH C18 Column (1.7 μm particle size, 2.1×50 mm) at a flow rate of 0.4 ml/min.

In general, the synthesis of the linker-drugs start from compound 11 and the cyclisation module, the synthesis of which is described in Elgersma et al. Mol. Pharmaceutics, 2015; 12: 1813-1835 and WO 2011/133039.

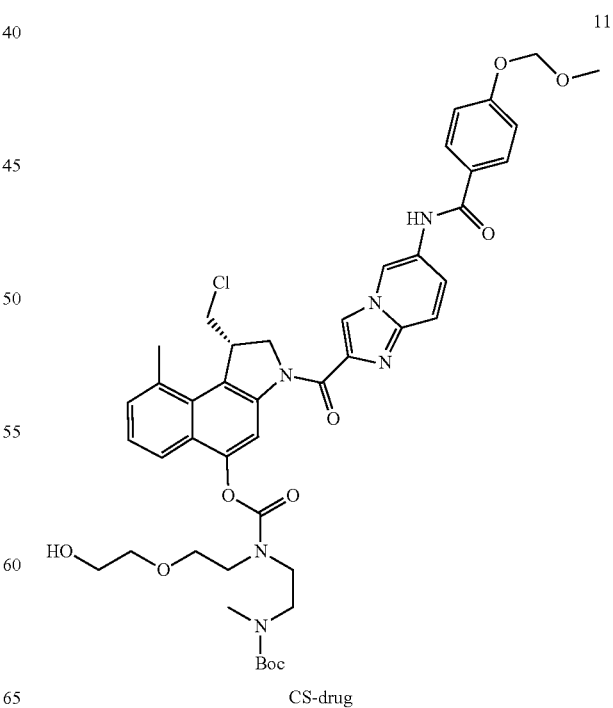

Synthesis of Compounds
Compound 12
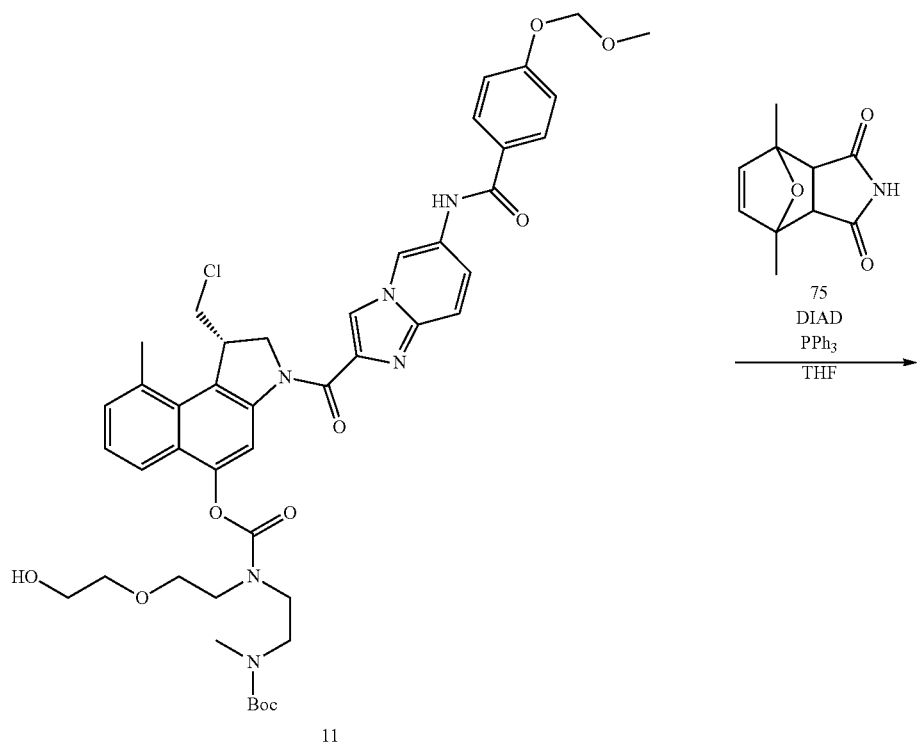
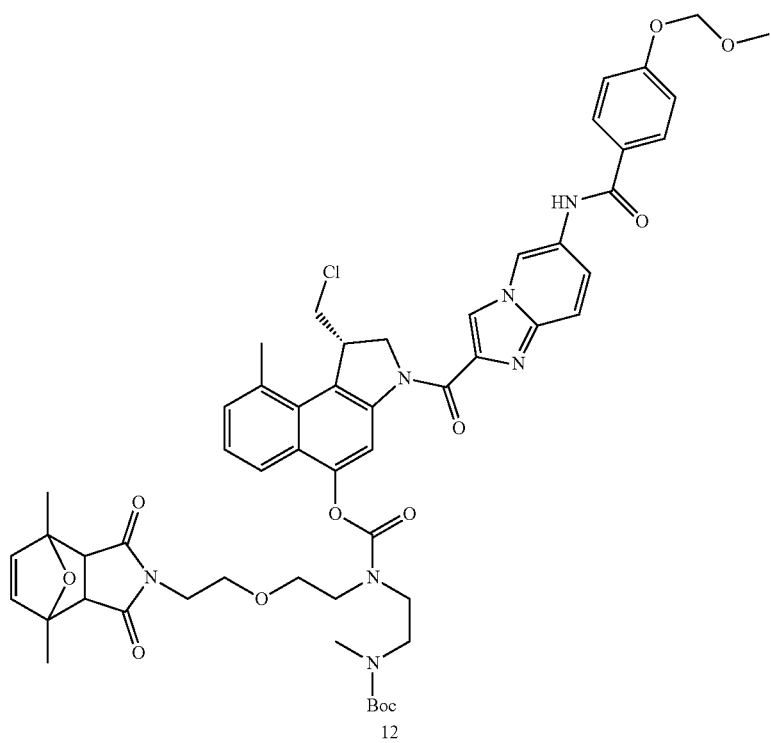

Compound 75, the protected maleimide, was synthesized as described in Elduque et al. Bioconjugate Chem. 2013; 24: 832-839. The NMR spectrum was identical to the spectrum in this literature reference.

Boc-Mom protected Drug-CS (11) (1.0 g, 1.16 mmol, 1 eq.) and protected maleimide 75 (0.34 g, 1.75 mmol, 1.5 eq.) were dissolved in dry THF (20 ml), followed by concentration in vacuo and drying in vacuo. The solid residue was redissolved in dry THF (20 ml) under nitrogen atmosphere, triphenylphosphine (0.46 g, 1.75 mmol, 1.5 eq.) was added and the resulting mixture was cooled on an ice bath. Next, diisopropyl azodicarboxylate (DIAD) (0.35 g, 1.75 mmol, 1.5 eq.) was added dropwise to the mixture and gradually warmed to room temperature (RT), stirring was continued for 30 min at RT. The mixture was concentrated in vacuo, purified by silica gel column chromatography (DCM/MeOH, 1:0 to 95:5, v/v), the fractions containing product were combined and concentrated in vacuo, co-evaporated with toluene and dried in vacuo to yield compound 12 (1.06 mmol, 91%) as a white foam.

$^1$H NMR (DMSO-d$_6$, 400 MHz): δ=1.30-1.44 (9H, m, CH$_{3, Boc}$), 1.53 (3H, s, CCH$_3$), 1.56 (3H, s, CCH$_3$), 2.78-2.94 (8H, m, ArCH$_3$, NCH$_3$, 2×CH$_{exo}$), 3.35-3.74 (13H, m, CHCl, 4×NCH$_2$, 2×OCH$_2$), 3.41 (3H, s, OCH$_3$) 3.79-3.84 (1H, m, CHCl), 4.45 (1H, t, H1), 4.62-4.67 (1H, m, H2), 5.16-5.21 (1H, m, H2), 5.30 (2H, s, OCH$_2$O), 6.35 (2H, d, HC=CH), 7.17 (2H, d, H3"), 7.31-7.37 (1H, m, H7), 7.39-7.40 (1H, m, H8), 7.57-7.59 (1H, m, H8'), 7.71-7.82 (2H, m, H6, H7'), 7.99 (2H, d, H2"), 8.35 (1H, br s, H4), 8.68 (1H, s, H3'), 9.46 (1H, s, H5'), 10.30 (1H, s, Ar—NHC(O)—Ar).

$^{13}$C NMR (DMSO-d$_6$, 100 MHz): δ=15.6, 15.7 (CCH$_3$), 22.4 (Ar—CH$_3$), 28.0, 28.1 (CH$_{3, Boc}$), 34.1, 34.6 (NCH$_3$), 37.5, 37.6 ((C=O)$_2$NCH$_2$CH$_2$), 44.2 (C1), 45.1, 45.5, 45.9, 46.3, 47.0 (NCH$_2$), 47.4 (CH$_2$Cl), 52.1 (CH$_{exo}$), 54.5 (C2), 55.8 (OCH$_3$), 66.6, 68.0, 68.3 (OCH$_2$), 78.6, 78.6 (C$_{Boc}$), 86.9 (C$_{exo}$), 93.7 (OCH$_2$O), 110.6, 110.6 (C4), 115.6 (C3"), 117.3 (C5'), 117.5 (C7'), 119.0 (C3'), 120.7 (C6), 122.3 (C9b), 123.1 (C8'), 124.6 (C7), 125.8 (C5a), 127.3 (C6'), 127.4 (C1"), 129.6 (C2"), 129.7 (C9a), 130.5 (C8), 132.9, 132.9 (C9), 140.5 (C8a'), 140.6 (C=C$_{exo}$), 141.4 (C2'), 141.9 (C3a), 148.0, 148.1 (Ar—OC(O)N), 153.7 (C=O$_{Boc}$), 154.7, 155.0 (C5), 159.6 (C4"), 161.9 (NC=O), 165.1 (Ar—NHC(O)—Ar), 174.7, 174.7 (C=O$_{exo}$).

MS (ESI) m/z; calculated: 1034.41 [M+H]$^+$, found: 1034.84 [M+H]$^+$.

Compound 17

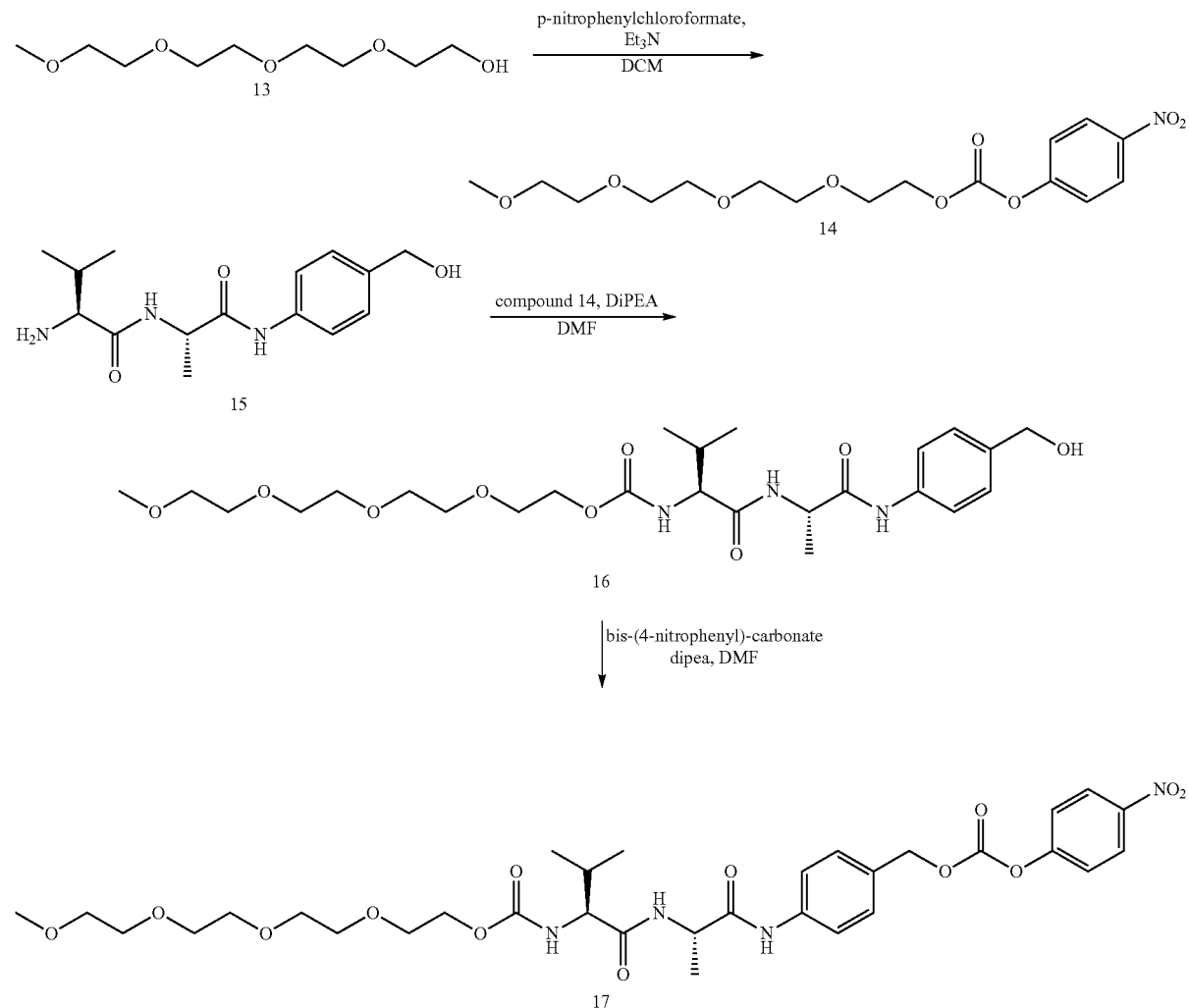

A solution of compound 13 (2.01 g, 9.65 mmol, 1 eq.) in THF (25 ml) was cooled to 0° C. in an ice bath, after which 4-nitrophenylchloroformate (2.14 g, 10.62 mmol, 1.1 eq.) and Et$_3$N (2.69 ml, 19.30 mmol, 2 eq.) were added and the resulting mixture was stirred for 2 hrs allowing it to warm to RT. The mixture was concentrated in vacuo and purified by silica gel column chromatography (DCM/EtOAc, 1:0 to 1:1, v/v), the fractions containing product were combined and concentrated in vacuo to yield intermediate 14 (2.5 g, 6.70 mmol, 69%) as a yellow oil. Compound 14 (1.34 g, 3.58 mmol, 1.05 eq.) and H-Val-Ala-PABA 15 (synthesized as described in US2014/0363454 (Igenica Biotherapeutics), 1.0 g, 3.41 mmol, 1 eq.) in DMF (20 ml) was cooled to 0° C. in an ice bath, N,N-diisopropylethylamine (DIPEA) (1.49 ml, 8.52 mmol, 2.5 eq.) was added to the solution and the mixture was stirred for 18 hrs allowing it to gradually warm to RT. The mixture was concentrated in vacuo, purified by silica gel column chromatography (DCM/MeOH, 1:0 to 9:1, v/v) to yield compound 16 (1.4 g, 2.65 mmol, 78%) as a white solid.

$^1$H NMR (DMSO-d$_6$, 400 MHz): δ=0.89 (3H, d, CH$_{3,Val}$), 0.91 (3H, d, CH$_{3,Val}$), 1.34 (3H, d, CH$_{3,Ala}$), 1.98-2.03 (1H, m, β-H$_{Val}$), 3.25 (3H, s, OCH$_3$), 3.41-3.62 (14H, m, O—CH$_2$), 3.92 (1H, t, α-H$_{Val}$), 4.08-4.12 (2H, m, CH$_2$OC(O)NH), 4.44-4.49 (3H, m, Ar—CH$_2$, α-H$_{Ala}$), 5.10-5.14 (1H, m, —OH), 7.12-7.30 (3H, m, H3, NH$_{Val}$), 7.57 (2H, d, H2), 8.14 (1H, d, NH$_{Ala}$), 9.91 (1H, s, NH$_{PABA}$).

$^{13}$C NMR (DMSO-d$_6$, 100 MHz): δ=18.1 (CH$_{3,Val}$), 18.2 (CH$_{3,Ala}$), 19.2 (CH$_{3,Val}$), 30.4 (β-CH$_{Val}$), 49.0 (α-CH$_{Ala}$), 58.1 (OCH$_3$), 60.1 (α-CH$_{Val}$), 62.7 (Ar—CH$_2$), 63.6 (CH$_2$OC(O)NH), 68.9 (OCH$_2$), 69.7 (OCH$_2$), 69.9 (OCH$_2$), 69.9 (OCH$_2$), 71.4 (OCH$_2$), 119.0 (C2), 127.0 (C3), 137.5 (C4), 137.6 (C1), 156.4 (OC(O)NH) 171.0 (C=O$_{Ala}$), 171.1 (C=O$_{Val}$).

MS (ESI) m/z; calculated: 528.62 [M+H]$^+$, found: 510.47 (—H$_2$O) [M+H]$^+$.

A solution of compound 16 (1.3 g, 2.46 mmol, 1 eq.) in DMF (20 ml) was cooled to 0° C. in an ice bath and bis(4-nitrophenyl) carbonate (1.50 g, 4.93 mmol, 2 eq.) and DIPEA (0.65 ml, 3.70 mmol, 1.5 eq.) were added. The mixture was stirred for 3 hrs and gradually warmed to RT. The crude mixture was concentrated in vacuo, purified by silica gel column chromatography (DCM/MeOH, 1:0 to 9:1, v/v) to yield compound 17 (1.7 g, 2.45 mmol, quantitative yield) as a white solid.

$^1$H NMR (DMSO-d$_6$, 400 MHz): δ=0.87 (3H, d, CH$_{3,Val}$), 0.92 (3H, d, CH$_{3,Val}$), 1.35 (3H, d, CH$_{3,Ala}$), 1.99-2.04 (1H, m, β-H$_{Val}$), 3.26 (3H, s, OCH$_3$), 3.36-3.62 (14H, m, O—CH$_2$), 3.92 (1H, t, α-CH$_{Val}$), 4.08-4.12 (2H, m, CH$_2$OC(O)NH), 4.47 (1H, m, α-CH$_{Ala}$), 5.27 (2H, s, Ar—CH$_2$), 7.16-7.30 (1H, m, NH$_{Val}$), 7.44 (2H, d, H3), 7.59 (2H, d, H6), 7.68 (2H, d, H2), 8.19 (1H, d, NH$_{Ala}$), 8.33 (2H, d, H7), 10.09 (1H, s, NH$_{PABA}$).

$^{13}$C NMR (DMSO-d$_6$, 100 MHz): δ=18.0 (CH$_{3,Val}$), 18.1 (CH$_{3,Ala}$), 19.2 (CH$_{3,Val}$), 30.4 (β-CH$_{Val}$), 49.1 (α-CH$_{Ala}$), 58.0 (OCH$_3$), 60.0 (α-CH$_{Val}$), 63.5 (CH$_2$OC(O)NH), 68.8 (OCH$_2$), 69.6 (OCH$_2$), 69.8 (OCH$_2$), 69.8 (OCH$_2$), 70.3 (Ar—CH$_2$), 71.3 (OCH$_2$), 119.1 (C2), 122.6 (C6), 125.4 (C7), 129.3 (C4), 129.5 (C3), 139.5 (C1), 145.2 (C5), 152.0 (OC(O)O), 155.3 (C8), 156.3 (OC(O)NH) 171.1 (C=O$_{Val}$), 171.3 (C=O$_{Ala}$).

MS (ESI) m/z; calculated: 693.73 [M+H]$^+$, found: 693.63 [M+H]$^+$.

Compound 19

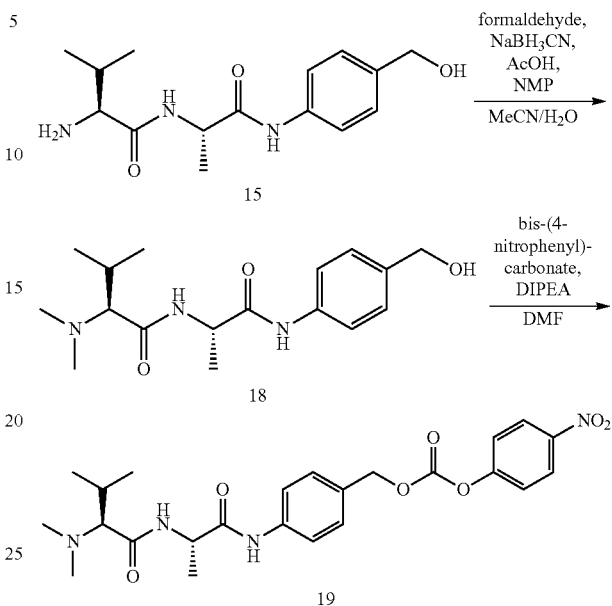

To a solution of H-Val-Ala-PABA 15 (synthesized as described in US2014/0363454 (Igenica Biotherapeutics), 1.4 g, 4.77 mmol, 1 eq.) in MeCN/H$_2$O (1:1) (100 ml) were subsequently added N-methylmorpholine (1.05 ml, 9.54 mmol, 2 eq.), formaldehyde (3.55 ml, 47.7 mmol, 10 eq.) and NaCNBH$_3$ (0.9 g, 14.32 mmol, 3 eq.) followed by dropwise addition of acetic acid (0.55 ml, 9.54 mmol, 2eq.). The resulting mixture was stirred for 30 min. Then, the crude mixture was concentrated in vacuo, co-evaporated with toluene and purified by silica gel column chromatography (DCM/MeOH, 1:0 to 7:3, v/v) to yield compound 18 (1.55 g, quantitative yield) as a white waxy solid.

$^1$H NMR (DMSO-d$_6$, 400 MHz): δ=0.84 (3H, d, CH$_{3,Val}$), 0.97 (3H, s, CH$_{3,Val}$), 1.35 (3H, d, CH$_{3,Ala}$), 1.98-2.11 (1H, m, β-H$_{Val}$), 2.39 (6H, br s, N(CH$_3$)$_2$), 3.20-3.60 (α-CH$_{Val}$), 4.45 (2H, ArCH$_2$), 4.46-4.55 (1H, m, α-CH$_{Ala}$), 5.12 (1H, s, OH), 7.26 (2H, d, H3), 7.56 (2H, d, H2), 8.29 (1H, br s, NH$_{Ala}$), 10.01 (1H, s, NH$_{PABA}$).

MS (ESI) m/z; calculated: 322.21 [M+H]$^+$, found: 322.16 [M+H]$^+$.

A solution of compound 18 (1.53 g, 4.77 mmol, 1 eq.) in DMF (20 ml) was cooled to 0° C. in an ice bath, bis(4-nitrophenyl) carbonate (2.90 g, 9.54 mmol, 2 eq.) and DIPEA (1.25 ml, 7.16 mmol, 1.5 eq.) were added. The resulting mixture was stirred for 3 hrs and gradually warmed to RT. The mixture was concentrated in vacuo, purified by silica gel column chromatography (DCM/MeOH, 1:0 to 8:2, v/v) to yield compound 19 (2.2 g, 4.52 mmol, 95%) as a yellow waxy solid.

$^1$H NMR (DMSO-d$_6$, 400 MHz): δ=0.81 (3H, d, CH$_{3,Val}$), 0.91 (3H, d, CH$_{3,Val}$), 1.34 (3H, d, CH$_{3,Ala}$), 1.93-2.01 (1H, m, β-H$_{Val}$), 2.29 (6H, br s, N(CH$_3$)$_2$), 3.20-3.60 (α-CH$_{Val}$), 4.50 (1H, m, α-CH$_{Ala}$), 5.24 (2H, s, ArCH$_2$), 7.42 (2H, d, H3), 7.56 (2H, d, H2'), 7.64 (2H, d, H2), 8.24 (1H, br s, NH$_{Ala}$), 8.30 (2H, d, H3'), 10.14 (1H, s, NH$_{PABA}$).

$^{13}$C NMR (DMSO-d$_6$, 100 MHz): δ=18.8 (CH$_{3,Ala}$), 20.0 (CH$_{3,Val}$), 27.1 (β-CH$_{Val}$), 41.8 (N(CH$_3$)$_2$), 49.3 (α-CH$_{Ala}$), 70.7 (Ar—CH$_2$), 73.1 (α-CH$_{Val}$), 119.5 (C2), 122.9, 123.0 (C2'), 125.8 (C3'), 129.7 (C4), 130.0 (C3), 139.9 (C1), 145.6 (C1'), 152.4 (OC(O)O), 155.8 (C4'), 162.8 (C=O$_{Val}$), 171.8 (C=O$_{Ala}$).

MS (ESI) m/z; calculated: 487.22 [M+H]⁺, found: 487.60 [M+H]⁺.

Compound 24

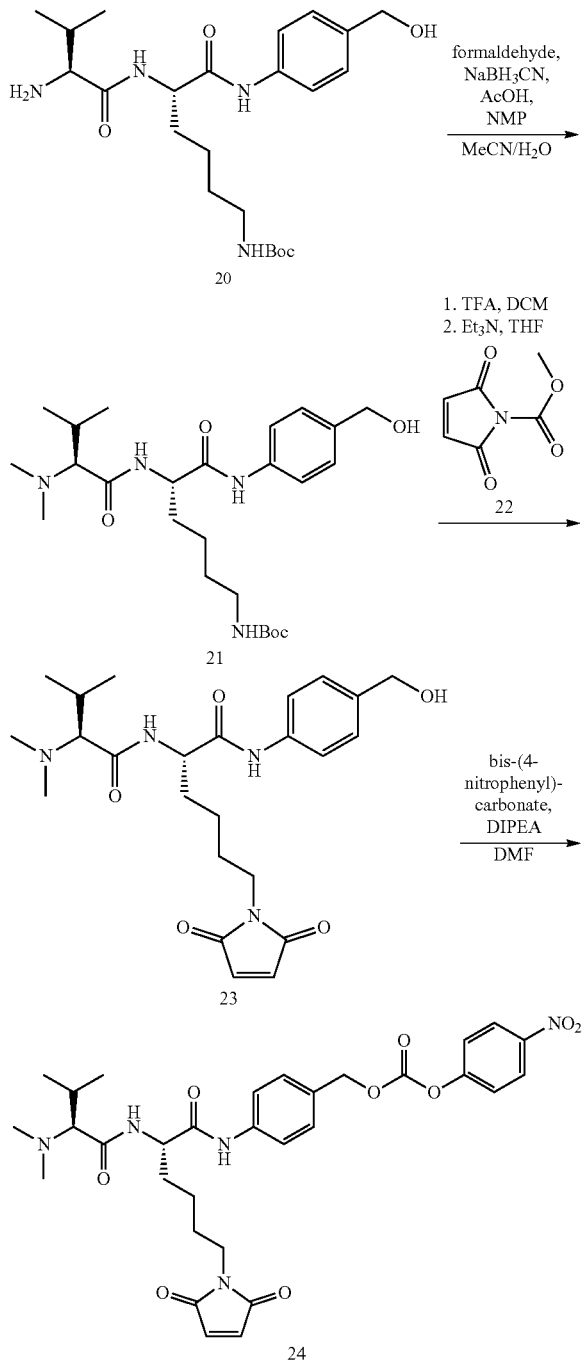

To a solution of H-Val-Lys(Boc)-PABA 20 (synthesized as described in WO2013/67597, page 80-82 (Ascend Biopharmaceuticals), 1.26 g, 2.80 mmol, 1 eq.) in MeCN/H$_2$O (1:1) (50 ml) were added N-methylmorpholine (0.62 ml, 5.59 mmol, 2 eq.), formaldehyde (2.08 ml, 28.0 mmol, 10 eq.) and NaCNBH$_3$ (0.53 g, 8.39 mmol, 3 eq.) followed by dropwise addition of acetic acid (0.32 ml, 5.59 mmol, 2 eq.).

The mixture was stirred for 30 min. The mixture was concentrated in vacuo and co-evaporated with toluene. The crude product was purified by silica gel column chromatography (DCM/MeOH, 1:0 to 7:3 v/v) to yield compound 21 (1.13 g, 2.36 mmol, 84%) as a white waxy solid.

$^1$H NMR (DMSO-d$_6$, 400 MHz): δ=0.80 (3H, d, CH$_{3,Val}$), 0.91 (3H, d, CH$_{3,Val}$), 1.22-1.53 (13H, m, CH$_3$,Boc 2×CH$_{2,Lys}$), 1.62-1.73 (2H, m, CH$_{2,Lys}$), 1.84-1.96 (1H, m, β-CH$_{Val}$), 2.26 (6H, br s, 2×NCH$_3$), 2.52 (1H, s, α-CH$_{Val}$), 3.41 (2H, t, CH$_{2,Lys}$), 4.45 (3H, s, Ar—CH$_2$, α-CH$_{Lys}$), 6.77 (1H, br s, ε-NH$_{Lys}$), 7.25 (2H, d, H3), 7.54 (2H, d, H2), 8.09 (1H, br s, NH$_{Lys}$), 10.00 (1H, s, NH$_{PABA}$), 11.99 (1H, br s, OH).

$^{13}$C NMR (DMSO-d$_6$, 100 MHz): δ=20.0 (CH$_{3,Val}$), 23.4 (CH$_{2,Lys}$), 27.2 (β-CH$_{Val}$), 28.7 (CH$_{3,\ Boc}$), 29.6 (CH$_{2,Lys}$), 32.0 (CH$_{2,Lys}$), 39.8 (CH$_2$,Lys), 41.8 (NCH$_3$), 53.5 (α-CH$_{Lys}$), 63.0 (Ar—CH$_2$), 73.4 (α-CH$_{Val}$), 77.8 (C$_{Boc}$), 119.3 (C2), 127.4 (C3), 137.8 (C4), 138.1 (C1), 156.0 (C=O$_{Boc}$), 171.2 (C=O$_{Val}$, C=O$_{Lys}$).

MS (ESI) m/z; calculated: 479.32 [M+H]⁺, found: 479.67 [M+H]⁺

A solution of compound 21 (1.06 g, 2.22 mmol, 1 eq.) in DCM (20 ml) was cooled to 0° C. in an ice bath, TFA (15 ml) was added and stirred for 30 min., then diluted with DCM, concentrated in vacuo and co-evaporated with DCM (twice). The obtained TFA-salt was dissolved in THF (10 ml), maleimide-carbamate 22 (0.34 g, 2.22 mmol, 1 eq.) was added followed by addition of Et$_3$N (1.24 ml, 8.86 mmol, 4 eq.). The reaction mixture was stirred for 48 hrs at 50° C., after which an additional 0.5 eq. of Et$_3$N was added and stirred for another 24 hrs. The mixture was concentrated in vacuo and the crude product was purified by silica gel column chromatography (DCM/MeOH, 1:0 to 7:3 v/v) to yield compound 23 which was immediately used in the next step.

MS (ESI) m/z; calculated: 459.26 [M+H]⁺, found: 459.53 [M+H]⁺

A solution of compound 23 (1.0 g, 2.18 mmol, 1 eq.) in DMF (10 ml) was cooled to 0° C. in an ice bath, and bis(4-nitrophenyl) carbonate (1.33 g, 4.36 mmol, 2 eq.) and DIPEA (0.57 ml, 3.27 mmol, 1.5 eq.) were added and the resulting mixture was stirred for 3 hrs at 0° C. in an ice bath. Then, the mixture was concentrated in vacuo and the crude product was purified by silica gel column chromatography (DCM/MeOH, 1:0 to 8:2 v/v) to yield compound 24 (0.55 g, 0.88 mmol, 40%) as an off-white solid.

$^1$H NMR (DMSO-d$_6$, 400 MHz): δ=0.77 (3H, d, CH$_{3,Val}$), 0.88 (3H, d, CH$_{3,Val}$), 1.20-1.42 (2H, m, CH$_{2,Lys}$), 1.44-1.76 (4H, m, 2×CH$_{2,Lys}$), 1.84-1.96 (1H, m, β-CH$_{Val}$), 2.18 (6H, br s, 2×NCH$_3$), 2.60 (1H, d, α-CH$_{Val}$), 3.41 (2H, t, CH$_{2,Lys}$), 4.39 (1H, m, α-CH$_{Lys}$), 5.25 (2H, s, Ar—CH$_2$), 7.00 (2H, s, HC=CH), 7.42 (2H, d, H3), 7.57 (2H, d, H6), 7.62 (2H, d, H2), 8.04 (1H, d, NH$_{Lys}$), 8.32 (2H, d, H7), 10.12 (1H, s, NH$_{PABA}$).

$^{13}$C NMR (DMSO-d$_6$, 100 MHz): δ=19.4, 19.5 (CH$_{3,Val}$), 23.0 (CH$_{2,Lys}$), 26.7 (β-CH$_{Val}$), 27.6 (CH$_{2,Lys}$), 31.1 (CH$_{2,Lys}$), 37.0 (CH$_{2,Lys}$), 41.3 (NCH$_3$), 52.8 (α-CH$_{Lys}$), 70.2 (Ar—CH$_2$), 72.9 (α-CH$_{Val}$), 119.0 (C2), 122.6 (C6), 125.4 (C7), 129.2 (C4), 129.5 (C3), 134.4 (HC=CH) 139.4 (C1), 145.2 (C5), 151.9 (OC(O)O), 155.3 (C8), 170.1 (C=O$_{Val}$), 171.0 (C=O$_{maleimide}$), 171.1 (C=O$_{Lys}$).

MS (ESI) m/z; calculated: 624.27 [M+H]⁺, found: 624.61 [M+H]⁺.

Compound 34

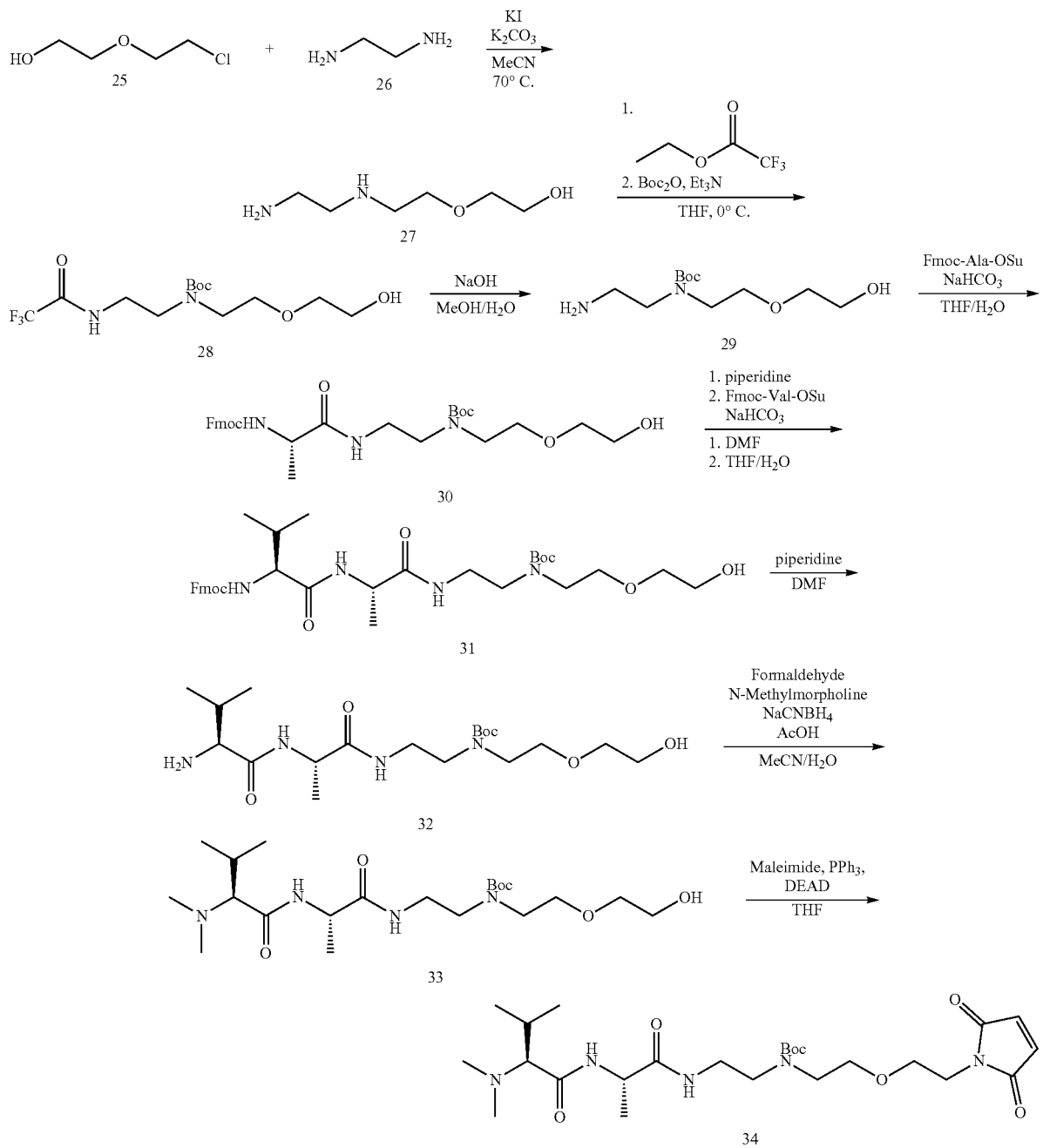

To a mixture of ethane-1,2-diamine 26 (2.15 ml, 32.1 mmol, 4 eq.), potassium iodide (1.33 g, 8.03 mmol, 1 eq.) and potassium carbonate (2.22 g, 16.06 mmol, 2 eq.) in MeCN (25 ml) was added dropwise a solution of 2-(2-chloroethoxy)ethanol 25 (0.85 ml, 8.03 mmol, 1 eq.). The resulting mixture was stirred at 60° C. for 2 days. Next, the crude mixture was concentrated in vacuo, co-evaporated with toluene and the residue was taken up in EtOAc and stirred for 10 min. The suspension was filtered and the filtrate was concentrated in vacuo to yield compound 27 2-(2-(2-aminoethylamino)ethoxy)ethanol (750 mg, 5.06 mmol, 63%) as a colorless oil.

MS (ESI) m/z; calculated: 149.13 [M+H]$^+$, found: 149.23 [M+H]$^+$

To a cooled (0° C.) solution of 2,2,2-trifluoroacetate (602 μl, 5.06 mmol, 1 eq.) in THF (10 ml) was added dropwise a solution of 2-(2-(2-aminoethylamino)ethoxy)ethanol 27 (750 mg, 5.06 mmol, 1 eq.) in THF (5 ml) and the mixture was stirred for 45 min. Then, di-tert-butyl dicarbonate (1.33 g, 6.07 mmol, 1.2 eq.) in THF (5 ml) was added dropwise followed by addition of Et$_3$N (846 μl, 6.07 mmol, 1.2 eq.) and stirred for 1 hr. The mixture was concentrated in vacuo and purified by silica gel column chromatography (DCM/EtOAc, 1:0 to 1:1, v/v) to yield compound 28 (980 mg, 2.85 mmol, 56%) as a yellow oil.

$^1$H NMR (DMSO-d$_6$, 400 MHz): δ=1.38 (9H, s, CH$_{3,Boc}$), 3.25-3.36 (6H, m, CH$_2$N$_{Boc}$, CH$_2$N), 3.39-3.43 (2H, m, CH$_2$O), 3.46-3.52 (4H, m, CH$_2$OH, CH$_2$O), 4.62 (1H, t, OH).

$^{13}$C NMR (DMSO-d$_6$, 100 MHz): δ=28.2, 28.4 (CH$_{3,Boc}$), 38.2, 38.4 (CH$_2$NH), 46.2, 46.5, 46.8, 47.2 (CH$_2$N$_{Boc}$), 60.6 (CH$_2$OH), 68.8, 69.2 (NCH$_2$CH$_2$O), 72.6 (CH$_2$O), 79.3 (C$_{Boc}$), 112.1, 114.9, 117.8, 120.7 (CF$_3$), 155.0, 155.3 (C=O$_{Boc}$), 156.3, 156.7, 157.0, 157.4 (C=O).

MS (ESI) m/z; calculated: 367.15 [M+Na]$^+$, found: 245.18 [M-Boc]$^+$, 367.29 [M+Na]$^+$ To a solution of compound 28 (900 mg, 2.61 mmol, 1 eq.) in MeOH (10 ml) was added, NaOH (157 mg, 3.92 mmol, 1.5 eq., dissolved in water (5 ml)) and the mixture was stirred for 4 hrs at RT. The mixture was concentrated in vacuo and DCM and water (saturated with NaCl) were added. The DCM-layer was dried on MgSO$_4$, filtered and concentrated in vacuo to yield compound 29 (660 mg, 100%) as a yellow oil.

$^1$H NMR (DMSO-d$_6$, 400 MHz): δ=1.39 (9H, s, CH$_{3,Boc}$), 2.64 (2H, t, CH$_2$NH$_2$), 3.10 (3H, br s, NH$_2$, OH) 3.12-3.19 (2H, m, CH$_2$N$_{Boc}$), 3.27-3.33 (2H, m, CH$_2$N$_{Boc}$), 3.39-3.44 (2H, m, CH$_2$O), 3.45-3.51 (4H, m, CH$_2$OH, CH$_2$O).

$^{13}$C NMR (DMSO-d$_6$, 100 MHz): δ=28.5 (CH$_{3,Boc}$), 40.9 (CH$_2$NH$_2$), 47.3, 47.4 (CH$_2$N$_{Boc}$), 50.6, 51.1 (CH$_2$N$_{Boc}$), 60.7 (CH$_2$OH), 68.9, 69.3 (NCH$_2$CH$_2$O), 72.6 (CH$_2$O), 78.9 (C$_{Boc}$), 155.2 (C=O$_{Boc}$).

MS (ESI) m/z; calculated: 249.18 [M+H]$^+$, found: 249.30 [M+H]$^+$

To a solution of compound 29 (650 mg, 2.62 mmol, 1 eq.) and NaHCO$_3$ (440 mg, 5.24 mmol, 2 eq.) in water (6 ml) was added Fmoc-Ala-OSu (1.18 g, 2.88 mmol, 1.1 eq.) in THF (6 ml) and the mixture was stirred at RT overnight. Then, THF was evaporated, water was added and extracted with EtOAc (twice). The combined organic layer was washed with brine, dried (on MgSO$_4$), filtered and concentrated in vacuo. The crude product was purified by silica gel column chromatography (DCM/MeOH, 1:0 to 9:1, v/v) to yield compound 30 (1.2 g, 2.22 mmol, 85%) as a white solid.

$^1$H NMR (DMSO-d$_6$, 400 MHz): δ=1.21 (3H, d, CH$_{3,Ala}$), 1.39 (9H, s, CH$_{3,Boc}$), 3.11-3.52 (12H, m, CH$_2$NH, CH$_2$N$_{Boc}$, CH$_2$O, CH$_2$OH), 3.94-4.06 (1H, m, α-CH$_{Ala}$), 4.18-4.30 (3H, m, CH$_{Fmoc}$, CH$_{2,Fmoc}$), 4.60 (1H, t, OH), 7.31-7.36 (2H, m, CH$_{Ar}$), 7.39-7.50 (3H, m, CH$_{Ar}$, NH$_{Ala}$), 7.71-7.76 (2H, m, CH$_{Ar}$), 7.86-7.95 (3H, m, CH$_{Ar}$, NH).

$^{13}$C NMR (DMSO-d$_6$, 100 MHz): δ=18.7 (CH$_{3,Ala}$), 28.5 (CH$_{3,Boc}$), 37.7, 38.0 (CH$_2$NH), 47.1 (CH$_{Fmoc}$), 47.3, 47.5 (CH$_2$N$_{Boc}$), 50.6 (α-CH$_{Ala}$), 60.7 (CH$_2$OH), 66.1 (CH$_{2,Fmoc}$), 68.8, 69.2 (NCH$_2$CH$_2$O), 72.6 (CH$_2$O), 79.1 (C$_{Boc}$), 120.6 (CH$_{Ar}$), 125.8 (CH$_{Ar}$), 127.5 (CH$_{Ar}$), 128.1 (CH$_{Ar}$), 141.2 (C$_{Ar}$), 144.3, 144.4 (C$_{Ar}$), 155.1, 155.2 (C=O$_{Boc}$), 156.1 (C=O$_{Fmoc}$), 173.0 (C=O$_{Ala}$).

MS (ESI) m/z; calculated: 564.27 [M+Na]$^+$, found: 442.47 [M-Boc]$^+$, 564.55 [M+Na]$^+$ To a solution of compound 30 (1.2 g, 2.16 mmol, 1 eq.) in DMF (10 ml) was added piperidine (4.4 ml, 44.3 mmol, 20 eq.) and stirred for 90 min. The mixture was concentrated in vacuo, co-evaporated with toluene and re-dissolved in water (12 ml) and extracted twice with ether. A solution of Fmoc-Val-OSu (0.94 g, 2.16 mmol, 1 eq.) in THF (16 ml) was then added to the water layer, followed by addition of sodium bicarbonate (0.2 g, 2.38 mmol, 1.1 eq.) and the resulting mixture was stirred for 4 hrs at RT. Next, THF was evaporated, water was added and extracted twice with EtOAc. The combined organic layers were dried on Na$_2$SO$_4$, filtered and concentrated in vacuo. The crude product was purified by silica gel column chromatography (DCM/MeOH, 1:0 to 9:1, v/v) to yield compound 31 (1.4 g, 2.19 mmol, quantitative yield) as a white foam.

$^1$H NMR (DMSO-d$_6$, 400 MHz): δ=0.83-0.89 (6H, m, CH$_{3,Val}$), 1.21 (3H, d, CH$_{3,Ala}$), 1.39 (9H, s, CH$_{3,Boc}$), 1.95-2.03 (1H, m, β-H$_{Val}$), 3.10-3.51 (14H, m, CH$_2$NH$_2$, CH$_2$N$_{Boc}$, CH$_2$O, CH$_2$OH), 4.18-4.30 (4H, m, α-CH$_{Ala}$, CH$_{Fmoc}$, CH$_{2,Fmoc}$), 4.60 (1H, t, OH), 7.30-7.36 (2H, m, CH$_{Ar}$), 7.39-7.47 (3H, m, CH$_{Ar}$, NH$_{Val}$), 7.72-7.77 (2H, m, CH$_{Ar}$), 7.87-7.99 (4H, m, CH$_{Ar}$, NH$_{Ala}$, NH).

$^{13}$C NMR (DMSO-d$_6$, 100 MHz): δ=18.6 (CH$_{3,Val}$), 18.9 (CH$_{3,Ala}$), 19.7 (CH$_{3,Val}$), 28.5 (CH$_{3,Boc}$), 30.8 (β-CH$_{Val}$), 37.5, 38.0 (CH$_2$NH), 47.2 (CH$_{Fmoc}$), 47.0, 47.3 (CH$_2$N$_{Boc}$), 48.6 (α-CH$_{Ala}$), 60.5 (α-CH$_{Val}$), 60.7 (CH$_2$OH), 66.2 (CH$_{2,Fmoc}$), 68.9, 69.2 (NCH$_2$CH$_2$O), 72.6 (CH$_2$O), 79.1 (C$_{Boc}$), 120.5 (CH$_{Ar}$), 125.8 (CH$_{Ar}$), 127.5 (CH$_{Ar}$), 128.1 (CH$_{Ar}$), 141.2, 141.2 (C$_{Ar}$), 144.2, 144.4 (C$_{Ar}$), 155.1 (C=O$_{Boc}$), 156.6 (C=O$_{Fmoc}$), 171.1 (C=O$_{Val}$), 172.5 (C=O$_{Ala}$).

MS (ESI) m/z; calculated: 641.35 [M+H]$^+$, found: 641.59 [M+H]$^+$

To a solution of compound 31 (1.4 g, 2.19 mmol, 1 eq.) in DMF (10 ml) was added piperidine (4.3 ml, 43.7 mmol, 20 eq.) and stirred for 2 hrs. The crude mixture was concentrated in vacuo, co-evaporated with toluene and the solid residue washed with Et$_2$O, filtered and dried in vacuo to yield compound 32 (0.68 g, 1.63 mmol, 74%) as a grey solid.

$^1$H NMR (DMSO-d$_6$, 400 MHz): δ=0.76 (3H, d, CH$_{3,Val}$), 0.88 (3H, d, CH$_{3,Val}$), 1.18 (3H, d, CH$_{3,Ala}$), 1.39 (9H, s, CH$_{3,Boc}$), 1.90-1.97 (1H, m, β-H$_{Val}$), 2.99 (1H, d, α-CH$_{Val}$), 3.10-3.52 (12H, m, CH$_2$NH, CH$_2$N$_{Boc}$, CH$_2$O, CH$_2$OH), 4.22-4.30 (1H, m, α-CH$_{Ala}$), 4.62 (1H, br s, OH), 7.98-8.05 (2H, m, NH$_{Ala}$, NH).

$^{13}$C NMR (DMSO-d$_6$, 100 MHz): δ=17.2 (CH$_{3,Val}$), 19.3 (CH$_{3,Ala}$), 19.9 (CH$_{3,Val}$), 28.5 (CH$_{3,Boc}$), 31.7 (β-CH$_{Val}$), 37.6, 38.0 (CH$_2$NH), 47.0, 47.2, 47.4 (CH$_2$N$_{Boc}$), 48.1 (α-CH$_{Ala}$), 60.1 (α-CH$_{Val}$), 60.7 (CH$_2$OH), 68.9, 69.2 (NCH$_2$CH$_2$O), 72.6 (CH$_2$O), 79.1 (C$_{Boc}$), 155.1, 155.2 (C=O$_{Boc}$), 172.7 (C=O$_{Ala}$), 174.3 (C=O$_{Val}$).

MS (ESI) m/z; calculated: 419.29 [M+H]$^+$, found: 419.58 [M+H]$^+$

To a solution of compound 32 (680 mg, 1.63 mmol, 1 eq.) in MeCN/H$_2$O (50 ml, 1:1, v/v) were subsequently added N-methylmorpholine (357 μl, 3.25 mmol, 2 eq.), formaldehyde (1.21 ml, 16.25 mmol, 10 eq.) and NaCNBH$_3$ (306 mg, 4.87 mmol, 3 eq.) followed by dropwise addition of acetic acid (186 μl, 3.25 mmol, 2 eq.). The resulting mixture was stirred for 15 min. The crude mixture was concentrated in vacuo, co-evaporated with toluene, and purified by silica gel column chromatography (DCM/MeOH, 1:0 to 8:2, v/v). The product was again co-evaporated with toluene to yield compound 33 (680 mg, 1.52 mmol, 94%) as a colorless oil.

$^1$H NMR (DMSO-d$_6$, 400 MHz): δ=0.77 (3H, d, CH$_{3,Val}$), 0.88 (3H, d, CH$_{3,Val}$), 1.20 (3H, d, CH$_{3,Ala}$), 1.38 (9H, s, CH$_{3,Boc}$), 1.89-1.98 (1H, m, β-H$_{Val}$), 2.24 (6H, s, N(CH$_3$)$_2$), 2.63-2.72 (1H, d, α-CH$_{Val}$), 3.08-3.62 (12H, m, CH$_2$NH, CH$_2$N$_{Boc}$, CH$_2$O, CH$_2$OH), 4.28-4.34 (1H, m, α-CH$_{Ala}$), 7.87-8.01 (2H, m, NH$_{Ala}$, NH).

$^{13}$C NMR (DMSO-d$_6$, 100 MHz): δ=19.4 (CH$_{3,Val}$), 19.4 (CH$_{3,Ala}$), 20.0 (CH$_{3,Val}$), 27.0 (β-CH$_{Val}$), 28.5 (CH$_{3,Boc}$), 37.5, 37.9 (CH$_2$NH), 41.8 (NCH$_3$), 46.9, 47.3, 47.5 (CH$_2$N$_{Boc}$), 48.2 (α-CH$_{Ala}$), 60.7 (CH$_2$OH), 68.9, 69.2 (NCH$_2$CH$_2$O), 72.6 (CH$_2$O), 73.4 (α-CH$_{Val}$), 79.1 (C$_{Boc}$), 155.1 (C=O$_{Boc}$), 169.2 (C=O$_{Val}$), 172.6 (C=O$_{Ala}$).

MS (ESI) m/z; calculated: 447.32 [M+H]$^+$, found: 447.85 [M+H]$^+$

A solution of compound 33 (680 mg, 1.52 mmol, 1 eq.) in dry THF (20 ml) was put under a nitrogen atmosphere and maleimide (192 mg, 1.98 mmol, 1.3 eq.) and triphenylphosphine (519 mg, 1.98 mmol, 1.3 eq.) were added. The mixture was cooled to 0° C. in an ice bath and DEAD (2.2 M in toluene) (900 μl, 1.98 mmol, 1.3 eq.) was added dropwise and stirred for 30 min at RT. The crude mixture was concentrated in vacuo and purified by silica gel column chromatography (DCM/MeOH, 1:0 to 9:1, v/v) to yield compound 34 (280 mg, 0.53 mmol, 35%) as a colorless waxy solid.

13C NMR (DMSO-d6, 400 MHz): δ=0.76 (3H, dd, CH3, Val), 0.87 (3H, dd, CH3,Val), 1.13-1.30 (3H, m, CH3,Ala) 1.38 (9H, s, CH3,Boc), 1.86-2.01 (1H, m, β-H$_{Val}$), 2.18 (6H, br s, N(CH3)2), 2.57 (1H, d, α-CH$_{Val}$), 3.05-3.71 (12H, m, NCH2, OCH2), 4.27-4.35 (1H, m, α-CH$_{Ala}$), 7.02 (2H, s, HC=CH), 7.87 (2H, br s, NH$_{Ala}$, C(=O)NHCH2).

13C NMR (DMSO-d6, 100 MHz): δ=19.4 (CH$_{3,Ala}$), 19.7 (CH$_{3,Val}$), 20.0 (CH$_{3,Val}$), 27.1 (β-CH$_{Val}$), 28.5 (CH$_{3,Boc}$), 37.3, 37.4 ((C=O)2NCH2CH2), 37.8 (NHCH2), 41.8 (N(CH3)2), 46.9, 47.1, 46.5 (NCH2), 48.0 (α-CH$_{Ala}$), 67.3, 68.6, 68.9 (OCH2), 73.5 (α-CH$_{Val}$), 79.1 (C$_{Boc}$), 135.0 (HC=CH), 155.7 (C=O$_{Boc}$), 169.7 (C=O$_{Val}$), 171.3 (C=O$_{maleimide}$), 172.7 (C=O$_{Ala}$).

MS (ESI) m/z; calculated: 526.32 [M+H]+, found: 526.65 [M+H]+.

Compound 40

A mixture of tert-butyl 2-(benzylamino)ethyl(methyl)carbamate 38 (664 mg, 2.51 mmol, 1 eq.), phthalimide-tetraethyleneglycol-tosylate 37 (1.2 g, 2.51 mmol, 1 eq.), K2CO3 (695 mg, 5.03 mmol, 2 eq.) and KI (417 mg, 2.51 mmol, 1 eq.) in acetonitrile (20 ml) was refluxed for 3 days. The mixture was concentrated in vacuo and the crude product was purified by silica gel column chromatography (DCM/MeOH, 1:0 to 8:2, v/v) to yield compound 39 (1.4 g, 2.46 mmol, 98%) as a colorless oil.

MS (ESI) m/z; calculated: 570.32 [M+H]+, found: 570.50 [M+H]+.

Palladium on carbon (262 mg, 0.25 mmol, 0.1 eq.) was suspended in MeOH (10 ml) followed by the addition of compound 39 (1.4 g, 2.46 mmol, 1 eq. in MeOH ((10 ml)) and acetic acid (422 μl, 7.37 mmol, 3 eq.). The resulting mixture was stirred under hydrogen for 3 hrs. The mixture was filtered over Celite, concentrated in vacuo, co-evaporated with toluene and dried in vacuo to yield compound 40 (850 mg, 1.77 mmol, 72%).

1H NMR (DMSO-d6, 400 MHz): δ=1.38 (CH$_{3,Boc}$), 2.59-2.65 (4H, m, CH2NHCH2), 2.77 (3H, br s, NCH3), 3.19 (2H, t, NCH2), 3.35-3.68 (10H, M, OCH2), 3.62 (2H, t, (C=O)2NCH2CH2), 3.75 (2H, t, (C=O)2NCH2), 7.82-7.89 (4H, m, H$_{Ar}$).

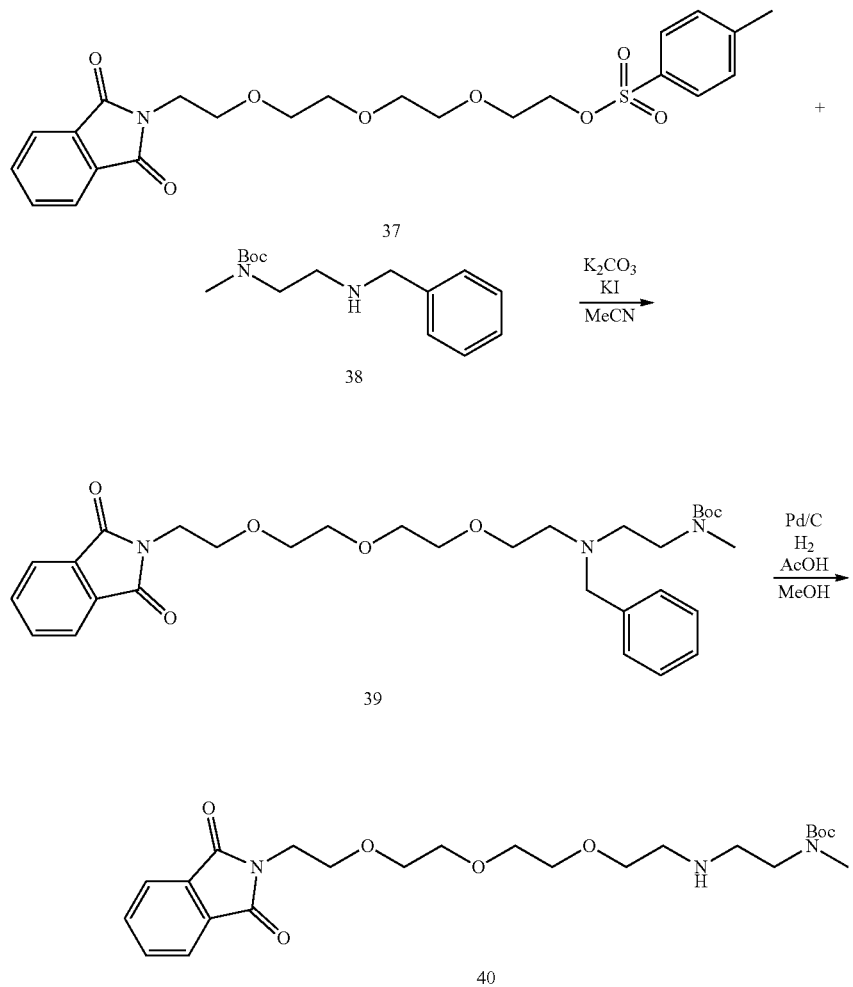

The synthesis of phthalimide-tetraethyleneglycol-toslyate 37 is described in several literature procedures. For example in Kim et al. Organic Letters, 2007, 9 (22): 4419-4422.

13C NMR (DMSO-d6, 100 MHz): δ=28.5 (CH$_{3,Boc}$), 34.7 (NCH3), 37.6 ((C=O)2NCH2CH2), 47.5 (NHCH2), 48.8 (NCH2), 67.4 ((C=O)2NCH2CH2O), 70.0, 70.0, 70.1, 70.2, 70.4 (OCH$_2$), 78.7 (C$_{Boc}$), 123.5 (CH$_{Ar}$), 132.0 (C$_{Ar}$), 134.9 (CH$_{Ar}$), 155.3 (C=O$_{Boc}$), 168.2 (C=O$_{Phthalimide}$).

MS (ESI) m/z; calculated: 480.27 [M+H]$^+$, found: 480.44 [M+H]$^+$.

Compound 50

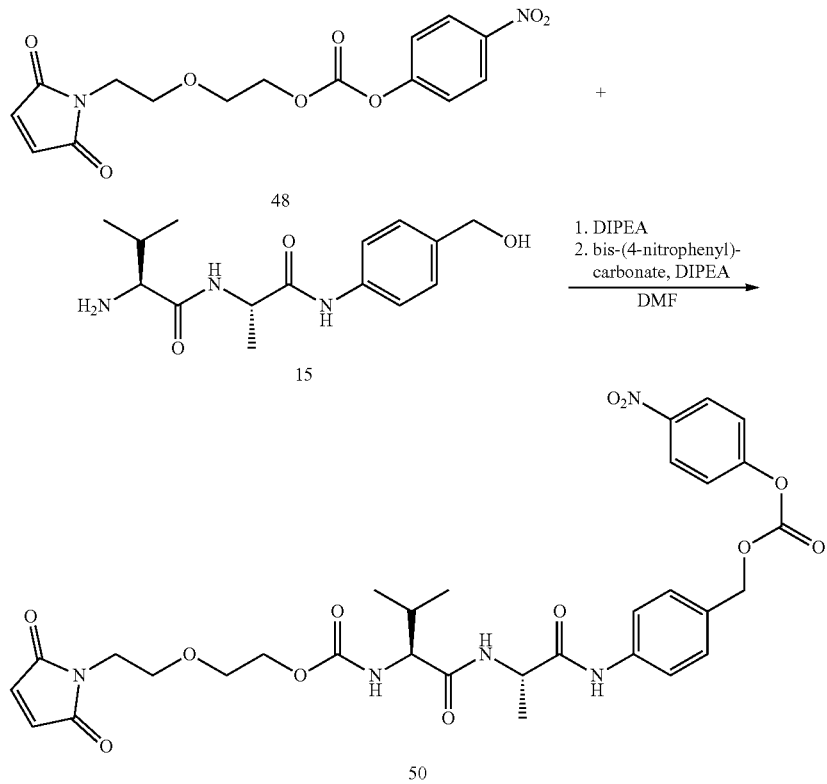

To a solution of compound 15 (3.58 g, 10.2 mmol, 1 eq.) in DMF (20 ml) was added compound 48 (3.16 g, 10.2 mmol, 1 eq.) and DIPEA (2.0 ml, 11.5 mmol, 1.1 eq.) and the resulting mixture stirred for 2 hrs. Then, bis-(4-nitrophenyl)carbonate (4.68 g, 15.4 mmol, 1.5 eq.) and stirred for 18 hrs. The mixture was concentrated in vacuo and the crude product was purified by silica gel column chromatography (DCM/MeOH, 1:0, 9:1, v/v), taken up in dioxane/water and freeze dried to yield compound 50 (5.16 g, 7.7 mmol, 75%) as an off-white solid.

$^1$H NMR (DMSO-d$_6$, 400 MHz): δ=0.82-0.90 (6H, m, CH$_3$,val), 1.32 (3H, d, CH$_{3,Ala}$), 1.92-2.03 (1H, m, β-H$_{Val}$), 3.50-3.60 (6H, m, NCH$_2$, OCH$_2$), 3.85-3.91 (1H, m, α-CH$_{Val}$), 3.96-4.07 (2H, m, CH$_2$OC(O)NH), 4.38-4.47 (1H, m, α-CH$_{Ala}$), 5.25 (1H, s, Ar—CH$_2$), 7.02 (2H, s, HC=CH), 7.17 (1H, d, NH$_{Val}$), 7.42 (2H, d, H3), 7.57 (2H, d, H2'), 7.64 (2H, d, H2), 8.16 (1H, d, NH$_{Ala}$), 8.31 (2H, d, H3'), 10.06 (1H, s, NH$_{PABA}$).

$^{13}$C NMR (DMSO-d$_6$, 100 MHz): δ=18.5 (CH$_{3,Val}$, CH$_{3,Ala}$), 19.6 (CH$_{3,Val}$), 30.8 (β-CH$_{Val}$), 37.1 ((C=O)$_2$NCH$_2$CH$_2$), 49.5 (α-CH$_{Val}$), 60.4 (α-CH$_{Val}$), 63.8 (CH$_2$OC(O)NH), 67.4, 68.8 (OCH$_2$), 70.7 (ArCH$_2$O), 119.5 (C2), 123.1 (C2'), 125.9 (C3'), 129.8 (4), 129.9 (C3), 135.0 (HC=CH), 139.9 (C1), 145.6 (C1'), 152.4 (OC(O)O), 155.8 (C4'), 156.6 (OC(O)NH), 171.3 (C=O$_{maleimide}$), 171.5 (C=O$_{Val}$), 171.7 (C=O$_{Ala}$).

MS (ESI) m/z; calculated: 670.24 [M+H]$^+$, found: 670.30 [M+H]$^+$.

Compound 56

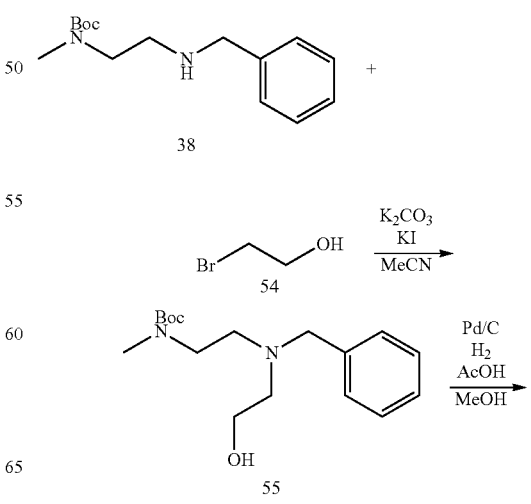

-continued

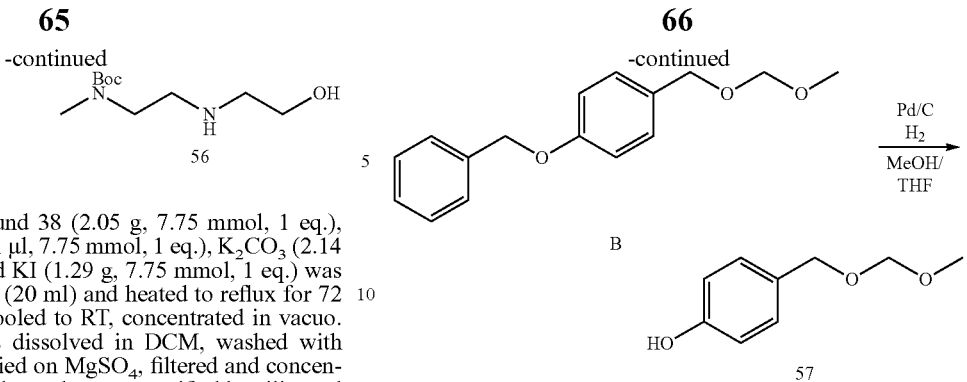

A mixture of compound 38 (2.05 g, 7.75 mmol, 1 eq.), 2-bromoethanol (54, 551 μl, 7.75 mmol, 1 eq.), K₂CO₃ (2.14 g, 15.5 mmol, 2 eq.) and KI (1.29 g, 7.75 mmol, 1 eq.) was dissolved in acetonitrile (20 ml) and heated to reflux for 72 hrs. The mixture was cooled to RT, concentrated in vacuo. The crude product was dissolved in DCM, washed with water (2×) and brine, dried on MgSO₄, filtered and concentrated in vacuo. The crude product was purified by silica gel column chromatography (heptane/EtOAc, 1:0 to 0:1 v/v), the fractions containing product were combined and concentrated in vacuo to yield compound 55 (1 g, 3.24 mmol, 42%) as an orange oil.

MS (ESI) m/z; calculated: 309.22 [M+H]⁺, found: 309.38 [M+H]⁺.

To a suspension of Pd/C (345 mg, 0.32 mmol, 0.1 eq.) in MeOH (50 ml) was added a solution of compound 55 (1 g, 3.24 mmol, 1 eq. in MeOH 50 ml) followed by addition of acetic acid (557 μl, 9.73 mmol, 3 eq.). The resulting mixture was stirred for 4 hrs under a hydrogen atmosphere. Then, the mixture was filtered over Celite, concentrated in vacuo, co-evaporated with toluene and purified by silica gel column chromatography (DCM/MeOH, gradient), the fractions containing product were combined and concentrated in vacuo to yield OEGCS (56) (720 mg, 3.3 mmol, quantitative yield) as an oil.

¹H NMR (DMSO-d₆, 400 MHz): δ=1.39 (9H, s, $CH_{3,Boc}$), 2.63 (2H, t, $NCH_2CH_2OH$), 2.68 (2H, t, $NCH_2CH_2N$), 2.78 (3H, br s, $NCH_3$), 3.24 (2H, t, $NCH_2$), 3.46 (2H, t, $CH_2OH$), 4.25 (2H, br s, NH, OH).

¹³C NMR (DMSO-d₆, 100 MHz): δ=28.5 ($CH_{3,Boc}$), 34.7 ($NCH_3$), 46.8, 47.2, 47.8, 48.3 ($NHCH_2$), 51.5 ($NCH_2$), 60.3 ($CH_2OH$), 78.8 ($C_{Boc}$), 155.3 ($C=O_{Boc}$).

MS (ESI) m/z; calculated: 219.17 [M+H]⁺, found: 219.28 [M+H]⁺.

Compound 57

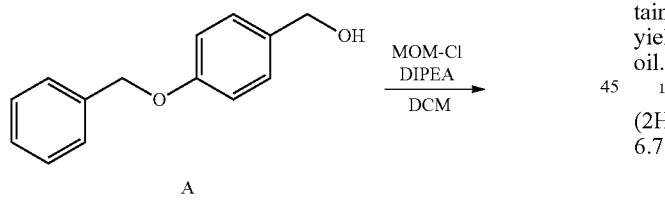

Compound A is commercially available from Acros Organics (CAS nr. 836-43-1, suppl. Code 18196).

A solution of compound A (2.73 g, 12.7 mmol, 1 eq.) in DCM (20 ml) was cooled to 0° C. in an ice bath, and DIPEA (6.68 ml, 38.2 mmol, 3 eq.) was added followed by dropwise addition of MOM-Cl (1.45 ml, 19.1 mmol, 1.5 eq.). The mixture was stirred for 24 hrs at RT. Next, water and DCM were added and the layers were separated. The DCM-layer was washed with a 1M HCl-solution, a saturated NaHCO₃-solution, water and brine and dried on Na₂SO₄. The DCM-layer was filtered and the filtrate concentrated in vacuo. The crude product was purified by silica gel column chromatography (C7/EtOAc, 1:0 to 9:1, v/v) and the fractions containing product were combined and concentrated in vacuo to yield compound B (2.6 g, 10.1 mmol, 79%) as a colorless oil.

¹H NMR (CDCl₃, 400 MHz): 3.40 (3H, s, OCH₃), 4.52 (2H, s, ArCH₂), 4.68 (2H, s, OCH₂O), 5.06 (ArCH₂, benzyl), 6.96 (2H, d, H2), 7.26-7.44 (7H, m, H3, $H_{benzyl}$).

To a suspension of Pd/C (0.21 g, 2.01 mmol, 0.2 eq.) in MeOH (6 ml) was added compound B (2.6 g, 10.07 mmol, 1 eq.) in THF (12 ml). The mixture was purged with hydrogen 3 times and stirred under a hydrogen atmosphere for 4 hrs. The suspension was filtered over Celite, concentrated in vacuo and purified by silica gel column chromatography (C7/EtOAc, 1:0 to 3:1, v/v). The fractions containing product were combined and concentrated in vacuo to yield compound 57 (1.68 g, 9.99 mmol, 99%) as a colorless oil.

¹H NMR (CDCl₃, 400 MHz): 3.42 (3H, s, OCH₃), 4.52 (2H, s, ArCH₂), 4.70 (2H, s, OCH₂O), 6.55 (1H, br s, OH), 6.75 (2H, d, H2), 7.20 (2H, d, H3).

Compound 61

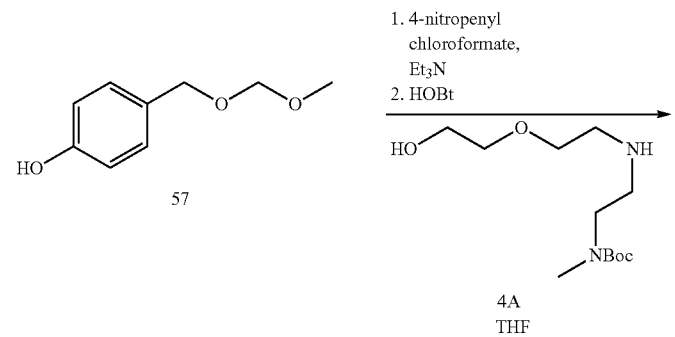

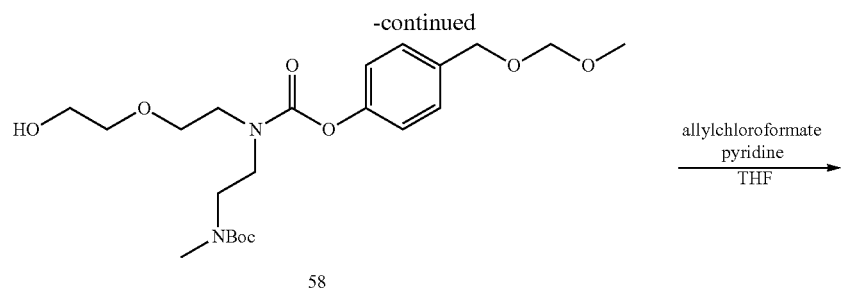
58
allylchloroformate
pyridine
THF
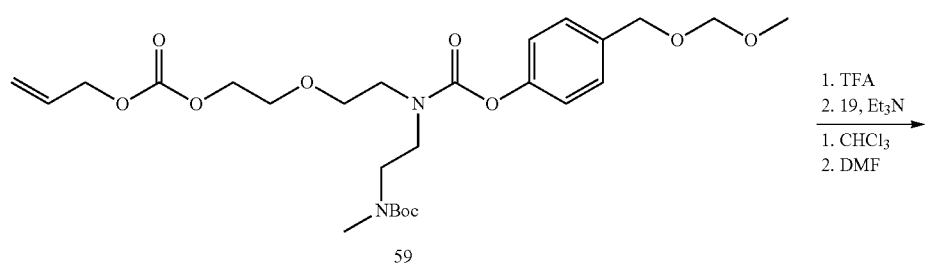
59
1. TFA
2. 19, Et₃N
1. CHCl₃
2. DMF
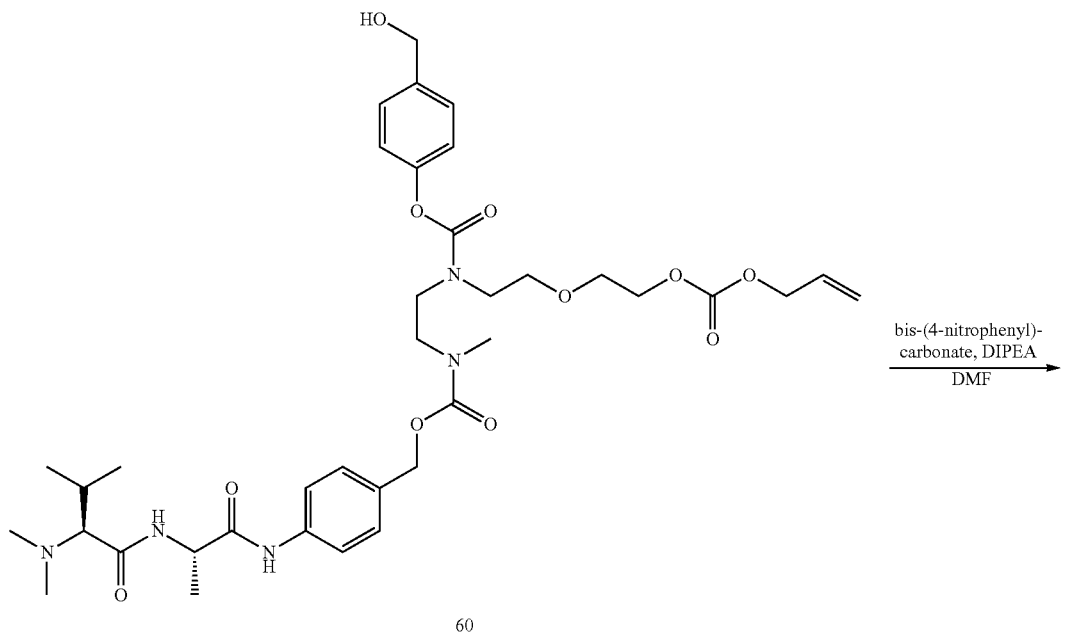
60
bis-(4-nitrophenyl)-
carbonate, DIPEA
DMF

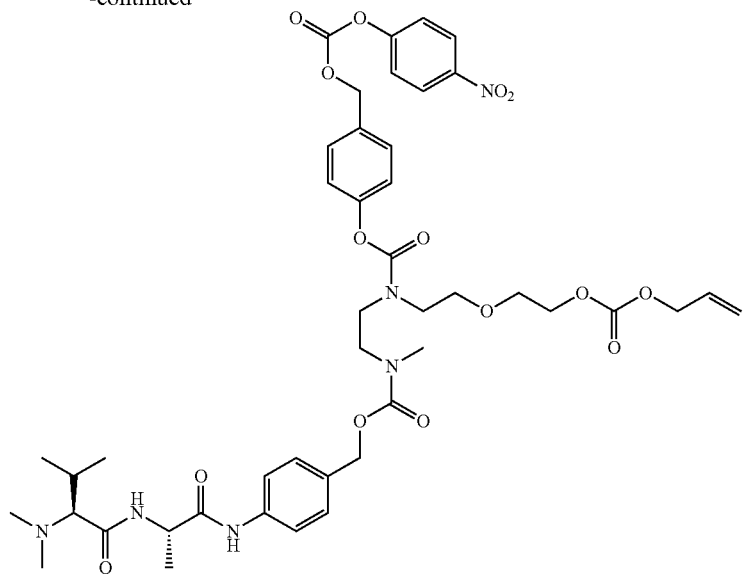

61

A solution of compound 57 (1.68 g, 10 mmol, 1 eq.) in THF (25 ml) was cooled to 0° C. in an ice bath and 4-nitrophenylchloroformate (2.12 g, 10.5 mmol, 1.05 eq.) and Et$_3$N (4.18 ml, 30 mmol, 3 eq.) were added and the mixture was stirred at 0° C. in an ice bath for 30 min. Next, HOBt (1.53 g, 10 mmol, 1 eq.) and cyclisation spacer 4A (synthesized as described in WO2011/133039, example 1 (Syntarga), 2.62 g, 10 mmol, 1 eq. in THF (10 ml)) were added and stirred at 50° C. for 90 min. The mixture was concentrated in vacuo and the crude product was purified by silica gel column chromatography (DCM/EtOAc, 1:0 to 1:1, v/v), the fractions containing product combined and concentrated in vacuo to yield compound 58 (3.1 g, 6.8 mmol, 68%) as a yellow oil.

$^1$H NMR (DMSO-d$_6$, 400 MHz): δ=1.34-1.43 (9H, m, CH$_{3,Boc}$), 2.80-2.87 (3H, m, NCH$_3$), 3.31 (3H, s, OCH$_3$), 3.29-3.66 (12H, m, CH$_2$N, CH$_2$O), 4.52 (2H, s, ArCH$_2$), 4.66 (2H, s, OCH$_2$O), 7.06-7.11 (2H, m, H2), 7.33-7.38 (2H, m, H3).

$^{13}$C NMR (DMSO-d$_6$, 100 MHz): δ=28.4 (CH$_{3,Boc}$), 34.4, 34.7, 34.9 (NCH$_3$), 45.7, 46.5, 46.6, 47.1, 47.3, 47.4 (NCH$_2$), 55.2 (OCH$_3$), 60.7, 60.7 (CH$_2$OH), 68.4 (ArCH$_2$), 68.7, 69.2 (NCH$_2$CH$_2$O), 72.7, 72.8 (OCH$_2$), 79.0, 79.0 (C$_{Boc}$), 95.7 (OCH$_2$O), 122.0, 122.2 (C2), 128.9, 129.0 (C3), 135.4 (C4), 151.0 (C1), 154.3 (C=O), 155.2 (C=O$_{Boc}$).

MS (ESI) m/z; calculated: 457.25 [M+H]$^+$, found: 357.16 (–Boc), 457.58 [M+H]$^+$.

A solution of compound 58 (1 g, 2.19 mmol, 1 eq.) in THF (20 ml) was cooled in an ice bath and allyl chloroformate (0.26 ml, 2.41 mmol, 1.1 eq.) and pyridine (0.35 ml, 4.38 mmol, 2 eq.) were added dropwise. The mixture was stirred for 5 hrs at 0° C. in an ice bath. The crude mixture was concentrated in vacuo and purified by silica gel column chromatography (DCM/EtOAc, 1:0 to 1:1, v/v), the fractions containing product combined and concentrated in vacuo to yield compound 59 (1.1 g, 2.0 mmol, 92%) as a colorless oil.

$^1$H NMR (DMSO-d$_6$, 400 MHz): δ=1.33-1.41 (9H, m, CH$_{3,Boc}$), 2.78-2.86 (3H, m, NCH$_3$), 3.30 (3H, s, OCH$_3$), 3.29-3.70 (10H, m, CH$_2$N, CH$_2$O), 4.22-4.26 (2H, m, (C=O)OCH$_2$CH$_2$O), 4.51 (2H, s, ArCH$_2$), 4.57-4.62 (2H, m, CH$_{2,Aloc}$), 4.65 (2H, s, OCH$_2$O), 5.22-5.35 (2H, m, C=CH$_{2,Aloc}$), 5.86-5.99 (1H, m, CH$_{Aloc}$), 7.05-7.11 (2H, m, H2), 7.32-7.36 (2H, m, H3).

$^{13}$C NMR (DMSO-d$_6$, 100 MHz): δ=28.5 (CH$_{3,Boc}$), 34.5, 35.0 (NCH$_3$), 45.7, 46.5, 47.2 (NCH$_2$), 55.2 (OCH$_3$), 67.2 (C=O)OCH$_2$CH$_2$O), 68.3 (CH$_{2,Aloc}$), 68.4 (ArCH$_2$), 68.6, 69.2 (OCH$_2$), 79.0, 79.0 (C$_{Boc}$), 95.7 (OCH$_2$O), 118.8 (C=CH$_{2,Aloc}$), 122.0, 122.2 (C2), 129.0 (C3), 132.6 (CH$_{Aloc}$), 135.5 (C4), 151.0 (C1), 154.3 (C=O), 154.9 (C=O$_{Aloc}$), 155.2 (C=O$_{Boc}$).

MS (ESI) m/z; calculated: 563.26 [M+Na]$^+$, found: 441.50 [M-Boc]$^+$, 563.57 [M+Na]$^+$.

Compound 59 (250 mg, 0.46 mmol, 1 eq.) was dissolved in chloroform (6 ml), cooled to 0° C. in an ice bath, TFA (6 ml) was added and stirred for 8 hrs. The mixture was diluted with chloroform, concentrated in vacuo, co-evaporated with toluene and dried in vacuo. The resulting TFA-salt was redissolved in dry DMF (2 ml), cooled to 0° C. in an ice bath. A solution of compound 19 (225 mg, 0.46 mmol, 1 eq.) in dry DMF (2 ml) was added followed by dropwise addition of Et$_3$N (0.14 ml, 1.39 mmol, 3 eq.). The resulting mixture was stirred for 3 hrs followed by addition of MeOH (2 ml) and additional stirring for 15 min. The mixture was concentrated in vacuo and purified by silica gel column chromatography (DCM/MeOH, 1:0 to 8:2, v/v), the fractions containing product combined and concentrated in vacuo to yield compound 60 (190 mg, 0.26 mmol, 55%) as a light yellow oil.

$^1$H NMR (DMSO-d$_6$, 400 MHz): δ=0.82-0.86 (3H, m, CH$_{3,Val}$), 0.94-0.98 (3H, m, CH$_{3,Val}$), 1.33-1.37 (3H, m, CH$_{3,Ala}$), 2.06 (1H, br s, β-H$_{Val}$), 2.30 (6H, br s, N(CH$_3$)$_2$), 2.85-2.90 (3H, m, NCH$_3$), 3.30-3.72 (10H, m, CH$_2$N, CH$_2$O), 4.21-4.26 (2H, m, (C=O)OCH$_2$CH$_2$O), 4.46-4.61 (5H, m, α-CH$_{Ala}$, ArCH$_2$, CH$_{2,Aloc}$), 4.95-5.03 (2H, m, CH$_2$,PABA) 5.20-5.35 (2H, m, OH, C=CH$_{2,Aloc}$), 5.86-5.96 (1H, m, CH$_{Aloc}$), 6.96-7.04 (2H, m, H2'), 7.23-7.32 (4H, m, H3, H3'), 7.52-7.61 (2H, m, H2), 8.55 (1H, br s, NH$_{Ala}$), 9.74 (1H, br s, OH), 10.16 (NH$_{PABA}$).

$^{13}$C NMR (DMSO-d$_6$, 100 MHz): δ=18.6 (CH$_{3,Val}$), 18.6 (CH$_{3,Ala}$), 19.8 (CH$_{3,Val}$), 27.1 (β-CH$_{Val}$), 34.5, 34.7, 35.1, 35.2 (NCH$_3$), 41.7 (NCH$_{3,Val}$), 45.7, 46.4, 46.7, 47.1, 47.3 (NCH$_2$), 49.5 (α-CH$_{Ala}$), 62.9 (ArCH$_2$OH), 66.5, 66.7 (ArCH$_{2,PABA}$), 67.2 (C=O)OCH$_2$CH$_2$O), 68.3, 68.3

(CH$_{2,Aloc}$), 68.5, 68.6, 69.1 (OCH$_2$), 72.7 (α-CH$_{Val}$), 118.7 (C=CH$_{2,Aloc}$), 119.5 (C2) 121.8 (CT), 127.6, 127.7 (C3), 128.9 (C3'), 132.0, 132.1 (C4, C4'), 132.6 (CH$_{Aloc}$), 139.2 (C1), 139.8 (C4'), 150.3 (C1'), 154.3 (Ar—OC(O)N), 154.9 (C=O$_{Aloc}$), 156.0, 156.1 (Ar—CH$_2$OC(O)N), 171.4 (C=O$_{Ala}$).

MS (ESI) m/z; calculated: 744.38 [M+H]$^+$, found: 744.72 [M+H]$^+$.

A solution of compound 60 (190 mg, 0.26 mmol, 1 eq.) in dry DMF (2 ml) was cooled to 0° C. in an ice bath and bis(4-nitrophenyl)carbonate (155 mg, 0.51 mmol, 2 eq.) and DIPEA (67 μl, 0.38 mmol, 1.5 eq.) were added and stirred for 4 hrs. The mixture was concentrated in vacuo and purified by silica gel column chromatography (DCM/MeOH, 1:0 to 9:1, v/v), the fractions containing product combined and concentrated in vacuo to yield compound 61 (202 mg, 0.22 mmol, 87%).

$^1$H NMR (DMSO-d$_6$, 400 MHz): δ=0.80 (3H, d, CH$_{3,Val}$), 0.90 (3H, d, CH$_{3,Val}$), 1.32 (3H, d, CH$_{3,Ala}$), 1.94 (1H, br 2.25 (6H, br s, N(CH$_3$)$_2$), 2.85-2.91 (3H, m, NCH$_3$), 3.30-3.71 (10H, m, CH$_2$N, CH$_2$O), 4.23 (2H, br s, (C=O) OCH$_2$CH$_2$O), 4.45-4.54 (1H, m, α-CH$_{Ala}$), 4.59 (2H, br s, CH$_{2,Aloc}$), 4.95-5.03 (2H, m, CH$_{2,PABA}$), 5.31 (2H, s ArCH$_2$), 5.20-5.34 (2H, m, C=CH$_{2,Aloc}$), 5.86-5.96 (1H, m, CH$_{Aloc}$), 7.07-7.15 (2H, m, H2'), 7.23-7.33 (2H, m, H3), 7.45-7.49 (2H, m, H3'), 7.52-7.60 (4H, m, H2, H2''), 8.14 (1H, br s, NH$_{Ala}$), 8.29-8.35 (2H, m, H3''), 10.09 (NH$_{PABA}$).

$^{13}$C NMR (DMSO-d$_6$, 100 MHz): δ=18.5 (CH$_{3,Ala}$), 20.0 (CH$_{3,Val}$), 27.1 (β-CH$_{Val}$), 34.5, 34.8, 35.1, 35.3 (NCH$_3$), 41.8 (NCH$_{3,Val}$), 45.7, 45.9, 46.4, 46.7, 47.1, 4743 (NCH$_2$), 49.2 (α-CH$_{Ala}$), 66.5, 66.7 (ArCH$_{2,PABA}$), 67.2 (C=O) OCH$_2$CH$_2$O), 68.3 (CH$_{2,Aloc}$), 68.5, 68.6, 69.0 (OCH$_2$), 70.4 (ArCH$_2$), 73.3 (α-CH$_{Val}$), 118.8 (C=CH$_{2,Aloc}$), 119.5 (C2) 122.3, 122.4 (C2'), 123.0 (C2''), 125.9 (C3''), 128.9, 128.9 (C3), 130.1 (C3'), 131.9, 132.0 (C4, C4'), 132.6 (CH$_{Aloc}$), 139.2 (C1), 145.7 (C1''), 151.9 (C1'), 152.4 (OC(O)O) 154.3 (Ar—OC(O)N), 154.9 (C=O$_{Aloc}$), 155.8 (C4''), 156.0, 156.1 (Ar—CH$_2$OC(O)N), 171.7 (C=O$_{Ala}$).

MS (ESI) m/z; calculated: 909.39 [M+H]$^+$, found: 909.77 [M+H]$^+$.

Compound 68

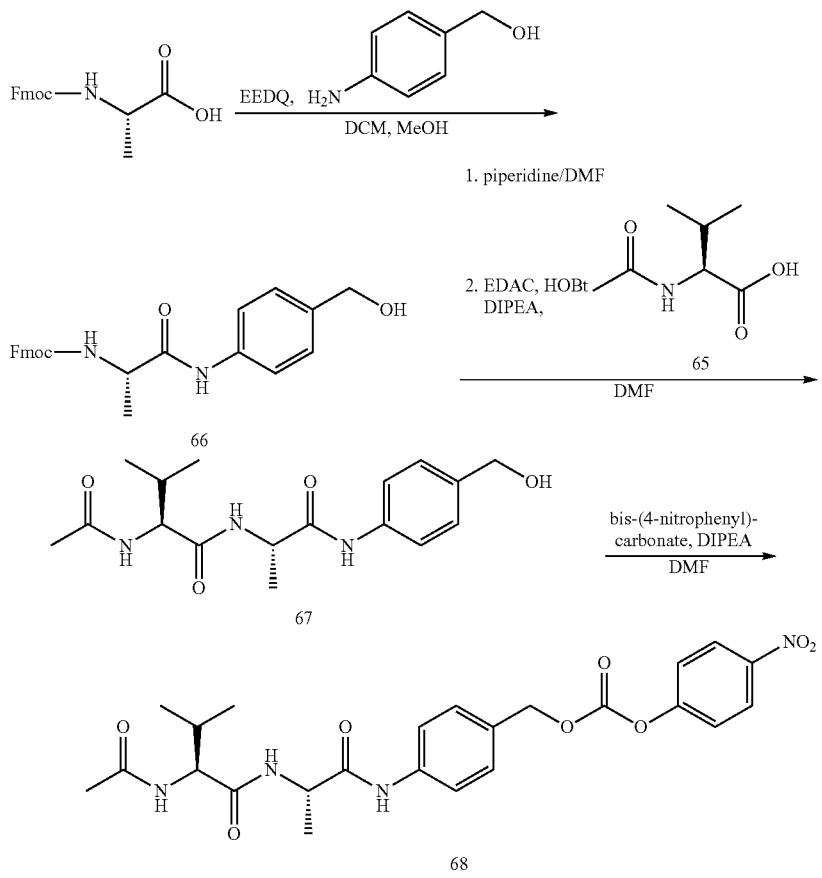

A solution of (S)-2-(((9H-fluoren-9-yl)methoxy)carbonylamino)propanoic acid (5 g, 16.1 mmol) and (4-aminophenyl)methanol (2.77 g, 22.5 mmol, 1.4 eq) in DCM (90 ml) and MeOH (30 ml) was cooled to 0° C., ethyl 2-ethoxyquinoline-1(2H)-carboxylate (7.94 g, 32.1 mmol, 2 eq) was added and stirred for 18 hrs. The mixture was concentrated in vacuo, stirred in ether (100 ml) and filtered to yield (S)-(9H-fluoren-9-yl)methyl 1-(4-(hydroxymethyl)phenylamino)-1-oxopropan-2-ylcarbamate (6 g, 14.41 mmol, 90%) as an off white solid.

$^1$H NMR (DMSO-d$_6$, 400 MHz): δ=1.32 (3H, d, CH$_{3,Ala}$) 4.17-4.29 (4H, m, α-CH$_{Ala}$, CH$_{Fmoc}$, CH$_{2\ Fmoc}$), 4.44 (2H, s, ArCH$_2$), 7.24-7.90 (13H, m, CH$_{ArFmoc}$, H2, H3, NH$_{Ala}$), 9.95 (1H, s, NH$_{PABA}$).

$^{13}$C NMR (DMSO-d$_6$, 100 MHz): δ=18.1 (CH$_{3,Ala}$), 46.6 (CH$_{2,Fmoc}$), 50.7 (α-CH$_{Ala}$), 62.6 (CH$_2$), 65.6 (CH$_{2\ Fmoc}$), 118.9 (C2), 120.1 (CH$_{Fmoc}$), 125.3 (CH$_{Fmoc}$), 126.9 (CH$_{Fmoc}$), 127.1 (C3), 127.6 (CH$_{Fmoc}$), 137.4, 137.6 (C1, C4), 140.7 (C$_{Fmoc}$), 143.8 (C$_{Fmoc}$), 143.9 (C$_{Fmoc}$), 155.8 (C=O$_{Fmoc}$), 171.4 (C=O$_{Ala}$).

MS (ESI) m/z; calculated: 417.18 [M+H]⁺, found: 417.48 [M+H]⁺.

(S)-(9H-fluoren-9-yl)methyl 1-(4-(hydroxymethyl)phenylamino)-1-oxopropan-2-ylcarbamate (6 g, 14.41 mmol) was dissolved in DMF (25 ml), piperidine (9.81 g, 115 mmol) added and stirred for 1 hr. The mixture was concentrated and coevaporated with toluene. The crude product (solid) was stirred in ether (150 ml) for 1 hr and filtered. This procedure was repeated once and the obtained solid product was dried on high vacuum to yield deprotected compound 66 (2.4 g, 12.36 mmol, 86%) as a white solid and used directly in the next step.

A solution of compound 65 (224 mg, 1.55 mmol, 1 eq.) and deprotected compound 66 (300 mg, 1.55 mmol, 1 eq.) in DMF (5 ml) was cooled to 0° C. in an ice bath and EDAC (474 mg, 2.47 mmol, 1.6 eq.), HOBt (284 mg, 1.85 mmol, 1.2 eq.) and DIPEA (1.35 ml, 7.72 mmol, 5 eq.) were added. The resulting mixture was stirred for 18 hrs allowing it to warm to RT. The crude mixture concentrated in vacuo and purified by silica gel column chromatography (DCM/MeOH, 1:0 to 9:1, v/v) to yield compound 67 in quantitative yield.

MS (ESI) m/z; calculated: 336.19 [M+H]⁺, found: 336.36 [M+H]⁺.

Compound 67 (150 mg, 0.45 mmol, 1 eq.) was dissolved in DMF (2.5 ml), cooled to 0° C. in an ice bath and bis(4-nitrophenyl)carbonate (272 mg, 0.89 mmol, 2 eq.) and DIPEA (117 µl, 0.67 mmol, 1.5 eq.) were added and the resulting solution was stirred for 3 hrs allowing it to warm to RT. Then, the mixture was concentrated in vacuo and the crude product was purified by silica gel column chromatography (DCM/MeOH, 1:0 to 95:5, v/v) to yield compound 68 (200 mg, 0.4 mmol, 89%) as an off white solid.

¹H NMR (DMSO-d₆, 400 MHz): δ=0.85 (3H, d, $CH_{3,Val}$), 0.89 (3H, d, $CH_{3,Val}$), 1.32 (3H, d, $CH_{3,Ala}$) 1.89 (3H, s, $CH_{3,Acetyl}$), 1.90-1.99 (1H, m, β-$H_{Val}$), 4.15-4.21 (1H, m, α-$CH_{Val}$), 4.37-4.43 (1H, m, α-$CH_{Ala}$), 5.25 (2H, s, $ArCH_2$), 7.42 (2H, d, H3), 7.57 (2H, d, H2'), 7.65 (2H, d, H2), 7.90 (1H, d, $NH_{Val}$), 8.23 (1H, d, $NH_{Ala}$), 8.31 (2H, d, H3'), 9.99 (1H, s, $NH_{PABA}$).

¹³C NMR (DMSO-d₆, 100 MHz): δ=18.3 ($CH_{3,Ala}$), 18.7 ($CH_{3,Val}$), 19.6 ($CH_{3,Val}$), 23.1 ($CH_{3,Acetyl}$), 30.9 (β-$CH_{Val}$), 49.5 (α-$CH_{Ala}$), 58.2 (α-$CH_{Val}$), 70.7 (Ar—$CH_2$), 119.5 (C2), 123.1 (C2'), 125.9 (C3'), 129.7 (C4), 129.9 (C3), 139.9 (C1), 145.7 (C1'), 152.4 (OC(O)O), 155.8 (C4'), 170.0 (C=$O_{Acetyl}$), 171.5 (C=$O_{Val}$), 171.7 (C=$O_{Ala}$).

MS (ESI) m/z; calculated: 501.20 [M+H]⁺, found: 501.40 [M+H]⁺.

Compound 73

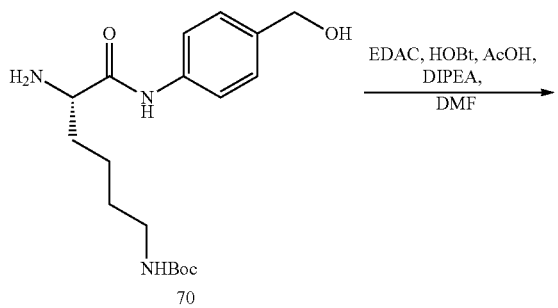

70

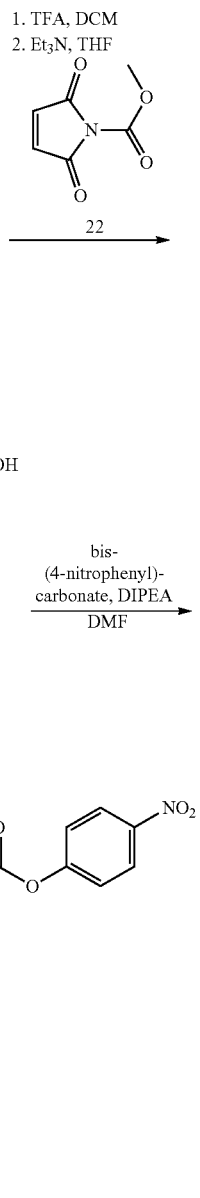

The synthesis of H-Lys(Boc)-PABA, compound 70, is described in Nair et al. Chem. Commun. 2015; 51: 2403-2406.

Compound 71 was obtained as a side product of the coupling of H-Lys(Boc)-PABA 70 (1 eq.) and Me₂ValOH (1.2 eq.) using EDAC (1.6 eq.), HOBt (1.2 eq.) and DIPEA (5 eq.) in DMF (20 ml) for 18 hrs. This side reaction was caused by the presence of AcOH in the Me₂ValOH. The mixture was concentrated in vacuo and purified by silica gel column chromatography (DCM/MeOH, 1:0 to 9:1, v/v), the fractions containing product combined and concentrated in vacuo to yield compound 71 (540 mg, 1.37 mmol, 40%) as a white solid after crystallization from ether.

MS (ESI) m/z; calculated: 394.24 [M+H]⁺, found: 394.23 [M+H]⁺.

A solution of compound 71 (540 mg, 1.37 mmol, 1 eq.) in chloroform (12 ml) was cooled to 0° C. in an ice bath, diluted with TFA (8 ml) and the mixture was stirred for 45 min. Then, the reaction mixture was diluted with DCM, concentrated in vacuo and purified by silica gel column chromatography (DCM/MeOH, 1:0 to 1:1, v/v), the fractions containing product combined and concentrated in vacuo to give the intermediate amine (300 mg, 1.02 mmol, 75%) as a light yellow oil. The oil was suspended in THF (20 ml), cooled to 0° C. in an ice bath and compound 22 (159 mg, 1.02 mmol, 1 eq.) and Et$_3$N (570 µl, 4.09 mmol, 4 eq.) were added and stirred for 20 min. The reaction mixture was warmed to 50° C. for 48 hrs. The mixture was concentrated in vacuo and the crude product was purified by silica gel column chromatography (DCM/MeOH, 1:0 to 9:1, v/v), the fractions containing product combined and concentrated in vacuo to yield compound 72 (90 mg, 0.24 mmol, 24%) as a colorless waxy solid.

MS (ESI) m/z; calculated: 374.17 [M+H]$^+$, found: 374.38 [M+H]$^+$.

A solution of compound 72 (90 mg, 0.24 mmol, 1 eq.) in DMF (2.5 ml) was cooled to 0° C. in an ice bath and bis(4-nitrophenyl)carbonate (147 mg, 0.48 mmol, 2 eq.) and DIPEA (63 µl, 0.36 mmol, 1.5 eq.) were added and the resulting solution was stirred for 3 hrs allowing it gradually to warm to RT. Then, the mixture was concentrated in vacuo and purified by silica gel column chromatography (DCM/MeOH, 1:0 to 9:1 v/v), the fractions containing product combined and concentrated in vacuo to yield compound 73 (56 mg, 0.10 mmol, 43%) as a colorless solid.

MS (ESI) m/z; calculated: 539.18 [M+H]$^+$, found: 539.40 [M+H]$^+$.

Synthesis of Linker-Drug Compounds

Linker-Drug Compound 3

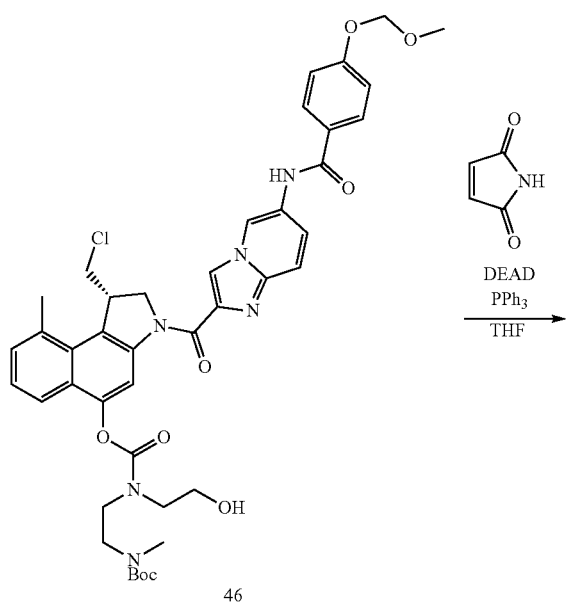

46

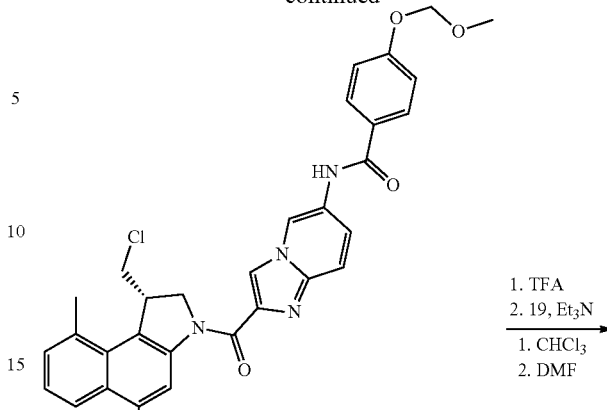

47

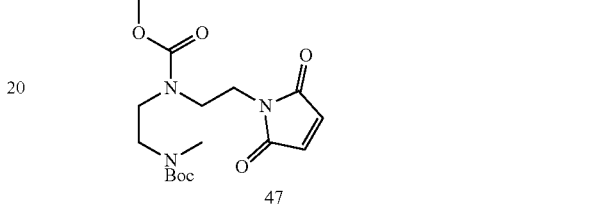

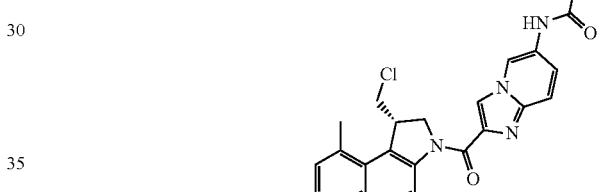

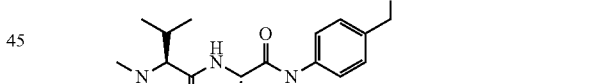

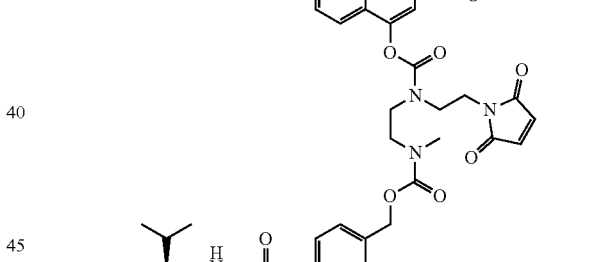

3

Compound 11 (530 mg, 0.93 mmol, 1 eq.) was dissolved in dry THF (15 ml), cooled to 0° C. in an ice bath, 4-nitrophenylchloroformate (206 mg, 1.02 mmol, 1.1 eq.) and Et$_3$N (647 µl, 1.49 mmol, 5 eq.) were added and stirred for 45 min. Then compound 56 (263 mg, 1.21 mmol, 1.3 eq.) in dry THF (3 ml) and HOBt (156 mg, 1.02 mmol, 1.1 eq.) were added and the resulting mixture was warmed to 45° C. for 2 hrs. Afterwards the crude mixture was cooled to RT, concentrated in vacuo and purified by silica gel column chromatography (DCM/MeOH, 1:0 to 93:7, v/v), the fractions containing product combined and concentrated in vacuo to yield product 46 (580 mg, 0.71 mmol, 77%) as a white foam.

$^1$H NMR (DMSO-d$_6$, 400 MHz): δ=1.32-1.45 (9H, m, CH$_{3,Boc}$), 2.78-2.95 (6H, m, ArCH$_3$, NCH$_3$), 3.30-3.79 (9H, m, CHCl, NCH$_2$, OCH$_2$), 3.41 (3H, s, OCH$_3$), 3.81-3.86 (1H, m, CHCl), 4.47 (1H, t, H1), 4.64-4.70 (1H, m, H2), 4.89, 5.04 (1H, 2×br s, OH) 5.17-5.21 (1H, m, H2), 5.31 (2H, s, OCH$_2$O), 7.18 (2H, d, H3″), 7.31-7.37 (1H, m, H7), 7.37-7.44 (1H, m, H8), 7.56-7.60 (1H, m, H8′), 7.71-7.86 (2H, m, H6, H7′), 8.00 (2H, d, H2″), 8.37 (1H, br s, H4), 8.70 (1H, s, H3′), 9.47 (1H, s, H5′), 10.32 (1H, s, Ar—NHC(O)—Ar).

$^{13}$C NMR (DMSO-d$_6$, 100 MHz): δ=22.9 (Ar—CH$_3$), 28.5, 28.6 (CH$_{3,Boc}$), 34.5 (NCH$_3$), 44.7 (C1), 45.8, 46.2, 46.4 (NCH$_2$), 48.0 (CH$_2$Cl), 55.1 (C2), 56.3 (OCH$_3$), 59.1, 59.7 (CH$_2$OH), 79.1, 79.2 (C$_{Boc}$), 93.7 (OCH$_2$O), 111.0, 111.1 (C4), 116.2 (C3″), 117.8 (C5′), 118.0 (C7′), 119.6 (C3′), 121.3 (C6), 122.8 (C9b), 123.6 (C8′), 125.1 (C7), 126.3 (C5$_a$), 127.8 (C6′), 127.9 (C1″), 130.1 (C2″), 130.3 (C9a), 131.0 (C8), 133.4 (C9), 141.0 (C2′), 141.9 (C8a′), 142.4 (C3$_a$), 148.6, 148.6 (Ar—OC(O)N), 154.3, 154.4 (C5), 155.2 (C=O$_{Boc}$), 160.1 (C4″), 162.4 (NC=O), 165.6 (Ar—NHC(O)—Ar).

MS (ESI) m/z; calculated: 815.32 [M+H]$^+$, found: 815.60 [M+H]$^+$.

A solution of compound 46 (200 mg, 0.25 mmol, 1 eq.), maleimide (31 mg, 0.32 mmol, 1.3 eq.) and triphenylphosphine (84 mg, 0.32 mmol, 1.3 eq) in dry THF (4 ml) was cooled to 0° C. in an ice bath and DEAD (2.2 M in toluene, 145 µl, 0.32 mmol, 1.3 eq.) was added dropwise and the mixture was stirred for 45 min at RT. The mixture was concentrated in vacuo and purified by silica gel column chromatography (DCM/MeOH, 1:0 to 95:5, v/v), the fractions containing product combined and concentrated in vacuo, co-evaporated with toluene to yield compound 47 (150 mg, 0.17 mmol, 68%) as a white foam.

MS (ESI) m/z; calculated: 894.32 [M+H]$^+$, found: 894.62 [M+H]$^+$.

A solution of compound 47 (150 mg, 0.17 mmol, 1 eq.) in chloroform (4 ml) was cooled to 0° C. in an ice bath and diluted with TFA (2 ml) and stirred for 3 hrs. The mixture was concentrated in vacuo, co-evaporated with toluene and dried in vacuo. The intermediate was dissolved in dry DMF (2 ml) and cooled to 0° C. in an ice bath followed by addition of activated linker 19 (98 mg, 0.20 mmol, 1.2 eq.) and Et$_3$N (47 µl, 0.34 mmol, 2 eq.). The reaction mixture was stirred for 2 hrs. The mixture was concentrated in vacuo and purified by silica gel column chromatography (DCM/MeOH, 1:0 to 7:3, v/v), the fractions containing product combined and concentration in vacuo to yield the crude compound 3, which was further purified by preparative HPLC (Sunfire C-18, MeCN/MilliQ 0.1% m/m TFA). The acetonitrile was evaporated and the aqueous residue freeze dried, the obtained solid was taken up in dioxane/water (6 ml, 2:1) and freeze dried to yield the TFA salt of linker-drug compound 3 (69 mg, 0.06 mmol, 38%) as a white solid.

$^1$H NMR (DMSO-d$_6$, 400 MHz): δ=0.89 (3H, d, CH$_{3,Val}$), 1.07 (3H, d, CH$_{3,Val}$), 1.37 (3H, d, CH$_{3,Ala}$), 2.24-2.34 (1H, m, β-H$_{Val}$), 2.78 (6H, br s, N(CH$_3$)$_2$), 2.84 (3H, br s, ArCH$_3$), 2.84-2.98 (3H, d, C(O)NCH$_3$), 3.35-3.88 (11H, m, CH$_2$Cl, α-CH$_{Val}$, NCH$_2$), 4.44-4.51 (1H, m, H1), 4.55 (1H, t, α-CH$_{Ala}$), 4.61-4.69 (1H, m, H2), 4.97-5.10 (3H, m, H2, Ar—CH$_2$), 6.92 (2H, d, H3″), 6.98 (1H, s, HC=CH), 7.08 (1H, s, HC=CH), 7.19-7.80 (9H, m, H6, H7, H8, H7′, H8′, H2‴, H3‴), 7.91 (2H, d, H2″), 8.21-8.32 (1H, m, H4), 8.78-8.83 (1H, m, H3′), 8.99 (1H, d, NH$_{Ala}$), 9.54-9.68 (2H, m, H5′, OH), 10.11-10.20 (1H, m, NH$_{PABA}$), 10.30 (1H, s, Ar—NHC(O)—Ar).

$^{13}$C NMR (DMSO-d$_6$, 100 MHz): 17.1 (CH$_{3,Val}$), 18.5 (CH$_{3,Ala}$), 19.6 (CH$_{3,Val}$), 22.8 (Ar—CH$_3$), 27.0 (β-CH$_{Val}$), 34.7 (NCH$_3$), 35.5 ((C=O)$_2$NCH$_2$CH$_2$), 41.5 (NCH$_{3,Val}$), 42.1 (NCH$_{3,Val}$), 44.8 (C1), 45.6 (NCH$_2$), 47.9 (CH$_2$Cl), 49.8 (α-CH$_{Ala}$), 54.9 (C2), 66.4 (Ar—CH$_2$OC(O)N), 72.0 (α-CH$_{Val}$), 111.0 (C4), 115.6 (C3″), 117.0 (C7′), 117.8 (C5′), 119.3 (C3′), 119.5 (C2‴), 121.1 (C6), 123.1 (C9b), 125.0 (C1″), 125.3 (C7, C8′), 126.3 (5a), 128.7 (C6′), 128.9 (C3‴), 130.2 (C9a), 130.3 (C2″), 131.1 (C8), 132.3 (C4‴), 133.4 (C9), 135.1, 135.2 (HC=CH), 138.9 (C1‴), 141.1 (C2′, C8a′), 142.1 (C3a), 148.4 (Ar—OC(O)N), 154.2 (C5), 154.7 (Ar—CH$_2$OC(O)N), 161.4 (NC=O), 161.4 (C4″), 165.4 (C=O$_{Val}$), 165.9 (Ar—NHC(O)—Ar), 170.7 (C=O$_{Ala}$), 171.4, 171.5 (C=O$_{maleimide}$).

MS (ESI) m/z; calculated: 1097.43 [M+H]$^+$, found: 1097.76 [M+H]$^+$.

Linker-Drug Compound 4

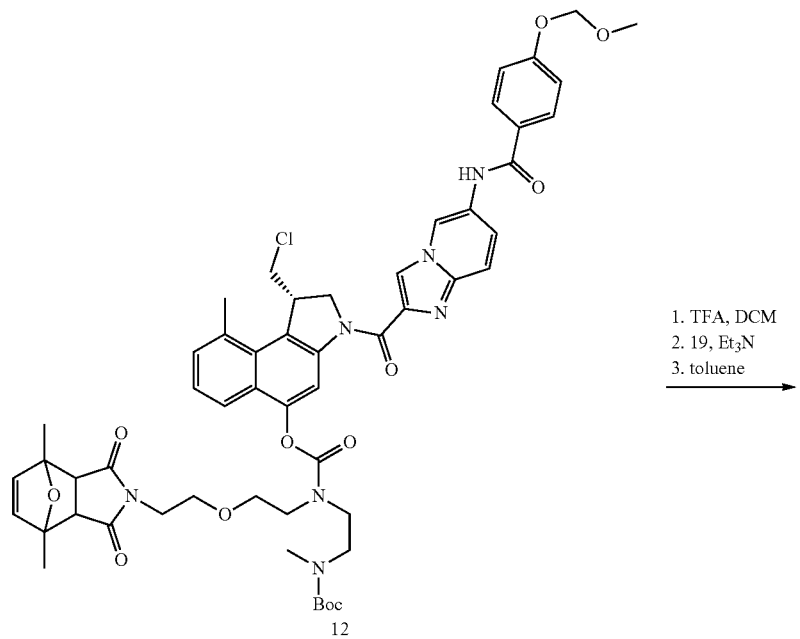

1. TFA, DCM
2. 19, Et$_3$N
3. toluene

12

-continued

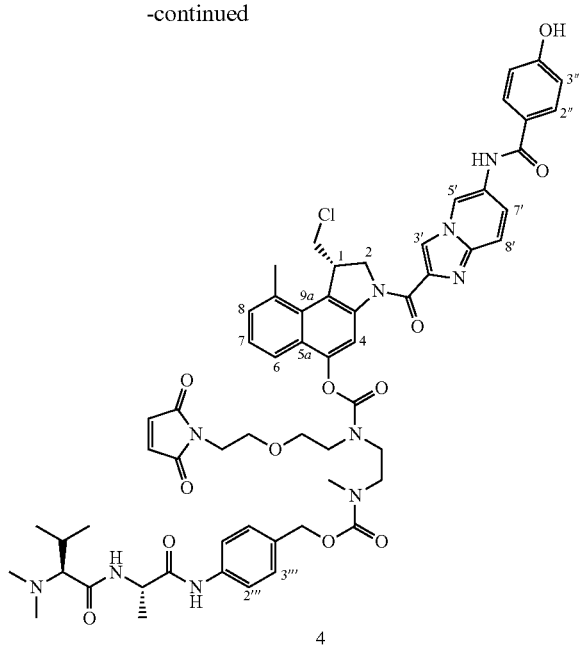

4

A solution of compound 12 (990 mg, 0.96 mmol, 1 eq.) in DCM (5 ml) was cooled to 0° C. in an ice bath and diluted with TFA (5 ml). The mixture was stirred for 2.5 hrs and then diluted with DCM, concentrated in vacuo and co-evaporated with toluene. Activated compound 19 (512 mg, 1.05 mmol, 1.1 eq.) was dissolved in dry DMF (10 ml), cooled to 0° C. in an ice bath and subsequently Et$_3$N (533 µl, 4.06 mmol, 4 eq.) was added followed by dropwise addition of the TFA-salt (which was dissolved in dry DMF (10 ml)). The resulting mixture was stirred for 3 hrs and gradually warmed from 0° C. in an ice bath to RT. Next, the mixture was concentrated in vacuo and the crude product was purified by silica gel column chromatography (DCM/MeOH, gradient), the fractions containing product combined, concentrated in vacuo and co-evaporated with toluene. Then, the obtained solid was suspended in toluene (120 ml) and gradually warmed to 90° C. in 5 hrs. The mixture was concentrated in vacuo and the crude product was purified by preparative HPLC (Sunfire C-18, MeCN/MilliQ 0.1% m/m TFA). Acetonitrile was evaporated and the water residue freeze dried. The obtained product was dissolved in dioxane/water (18 ml, 2:1) and freeze dried a second time to yield the TFA salt of linker-drug compound 4 (475 mg, 0.42 mmol, 44%) as a white solid.

$^1$H NMR (DMSO-d$_6$, 400 MHz): δ=0.88 (3H, d, CH$_{3,Val}$), 1.06 (3H, d, CH$_{3,Val}$), 1.36 (3H, d, CH$_{3,Ala}$), 2.25-2.30 (1H, m, β-H$_{Val}$), 2.77 (6H, br s, N(CH$_3$)$_2$), 2.85 (3H, br s, ArCH$_3$), 2.85-2.92 (3H, d, C(O)NCH$_3$), 3.33-3.71 (14H, m, CHCl, α-CH$_{Val}$, NCH$_2$, OCH$_2$), 3.83 (1H, d, CHCl), 4.47-4.51 (1H, m, H1), 4.51-4.57 (1H, m, α-CH$_{Ala}$), 4.63-4.69 (1H, m, H2), 4.96-5.07 (3H, m, H2, Ar—CH$_2$), 6.89-6.97 (3H, m, HC=CH, H3″), 7.03 (1H, d, CH=CH), 7.17-7.59 (6H, m, H7, H8, H2‴, H3‴), 7.62-7.80 (3H, m, H6, H7′, H8′), 7.91 (2H, d, H2″), 8.28-8.39 (1H, m, H4), 8.79-8.81 (1H, m, H3′), 8.99 (1H, d, NH$_{Ala}$), 9.55-9.62 (2H, m, H5′, OH), 10.11-10.18 (1H, m, NH$_{PABA}$), 10.30 (1H, s, Ar—NHC(O)—Ar).

$^{13}$C NMR (DMSO-d$_6$, 100 MHz): δ=17.1 (CH$_{3,Val}$), 18.5 (CH$_{3,Ala}$), 19.6 (CH$_{3,Val}$), 22.9 (Ar—CH$_3$), 27.0 (β-CH$_{Val}$), 34.4, 34.8, 35.2 (NCH$_3$), 37.1, 37.4 ((C=O)$_2$NCH$_2$CH$_2$), 41.5 (NCH$_{3,Val}$), 42.1 (NCH$_{3,Val}$), 44.8 (C1), 47.4, 47.6 (NCH$_2$), 47.9 (CH$_2$Cl), 49.8 (α-CH$_{Ala}$), 54.9 (C2), 66.4, 66.5 (Ar—CH$_2$OC(O)N), 67.6, 68.4, 68.6 (OCH$_2$), 71.9 (α-CH$_{Val}$), 111.0 (C4), 115.6 (C3″), 117.0 (C7′), 117.8 (C5′), 119.5 (C3′, C2‴), 121.2 (C6), 123.0 (C9b), 124.9 (C1″), 125.3 (C7, C8′), 126.3 (C5a), 128.8 (C6′), 128.9, 129.0 (C3‴), 130.2 (C9a), 130.3 (C2″), 131.1 (C8), 132.4 (C4‴), 133.5 (C9), 134.9, 135.0 (HC=CH), 138.9 (C1‴), 139.0 (C2′), 140.9 (C8a′), 142.1 (C3a), 148.5 (Ar—OC(O)N), 154.1, 154.3 (C5), 156.2 (Ar—CH$_2$OC(O)N), 161.3 (NC=O), 161.4 (C4″), 165.4 (C=O$_{Val}$), 165.9 (Ar—NHC(O)—Ar), 170.8 (C=O$_{Ala}$), 171.4 (C=O$_{maleimide}$).

MS (ESI) m/z; calculated: 1141.45 [M+H]$^+$, found: 1141.90 [M+H]$^+$.

Linker-Drug Compound 5

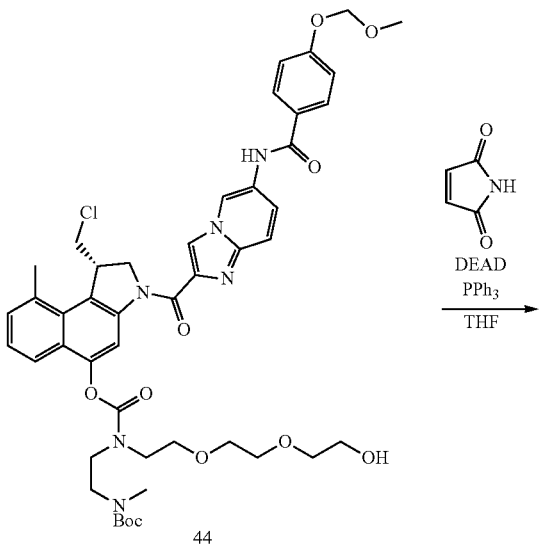

44

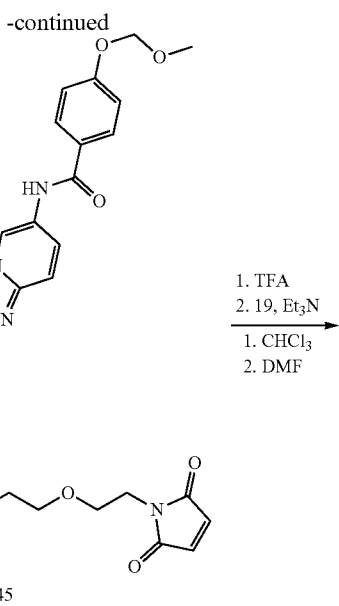

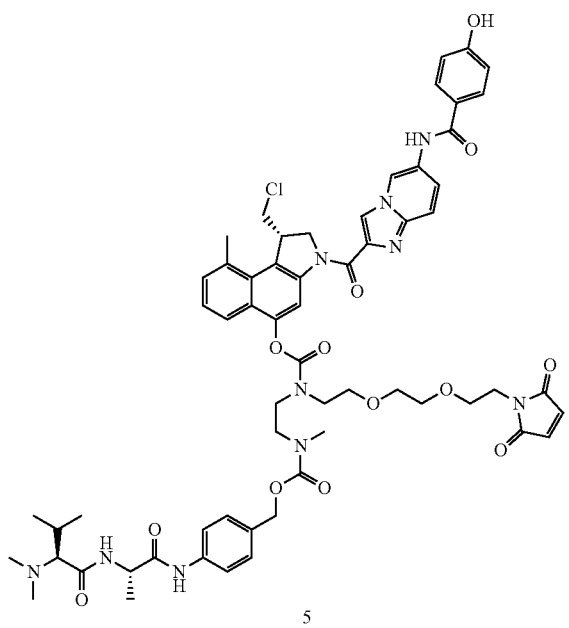 [SMILES: Cc1cccc2c(OC(=O)N(CCOCCOCCN3C(=O)C=CC3=O)CCN(C)C(=O)OCc3ccc(NC(=O)[C@H](C)NC(=O)[C@H](C(C)C)N(C)C)cc3)cc3c(c12)[C@H](CCl)CN3C(=O)c1cn2cc(NC(=O)c3ccc(O)cc3)ccc2n1]

A solution of compound 44 (720 mg, 0.80 mmol, 1 eq.), maleimide (10 mg, 1.04 mmol, 1.3 eq.) and triphenylphosphine (272 mg, 1.04 mmol, 1.3 eq) in dry THF (10 ml) was cooled to 0° C. in an ice bath and DEAD (2.2 M in toluene, 471 µl, 1.04 mmol, 1.3 eq.) was added dropwise and stirred for 45 min at RT. The mixture was concentrated in vacuo and purified by silica gel column chromatography (DCM/MeOH, 1:0 to 95:5, v/v), the fractions containing product combined and concentrated in vacuo, co-evaporated with toluene to yield compound 45 (590 mg, 0.60 mmol, 75%) as a white foam.

$^1$H NMR (DMSO-d$_6$, 400 MHz): δ=1.29-1.45 (9H, m, CH$_{3,Boc}$), 2.78-2.95 (6H, m, ArCH$_3$, NCH$_3$), 3.42 (3H, s, OCH$_3$), 3.35-3.74 (17H, m, CHCl, NCH$_2$, OCH$_2$), 3.80-3.86 (1H, m, CHCl), 4.47 (1H, t, H1), 4.63-4.70 (1H, m, H2), 5.16-5.21 (1H, m, H2), 5.31 (2H, s, OCH$_2$O), 6.97-7.02 (2H, m, HC=CH), 7.18 (2H, d, H3″), 7.31-7.44 (2H, m, H7, H8), 7.57-7.61 (1H, m, H8′), 7.68-7.84 (2H, m, H6, H7′), 7.99 (2H, d, H2″), 8.35 (1H, br s, H4), 8.70 (1H, s, H3′), 9.47 (1H, s, H5′), 10.32 (1H, s, Ar—NHC(O)—Ar).

$^{13}$C NMR (DMSO-d$_6$, 100 MHz): δ=22.9 (Ar—CH$_3$), 28.5, 28.6 (CH$_{3,Boc}$), 34.6 (NCH$_3$), 37.2, 37.3 ((C=O)$_2$NCH$_2$CH$_2$), 44.7 (C1), 45.5, 46.0, 47.5 (NCH$_2$), 47.9 (CH$_2$Cl), 55.1 (C2), 56.3 (OCH$_3$), 67.5, 68.6, 69.1, 69.9, 70.2, 70.3 (OCH$_2$), 79.1, 79.1 (C$_{Boc}$), 94.2 (OCH$_2$O), 111.0, 111.1 (C4), 116.2 (C3″), 117.8 (C5′), 118.0 (C7′), 119.6 (C3′), 121.2 (C6), 122.8 (C9b), 123.6 (C8′), 125.1 (C7), 126.3 (C5a), 127.8 (C6′), 127.9 (C1″), 130.1 (C2″), 130.3 (C9a), 131.0 (C8), 133.5 (C9), 134.9, 134.9 (HC=CH), 141.0 (C2′), 141.9 (C8a′), 142.4 (C3$_a$), 148.5, 148.6 (Ar—OC(O)N), 154.3 (C5), 155.2 (C=O$_{Boc}$), 160.1 (C4″), 162.3 (NC=O), 165.6 (Ar—NHC(O)—Ar), 171.3, 171.3 (C=O$_{Maleimide}$).

MS (ESI) m/z; calculated: 982.37 [M+H]$^+$, found: 982.80 [M+H]$^+$.

A solution of compound 45 (200 mg, 0.20 mmol, 1 eq.) in chloroform (2 ml) was cooled to 0° C. in an ice bath and diluted with TFA (2 ml) and stirred for 3 hrs. The mixture was concentrated in vacuo, co-evaporated with toluene and dried in vacuo. The intermediate was dissolved in dry DMF (2 ml), cooled to 0° C. in an ice bath and activated linker 19 (119 mg, 0.24 mmol, 1.2 eq.) and Et$_3$N (85 µl, 0.61 mmol, 3 eq.) were added and the mixture was stirred for 2 hrs. The mixture was concentrated in vacuo and purified by silica gel column chromatography (DCM/MeOH, 1:0 to 7:3, v/v) to yield the crude compound 5, which was purified by preparative HPLC (Sunfire C-18, MeCN/MilliQ 0.1% m/m TFA). MeCN was evaporated and the aqueous residue freeze dried, the obtained solid was taken up in dioxane/water (6 ml, 2:1) and freeze dried to yield the TFA salt of linker-drug compound 5 (18 mg, 0.013 mmol, 7%) as a white solid.

$^1$H NMR (DMSO-d$_6$, 400 MHz): δ=0.88 (3H, d, CH$_{3,Val}$), 1.06 (3H, d, CH$_{3,Val}$), 1.37 (3H, d, CH$_{3,Ala}$), 2.23-2.33 (1H, m, β-H$_{Val}$), 2.77 (6H, br s, N(CH$_3$)$_2$), 2.85 (3H, br s, ArCH$_3$), 2.85-2.98 (3H, d, C(O)NCH$_3$), 3.36-3.99 (19H, m, CH$_2$Cl, α-CH$_{Val}$, NCH$_2$, OCH$_2$), 4.46-4.51 (1H, m, H1), 4.55 (1H, t, α-CH$_{Ala}$), 4.63-4.69 (1H, m, H2), 4.97-5.18 (3H, m, H2, Ar—CH$_2$), 6.91 (2H, d, H3″), 6.95-7.01 (2H, m, HC=CH), 7.18-7.59 (6H, m, H7, H8, H2‴, H3‴), 7.62-7.80 (3H, m, H6, H7′, H8′), 7.91 (2H, d, H2″), 8.28-8.39 (1H, m, H4), 8.72 (1H, s, H3′), 8.99 (1H, d, NH$_{Ala}$), 9.50 (1H, br s, H5′), 9.64 (1H, br s, OH), 10.11-10.30 (2H, m, NH$_{PABA}$, Ar—NHC(O)—Ar).

$^{13}$C NMR (DMSO-d$_6$, 100 MHz): δ=17.2 (CH$_{3,Val}$), 18.5 (CH$_{3,Ala}$), 19.7 (CH$_{3,Val}$), 22.9 (Ar—CH$_3$), 27.0 (β-CH$_{Val}$), 34.9, 35.3 (NCH$_3$), 37.3 ((C=O)$_2$NCH$_2$CH$_2$), 41.6 (NCH$_{3,Val}$), 42.0 (NCH$_{3,Val}$), 44.8 (C1), 47.4, 47.6 (NCH$_2$), 47.9 (CH$_2$Cl), 49.8 (α-CH$_{Ala}$), 55.0 (C2), 66.5 (Ar—CH$_2$OC(O)N), 67.5, 69.0, 69.8, 70.1, 70.3 (OCH$_2$), 71.9 (α-CH$_{Val}$), 111.0 (C4), 115.5 (C3″), 117.7 (C7′), 117.7 (C5′), 119.5 (C3′, C2‴), 121.3 (C6), 122.9 (C9b), 124.1 (C8′), 125.1 (C7), 126.3 (C5a, C1″), 128.3 (C6′), 128.8 (C3‴), 130.3 (C9a), 130.3 (C2″), 131.1 (C8), 132.6 (C4‴), 133.5 (C9), 134.9, 135.0 (HC=CH), 138.9 (C1‴), 141.6 (C2′, C8a′), 142.3 (C3a), 148.5 (Ar—OC(O)N), 154.5 (C5), 156.3 (Ar—CH$_2$OC(O)N), 158.1, 158.4, 158.8, 159.1 (TFA), 161.4 (NC=O), 161.4 (C4″), 165.4 (C=O$_{Val}$), 165.9 (Ar—NHC(O)—Ar), 170.7 (C=O$_{Ala}$), 171.3 (C=O$_{maleimide}$).

MS (ESI) m/z; calculated: 1185.48 [M+H]$^+$, found: 1186.79 [M+H]$^+$.

Linker-Drug Compound 6
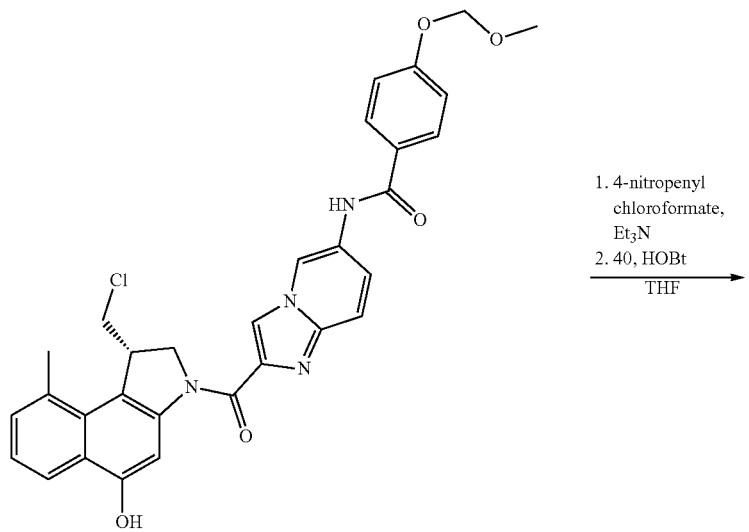
35
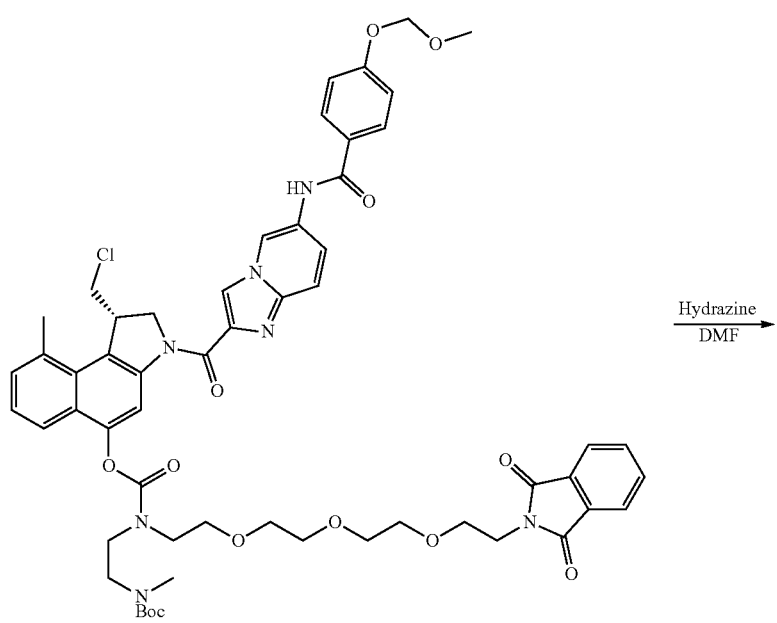
41

-continued
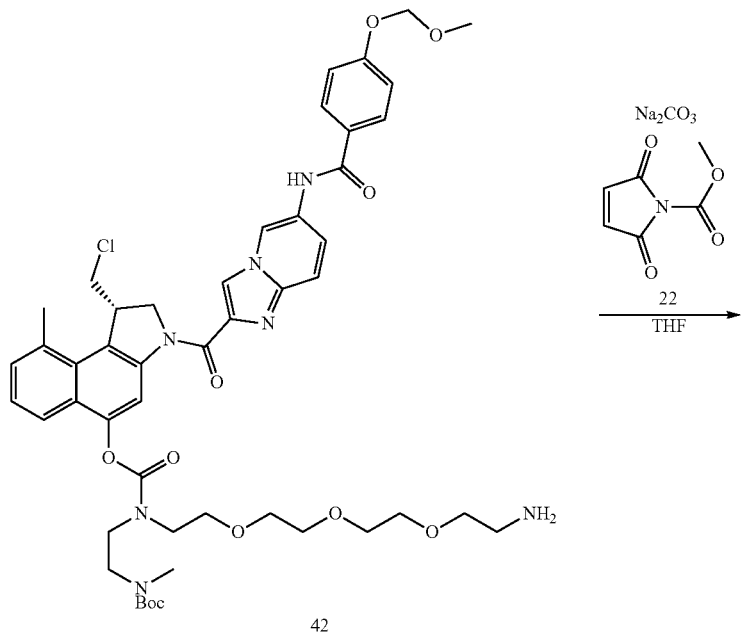
42
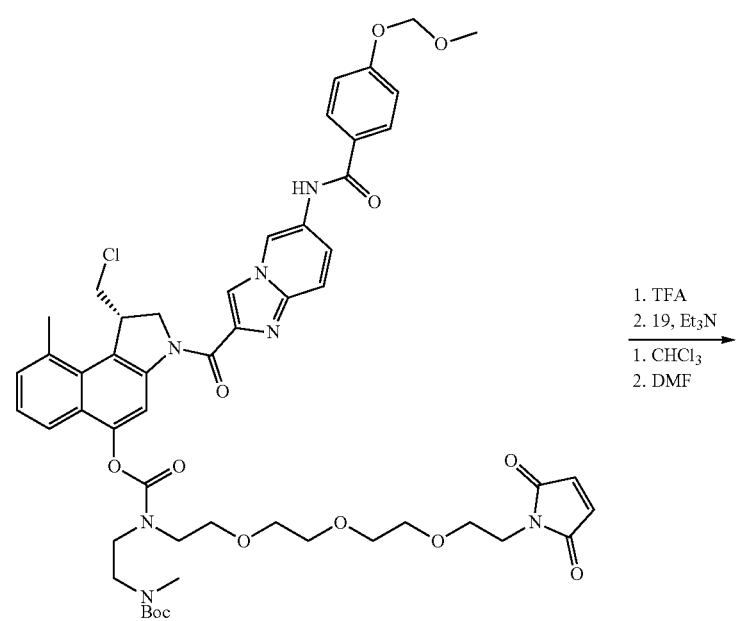
43

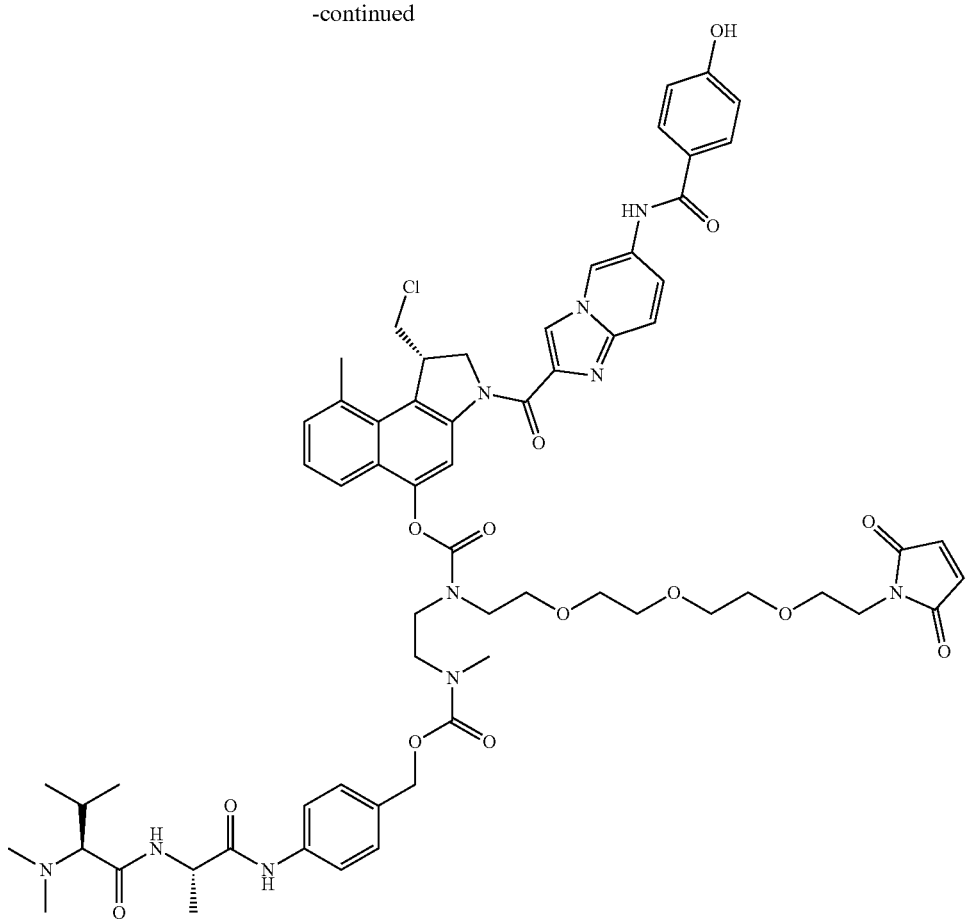

A solution of compound 35 (170 mg, 0.30 mmol, 1 eq.) in dry THF (5 ml) was cooled to 0° C. in an ice bath and 4-nitrophenylchloroformate (66 mg, 0.33 mmol, 1.1 eq.) and Et$_3$N (207 μl, 1.49 mmol, 5 eq.) were added and stirred for 30 min. Next, a solution of compound 40 (186 mg, 0.39 mmol, 1.3 eq.) in dry THF (3 ml) and HOBt (50 mg, 0.33 mmol, 1.1 eq.) were added and the resulting mixture was warmed to 45° C. for 2 hrs. The mixture was cooled to RT, concentrated in vacuo and the crude product was purified by silica gel column chromatography (DCM/MeOH, 1:0 to 95:5, v/v) to yield compound 41 (325 mg, quantitative yield).

H NMR (DMSO-d$_6$, 400 MHz): δ=1.30-1.44 (9H, m, CH$_{3, Boc}$), 2.78-2.95 (6H, m, ArCH$_3$, NCH$_3$), 3.35-3.77 (21H, m, CHCl, 4×NCH$_2$, 6×OCH$_2$), 3.41 (3H, s, OCH$_3$) 3.79-3.85 (1H, m, CHCl), 4.42-4.48 (1H, m, H1), 4.62-4.69 (1H, m, H2), 5.16-5.21 (1H, m, H2), 5.30 (2H, s, OCH$_2$O), 7.18 (2H, d, H3"), 7.29-7.41 (2H, m, H7, H8), 7.56-7.80 (1H, m, H8'), 7.67-7.86 (6H, m, H6, H7', H$_{Phthalimide}$), 7.99 (2H, d, H2"), 8.36 (1H, br s, H4), 8.68 (1H, s, H3'), 9.46 (1H, s, H5'), 10.30 (1H, s, Ar—NHC(O)—Ar).

$^{13}$C NMR (DMSO-d$_6$, 100 MHz): δ=22.9 (Ar—CH$_3$), 28.4, 28.6 (CH$_{3,Boc}$), 34.5 (NCH$_3$), 37.5, 37.6 ((C=O)$_2$NCH$_2$CH$_2$), 44.7 (C1), 45.5, 46.0, 46.4, 47.5 (NCH$_2$), 47.9 (CH$_2$Cl), 55.1 (C2), 56.3 (OCH$_3$), 67.4, 68.5, 69.1, 70.0, 70.0, 70.2, 70.3, 70.3 (OCH$_2$), 79.1, 79.1 (C$_{Boc}$), 94.2 (OCH$_2$O), 111.0, 111.1 (C4), 116.1 (C3"), 117.8 (C5'), 118.0 (C7'), 121.2 (C3'), 121.3 (C6), 122.8 (C9b), 123.4 (CH$_{Phthalimide}$) 123.5 (C8'), 125.1 (C7), 126.3 (C5a), 127.8 (C6'), 127.9 (C1"), 130.1 (C2"), 130.2 (C9a), 131.0 (C8), 132.0 (C$_{Phthalimide}$), 133.4, 133.4 (C9), 134.8 (CH$_{Phthalimide}$) 141.0 (C2'), 141.9 (C8a'), 142.4 (C3a), 148.5, 148.6 (Ar—OC(O)N), 154.3 (C5), 155.2, 155.5 (C=O$_{Boc}$), 160.1 (C4"), 162.3 (NC=O), 165.6 (Ar—NHC(O)—Ar), 168.2, 168.2 (C=O$_{Phthalimide}$).

MS (ESI) m/z; calculated: 1076.42 [M+H]+, found: 1076.77 [M+H]+.

To a solution of compound 41 (323 mg, 0.3 mmol, 1 eq.) in DMF (3 ml) was added hydrazine (44 μl, 0.9 mmol, 3 eq.) and the mixture was warmed to 35° C. for 5.5 hrs with regular addition of fresh hydrazine (30 μl, 0.6 mmol, 2 eq.) every 45 min. The crude mixture was concentrated in vacuo and purified by silica gel column chromatography (DCM/MeOH, 1:0 to 7:3, v/v) to yield compound 42 (284 mg, 0.17 mmol, 56%) as a yellow/orange waxy solid.

$^1$H NMR (DMSO-$d_6$, 400 MHz): δ=1.29-1.45 (9H, m, $CH_{3,Boc}$), 2.74-2.96 (8H, m, $ArCH_3$, $NCH_3$, $CH_2NH_2$), 3.34 (2H, br s, $NH_2$), 3.41 (3H, s, $OCH_3$), 3.40-3.79 (19H, m, CHCl, $NCH_2$, $OCH_2$), 3.81-3.86 (1H, m, CHCl), 4.48 (1H, t, H1), 4.64-4.71 (1H, m, H2), 5.15-5.20 (1H, m, H2), 5.31 (2H, s, $OCH_2O$), 7.18 (2H, d, H3"), 7.34-7.46 (2H, m, H7, H8), 7.63-8.08 (5H, m, H6, H7', H8', H2"'), 8.35 (1H, br s, H4), 8.70 (1H, s, H3'), 9.49 (1H, s, H5'), 10.43 (1H, s, Ar—NHC(O)—Ar).

$^{13}$C NMR (DMSO-$d_6$, 100 MHz): δ=22.9 (Ar—$CH_3$), 28.5, 28.6 ($CH_{3,Boc}$), 34.6 ($NCH_3$), 39.1 ($CH_2NH_2$), 44.7 (C1), 45.5, 45.9, 47.4 ($NCH_2$), 48.0 ($CH_2Cl$), 55.1 (C2), 56.3 ($OCH_3$), 67.3, 68.4, 69.0, 70.2, 70.2, 70.4 ($OCH_2$), 79.1, 79.2 ($C_{Boc}$), 94.2 ($OCH_2O$), 111.0, 111.1 (C4), 116.1 (C3"), 117.8 (C5'), 118.0 (C7'), 119.5 (C3'), 121.2, 121.3 (C6), 122.9 (C9b), 123.7 (C8'), 125.1 (C7), 126.3 (C5$_a$), 127.7 (C6'), 128.0 (C1"), 130.1 (C2"), 130.3 (C9a), 131.0 (C8), 133.5 (C9), 141.0 (C2'), 141.9 (C8a'), 142.4 (C3$_a$), 148.5, 148.6 (Ar—OC(O)N), 154.3 (C5), 155.2 (C=$O_{Boc}$), 160.1 (C4"), 162.4 (NC=O), 165.6 (Ar—NHC(O)—Ar).

MS (ESI) m/z; calculated: 946.41 [M+H]+, found: 946.71 [M+H]+.

Compound 42 (160 mg, 0.17 mmol, 1 eq.) was dissolved in a mixture of THF (5 ml) and a saturated $NaHCO_3$ solution (1 ml), cooled to 0° C. in an ice bath and maleimide-carbamate 22 (26 mg, 0.17 mmol, 1 eq.) was added. The mixture was stirred for 30 min. Then, $Na_2CO_3$ (1 M in $H_2O$) (169 μl, 0.17 mmol, 1 eq.) was added and stirred for an additional 45 min. Then, $H_2O$ was added to the mixture, extracted twice with EtOAc and dried on $MgSO_4$. The solution was filtered and concentrated in vacuo followed by purification of the crude product by silica gel column chromatography (DCM/MeOH, 1:0 to 95:5 v/v) to yield compound 43 (100 mg, 0.10 mmol, 58%) as a white waxy solid.

$^1$H NMR (DMSO-$d_6$, 400 MHz): δ=1.31-1.45 (9H, m, $CH_{3,Boc}$), 2.76-2.95 (6H, m, $ArCH_3$, $NCH_3$), 3.41 (3H, s, $OCH_3$), 3.40-3.79 (21H, m, CHCl, $NCH_2$, $OCH_2$), 3.79-3.85 (1H, m, CHCl), 4.46 (1H, t, H1), 4.63-4.70 (1H, m, H2), 5.16-5.21 (1H, m, H2), 5.30 (2H, s, $OCH_2O$), 6.99 (2H, d, HC=CH), 7.11-7.27 (4H, d, H3"), 7.32-7.43 (2H, m, H7, H8), 7.56-7.60 (1H, m, H8'), 7.68-7.84 (2H, m, H6, H7'), 7.99 (2H, d, H2"), 8.35 (1H, br s, H4), 8.69 (1H, s, H3'), 9.47 (1H, s, H5'), 10.31 (1H, s, Ar—NHC(O)—Ar).

$^{13}$C NMR (DMSO-$d_6$, 100 MHz): δ=22.9 (Ar—$CH_3$), 28.5, 28.6 ($CH_{3,Boc}$), 34.5 ($NCH_3$), 37.2, 37.3 ((C=O)$_2NCH_2CH_2$), 44.7 (C1), 45.5, 46.0, 46.4, 47.5 ($NCH_2$), 47.9 ($CH_2Cl$), 55.1 (C2), 56.3 ($OCH_3$), 67.4, 67.4, 68.5, 69.1, 69.9, 69.9, 70.2, 70.2, 70.3, 70.4 ($OCH_2$), 79.1, 79.1 ($C_{Boc}$), 94.2 ($OCH_2O$), 111.0, 111.1 (C4), 116.2 (C3"), 117.8 (C5'), 118.0 (C7'), 119.5 (C3'), 121.2, 121.3 (C6), 122.8 (C9b), 123.6 (C8'), 125.1 (C7), 126.3 (C5a), 127.8 (C6'), 127.9 (C1"), 130.1 (C2"), 130.3 (C9a), 131.0 (C8), 133.5 (C9), 135.0 (HC=CH), 141.0 (C2'), 141.9 (C8a'), 142.4 (C3a), 148.5, 148.6 (Ar—OC(O)N), 154.3 (C5), 155.2, 155.5 (C=$O_{Boc}$), 160.1 (C4"), 162.4 (NC=O), 165.6 (Ar—NHC(O)—Ar), 171.3 (C=$O_{Maleimide}$).

MS (ESI) m/z; calculated: 1026.40 [M+H]+, found: 1026.59 [M+H]+.

A solution of compound 43 (100 mg, 0.097 mmol, 1 eq.) in chloroform (4 ml) was cooled to 0° C. in an ice bath, diluted with TFA (2 ml) and stirred for 3 hrs. The mixture was concentrated in vacuo, co-evaporated with toluene and dried in vacuo. Then, the intermediate was dissolved in dry DMF (2 ml), cooled to 0° C. in an ice bath and activated linker 19 (57 mg, 0.117 mmol, 1.2 eq.) and $Et_3N$ (27 μl, 0.195 mmol, 2 eq.) were added and the mixture was stirred for 2 hrs. The mixture was concentrated in vacuo and the crude product was purified by silica gel column chromatography (DCM/MeOH, 1;0 to 7:3, v/v) to yield the compound 6, which was further purified by preparative HPLC (Sunfire C-18, MeCN/MilliQ 0.1% m/m TFA). The acetonitrile was evaporated and the aqueous residue freeze dried, the obtained solid was taken up in dioxane/water (6 ml, 2:1) and freeze dried to yield the TFA salt of linker-drug compound 6 (19 mg, 0.015 mmol, 15%) as a white solid.

$^1$H NMR (DMSO-$d_6$, 400 MHz): δ=0.88 (3H, d, $CH_{3,Val}$), 1.06 (3H, d, $CH_{3,Val}$), 1.37 (3H, d, $CH_{3,Ala}$), 2.18-2.32 (1H, m, β-$H_{Val}$), 2.77 (6H, br s, $N(CH_3)_2$), 2.85 (3H, br s, $ArCH_3$), 2.85-2.98 (3H, d, C(O)$NCH_3$), 3.39-4.11 (23H, m, $CH_2Cl$, α-$CH_{Val}$, $NCH_2$, $OCH_2$), 4.46-4.51 (1H, m, H1), 4.51-4.58 (1H, m, α-$CH_{Ala}$), 4.63-4.69 (1H, m, H2), 4.97-5.15 (3H, m, H2, Ar—$CH_2$), 6.91 (2H, d, H3"), 6.99 (2H, s, HC=CH), 7.18-7.59 (6H, m, H7, H8, H2"', H3"'), 7.63-7.82 (3H, m, H6, H7', H8'), 7.91 (2H, d, H2"), 8.28-8.39 (1H, m, H4), 8.76 (1H, s, H3'), 8.97 (1H, d, $NH_{Ala}$), 9.53 (2H, br s, H5', OH), 10.11-10.30 (2H, m, $NH_{PABA}$, Ar—NHC(O)—Ar).

$^{13}$C NMR (DMSO-$d_6$, 100 MHz): δ=17.1 ($CH_{3,Val}$), 18.6 ($CH_{3,Ala}$), 19.7 ($CH_{3,Val}$), 22.9 (Ar—$CH_3$), 27.0 (β-$CH_{Val}$), 34.6, 35.2 ($NCH_3$), 37.2 ((C=O)$_2NCH_2CH_2$), 41.5 ($NCH_{3,Val}$), 42.2 ($NCH_{3,Val}$), 44.8 (C1), 47.4, 47.6 ($NCH_2$), 47.9 ($CH_2Cl$), 49.8 (α-$CH_{Ala}$), 55.0 (C2), 66.5 (Ar—$CH_2OC(O)N$), 67.4, 68.5, 69.9, 70.2, 70.3 ($OCH_2$), 72.0 (α-$CH_{Val}$), 111.1 (C4), 115.5 (C3"), 117.4 (C7'), 117.7 (C5'), 119.5 (C3', C2"'), 121.2 (C6), 122.9 (C9b), 124.4 (C8'), 125.0 (C1"), 125.2 (C7), 126.3 (C5a), 128.5 (C6'), 128.8 (C3"), 130.3 (C9a), 130.3 (C2"), 131.0 (C8), 132.5 (C4"), 133.5 (C9), 135.0 (HC=CH), 138.8 (C1"'), 141.4 (C2'), 141.4 (C8a'), 142.2 (C3a), 148.5 (Ar—OC(O)N), 154.2, 154.5 (C5), 156.2 (Ar—$CH_2OC(O)N$), 158.1, 158.4, 158.8, 159.1 (TFA), 161.4 (NC=O), 161.4 (C4"), 165.4 (C=$O_{Val}$), 165.9 (Ar—NHC(O)—Ar), 170.7 (C=$O_{Ala}$), 171.3 (C=$O_{maleimide}$).

MS (ESI) m/z; calculated: 1229.51 [M+H]+, found: 1229.82 [M+H]+.

Linker-Drug Compound 7
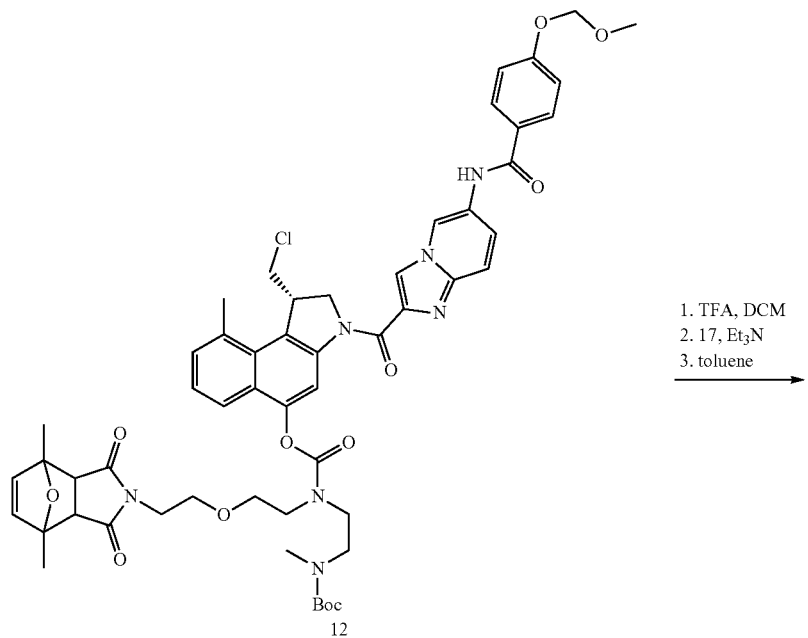
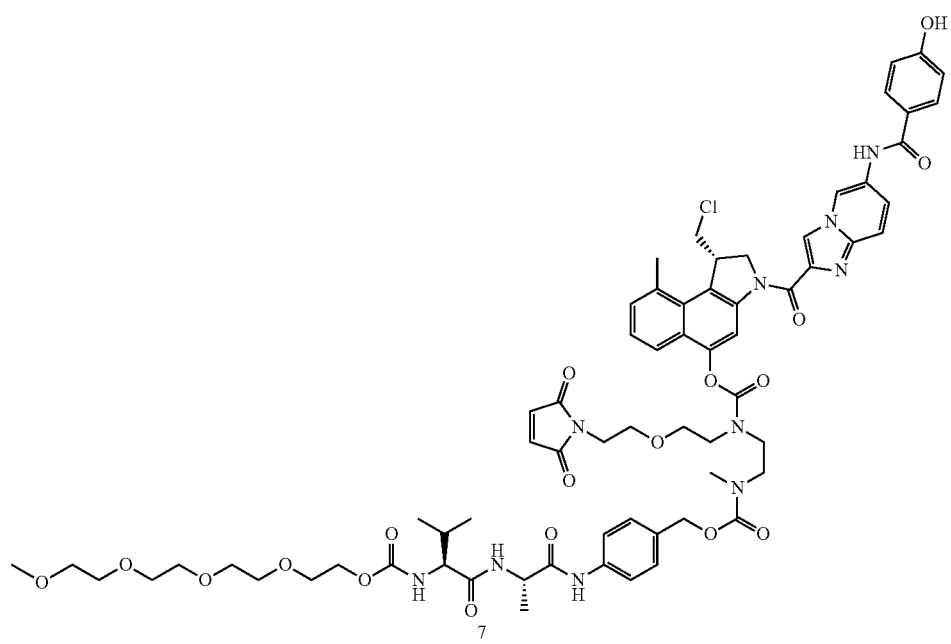

A solution of protected Drug-CS 12 (1.05 g, 1.02 mmol, 1 eq.) in DCM (5 ml) was cooled to 0° C. in an ice bath, after which TFA (5 ml) was added and the resulting mixture was stirred for 2.5 hrs, then diluted with DCM, concentrated in vacuo and co-evaporated with toluene. Next, activated linker 17 (0.70 g, 1.02 mmol, 1 eq.) was dissolved in dry DMF (10 ml), cooled to 0° C. in an ice bath, Et$_3$N (0.57 ml, 4.06 mmol, 4 eq.) was added followed by dropwise addition of the TFA-salt in dry DMF (10 ml). The resulting mixture was stirred for 3 hrs, allowing the mixture to warm to RT. The mixture was concentrated in vacuo and purified by silica gel column chromatography (DCM/MeOH, 1:0 to 7:3, v/v), the fractions containing product combined, concentrated in vacuo and co-evaporated with toluene. Then, the solid was suspended in toluene (120 ml) and gradually warmed to 90° C. over a period of 3 hrs. Next, the mixture was concentrated in vacuo and purified by preparative HPLC (Sunfire C-18, MeCN/MilliQ 0.1% m/m TFA). The acetonitrile of the collected fractions was evaporated and the water residue freeze dried. The obtained solid was dissolved in dioxane/water (18 ml, 2:1) and freeze dried a second time to yield the TFA salt of compound 7 (0.50 g, 0.37 mmol, 37%) as a white solid.

$^1$H NMR (DMSO-d$_6$, 400 MHz): δ=0.82 (3H, d, CH$_{3,Val}$), 0.87 (3H, d, CH$_{3,Val}$), 1.28 (3H, d, CH$_{3,Ala}$), 1.93-1.98 (1H, m, β-H$_{Val}$), 2.85 (3H, br s, Ar—CH$_3$), 2.84-2.93 (3H, m, NCH$_3$), 3.22 (3H, s, OCH$_3$), 3.34-3.72 (27H, m, CHCl, NCH$_2$, OCH$_2$), 3.82-3.89 (2H, m, CHCl, α-CH$_{Val}$), 4.03-4.06 (2H, m, CH$_2$OC(O)NH), 4.40 (1H, t, α-CH$_{Ala}$), 4.48-4.50 (1H, m, H1), 4.65-4.69 (1H, m, H2), 4.95-5.05 (3H, m, H2, Ar—CH$_2$), 6.89-6.97 (3H, m, CH=CH, H3"), 7.03 (1H, d, HC=CH), 7.17-7.58 (7H, m, H7, H8, H2'", H3'", NH$_{Val}$), 7.67-7.83 (3H, m, H6, H7', H8'), 7.91 (2H, d, H2"), 8.13-8.15 (1H, m, NH$_{Ala}$), 8.28-8.39 (1H, m, H4), 8.84-8.88 (1H, m, H3'), 9.59, (1H, s, H5'), 9.96-10.00 (1H, m, NH$_{PABA}$), 10.15-10.40 (1H, br s, OH), 10.33 (1H, s, Ar—NHC(O)—Ar).

$^{13}$C NMR (DMSO-d$_6$, 100 MHz): δ=18.5 (CH$_{3,Val}$), 18.6 (CH$_{3,Ala}$), 19.6 (CH$_{3,Val}$), 22.8 (Ar—CH$_3$), 30.8 (β-CH$_{Val}$), 34.4, 35.2 (NCH$_3$), 37.1, 37.4 ((C=O)$_2$NCH$_2$CH$_2$), 44.8 (C1), 47.4, 47.6 (NCH$_2$), 47.9 (CH$_2$Cl), 49.4 (α-CH$_{Ala}$), 54.9 (C2), 58.5 (OCH$_3$), 60.4 (α-CH$_{Val}$), 63.9 (CH$_2$OC(O)NH), 66.5 (Ar—CH$_2$OC(O)N), 66.6 (Ar—CH$_2$OC(O)N), 68.4, 68.5, 68.7 (OCH$_{2, maleimide}$ PEG), 69.3, 70.0, 70.2, 70.3, 71.7 (OCH$_2$), 111.0 (C4), 115.6 (C3"), 116.4 (C7'), 117.9 (C5'), 119.4 (C3', C21, 121.2 (C6), 123.1 (C9b), 124.9 (C1"), 125.4 (C7), 126.4 (C8'), 126.5 (C5a) 128.8, 129.0 (C3"), 129.1 (C6'), 130.2 (C9a), 130.4 (C2"), 131.1 (C8), 132.2 (C4'"), 133.5, 133.6 (C9), 134.9, 135.0 (HC=CH), 139.0 (C1'"), 139.1 (C2'), 140.4 (C8a'), 141.9 (C3a), 148.5 (Ar—OC(O)N), 154.1, 154.3 (C5), 155.8, 155.9 (Ar—CH$_2$OC(O)N) 156.7 (OC(O)NH), 158.4, 158.8 (TFA), 161.5 (C4"), 165.9 (Ar—NHC(O)—Ar), 171.4 (C=O$_{Val}$), 171.5 (C=O$_{maleimide}$), 171.5 (C=O$_{Ala}$).

MS (ESI) m/z; calculated: 1347.53 [M+H]$^+$, found: 1347.84 [M+H]$^+$.

Linker-Drug Compound 8

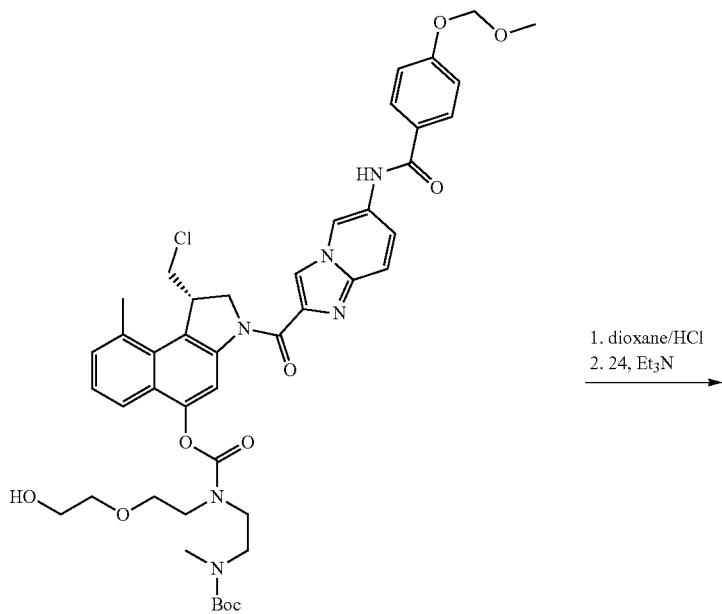

1. dioxane/HCl
2. 24, Et$_3$N

11

-continued

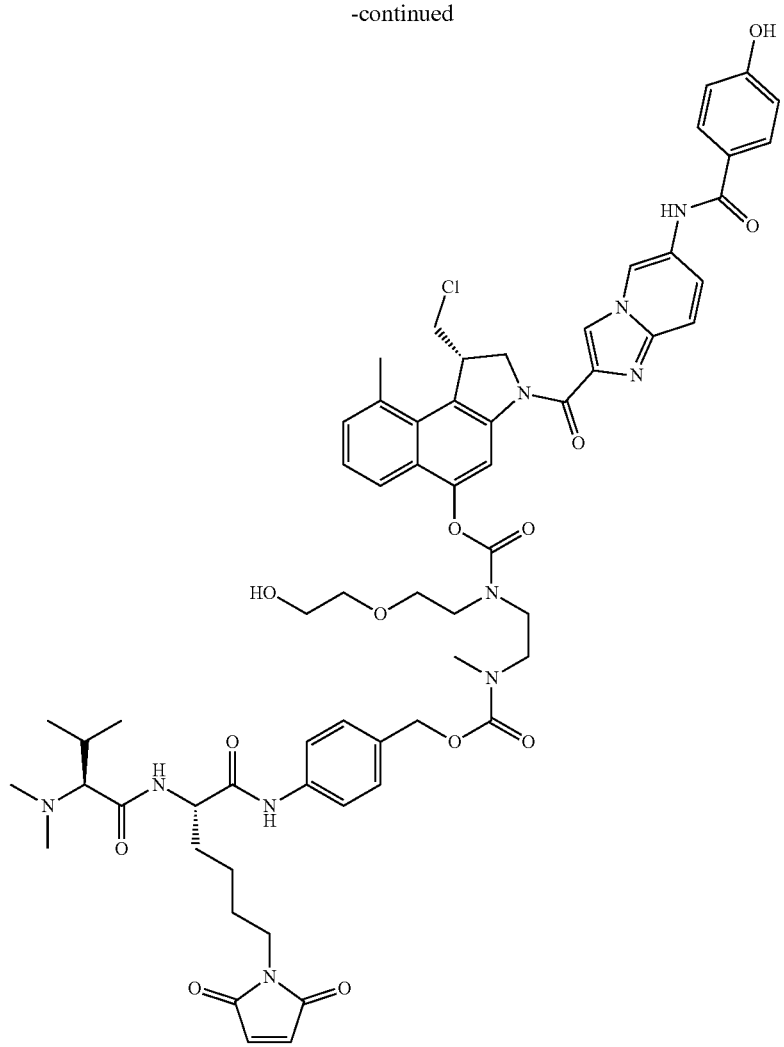

8

To a solution of compound 11 (630 mg, 0.73 mmol, 1 eq.) in dioxane (6 ml) was added 4M HCl in dioxane (15 ml) and the mixture was stirred for 2 hrs. Then, the mixture was concentrated and dried in vacuo. Next, activated compound 24 (503 mg, 0.81 mmol, 1.1 eq.) was dissolved in dry DMF (5 ml), cooled to 0° C. in an ice bath and Et$_3$N (307 µl, 2.20 mmol, 3 eq.) was added. Then, the HCl-salt (dissolved in 5 ml DMF) was added dropwise and the mixture was stirred for 3 hrs and gradually warmed to RT. Next, the mixture was concentrated in vacuo and the crude product was purified by silica gel column chromatography (DCM/MeOH, 1:0 to 7:3, v/v) to yield the crude compound 8 which was further purified by preparative HPLC (Sunfire C-18, MeCN/MilliQ 0.1% m/m TFA). Acetonitrile of the collected fractions was evaporated and the water residue freeze dried. The obtained solid was dissolved in dioxane/water (12 ml, 2:1) and freeze dried a second time to yield the TFA salt of linker-drug compound 8 (217 mg, 0.18 mmol, 25%) as a white solid.

$^1$H NMR (DMSO-d$_6$, 400 MHz): δ=0.88 (3H, d, CH$_{3,Val}$), 1.04 (3H, d, CH$_{3,Val}$), 1.20-1.38 (2H, m, CH$_{Lys}$), 1.46-1.59 (2H, m, CH$_{2,Lys}$), 1.61-1.81 (2H, m, CH$_{2\ Lys}$), 2.26-2.32 (1H, m, β-H$_{Val}$), 2.78 (6H, br s, N(CH$_3$)$_2$), 2.85 (3H, br s, ArCH$_3$), 2.85-2.98 (3H, d, C(O)NCH$_3$), 3.36-3.86 (17H, m, 2×CHCl, α-CH$_{Val}$, CH$_{2,Lys}$, 2×NCH$_2$, OCH$_2$), 4.48-4.53 (2H, m, H1, α-CH$_{Lys}$), 4.63-4.69 (1H, m, H2), 4.97-5.08 (3H, m, H2, Ar—CH$_2$), 6.92 (2H, d, H3''), 6.99 (2H, s, HC=CH), 7.19-7.58 (6H, m, H7, H8, H2''', H3'''), 7.70-7.81 (3H, m, H6, H7', H8'), 7.92 (2H, d, H2''), 8.30-8.42 (1H, m, H4), 8.79-8.81 (1H, m, H3'), 8.94 (1H, d, NH$_{Lys}$), 9.56 (1H, s, H5'), 9.62 (1H, br s, OH), 10.14-10.22 (1H, m, NH$_{PABA}$), 10.30 (1H, s, Ar—NHC(O)—Ar).

$^{13}$C NMR (DMSO-d$_6$, 100 MHz): δ=17.2 (CH$_{3,Val}$), 19.7 (CH$_{3,Val}$), 22.9 (Ar—CH$_3$), 23.2 (CH$_{2\ Lys}$), 27.0 (β-CH$_{Val}$), 28.1 (CH$_{2\ Lys}$), 31.8 (CH$_{2\ Lys}$), 34.4, 34.8, 35.2 (NCH$_3$), 37.4 (CH$_{2,Lys}$), 41.6, 41.9 (NCH$_{3,Val}$), 44.8 (C1), 47.5, 47.7 (NCH$_2$), 47.9 (CH$_2$Cl), 53.7 (α-CH$_{Lys}$), 54.9 (C2), 60.7, 60.7 (CH$_2$OH) 66.5 (ArCH$_2$), 68.5, 69.1 (NCH$_2$CH$_2$O), 72.0 (α-CH$_{Val}$), 72.7, 72.9 (OCH$_2$), 111.0 (C4), 115.6 (C3''), 117.0 (C7'), 117.8 (C5'), 119.6 (C3', C2'''), 121.3 (C6), 123.0 (C9b), 125.0 (C1''), 125.0 (C7), 125.3 (C8'), 126.3, 126.4 (C5a), 128.8 (C6'), 128.8 (C3'''), 130.2 (C9a), 130.3 (C2''), 131.1 (C8), 132.5 (C4''), 133.5 (C9), 134.9 HC=CH), 138.7 (C2', C1'''), 141.1 (C8a'), 142.1 (C3a), 148.5 (Ar—OC(O)N), 154.2, 154.4 (C5), 156.2 (Ar—CH$_2$OC(O)N), 161.3 (NC=O), 161.5 (C4''), 165.8 (C=O$_{Val}$), 165.9 (Ar—NHC(O)—Ar), 170.1 (C=O$_{Lys}$), 171.4 (C=O$_{maleimide}$).

MS (ESI) m/z; calculated: 1199.50 [M+H]$^+$, found: 1199.93 [M+H]$^+$.

Linker-Drug Compound 9
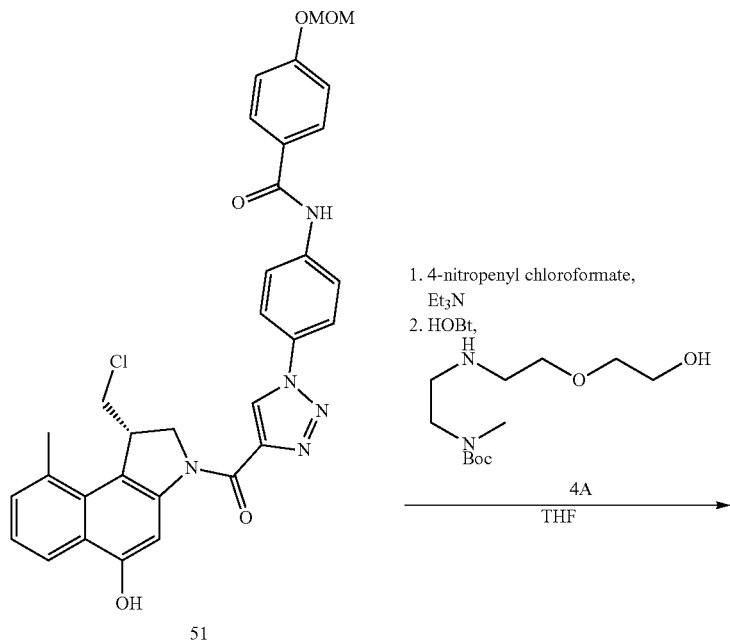
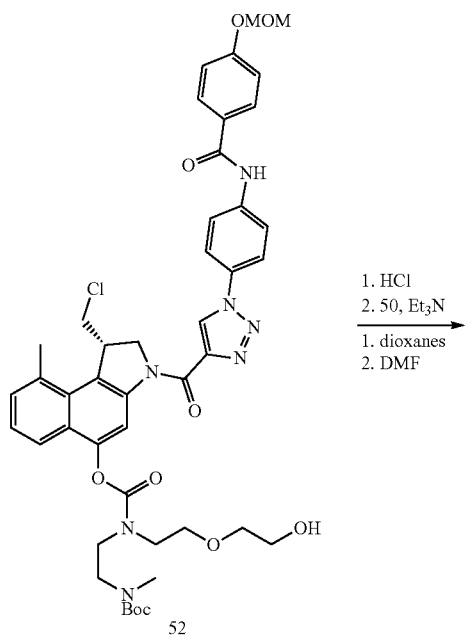

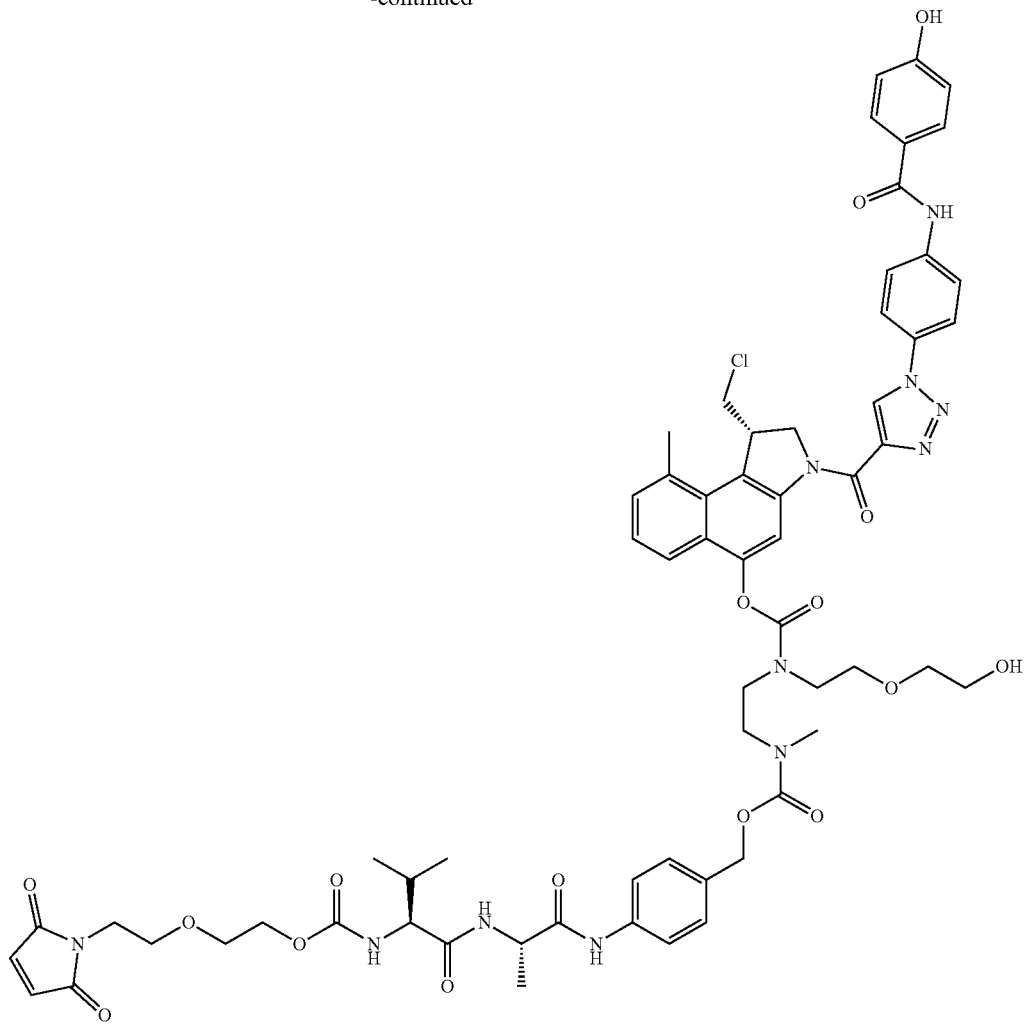

9

A solution of compound 51 (200 mg, 0.35 mmol, 1 eq.) in dry THF (5 ml) was cooled to 0° C. in an ice bath and 4-nitrophenylchloroformate (78 mg, 0.39 mmol, 1.1 eq.) and Et₃N (245 μl, 1.76 mmol, 5 eq.) were added and stirred for 30 min. Then, a solution of the cyclisation spacer 4A (synthesized as described in WO2011/133039, example 1 (Syntarga), 138 mg, 0.53 mmol, 1.5 eq.) in dry THF (3 ml) and HOBt (60 mg, 0.39 mmol, 1.1 eq.) were added and the resulting mixture was warmed to 50° C. for 2 hrs. The mixture was cooled to RT, concentrated in vacuo and the crude product was purified by silica gel column chromatography (DCM/MeOH, 1:0 to 93:7, v/v) to yield compound 52 (250 mg, 0.28 mmol, 80%) as a white solid.

$^1$H NMR (DMSO-d₆, 100 MHz): δ=1.33-1.45 (9H, m, $CH_{3,Boc}$), 2.86 (3H, s, Ar—CH₃), 2.79-2.96 (3H, m, NCH₃), 3.41 (3H, s, OCH₃), 3.39-3.80 (13H, m, CHCl, CH₂OH, OCH₂, NCH₂), 3.84-3.91 (1H, m, CHCl), 4.50-4.55 (1H, m, H1), 4.62-4.73 (2H, m, H2, OH), 5.01-5.06 (1H, m, H2), 5.31 (2H, s, OCH₂O), 7.18 (2H, d, H3"), 7.37-7.46 (2H, m, H7, H8), 7.68-7.89 (1H, m, H6), 7.97-8.06 (6H, m, H2', H3', H2"), 8.31-8.42 (1H, m, H4), 9.43 (1H, s, $H_{triazole}$), 10.41 (1H, s, Ar—NHC(O)—Ar).

$^{13}$C NMR (DMSO-d₆, 100 MHz): δ=22.8 (Ar—CH₃), 28.5, 28.6 ($CH_{3,Boc}$), 34.6 (NCH₃), 44.6 (C1), 45.5, 46.0, 47.6 (NCH₂), 48.1 (CH₂Cl), 54.8 (C2), 56.3 (OCH₃), 60.7, 60.7 (CH₂OH), 68.5, 69.0, 72.7, 72.9 (OCH₂), 79.1 ($C_{Boc}$), 94.2 (OCH₂O), 110.8, 110.9 (C4), 116.1 (C3"), 121.2 (C6), 121.4, 121.5 (CT, C3'), 123.2 (C9b), 125.4 (C7), 125.5 (C1"), 126.5 (C5a), 127.6 ($CH_{triazole}$), 130.1 (C2"), 130.3 (C9a), 131.2 (C8), 131.9 (C4'), 133.5 (C9), 140.7 (C1'), 141.8 (C3a), 145.0 ($C_{Triazole}$), 148.6 (Ar—OC(O)N), 154.3 (C5), 155.2 (C=$O_{Boc}$), 159.3 (NC(O)C), 160.0 (C4"), 165.6 (Ar—NHC(O)—Ar).

MS (ESI) m/z; calculated: 886.35 [M+H]⁺, found: 886.68 [M+H]⁺.

A solution of compound 52 (125 mg, 0.14 mmol, 1 eq.) in dioxane (2 ml) was diluted with 4 M HCl in dioxane (8 ml) and stirred for 10 min at RT. The mixture was concentrated in vacuo, co-evaporated with DCM and dried in vacuo. The obtained HCl-salt was dissolved in dry DMF (2.5 ml), cooled to 0° C. in an ice bath, followed by addition of activated compound 50 (142 mg, 0.21 mmol, 1.5 eq.) and Et₃N (39 μl, 0.28 mmol, 2 eq.). The mixture was stirred for 1.5 hrs allowing it to warm to RT. The mixture was concentrated in vacuo and the crude product was purified by silica gel column chromatography (DCM/MeOH, 1:0 to 7:3, v/v), the fractions containing product combined and concentrated in vacuo to yield compound 9, which was purified further by preparative HPLC (Sunfire C-18, MeCN/MilliQ 0.1% m/m TFA, gradient). The acetonitrile was evaporated and the aqueous residue freeze dried, the obtained solid was taken up in dioxane/water and freeze dried to yield the TFA salt of linker-drug compound 9 (57 mg, 0.05 mmol, 32%) as a white solid.

$^1$H NMR (DMSO-d$_6$, 400 MHz): δ=0.82 (3H, d, CH$_{3,Val}$), 0.86 (3H, d, CH$_{3,Val}$), 1.29 (3H, d, CH$_{3,Ala}$), 1.89-2.02 (1H, m, β-H$_{Val}$), 2.85 (3H, br s, ArCH$_3$), 2.83-2.99 (3H, m, NCH$_3$), 3.20-3.80 (20H, m, CHCl, CH$_2$OH, OCH$_2$, NCH$_2$), 3.82-3.90 (2H, m, CHCl, α-CH$_{Val}$), 3.98-4.03 (2H, m, CH$_2$OC(O)NH), 4.40 (1H, t, α-CH$_{Ala}$), 4.49-4.55 (1H, m, H1), 4.67-4.73 (1H, m, H2), 4.95-5.07 (3H, m, H2, Ar—CH$_2$), 6.90 (2H, d, H3"), 7.00 (2H, s, HC=CH), 7.15-7.58 (7H, m, H7, H8, H2'", H3'", NH$_{Val}$), 7.69-7.83 (1H, m, H6), 7.90 (2H, d, H2"), 7.97-8.05 (4H, m, H2', H3'), 8.13 (1H, d, NH$_{Ala}$), 8.30-8.42 (1H, m, H4), 9.37-9.42 (1H, m, H$_{triazole}$), 9.88-10.02 (1H, m, NH$_{PABA}$), 10.19 (1H, br s, Ar—OH), 10.30 (1H, s, Ar—NHC(O)—Ar).

$^{13}$C NMR (DMSO-d$_6$, 100 MHz): δ=18.5 (CH$_{3,Val}$, CH$_{3,Ala}$), 19.6 (CH$_{3,Val}$), 22.8 (Ar—CH$_3$), 30.8 (β-CH$_{Val}$), 35.2 (NCH$_3$), 37.1 ((C=O)$_2$NCH$_2$CH$_2$), 44.6 (C1), 47.7 (NCH$_2$), 48.1 (CHCl), 49.4 (α-CH$_{Ala}$), 54.8 (C2), 60.4 (α-CH$_{Val}$), 60.7, 60.7 (CH$_2$OH), 63.8 (CH$_2$OC(O)NH), 66.6 (Ar—CH$_2$OC(O)N), 68.4, 68.8, 68.9, 72.7, 72.9 (OCH$_2$), 110.8 (C4), 115.5 (C3"), 119.4 (C2'"), 121.3 (C6), 121.5 (C2', C3'), 123.2 (C9b), 125.4 (C7), 125.5 (C1"), 126.4 (C5a), 127.7 (CH$_{triazole}$), 128.8, 129.0 (C3"), 130.2 (C9a), 130.3 (C2"), 131.1 (C8), 131.7 (C4'), 132.2 (C4'"), 133.5 (C9), 135.0 (HC=CH), 139.0 (C1'"), 140.8 (C1'), 141.8 (C3a), 145.0 (C$_{Triazole}$), 148.6 (Ar—OC(O)N), 154.2 (C5), 154.4 (Ar—CH$_2$OC(O)N), 156.6 (OC(O)NH), 159.3 (NC(O)C), 161.3 (C4"), 165.8 (Ar—NHC(O)—Ar), 171.3 (C=O$_{Val}$), 171.4 (C=O$_{maleimide}$), 171.5 (C=O$_{Ala}$).

MS (ESI) m/z; calculated: 1272.48 [M+H]$^+$, found: 1272.57 [M+H]$^+$.

Linker-Drug Compound 10

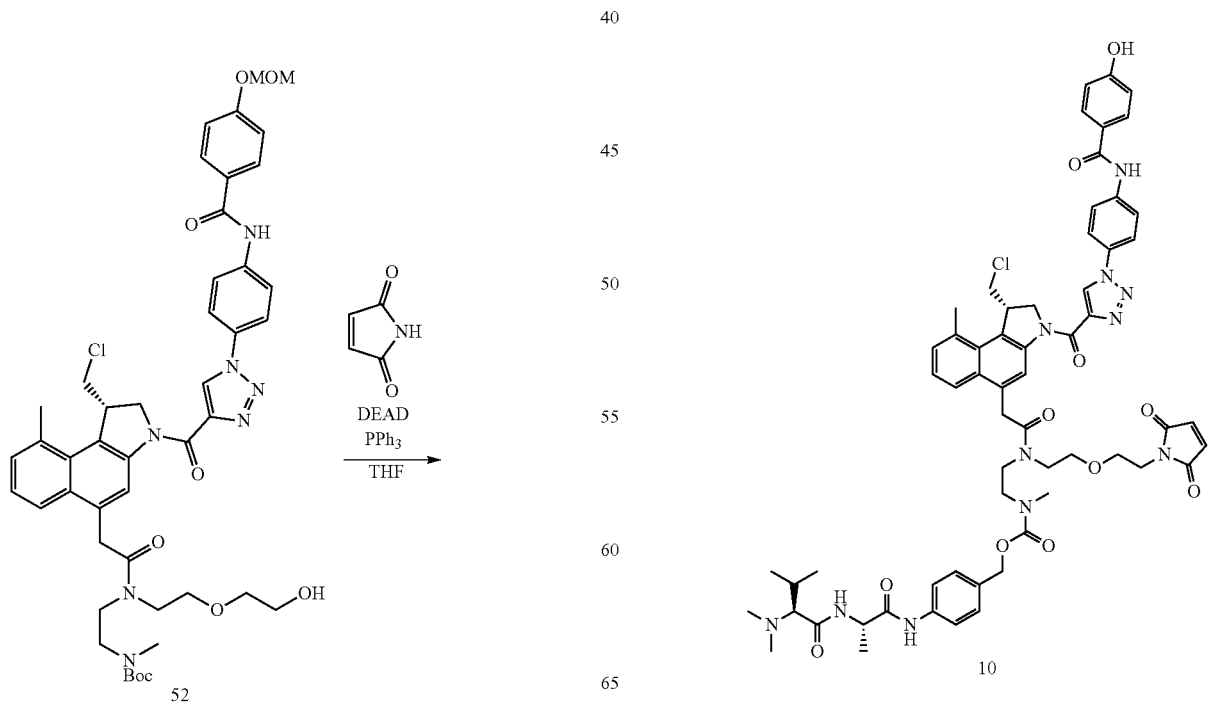

Compound 52 (200 mg, 0.23 mmol, 1 eq.), maleimide (29 mg, 0.29 mmol, 1.3 eq.) and triphenylphosphine (77 mg, 0.29 mmol, 1.3 eq.) were dissolved in dry THF (5 ml), cooled to 0° C. in an ice bath and DEAD (2.2 M in toluene, 133 µl, 0.29 mmol, 1.3 eq.) was added dropwise. The mixture was stirred for 100 min at RT. The mixture was concentrated in vacuo and the crude product was purified by silica gel column chromatography (DCM/MeOH, 1:0 to 97:3, v/v), the fractions containing product combined and concentrated in vacuo to yield compound 53 (100 mg, 0.10 mmol, 46%) as a orange foam.

MS (ESI) m/z; calculated: 965.36 [M+H]$^+$, found: 965.70 [M+H]$^+$.

A solution of compound 53 (80 mg, 0.08 mmol, 1 eq.) in chloroform (2 ml) was cooled to 0° C. in an ice bath, diluted with TFA (2 ml) and stirred for 3 hrs. The mixture was then concentrated in vacuo, co-evaporated with toluene and dried in vacuo. The obtained TFA salt was dissolved in dry DMF (2 ml), cooled to 0° C. in an ice bath and activated compound 19 (48 mg, 0.10 mmol, 1.2 eq.) and Et$_3$N (58 µl, 0.41 mmol, 5 eq.) were added and the mixture was stirred for 2 hrs. The mixture was concentrated in vacuo and purified by silica gel column chromatography (DCM/MeOH, 1:0 to 7:3, v/v), the fractions containing product combined and concentrated in vacuo to yield the crude compound 10 which was further purified by preparative HPLC (Sunfire C-18, MeCN/MilliQ 0.1% m/m TFA). MeCN was evaporated and the aqueous residue freeze dried, the obtained solid was taken up in dioxane/water (6 ml, 2:1) and freeze dried to yield the TFA salt of linker-drug compound 10 (33 mg, 0.03 mmol, 34%) as a white solid.

$^1$H NMR (DMSO-d$_6$, 400 MHz): δ=0.94 (3H, d, CH$_{3,Val}$), 1.11 (3H, d, CH$_{3,Val}$), 1.42 (3H, d, CH$_{3,Ala}$), 2.28-2.36 (1H, m, β-H$_{Val}$), 2.82 (6H, br s, N(CH$_3$)$_2$), 2.91 (3H, br s, ArCH$_3$), 2.90-3.02 (3H, d, C(O)NCH$_3$), 3.38-3.80 (14H, m, CHCl, α-CH$_{Val}$, NCH$_2$, OCH$_2$), 3.89-3.94 (1H, m, CHCl), 4.55-4.63 (2H, m, H1, α-CH$_{Ala}$), 4.71-4.79 (1H, m, H2), 5.03-5.12 (3H, m, H2, Ar—CH$_2$), 6.96 (2H, d, H3''), 7.01 (1H, d, CH=CH), 7.08 (1H, d, CH=CH), 7.23-7.64 (6H, m, H7, H8, H2''', H3'''), 7.72-7.83 (1H, m, H6), 7.96 (2H, d, H2''), 8.03-8.11 (4H, m, H2', H3'), 8.36-8.45 (1H, m, H4), 9.02 (1H, d, NH$_{Ala}$), 9.42-9.48 (1H, m, H$_{triazole}$), 9.61 (1H, br s, CN(CH$_3$)$_2$H$^+$ CF$_3$COO$^-$), 10.16-10.28 (2H, m, NH$_{PABA}$, OH), 10.36 (1H, s, Ar—NHC(O)—Ar).

$^{13}$C NMR (DMSO-d$_6$, 100 MHz): δ=17.1 (CH$_{3,Val}$), 18.6 (CH$_{3,Ala}$), 19.7 (CH$_{3,Val}$), 22.8 (Ar—CH$_3$), 27.0 (β-CH$_{Val}$), 34.5, 34.8 (NCH$_3$), 37.2, 37.4 ((C=O)$_2$NCH$_2$CH$_2$), 41.5 (NCH$_{3,Val}$), 42.2 (NCH$_{3,Val}$), 44.6 (C1), 45.9, 46.4, 47.4 (NCH$_2$), 48.0 (CH$_2$Cl), 49.8 (α-CH$_{Ala}$), 54.8 (C2), 66.5 (Ar—CH$_2$OC(O)N), 67.5, 68.4, 68.7 (OCH$_2$), 72.0 (α-CH$_{Val}$), 110.9 (C4), 115.5 (C3''), 119.5 (C2'''), 121.3 (C6), 121.3, 121.5 (C2', C3'), 123.1 (C9b), 125.4 (C7), 125.5 (C1''), 126.4 (C5a), 127.7 (CH$_{triazole}$), 128.8, 129.0 (C3''), 130.2 (C9a), 130.3 (C2''), 131.1 (C8), 131.7 (C4'), 132.4 (C4''), 133.6 (C9), 134.9, 135.0 (HC=CH), 138.8 (C1'''), 140.9 (C1'), 141.8 (C3a), 145.0 (C$_{Triazole}$), 148.5 (Ar—OC(O)N), 154.1, 154.3 (C5), 155.7, 156.1 (Ar—CH$_2$OC(O)N), 159.3 (NC(O)C), 161.3 (C4''), 165.4 (C=O$_{Val}$), 165.9 (Ar—NHC(O)—Ar), 170.7 (C=O$_{Ala}$), 171.4 (C=O$_{maleimide}$).

MS (ESI) m/z; calculated: 1168.47 [M+H]$^+$, found: 1168.79 [M+H]$^+$.

Linker-Drug Compound 36

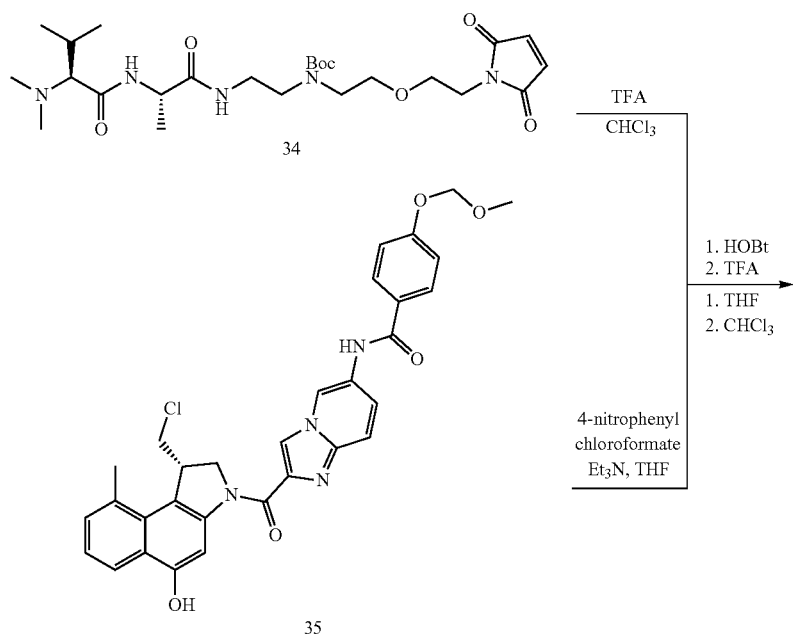

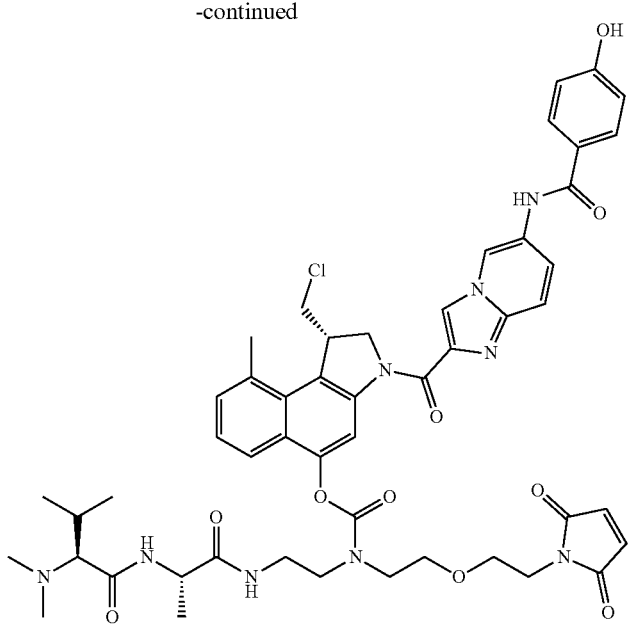

36

A solution of compound 34 (140 mg, 0.27 mmol, 1 eq.) in chloroform (4 ml) was cooled to 0° C. in an ice bath and TFA (2 ml) was added followed by stirring of the mixture for 1 hr. The mixture was concentrated in vacuo, co-evaporated with toluene and dried in vacuo. Separately, compound 35 (152 mg, 0.27 mmol, 1 eq.) was dissolved in dry THF (3 ml), cooled to 0° C. in an ice bath and 4-nitrophenylchloroformate (59 mg, 0.29 mmol, 1.1 eq.) and $Et_3N$ (186 μl, 1.33 mmol, 5 eq.) were added and stirred for 15 min. Then HOBt (41 mg, 0.27 mmol, 1 eq.) and the TFA-salt (of deprotected compound 34) in THF (3 ml) were added to the solution, which was warmed to 50° C. for 1 hr. The crude mixture was concentrated in vacuo and purified by silica gel column chromatography (DCM/MeOH, 1:0 to 7:3, v/v), the fractions containing product combined and concentrated in vacuo. The remaining solid dissolved in chloroform (3 ml), cooled to 0° C. in an ice bath, TFA (3 ml) added and stirred for 2 hrs. Then concentrated in vacuo and purified by silica gel column chromatography (DCM/MeOH, gradient), the fractions containing product combined and concentrated in vacuo to yield the crude product 36, which was purified by preparative HPLC (Sunfire C-18, MeCN/MilliQ 0.1% m/m TFA). The acetonitrile was evaporated and the aqueous residue freeze dried, the obtained solid taken up in dioxane/water (6 ml, 2:1, v/v) and freeze dried to yield the TFA salt of linker-drug compound 36 (65 mg, 0.07 mmol, 25%) as a white solid.

$^1$H NMR (DMSO-$d_6$, 400 MHz): δ=0.87 (3H, dd, $CH_{3,Val}$), 1.02 (3H, dd, $CH_{3,Val}$), 1.26-1.33 (3H, m, $CH_{3,Ala}$), 2.22-2.30 (1H, m, β-$H_{Val}$), 2.76 (6H, br s, $N(CH_3)_2$), 2.85 (3H, br s, Ar$CH_3$), 3.26-3.77 (14H, CHCl, α-$CH_{Val}$, $NCH_2$, $OCH_2$), 3.84 (1H, d, CHCl), 4.36-4.46 (1H, m, α-$CH_{Ala}$), 4.49 (1H, t, H1), 4.68 (1H, t, H2), 5.09 (1H, d, H2), 6.91 (2H, d, H3″), 6.95 (1H, s, HC=CH), 7.05 (1H, s, HC=CH), 7.32-7.39 (1H, m, H7), 7.40-7.46 (1H, m, H8), 7.66-7.72 (1H, m, H8′), 7.75-7.83 (2H, m, H6, H7′), 7.91 (2H, d, H2″), 8.25-8.44 (2H, m, H4, (C=O)NH—$CH_2$), 8.78 (1H, s, H3′), 8.86 (1H, d, $NH_{Ala}$), 9.54 (1H, s, H5′), 9.57 (1H, br s, OH), 10.28 (1H, s, Ar—NHC(O)—Ar).

$^{13}$C NMR (DMSO-$d_6$, 100 MHz): δ=17.1, 17.1 ($CH_{3,Val}$), 18.8, 18.9 ($CH_{3,Ala}$), 19.6, 19.6 ($CH_{3,Val}$), 22.9 (Ar—$CH_3$), 26.9, 26.9 (β-$CH_{Val}$), 37.1, 37.3 ((C=O)$_2NCH_2CH_2$), 38.1 ($CH_2NH$), 41.5 ($NCH_{3,Val}$), 42.1 ($NCH_{3,Val}$), 44.7 (C1), 47.4, 47.7 ($NCH_2$), 48.0 ($CH_2Cl$), 48.2 ($NCH_2$), 49.0 (α-$CH_{Ala}$), 55.0 (C2), 68.3, 68.5, 68.7, 68.9 ($OCH_{2, maleimide PEG}$), 72.0 (α-$CH_{Val}$), 111.0, 111.1 (C4), 115.6 (C3″), 117.3 (C7′), 117.7 (C5′), 119.3 (C3′), 121.3, 121.4 (C6), 122.9, 123.0 (C9b), 124.7 (C8′), 125.0 (C1″), 125.2 (C7), 126.4, 126.4 (C5a), 128.6 (C6′), 130.2 (C9a), 130.3 (C2″), 131.1 (C8), 133.5, 133.5 (C9), 134.9, 135.0 (HC=CH), 139.3 (C2′), 141.3 (C8a′), 142.2 (C3a), 148.5, 148.6 (Ar—OC(O)N), 154.1, 154.3 (C5), 161.4 (NC=O), 161.6 (C4″), 165.2 (C=$O_{Val}$), 165.9 (Ar—NHC(O)—Ar), 171.4 (C=$O_{maleimide}$), 172.0, 172.1 (C=$O_{Ala}$).

MS (ESI) m/z; calculated: 978.39 [M+H]$^+$, found: 978.70 [M+H]$^+$.

Linker-Drug Compound 64
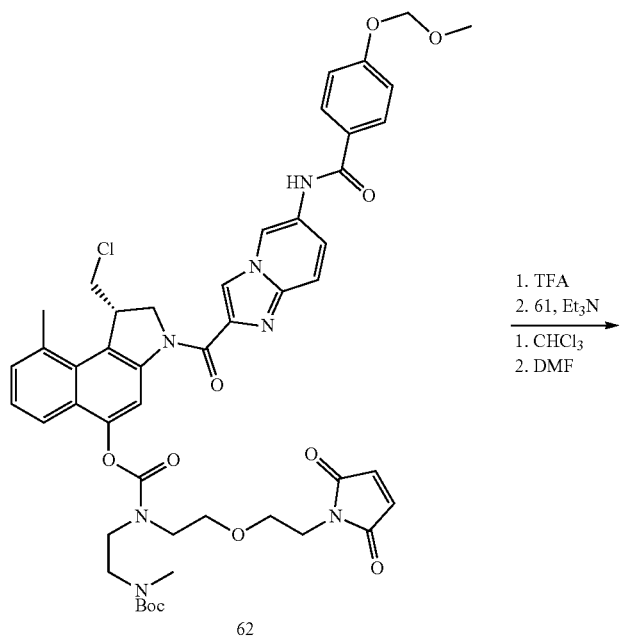 [SMILES: COCOc1ccc(C(=O)Nc2ccc3nc(C(=O)N4C[C@@H](CCl)c5c4cc(OC(=O)N(CCOCCN4C(=O)C=CC4=O)CCN(C)C(=O)OC(C)(C)C)c4cccc(C)c54)cn3c2)cc1]
1. TFA
2. 61, Et₃N
1. CHCl₃
2. DMF

-continued
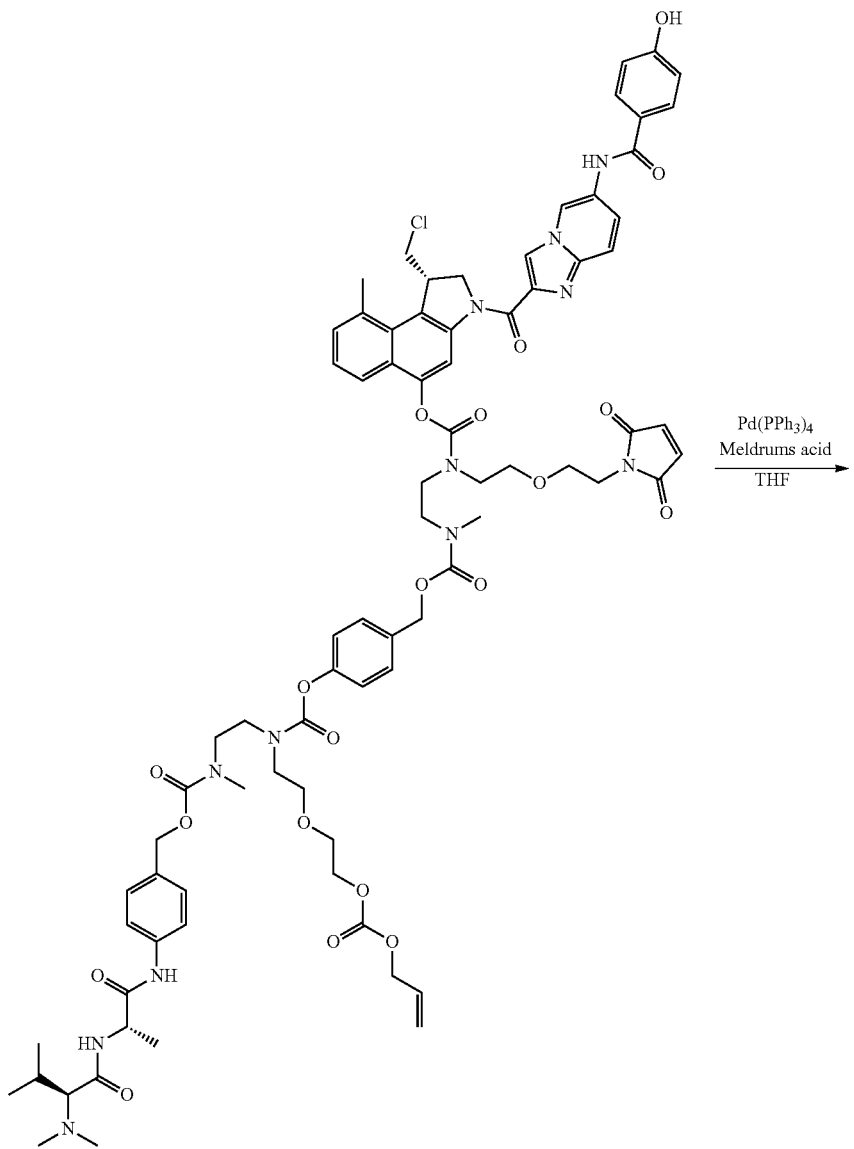
63

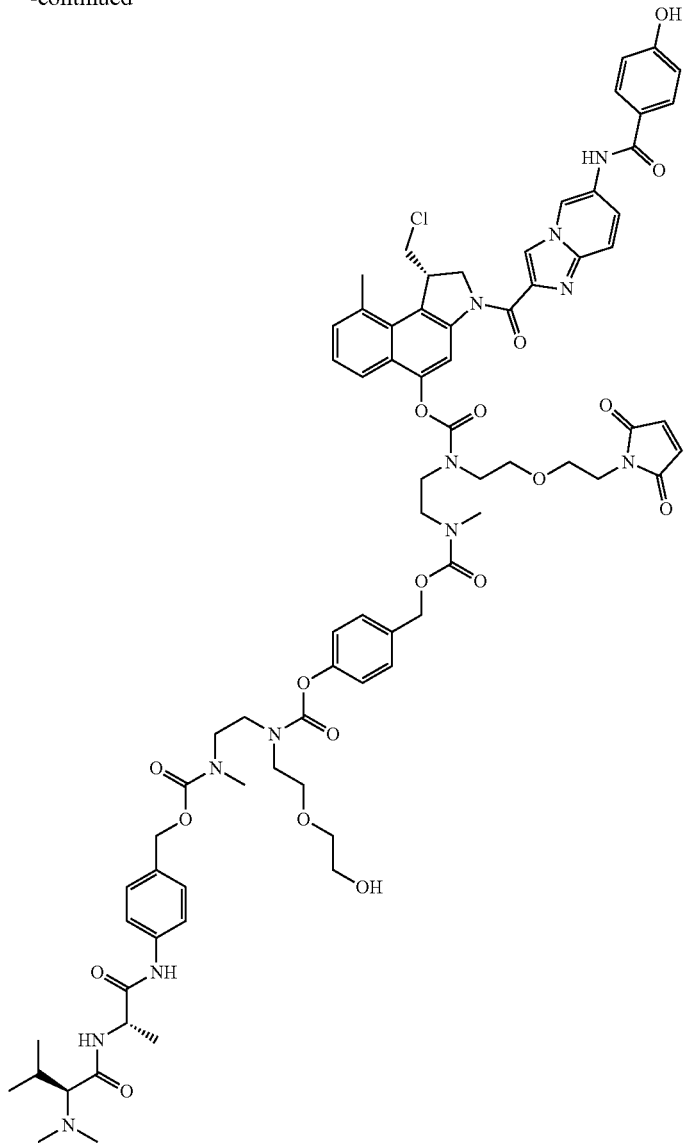

64

A solution of compound 62 (60 mg, 0.06 mmol, 1 eq.) in DCM (2 ml) was cooled to 0° C. in an ice bath and diluted with TFA (2 ml) and the mixture was stirred for 2 hrs. The mixture was concentrated in vacuo, co-evaporated with toluene and dried in vacuo. Next, a solution of compound 61 (64 mg, 0.07 mmol, 1.1 eq.) in DMF (1 ml) was cooled to 0° C. in an ice bath and Et$_3$N (36 ml, 0.26 mmol, 4 eq.) was added followed by dropwise addition of the TFA-salt (dissolved in 1 ml DMF). The resulting mixture was stirred for 2 hrs. The mixture was concentrated in vacuo and purified by silica gel column chromatography (DCM/MeOH, 1:0 to 7:3, v/v), the fractions containing product combined and concentrated in vacuo to yield intermediate 63.

(MS (ESI) m/z; calculated: 1563.62 [M+H]$^+$, found: 1563.31 [M+H]$^+$).

The intermediate 63 was dissolved (30 mg, 0.02 mmol, 1 eq.) in THF (5 ml), Pd(PPh$_3$)$_4$ (11 mg, 9.6 μmol, 0.5 eq.) was added, followed by 2,2-dimethyl-1,3-dioxane-4,6-dione (28 mg, 0.19 mmol, 10 eq.) and the mixture was stirred for 3 hrs at RT under a nitrogen atmosphere. The mixture was concentrated in vacuo and purified by silica gel column chromatography (DCM/MeOH, 1:0 to 7:3, v/v), the fractions containing product combined and concentrated in vacuo to yield the crude product 64, which was further purified by preparative HPLC (Sunfire C-18, MeCN/MilliQ 0.1% m/m TFA). MeCN evaporated and the aqueous residue freeze dried, the obtained solid was taken up in dioxane/water (6 ml, 2:1) and freeze dried to yield the TFA salt of linker-drug compound 64 (6 mg, 3.9 μmol, 20%) as a white solid.

$^1$H NMR (DMSO-d$_6$, 400 MHz): δ=0.87 (3H, m, CH$_{3,Val}$), 1.05 (3H, m, CH$_{3,Val}$), 1.34-1.39 (3H, m, CH$_{3,Ala}$), 2.24-2.33 (1H, br s, β-H$_{Val}$), 2.76 (6H, br s, N(CH$_3$)$_{2,Val}$), 2.84 (3H, s, ArCH$_3$), 2.82-2.97 (6H, m, NCH$_3$), 3.30-3.96 (26H, m, CH$_2$Cl, CH$_2$N, CH$_2$O), 4.43-4.49 (1H, m, H1), 4.50-4.59 (1H, m, α-CH$_{Ala}$), 4.60-4.69 (1H, m, H2), 4.92-5.12 (5H, m, H2, ArCH$_{2,PABA}$, ArCH$_2$), 6.86-7.04 (6H, m, HC=CH, H3", H2"), 7.22-7.43 (6H, m, H7, H8, H3''', H3"), 7.49-7.76 (5H, m, H6, H7', H8', H2"), 7.90 (2H, d, H2"), 8.30-8.38 (1H, m, H4), 8.71 (1H, br s, H3'), 8.96 (1H, d, NH$_{Ala}$), 9.46-9.57 (2H, m, H5', OH), 1.13-10.26 (3H, m, NH$_{PABA}$, Ar—NHC(O)—Ar).

¹³C NMR (DMSO-d₆, 100 MHz): δ=17.1 (CH₃,$_{Val}$), 18.6 (CH₃,$_{Ala}$), 19.6 (CH₃,$_{Val}$), 22.9 (Ar—CH₃), 27.0 (β-CH$_{Val}$), 35.2 (NCH₃), 37.2, 37.4 ((C=O)₂NCH₂CH₂), 41.5, 42.2 (NCH₃,$_{Val}$), 44.7 (C1), 46.0, 46.7, 47.4 (NCH₂), 47.9 (CH₂Cl), 49.8 (α-CH$_{Ala}$), 55.0 (C2), 60.7 (CH₂OH), 66.3 (Ar—CH₂OC(O)N), 67.6, 68.4, 68.6, 69.1 (OCH₂), 72.0 (α-CH$_{Val}$), 72.7 (OCH₂), 111.1 (C4), 115.5 (C3"'), 117.7 (C5', C7'), 119.6 (C3', C2"), 121.2 (C6), 122.1 (C21, 122.9 (C9b), 124.0 (C8'), 125.1 (C1"), 125.2 (C7), 126.3 (C5a), 128.3 (C6'), 128.9, 129.1 (C3"', C3"), 130.3 (C2"), 131.0 (C8), 131.7 (C9a), 132.4 (C4"', C4"), 133.5 (C9), 134.9, 135.0 (HC=CH), 138.9 (C1""), 140.4 (C2'), 141.7 (8a'), 142.3 (C3a), 148.5 (Ar—OC(O)N), 151.1 (C1"'), 154.1, 154.3 (C5), 155.9, 156.1 (Ar—CH₂OC(O)N), 161.4 (C4"), 162.1 (NC=O), 165.4 (C=O$_{Val}$), 165.9 (Ar—NHC(O)—Ar), 170.7 (C=O$_{Ala}$), 171.4 (C=O$_{maleimide}$).

MS (ESI) m/z; calculated: 1479.60 [M+H]⁺, found: 1480.86 [M+H]⁺.

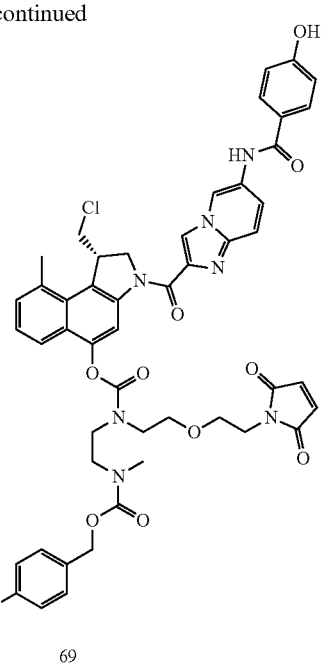

69

Linker-Drug Compound 69

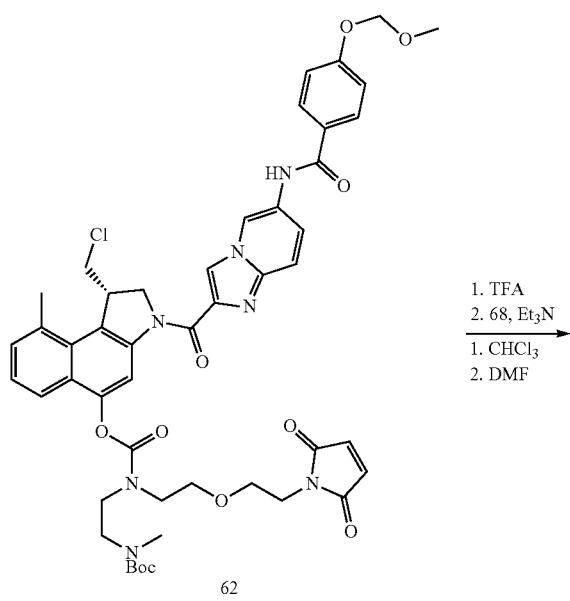

62

1. TFA
2. 68, Et₃N
1. CHCl₃
2. DMF

A solution of compound 62 (110 mg, 0.12 mmol, 1 eq.) in chloroform (3 ml) was cooled to 0° C. in an ice bath, diluted with TFA (3 ml) and stirred for 3 hrs. The reaction mixture was concentrated in vacuo, co-evaporated with toluene and dried in vacuo. Then, the resulting TFA-salt was dissolved in dry DMF (2 ml), cooled to 0° C. in an ice bath and activated linker 68 (65 mg, 0.13 mmol, 1.1 eq.) and Et₃N (33 μl, 0.23 mmol, 2 eq.) were added and the mixture was stirred for 3 hrs. The reaction mixture was concentrated in vacuo and the crude product was purified by silica gel column chromatography (DCM/MeOH, 1:0 to 7:3, v/v), the fractions containing product combined and concentration in vacuo to yield the crude compound 69, which was purified by preparative HPLC (Sunfire C-18, MeCN/MilliQ 0.1% m/m TFA). Acetonitrile was evaporated and the aqueous residue freeze dried, the obtained solid was taken up in dioxane/water (6 ml, 2:1) and freeze dried to yield the TFA salt of linker-drug compound 69 (28 mg, 0.02 mmol, 21%) as a white solid.

MS (ESI) m/z; calculated: 1155.43 [M+H]⁺, found: 1155.65 [M+H]⁺.

Linker-Drug Compound 74
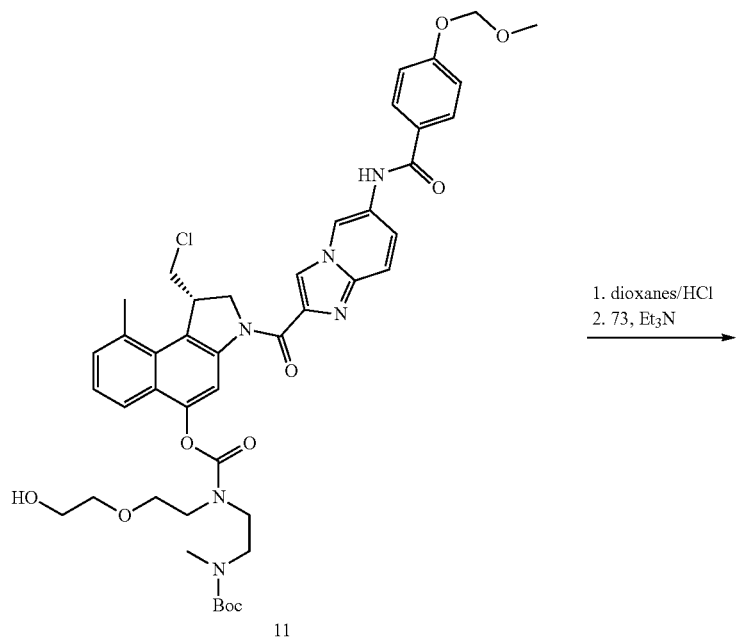

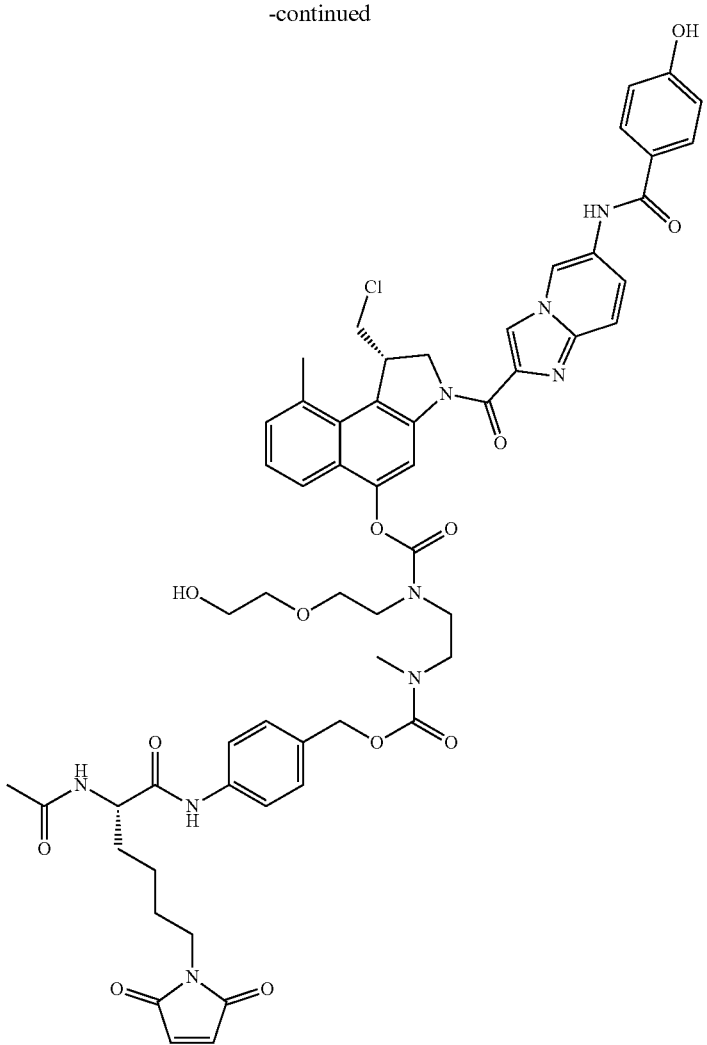

74

A solution of compound 11 (75 mg, 0.09 mmol, 1 eq.) in dioxane (2 ml) was diluted with 4 M HCl in dioxane (6 ml) and stirred for 2 hrs. The mixture was concentrated in vacuo and dried in vacuo. The obtained HCl-salt was dissolved in DMA (2 ml), cooled to 0° C. in an ice bath and compound 73 (56 mg, 0.10 mmol, 1.2 eq.) and Et$_3$N (24 µl, 0.17 mmol, 2 eq.) were added and the mixture was stirred for 1.5 hrs. The mixture was concentrated in vacuo and purified by silica gel column chromatography (DCM/MeOH, 1:0 to 7:3, v/v), the fractions containing product were combined and concentrated in vacuo to yield the crude compound 74, which was purified by preparative HPLC (Sunfire C-18, MeCN/MilliQ 0.1% m/m TFA). The acetonitrile was evaporated and the aqueous residue freeze dried. The obtained solid was taken up in dioxane/water (6 ml, 2:1) and freeze dried to yield linker-drug compound 74 (26 mg, 0.02 mmol, 27%) as a white solid.

$^1$H NMR (DMSO-d$_6$, 400 MHz): δ=1.15-1.28 (2H, m, CH$_{,Lys}$), 1.37-1.69 (4H, m, 2×CH$_{2,Lys}$), 1.86 (3H, s, CH$_{3,Acetyl}$), 2.85 (3H, br s, ArCH$_3$), 2.85-3.00 (3H, d, NCH$_3$), 3.37 (2H, t, (C=O)$_2$NCH$_{2,Lys}$), 3.36-4.05 (17H, m, CHCl, NCH$_2$, OCH$_2$), 4.29-4.36 (1H, m, α-CH$_{Lys}$), 4.46-4.52 (1H, m, H1), 4.64-4.70 (1H, m, H2), 4.96-5.07 (3H, m, H2, Ar—CH$_2$), 6.92 (2H, d, H3"), 6.98 (2H, s, HC=CH), 7.15-7.59 (6H, m, H7, H8, H2''', H3'''), 7.69-7.82 (3H, m, H6, H7', H8'), 7.92 (2H, d, H2''), 8.10 (1H, d, NH$_{Lys}$), 8.30-8.42 (1H, m, H4), 8.84 (1H, br s, H3'), 9.57 (1H, s, H5'), 9.96-10.04 (1H, m, NH$_{PABA}$), 10.24 (1H, br s, OH), 10.30 (1H, s, Ar—NHC(O)—Ar).

$^{13}$C NMR (DMSO-d$_6$, 100 MHz): δ=22.9 (Ar—CH$_3$), 23.2 (CH$_{2\ Lys}$), 28.2 (CH$_{2\ Lys}$), 30.9 (CH$_{3,Acetyl}$), 32.0 (CH$_{2\ Lys}$), 34.4, 35.0, 35.3 (NCH$_3$), 37.4 ((C=O)$_2$NCH$_{2,Lys}$), 44.8 (C1), 46.7, 47.5, 47.7 (NCH$_2$), 47.9 (CH$_2$Cl), 53.7 (α-CH$_{Lys}$), 54.9 (C2), 60.7, 60.7 (CH$_2$OH), 66.5 (ArCH$_2$), 68.5, 69.1 (OCH$_2$), 72.7, 72.9 (OCH$_2$), 111.0 (C4), 115.6 (C3"), 116.8 (C7'), 117.9 (C5'), 119.6 (C3', C2'''), 121.3 (C6), 123.1 (C9b), 125.0 (C1"), 125.4 (C7, C8'), 126.3 (C6'), 126.5 (C5a), 128.7 (C3"), 130.2 (C9a), 130.3 (C2"), 131.1 (C8), 132.2 (C4'''), 133.5, 133.6 (C9), 134.9 (HC=CH), 138.9 (C1'''), 140.9 (C2', C8a'), 142.0 (C3a), 148.5 (Ar—OC(O)N), 154.2, 154.4 (C5), 156.3 (Ar—CH$_2$OC(O)N), 161.4 (NC=O), 161.5 (C4"), 165.9 (Ar—NHC(O)—Ar), 169.9 (C=O$_{Acetyl}$), 171.3 (C=O$_{Lys}$), 171.4 (C=O$_{maleimide}$).

MS (ESI) m/z; calculated: 1114.41 [M+H]$^+$, found: 1114.66 [M+H]$^+$.

Protocols for Site-Specific and Wild-Type Conjugation

General Conjugation Protocol for Conjugation Via Partially Reduced Endogenous Disulfides (Wild-Type (wt) Conjugation)

A solution of antibody (5-10 mg/ml in 4.2 mM histidine, 50 mM trehalose, pH 6) was diluted with EDTA (25 mM in water, 4% v/v). The pH was adjusted to ~7.4 using TRIS (1 M in water, pH 8) after which TCEP (10 mM in water, 1-3 equivalents depending on the antibody and the desired DAR) was added and the resulting mixture was incubated at RT for 1-3 hrs. DMA was added followed by a solution of linker-drug (10 mM in DMA). The final concentration of DMA was 5-10%. The resulting mixture was incubated at RT in the absence of light for 1-16 hrs. In order to remove the excess of linker-drug, activated charcoal was added and the mixture was incubated at RT for 1 hr. The charcoal was removed using a 0.2 μm PES filter and the resulting ADC was formulated in 4.2 mM histidine, 50 mM trehalose, pH 6 using a Vivaspin centrifugal concentrator (30 kDa cut-off, PES). Finally, the ADC solution was sterile filtered using a 0.22 μm PES filter.

General Site-Specific Conjugation Protocol

Site-specific conjugates were synthesised according to the procedure as described in either Protocol A or Protocol B.

1) Protocol A

A solution of cysteine-engineered antibody (5-10 mg/ml in 4.2 mM histidine, 50 mM trehalose, pH 6) was diluted with EDTA (25 mM in water, 4% v/v). The pH was adjusted to ~7.4 using TRIS (1 M in water, pH 8) after which TCEP (10 mM in water, 20 equivalents) was added and the resulting mixture was incubated at room temperature (RT) for 1-3 hrs. The excess TCEP was removed by either a PD-10 desalting column or a centrifugal concentrator (Vivaspin filter, 30 kDa cut-off, PES) using 4.2 mM histidine, 50 mM trehalose, pH 6.

The pH of the resulting antibody solution was raised to ~7.4 using TRIS (1 M in water, pH 8) after which dehydroascorbic acid (10 mM in water, 20 equivalents) was added and the resulting mixture was incubated at RT for 1-2 hrs. At RT or 37° C., DMA was added followed by a solution of linker-drug (10 mM in DMA). The final concentration of DMA was 5-10%.

The resulting mixture was incubated at RT or 37° C. in the absence of light for 1-16 hrs. In order to remove the excess of linker-drug, activated charcoal was added and the mixture was incubated at RT for 1 hr. The charcoal was removed using a 0.2 μm PES filter and the resulting ADC was formulated in 4.2 mM histidine, 50 mM trehalose, pH 6 using a Vivaspin centrifugal concentrator (30 kDa cut-off, PES). Finally, the ADC solution was sterile filtered using a 0.22 μm PES filter.

2) Protocol B

A solution of cysteine-engineered antibody (500 μl, 40 mg/ml in 15 mM histidine, 50 mM sucrose, 0.01% polysorbate-20, pH 6) was diluted with 100 mM histidine, pH 5 (1300 μl). 2-(Diphenylphosphino)benzenesulfonic acid (DPPBS) (426 μl, 10 mM in water, 32 equivalents) was added and the resulting mixture was incubated at RT for 16-24 hrs. The excess DPPBS was removed by a centrifugal concentrator (Vivaspin filter, 30 kDa cut-off, PES) using 4.2 mM histidine, 50 mM trehalose, pH 6.

The pH of the resulting antibody solution was raised to ~7.4 using TRIS (1 M in water, pH 8). At RT or 37° C., DMA was added followed by a solution of linker-drug (10 mM in DMA). The final concentration of DMA was 5-10%. The resulting mixture was incubated at RT or 37° C. in the absence of light for 1-16 hrs. In order to remove the excess of linker-drug, activated charcoal was added and the mixture was incubated at RT for 1 hr. The charcoal was removed using a 0.2 μm PES filter and the resulting ADC was formulated in 4.2 mM histidine, 50 mM trehalose, pH 6 using a Vivaspin centrifugal concentrator (30 kDa cut-off, PES). Finally, the ADC solution was sterile filtered using a 0.22 μm PES filter.

Using the above general conjugation procedures, cysteine engineered and wild-type ADCs based on the linker-drugs of the invention and vc-seco-DUBA (SYD980, linker-drug compound 1) linker-drug were synthesized and characterized using analytical Hydrophobic Interaction Chromatography (HIC), Size Exclusion Chromatography (SEC), and Shielded Hydrophobic Phase Chromatography (SHPC).

As made apparent by analytical HIC, there were differences in the retention times (RTs) for the DAR2 species of the different ADCs (Tables 1A and 1B). Most interestingly, conjugating a drug to an antibody through a non-linear exo-linker gave rise to a (dramatic) decrease in the retention time as compared to drugs that were conjugated via a known linear linker. This decrease was more pronounced in ADCs comprising non-linear exo-linkers wherein the drug was positioned closer to the antibody, i.e. the number of atoms in the linker between the drug and the antibody is lower (number of atoms increasing from 7 for linker-drug compound 3 up to 16 for linker-drug compound 6).

As shown in WO2015/177360, conjugating a linker-drug at specific sites inside the Fab cavity or Fc cavity of an antibody decreases the retention time as compared to ADCs that are conjugated via partially reduced endogenous disulfides. Conjugation of the linker-drugs of the invention at these specific sites further reduced the retention time, i.e. further diminished the difference in hydrophobicity between a conjugated and an unconjugated antibody.

To further quantify this effect, the term relative hydrophobicity is introduced, which is defined as:

$$(RT_{DAR2} - RT_{DAR0})/(RT_{DAR2,reference-ADC} - RT_{DAR0,reference-ADC}).$$

In essence, the relative hydrophobicity is a measure that based on HIC data allows a facile comparison between the hydrophobicity of the ADCs comprising linker-drugs wherein the linker is a linear linker and ADCs comprising linker-drugs having a non-linear exo-linker. The data are summarized in Tables 1A and 1B.

TABLE 1A

The relative hydrophobicity of ADCs comprising various wild-type (wt) antibodies and various linker-drug compounds (LDs) on the previously specified analytical HIC column

| Antibody[1] | Cys mutation | | LD | DAR | HMW (%)[3] | $RT_{DAR2}$ | $RT_{DAR0}$ | Relative hydrophobicity[4] |
|---|---|---|---|---|---|---|---|---|
| | HC | LC | | | | | | |
| Trastuzumab | wt | wt | 1[2] | 1.7 | 1.1 | 9.9 | 6.9 | 1.0 |
| Trastuzumab | wt | wt | 3 | 1.9 | 2.4 | 8.5 | 6.9 | 0.5 |
| Trastuzumab | wt | wt | 4 | 2.3 | 4.0 | 8.9 | 6.9 | 0.7 |
| Trastuzumab | wt | wt | 5 | 1.9 | 2.5 | 9.2 | 6.9 | 0.8 |
| Trastuzumab | wt | wt | 6 | 2.1 | 1.9 | 9.9 | 6.9 | 0.8 |
| Trastuzumab | wt | wt | 7 | 2.1 | 3.6 | 9.5 | 6.9 | 0.9 |
| Trastuzumab | wt | wt | 8 | 1.9 | 2.8 | 9.3 | 6.9 | 0.8 |

TABLE 1A-continued

The relative hydrophobicity of ADCs comprising various wild-type (wt) antibodies and various linker-drug compounds (LDs) on the previously specified analytical HIC column

| Antibody[1] | Cys mutation HC | LC | LD | DAR | HMW (%)[3] | $RT_{DAR2}$ | $RT_{DAR0}$ | Relative hydrophobicity[4] |
|---|---|---|---|---|---|---|---|---|
| Rituximab | wt | wt | 1[2] | 2.1 | 4.1 | 10.4 | 7.9 | 1.0 |
| Rituximab | wt | wt | 3 | 2.0 | 4.1 | 9.1 | 7.8 | 0.5 |
| Rituximab | wt | wt | 4 | 2.0 | 3.9 | 9.4 | 7.9 | 0.6 |
| Rituximab | wt | wt | 5 | 1.9 | 4.3 | 9.7 | 7.9 | 0.7 |
| Rituximab | wt | wt | 6 | 2.0 | 6.9 | 9.8 | 7.9 | 0.8 |
| Rituximab | wt | wt | 7 | 1.9 | 6.0 | 10.0 | 7.9 | 0.8 |
| Rituximab | wt | wt | 8 | 2.0 | 1.6 | 9.9 | 7.9 | 0.8 |
| H8 | wt | wt | 1[2] | 1.8 | 6.0 | 9.8 | 6.4 | 1.0 |
| H8 | wt | wt | 3 | 1.8 | 1.3 | 8.3 | 6.4 | 0.6 |
| H8 | wt | wt | 4 | 1.8 | 1.7 | 8.7 | 6.4 | 0.7 |
| H8 | wt | wt | 5 | 1.8 | 1.4 | 9.0 | 6.4 | 0.8 |
| H8 | wt | wt | 6 | 1.9 | 3.3 | 9.1 | 6.4 | 0.8 |
| H8 | wt | wt | 7 | 1.9 | 1.3 | 9.1 | 6.4 | 0.8 |
| H8 | wt | wt | 8 | 1.8 | 1.7 | 9.4 | 6.4 | 0.9 |
| PSMA | wt | wt | 1[2] | 1.8 | 7.7 | 9.7 | 6.9 | 1.0 |
| PSMA | wt | wt | 3 | 1.7 | 4.6 | 8.5 | 7.2 | 0.5 |
| PSMA | wt | wt | 4 | 1.7 | 9.6 | 9.2 | 7.2 | 0.7 |
| PSMA | wt | wt | 5 | 1.7 | 5.1 | 9.5 | 7.2 | 0.8 |
| PSMA | wt | wt | 6 | 1.7 | 6.5 | 9.7 | 7.2 | 0.9 |

Figure 2:
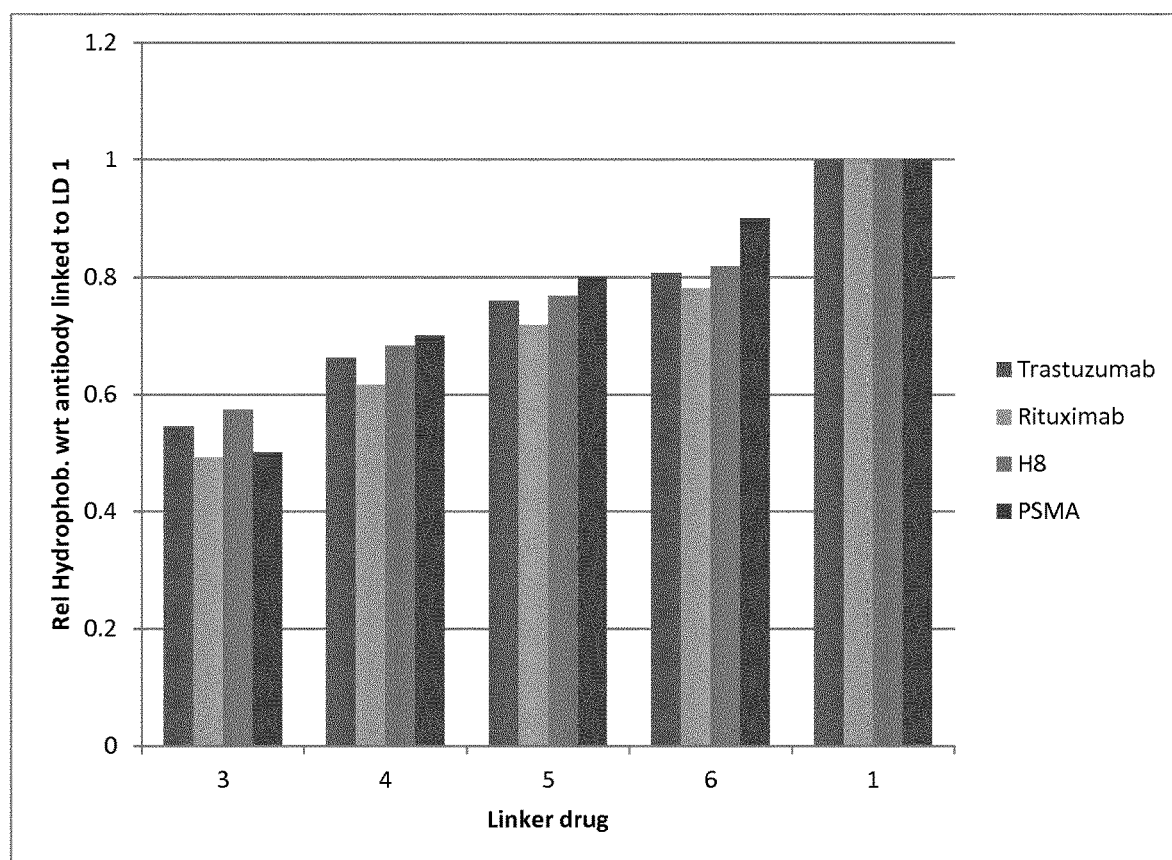
FIG. 2. Relative hydrophobicity of ADCs comprising non-linear linker-drugs of the invention versus comparator ADCs comprising linear vc-seco-DUBA (linker-drug compound 1).

[1]Random—non-site specific—conjugation
[2]Linker-drug with linear linker
[3]HMW are high molecular weight species, reflecting the amount of aggregates formed
[4]Defined as $(RT_{DAR2} - RT_{DAR0})/(RT_{DAR2, reference-ADC} - RT_{DAR0, reference-ADC})$, RT is retention time; the respective antibody linked to linker-drug compound 1 is the reference ADC FIG. 2 graphically shows the data of Table 1A. The (relative) hydrophobicity of the ADCs increases with the length of the linker, i.e., the smaller the number of atoms between the antibody's S-atom and the drug's O-atom the lower the (relative) hydrophobicity. ADCs with linker-drug compound 3 show the lowest relative hydrophobicity. Although the ADCs with linker-drug compound 7 have a lower relative hydrophobicity than the comparator ADCs with linker-drug compound 1, the polar PEG group attached to the cleavage site in linker-drug compound 7 does not further decrease the relative hydrophobicity of the ADC, when compared with ADCs comprising linker-drug compound 4 which has a similar linker, but lacks the PEG group.

TABLE 1B

The relative hydrophobicity of ADCs comprising anti-PSMA wild-type (wt) or cysteine engineered antibodies and various linker-drug compounds (LDs) on the previously specified analytical HIC column

| Antibody | Cys mutation HC | LC | LD | DAR | HMW (%)[3] | $RT_{DAR2}$ | $RT_{DAR0}$ | Relative hydrophobicity[4] |
|---|---|---|---|---|---|---|---|---|
| PSMA[1] | wt | wt | 1[2] | 1.8 | 7.7 | 9.7 | 6.9 | 1.0 |
| PSMA[1] | wt | wt | 3 | 1.7 | 4.6 | 8.5 | 7.2 | 0.5 |
| PSMA[1] | wt | wt | 4 | 1.7 | 9.6 | 9.2 | 7.2 | 0.7 |
| PSMA[1] | wt | wt | 5 | 1.7 | 5.1 | 9.5 | 7.2 | 0.8 |
| PSMA[1] | wt | wt | 6 | 1.7 | 6.5 | 9.7 | 7.2 | 0.9 |
| PSMA-LC40 | wt | P40C | 1[2] | 1.8 | 0.5 | 9.5 | 6.9 | 0.9 |
| PSMA-LC40 | wt | P40C | 3 | 1.8 | 0.7 | 7.9 | 7.2 | 0.3 |
| PSMA-LC40 | wt | P40C | 4 | 1.8 | 0.7 | 8.0 | 7.2 | 0.3 |
| PSMA-LC40 | wt | P40C | 5 | 1.7 | 0.8 | 8.2 | 7.2 | 0.4 |
| PSMA-LC40 | wt | P40C | 6 | 1.8 | 0.8 | 8.6 | 7.2 | 0.5 |
| PSMA-LC41 | wt | G41C | 1[2] | 1.8 | 0.6 | 8.7 | 6.9 | 0.6 |
| PSMA-LC41 | wt | G41C | 3 | 1.7 | 1.1 | 7.4 | 7.2 | 0.1 |
| PSMA-LC41 | wt | G41C | 4 | 1.7 | 0.9 | 7.5 | 7.2 | 0.1 |
| PSMA-LC41 | wt | G41C | 5 | 1.5 | 0.7 | 7.9 | 7.2 | 0.3 |
| PSMA-LC41 | wt | G41C | 6 | 1.8 | 1.2 | 8.2 | 7.2 | 0.4 |
| PSMA-HC41 | S41C | wt | 1[2] | 1.7 | 1.4 | 8.5 | 6.8 | 0.6 |
| PSMA-HC41 | S41C | wt | 3 | 1.8 | 1.0 | 7.2 | 7.0 | 0.1 |
| PSMA-HC41 | S41C | wt | 4 | 1.6 | 2.9 | 7.3 | 6.9 | 0.1 |
| PSMA-HC41 | S41C | wt | 5 | 1.6 | 0.9 | 7.6 | 7.1 | 0.2 |
| PSMA-HC41 | S41C | wt | 6 | 1.8 | 0.2 | 7.8 | 7.2 | 0.2 |
| PSMA-HC41 | S41C | wt | 7 | 1.7 | 2.5 | 7.8 | 7.1 | 0.3 |
| PSMA-HC41 | S41C | wt | 8 | 1.8 | 2.7 | 8.5 | 7.1 | 0.5 |
| PSMA-HC41 | S41C | wt | 9 | 1.6 | 3.3 | 9.5 | 7.1 | 0.9 |
| PSMA-HC41 | S41C | wt | 10 | 1.6 | 2.5 | 7.8 | 7.0 | 0.3 |
| PSMA-HC41 | S41C | wt | 36 | 2.0 | 0.6 | 7.2 | 7.0 | 0.1 |
| PSMA-HC41 | S41C | wt | 64 | 1.8 | 0.3 | 7.7 | 7.0 | 0.3 |

TABLE 1B-continued

The relative hydrophobicity of ADCs comprising anti-PSMA wild-type
(wt) or cysteine engineered antibodies and various linker-drug
compounds (LDs) on the previously specified analytical HIC column

| Antibody | Cys mutation | | LD | DAR | HMW (%)[3] | $RT_{DAR2}$ | $RT_{DAR0}$ | Relative hydrophobicity[4] |
|---|---|---|---|---|---|---|---|---|
| | HC | LC | | | | | | |
| PSMA-HC120[5] | T120C | wt | 1[2] | 1.8 | 0.9 | 11.3 | 6.8 | 1.6 |
| PSMA-HC120[5] | T120C | wt | 3 | 1.6 | 1.0 | 9.1 | 7.0 | 0.8 |
| PSMA-HC120[5] | T120C | wt | 4 | 1.7 | 0.7 | 9.7 | 7.0 | 1.0 |
| PSMA-HC120[5] | T120C | wt | 5 | 1.2 | 1.3 | 10.5 | 7.2 | 1.2 |
| PSMA-HC120[5] | T120C | wt | 6 | 1.6 | 0.8 | 10.7 | 7.2 | 1.3 |

[1] Random—non-site specific—conjugation
[2] Linker-drug with linear linker
[3] HMW are high molecular weight species, reflecting the amount of aggregates formed
[4] Defined as $(RT_{DAR2} - RT_{DAR0})/(RT_{DAR2, reference-ADC} - RT_{DAR0, reference-ADC})$, RT is retention time; PSMA linked to linker-drug compound 1 is the reference ADC
[5] Comparator ADCs with linker-drug conjugated to a cysteine residue pointing outwards FIGS. 3A-C and 4 graphically show the data of Table 1B.

Figure 3A:
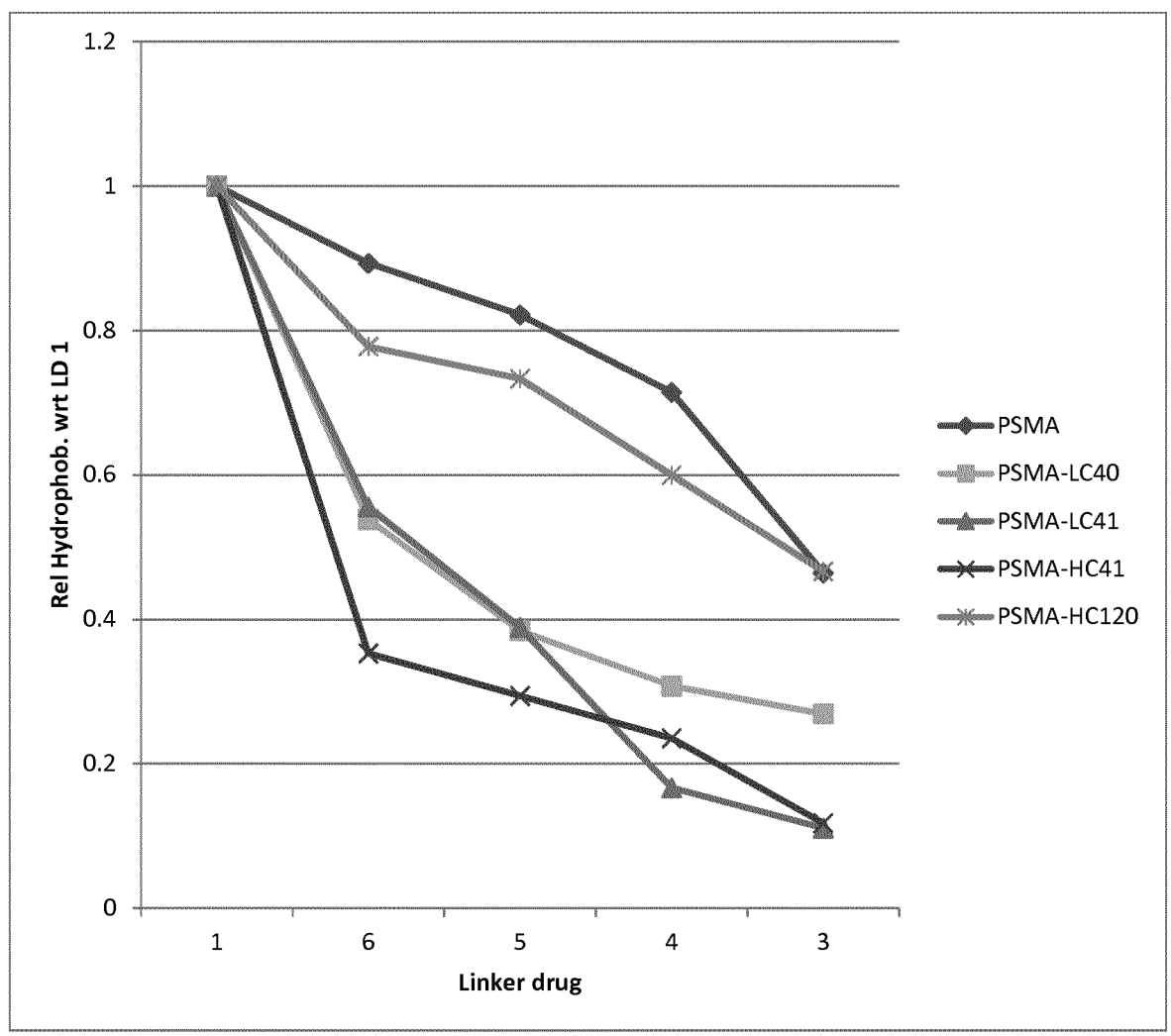
FIG. 3A. Relative hydrophobicity of wild-type and engineered cysteine anti-PSMA ADCs comprising non-linear linker-drugs of the invention versus comparator anti-PSMA ADCs comprising linear vc-seco-DUBA (linker-drug compound 1).

In FIG. 3A, the linker-drugs on the horizontal axis are arranged in the order of decreasing linker-drug hydrophobicity. The comparator ADC is an ADC with the same wild-type or cysteine engineered antibody conjugated to linear linker-drug compound 1. The (relative) hydrophobicity of the ADCs with linker-drugs of the invention is decreased with respect to the comparator ADC. This decrease in hydrophobicity is more pronounced in the ADCs in which the linker-drug is conjugated at a cysteine positioned in the Fab cavity.

Figure 3B:
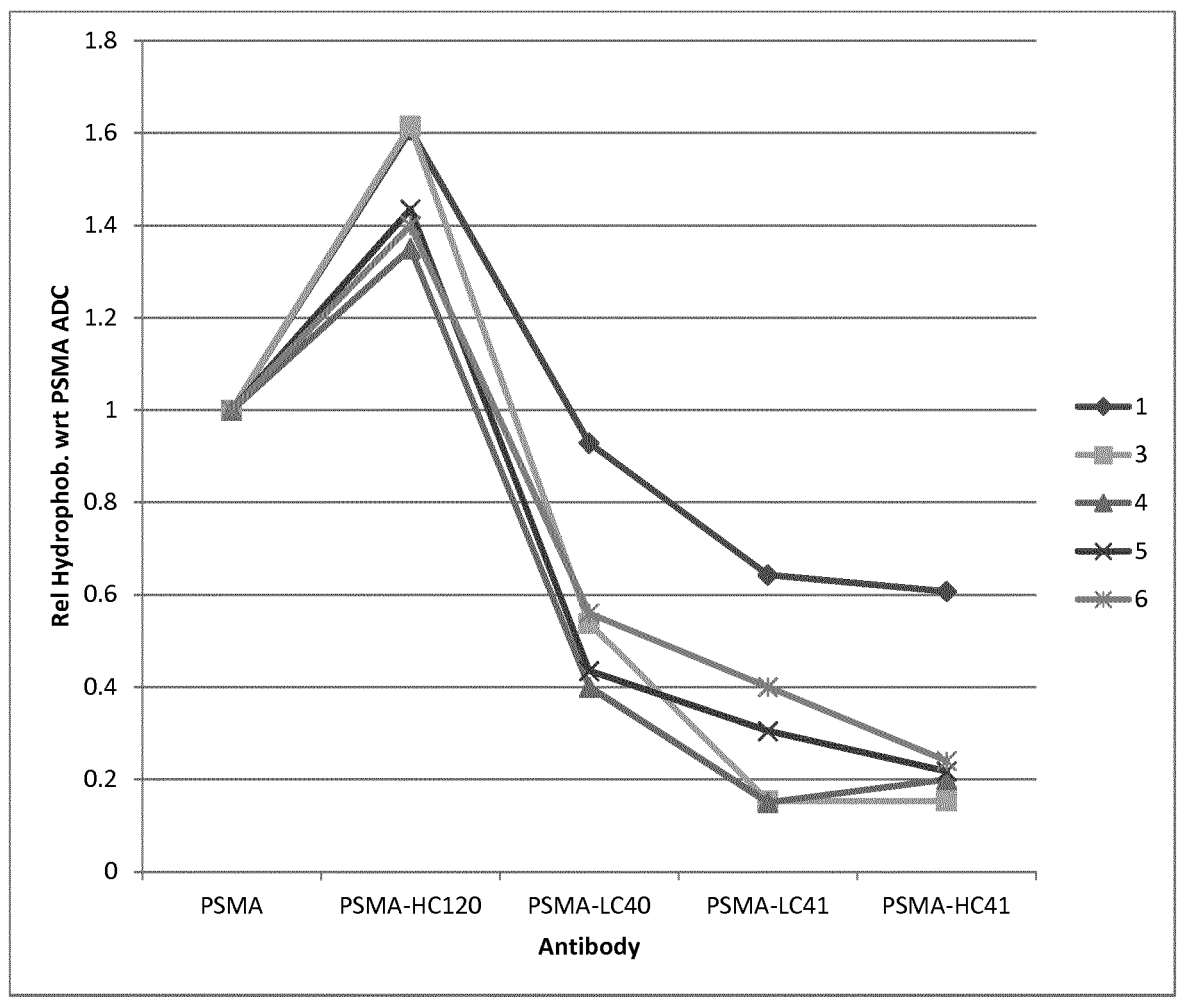
FIG. 3B. Relative hydrophobicity of engineered cysteine anti-PSMA ADCs comprising non-linear linker-drugs of the invention or linear vc-seco-DUBA (linker-drug compound 1) versus comparator non-engineered anti-PSMA wt ADC (PSMA) comprising said linker-drugs.

In FIG. 3B, the hydrophobicities of wt conjugated PSMA ADCs comprising linker-drugs of the invention and reference linker-drug 1 are taken as the reference values. This graph more clearly visualises the differences between various linker-drugs in one antibody. Especially for the ADCs in which the linker-drugs are conjugated at a cysteine positioned in the Fab cavity, there is a relatively large difference in relative hydrophobicity with the linker-drugs of the invention as compared with the linear reference linker-drug compound 1.

Figure 3C:
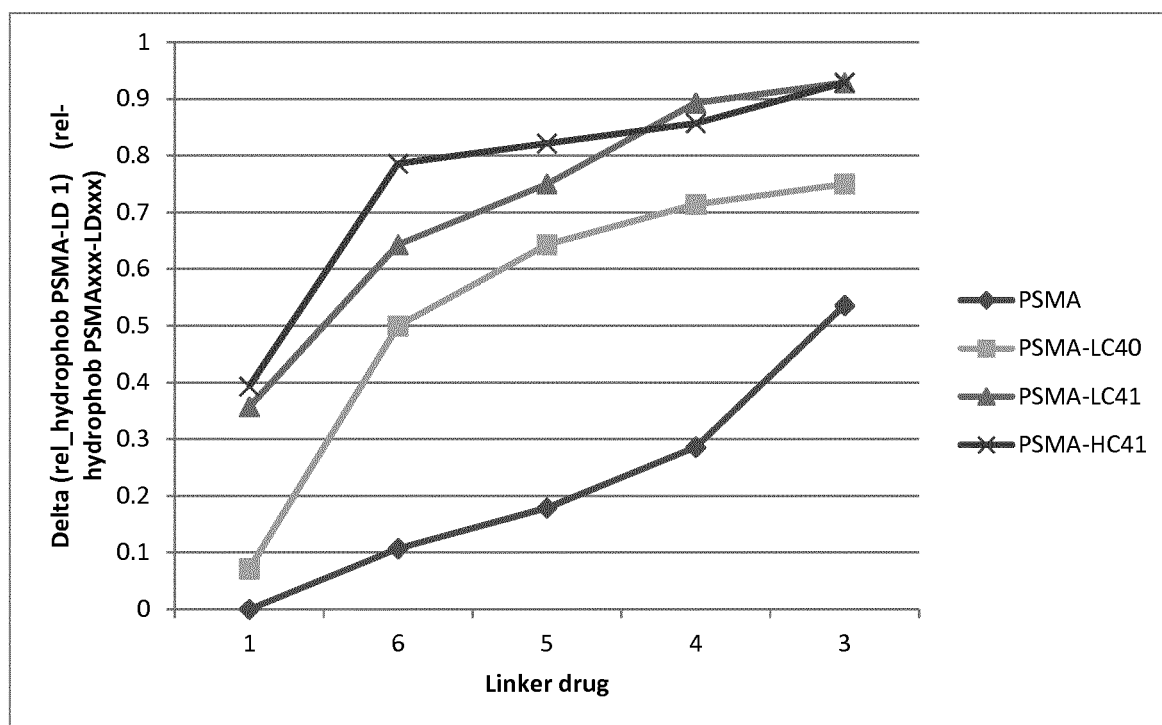
FIG. 3C. Delta in relative hydrophobicity of wild-type and engineered cysteine anti-PSMA ADCs comprising non-linear linker-drugs of the invention or linear vc-seco-DUBA (linker-drug compound 1) versus comparator non-engineered anti-PSMA wt ADC (PSMA) comprising linear vc-seco-DUBA (linker-drug compound 1).

FIG. 3C shows the differences in relative hydrophobicity of the various conjugates with respect to reference ADC PSMA-LD1. The difference between various antibodies comprising the same linker-drug of the invention at a cysteine positioned in the Fab cavity is small, but a significant decrease is observed with respect to the same antibodies comprising the linear reference linker-drug compound 1. Thus, the potential shielding effect of the Fab cavity is optimally used in combination with the non-linear linkers and linker-drugs of the invention.

Figure 4:
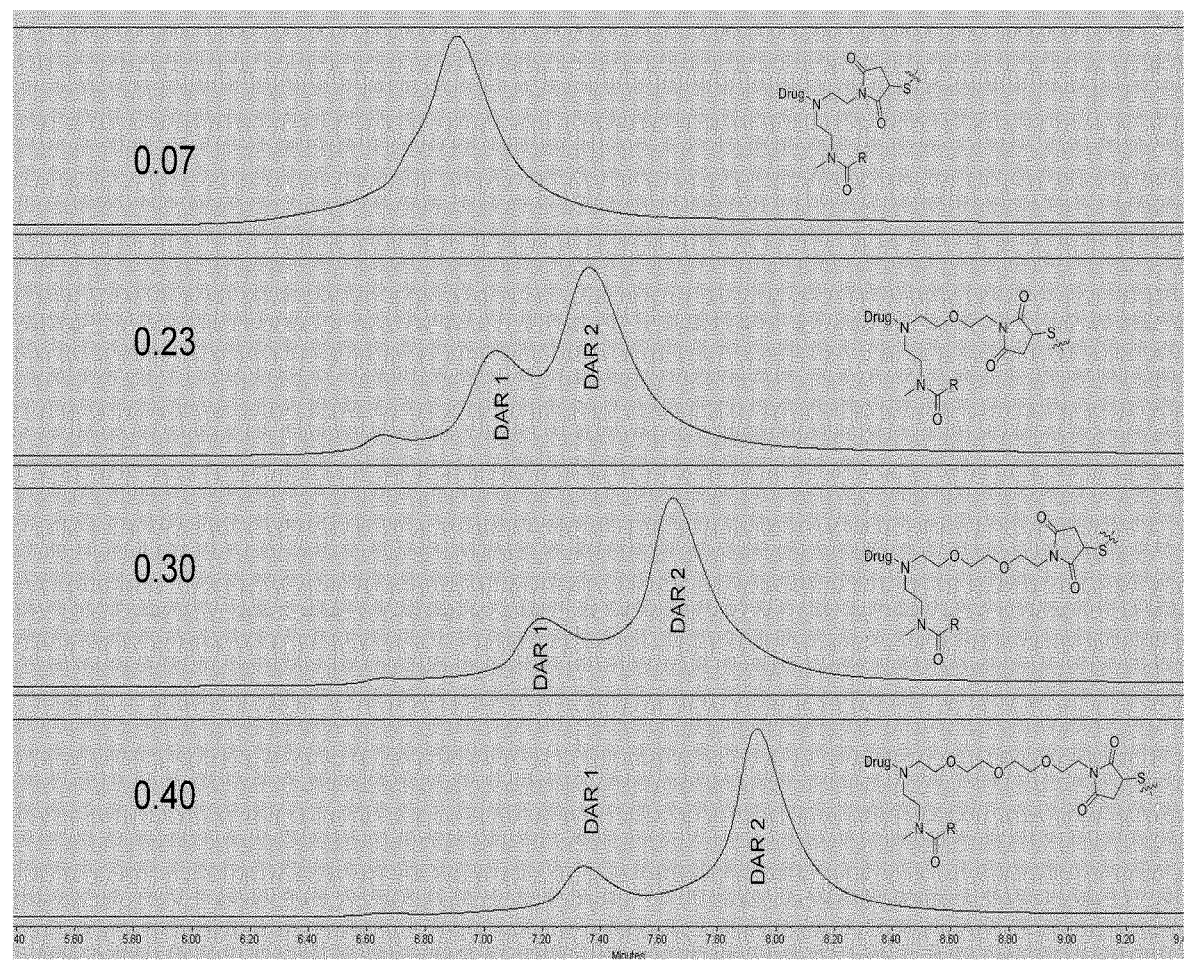
FIG. 4. HIC chromatogram of engineered cysteine anti-PSMA ADCs comprising non-linear linker-drugs of the invention.

FIG. 4 is a HIC chromatogram showing the difference in relative hydrophobicity of various conjugates with respect to reference naked antibody PSMA-HC41. The (relative) hydrophobicity of the ADCs with linker-drugs of the invention is increased with respect to the naked antibody. However, this increase is smaller when the distance between the antibody and drug is smaller, i.e. the number of atoms between the antibody's S-atom and the drug's O-atom is smaller.

Cellular Binding

Three anti-PSMA ADCs PSMA-LD1, PSMA-HC41-LD1 and comparator PSMA-HC120-LD1 had equal binding affinities on PSMA-expressing LNCaP-C4.2 cells ($EC_{50}$ in the range of 0.1-0.2 µg/ml) similar to the wild-type antibody, and all three ADCs were unable to bind to PSMA-negative DU-145 cells ($EC_{50}$>10 µg/ml).

Two anti-5T4 ADCs H8-LD1 and H8-HC40-LD1 had equal binding affinities on 5T4-expressing MDA-MB-468 cells ($EC_{50}$ in the range of 0.1-1.2 µg/ml) similar to the H8 antibody and both ADCs were unable to bind to 5T4-negative SK-MEL-30 cells ($EC_{50}$>10 µg/ml).

The binding of the ADCs was thus unaffected by the attached duocarmycin derivative linker-drug.

In Vitro Cytotoxicity

The potencies on PSMA-expressing LNCaP-C4.2 cells of anti-PSMA ADCs comprising the non-linear linker-drugs of the invention ($IC_{50}$ in the range of 0.2-2.1 nM, based on drug equivalents, see Table 2A below), either wild-type or site-specifically conjugated, were similar to the potencies of the respective comparator anti-PSMA ADCs comprising linear reference linker-drug compound 1.

All ADCs were inactive on PSMA-negative DU-145 cells ($IC_{50}$>70 nM) indicating selective killing of tumour cells through PSMA.

The four wild-type and site-specific non-binding control ADCs were at least 15-times less potent than the respective anti-PSMA ADCs comprising the non-linear linker-drugs of the present invention.

TABLE 2A

In vitro cytotoxicity of anti-PSMA ADCs in human tumour cells expressing PSMA

| | Cys mutation | | | PSMA-positive cell line LNCaP-C4.2 | | |
|---|---|---|---|---|---|---|
| Antibody | HC | LC | LD | $IC_{50}$ (nM)[7] | 95% CI[3] (nM) | % efficacy[4] |
| PSMA[1] | wt | wt | 1[2] | 0.23 | 0.20-0.27 | 82 |
| PSMA[1] | wt | wt | 3 | 1.23 | 0.79-1.94 | 73 |
| PSMA[1] | wt | wt | 4 | 1.18 | 0.79-1.74 | 78 |
| PSMA[1] | wt | wt | 5 | 1.79 | 1.04-3.08 | 87 |
| PSMA[1] | wt | wt | 6 | 0.85 | 0.61-1.18 | 73 |
| PSMA-LC40 | wt | P40C | 1[2] | 0.30 | 0.23-0.37 | 80 |

TABLE 2A-continued

In vitro cytotoxicity of anti-PSMA ADCs in human tumour cells expressing PSMA

| | | | | PSMA-positive cell line LNCaP-C4.2 | | |
|---|---|---|---|---|---|---|
| | Cys mutation | | | $IC_{50}$ | 95% $CI^3$ | % |
| Antibody | HC | LC | LD | $(nM)^7$ | (nM) | efficacy[4] |
| PSMA-LC40 | wt | P40C | 3 | 0.49 | 0.34-0.70 | 75 |
| PSMA-LC40 | wt | P40C | 4 | 0.37 | 0.27-0.49 | 78 |
| PSMA-LC40 | wt | P40C | 5 | 0.41 | 0.32-0.52 | 78 |
| PSMA-LC40 | wt | P40C | 6 | 0.39 | 0.31-0.48 | 77 |
| PSMA-LC41 | wt | G41C | $1^2$ | 0.31 | 0.25-0.38 | 80 |
| PSMA-LC41 | wt | G41C | 3 | 0.37 | 0.29-0.46 | 73 |
| PSMA-LC41 | wt | G41C | 4 | 0.24 | 0.20-0.30 | 77 |
| PSMA-LC41 | wt | G41C | 5 | 0.24 | 0.19-0.29 | 75 |
| PSMA-LC41 | wt | G41C | 6 | 0.31 | 0.25-0.39 | 78 |
| PSMA-HC41 | S41C | wt | $1^2$ | 0.25 | 0.21-0.28 | 78 |
| PSMA-HC41 | S41C | wt | 3 | 1.4 | 0.79-2.50 | 89 |
| PSMA-HC41 | S41C | wt | 4 | 0.48 | 0.40-0.58 | 88 |
| PSMA-HC41 | S41C | wt | 5 | 0.26 | 0.22-0.31 | 77 |
| PSMA-HC41 | S41C | wt | 6 | 0.47 | 0.39-0.58 | 79 |
| PSMA-HC41 | S41C | wt | 7 | 0.37 | 0.29-0.46 | 86 |
| PSMA-HC41 | S41C | wt | 8 | 0.52 | 0.42-0.66 | 88 |
| PSMA-HC41 | S41C | wt | 36 | >100 | n.a.[6] | 65 |
| PSMA-HC41 | S41C | wt | 64 | 2.07 | 0.97-4.44 | 80 |
| PSMA-HC120[5] | T120C | wt | $1^2$ | 0.14 | 0.13-0.16 | 82 |
| PSMA-HC120[5] | T120C | wt | 3 | 1.17 | 0.62-2.19 | 91 |
| PSMA-HC120[5] | T120C | wt | 4 | 0.76 | 0.52-1.10 | 85 |
| PSMA-HC120[5] | T120C | wt | 5 | 0.64 | 0.46-0.89 | 71 |
| PSMA-HC120[5] | T120C | wt | 6 | 0.47 | 0.38-0.60 | 74 |
| Non-binding control[1] | wt | wt | $1^2$ | 28.86 | 24.76-36.02 | 96 |
| Non-binding control-HC41 | P41C | wt | $1^2$ | >100 | n.a. | n.a. |
| Free drug | | | | 0.02 | 0.02-0.03 | 98 |

[1]Random—non-site specific—conjugation
[2]Linker-drug with linear linker
[3]95% CI is 95% confidence interval
[4]Percentage efficacy was given at the highest concentration tested (~100 nM) and calculated by dividing the measured luminescence for each drug or ADC with the average mean of untreated cells (only growth medium) multiplied by 100.
[5]Comparator ADCs with linker-drug conjugated to a cysteine residue pointing outwards
[6]n.a. is not applicable
[7]Relative $IC_{50}$ values were calculated as the concentration that gives a response half-way between bottom and top of the curve, when using a nonlinear regression sigmoidal dose-response equation with variable slope for curve fitting in GraphPad Prism.

The potencies of the wild-type anti-HER2 ADCs comprising the linker-drugs of the invention were similar to the ADC trastuzumab-LD1 on HER2-expressing SK-BR-3 cells ($IC_{50}$ between 0.1 and 0.3 nM, Table 2B). The anti-HER2 ADCs were inactive on HER2-negative SW620 cells ($IC_{50}$>100 nM).

The three non-binding control ADCs were at least 200-times less potent than the anti-HER2 ADCs.

TABLE 2B

In vitro cytotoxicity of anti-HER2 ADCs in human tumour cells expressing HER2

| | | | | HER2-positive cell line SK-BR-3 | | |
|---|---|---|---|---|---|---|
| | Cys mutation | | | $IC_{50}$ | 95% $CI^3$ | % |
| Antibody | HC | LC | LD | $(nM)^6$ | (nM) | efficacy[4] |
| Trastuzumab[1] | wt | wt | $1^2$ | 0.18 | 0.16-0.19 | 97 |
| Trastuzumab[1] | wt | wt | 3 | 0.29 | 0.27-0.31 | 97 |
| Trastuzumab[1] | wt | wt | 6 | 0.23 | 0.21-0.24 | 98 |
| Non-binding control[1] | wt | wt | $1^2$ | 168 | 17.11-1664 | 95 |
| Free drug | | | | 0.06 | 0.05-0.07 | 98 |

[1]Random—non-site specific—conjugation
[2]Linker-drug with linear linker
[3]95% CI is 95% confidence interval
[4]Percentage efficacy was given at the highest concentration tested (~100 nM) and calculated by dividing the measured luminescence for each drug or ADC with the average mean of untreated cells (only growth medium) multiplied by 100.
[5]n.a. is not applicable
[6]Relative $IC_{50}$ values were calculated as the concentration that gives a response half-way between bottom and top of the curve, when using a nonlinear regression sigmoidal dose-response equation with variable slope for curve fitting in GraphPad Prism.

Together, these data show that the ADCs comprising the linker-drug compounds of the invention have excellent tumour cell killing potency. Moreover, site-specific linkage of said linker-drugs in the variable region of the Fab part has no impact on the in vitro cytotoxicity with respect to site-specific linkage of linear comparator linker-drug compound 1, which releases the same duocarmycin drug unit after cleavage.

Tumour Xenograft Animal Model

The in vivo efficacy of four anti-PSMA ADCs was evaluated in the LNCaP-C4.2 prostate cancer xenograft model. The LNCaP-C4.2 cell line is a human prostate carcinoma epithelial cell line derived from a xenograft that was serially propagated in mice after castration-induced regression and relapse of the parental, androgen-dependent LNCaP-FGC xenograft cell line.

Tumours were induced subcutaneously by injecting $1 \times 10^7$ of LNCaP-C4.2 cells in 200 μL of RPMI 1640 containing matrigel (50:50, v:v) into the right flank of male CB17-SCID mice. LNCaP-C4.2 tumour cell implantation was performed 24 to 72 hours after a whole body irradiation with a γ-source (1.44 Gy, $^{60}$Co, BioMep, Breteniéres, France).

Treatments were started when the tumours reached a mean volume of 100-200 mm$^3$. Mice were randomized according to their individual tumour volume into groups and received a single i.v. injection of 2 mg/kg (FIG. 5A) or 5 mg/kg (FIG. 5B) anti-PSMA ADC, or vehicle in the tail vein. Changes in tumour volumes were monitored. All four ADCs have an average DAR of approximately 1.6-1.8.

Cachexia was observed in all groups; no significant differences were observed in the effects on body weights between the four ADCs.

Figure 5A:
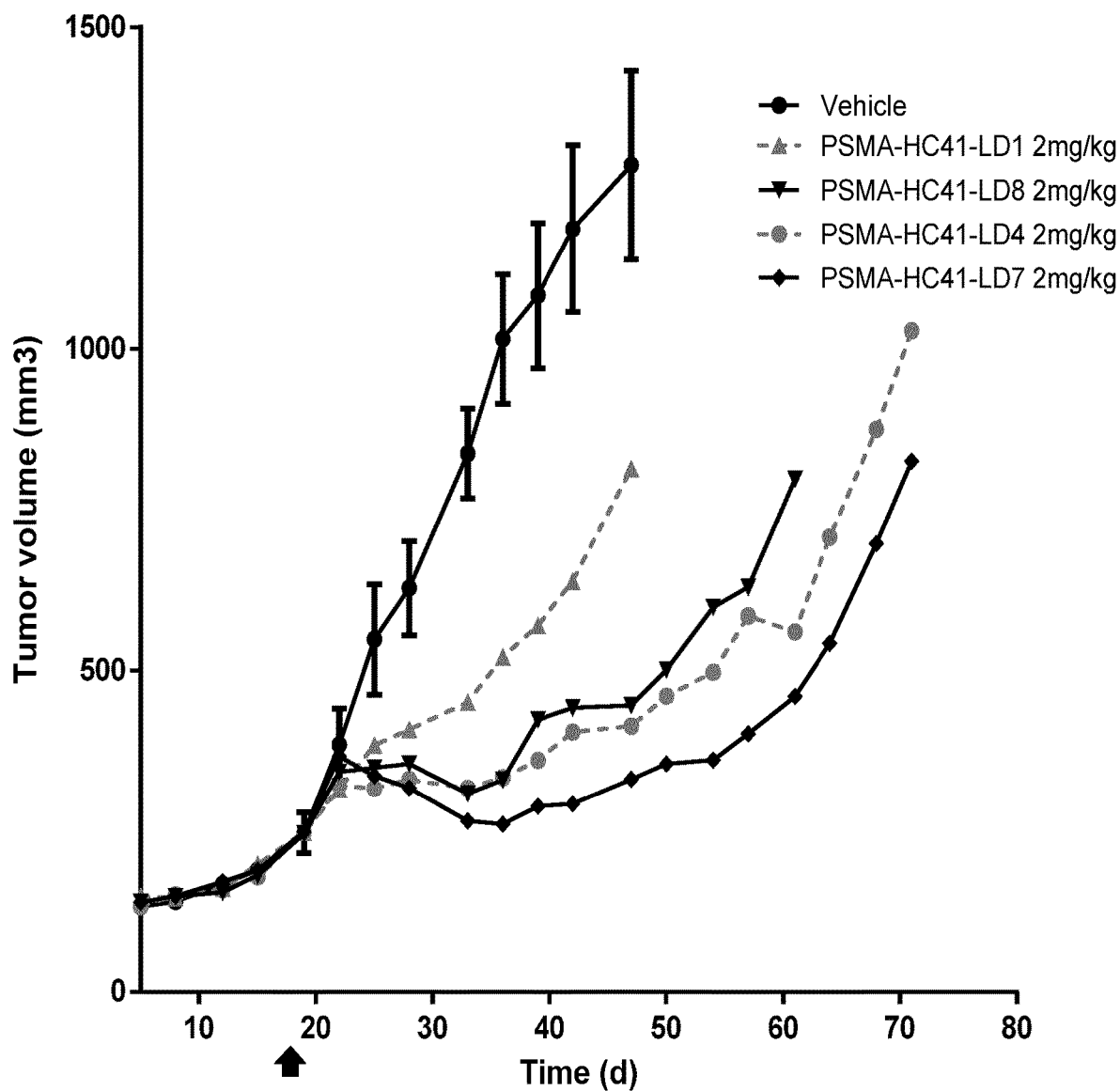
FIG. 5. In vivo LNCaP-C4.2 cell line xenograft efficacy in mice: engineered cysteine anti-PSMA (VH S41C) ADCs comprising linker-drug compounds 4, 7 or 8 versus vehicle control, and comparator engineered cysteine anti-PSMA (VH S41C) ADC comprising linear vc-seco-DUBA (linker-drug compound 1) after a single injection of 2 mg/kg (FIG. 5A) or 5 mg/kg (FIG. 5B) each.
Figure 5B:
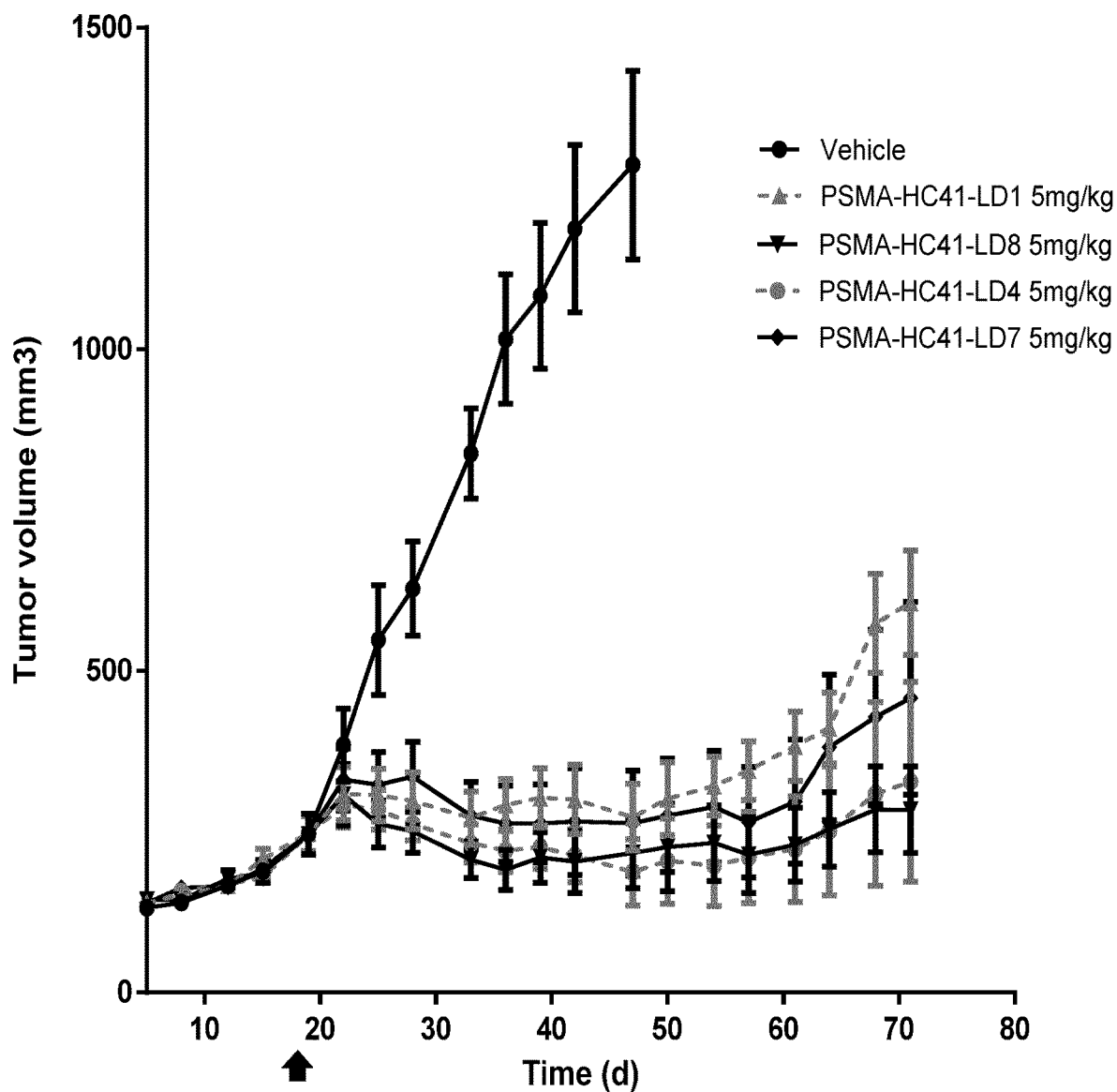

FIGS. 5A and 5B clearly demonstrate that the PSMA-H41C-LD4, -LD7, and -LD8 ADCs have better in vivo efficacy than the PSMA-H41C-LD1 ADC.

Together these data show that antibodies coupled to the non-linear linker-drugs of the invention (resulting in ADCs with reduced hydrophobicity) have advantageous in vivo properties with regard to their anti-tumour activity.

The invention claimed is:

1. A linker-drug compound of formula (I)

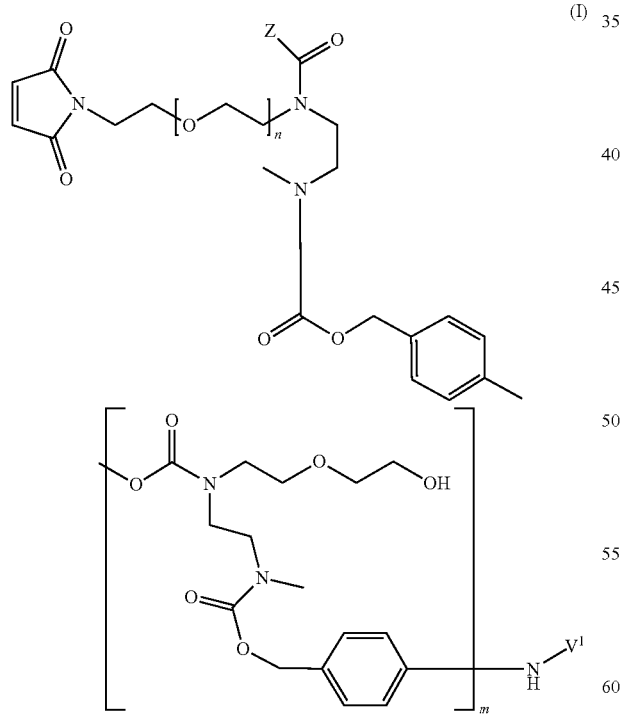

(I)

or a pharmaceutically acceptable salt, hydrate, or solvate thereof, wherein $V^1$ is a conditionally-cleavable or conditionally-transformable moiety, which can be cleaved or transformed by a chemical, photochemical, physical, biological, or enzymatic process;

Z is a cytotoxic drug comprising a phenolic hydroxyl group through which Z is attached to the linker;

n is 0, 1, 2, or 3; and m is 0 or 1.

2. The compound according to claim 1, wherein Z is

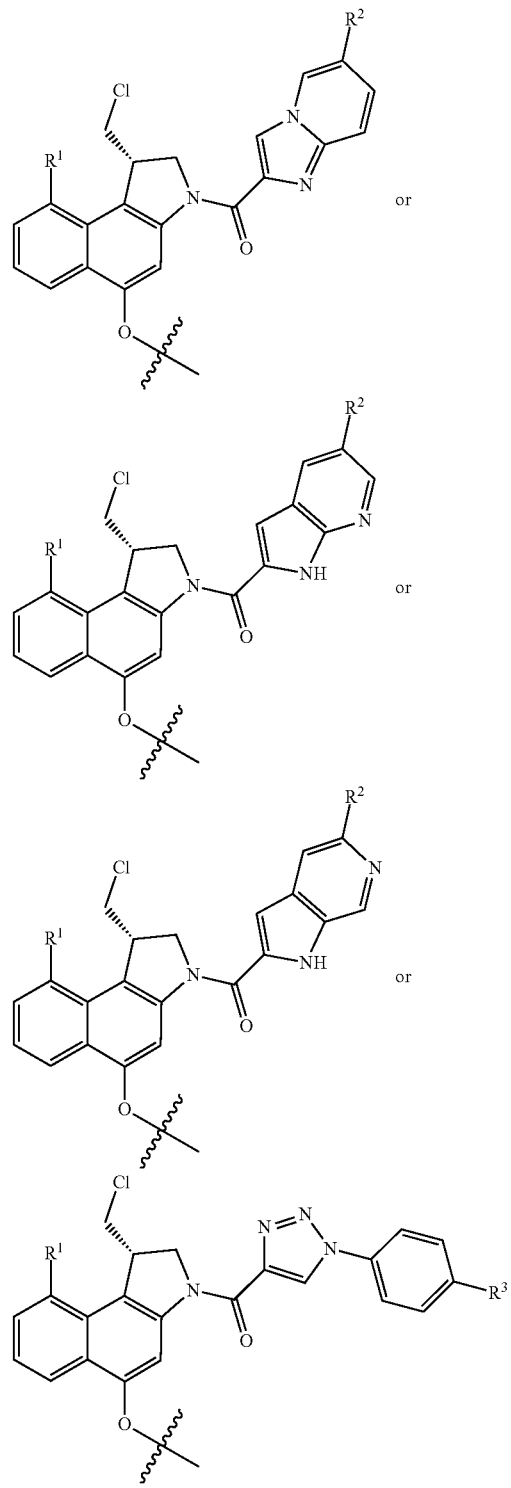

wherein $R^1$, $R^2$, and $R^3$ are independently selected from H, OH, SH, $NH_2$, $N_3$, $NO_2$, NO, $CF_3$, CN, $C(O)NH_2$, C(O)H, C(O)OH, halogen, $R^a$, $SR^a$, $S(O)R^a$, $S(O)_2R^a$, S(O)OR$^a$, S(O)$_2$OR$^a$, OS(O)R$^a$, OS(O)$_2$R$^a$, OS(O)OR$^a$, OS(O)$_2$OR$^a$, OR$^a$, NHR$^a$, N(R$^a$)R$^b$, $^+$N(R$^a$)(R$^b$)R$^c$, P(O)(OR$^a$)(OR$^b$), OP(O)(OR$^a$)(OR$^b$), SiR$^a$R$^b$R$^c$, C(O)R$^a$, C(O)OR$^a$, C(O)N(R$^a$)R$^b$, OC(O)R$^a$, OC(O)OR$^a$, OC(O)N(R$^a$)R$^b$, N(R$^a$)C(O)R$^b$, N(R$^a$)C(O)OR$^b$, N(R$^a$)C(O)N(R$^b$)R$^c$, and a water-soluble group, wherein R$^a$, R$^b$, and R$^c$ are independently selected from H and optionally substituted (CH$_2$CH$_2$O)$_{aa}$CH$_2$CH$_2$X$^1$R$^{a1}$, C$_{1-15}$ alkyl, C$_{1-15}$ heteroalkyl, C$_{3-15}$ cycloalkyl, C$_{1-15}$ heterocycloalkyl, C$_{5-15}$ aryl, or C$_{1-15}$ heteroaryl, wherein aa is selected from 1 to 1000, X$^1$ is selected from O, S, and NR$^{b1}$, and R$^{b1}$ and R$^{a1}$ are independently selected from H and C$_{1-3}$ alkyl, one or more of the optional substituents in R$^a$, R$^b$, and/or R$^c$ optionally being a water-soluble group, two or more of R$^a$, R$^b$, and R$^c$ optionally being joined by one or more bonds to form one or more optionally substituted carbocycles and/or heterocycles.

3. The compound according to claim 2, wherein Z is

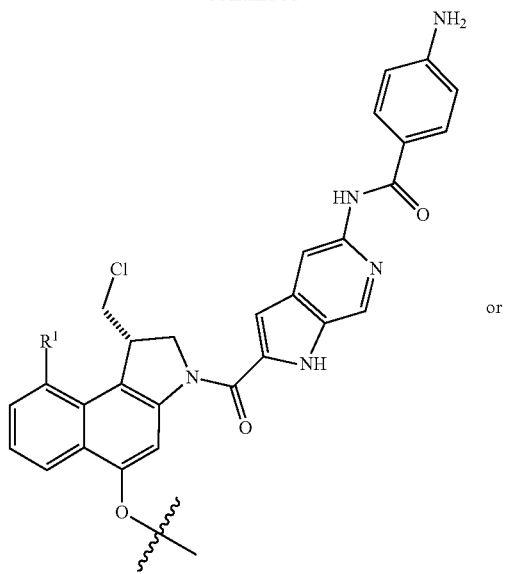

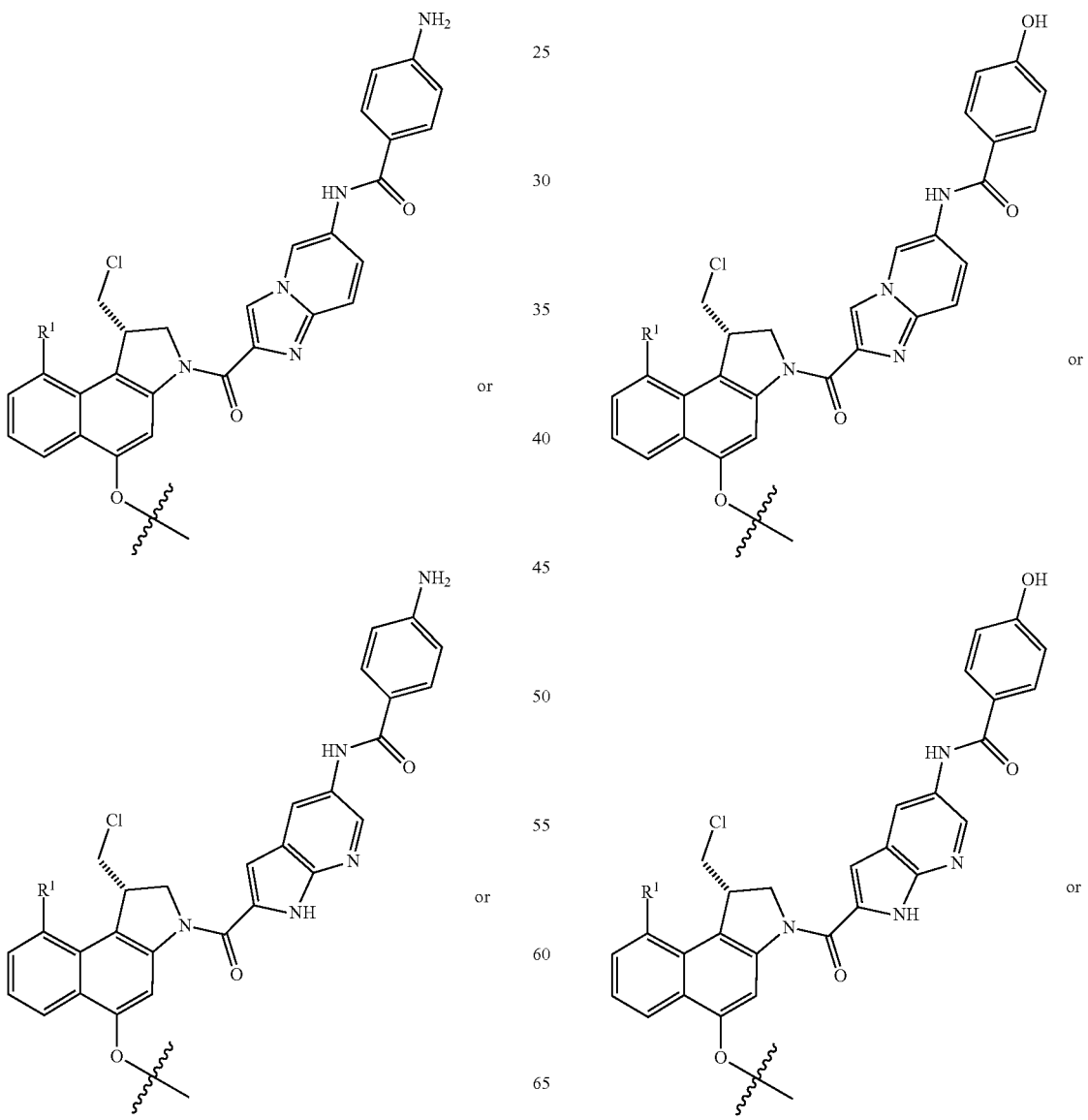

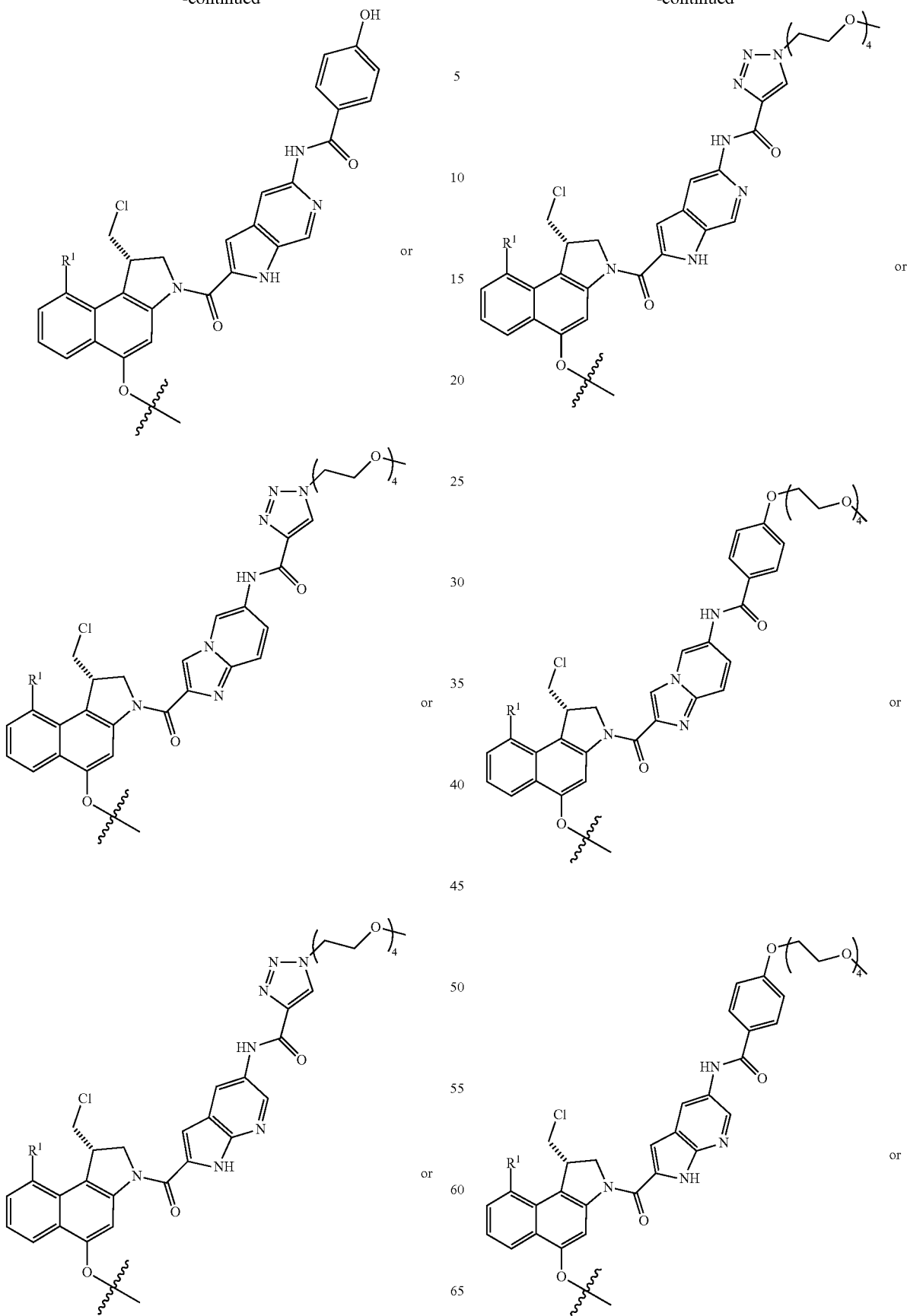

133
-continued
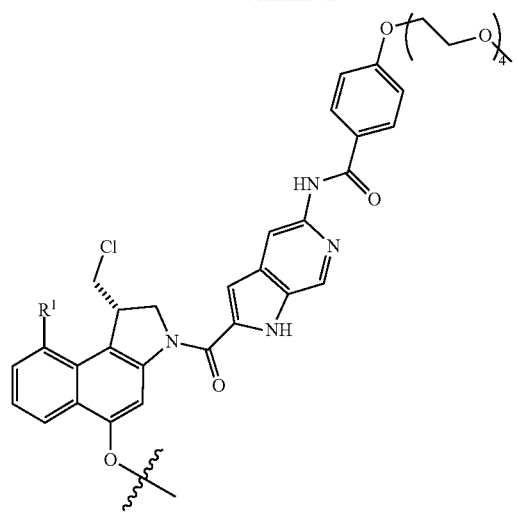
or
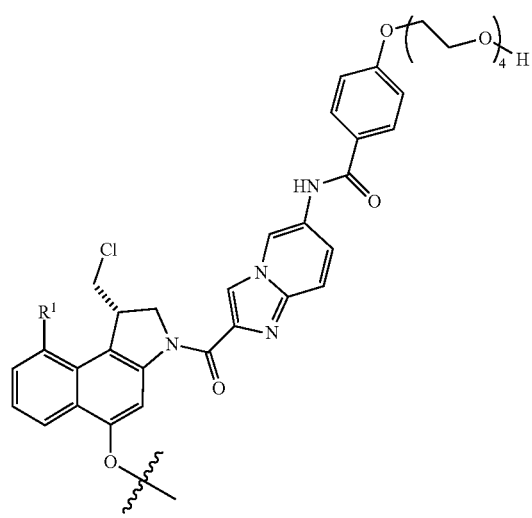
or
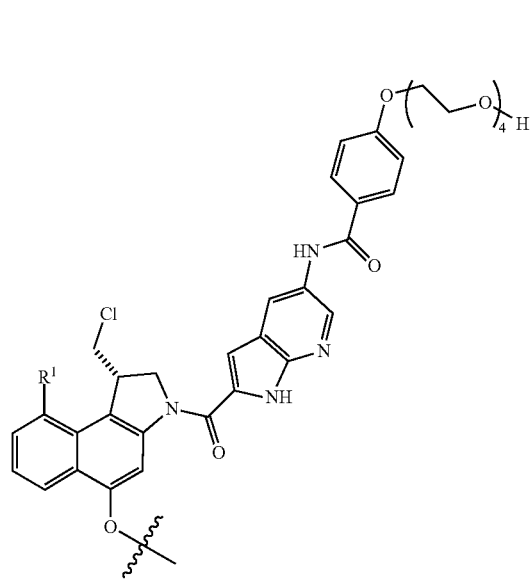
134
-continued
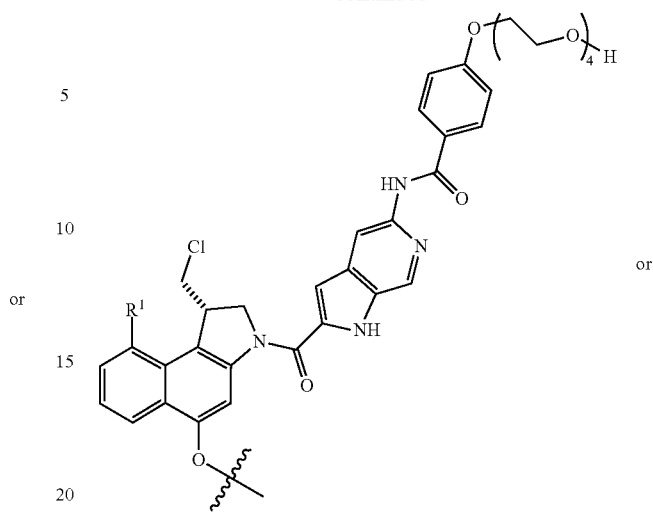
or
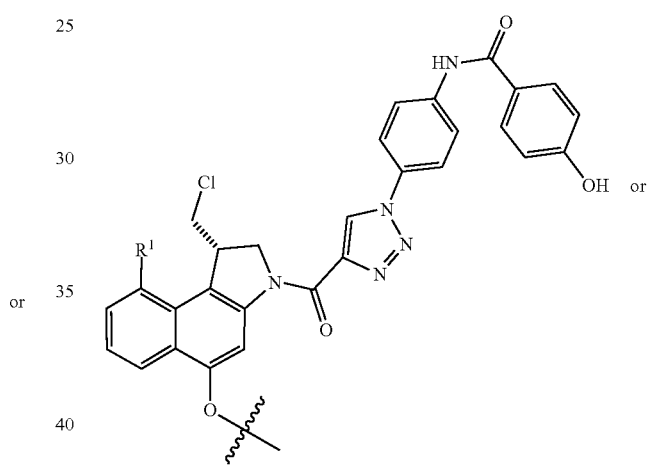
or
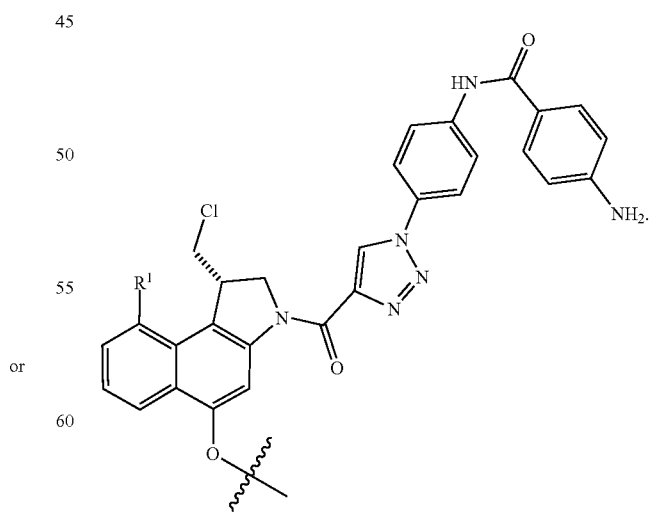
4. The compound according to claim 3, wherein $R^1$ is selected from H, methyl and methoxy.

5. The compound according to claim 4, wherein Z is
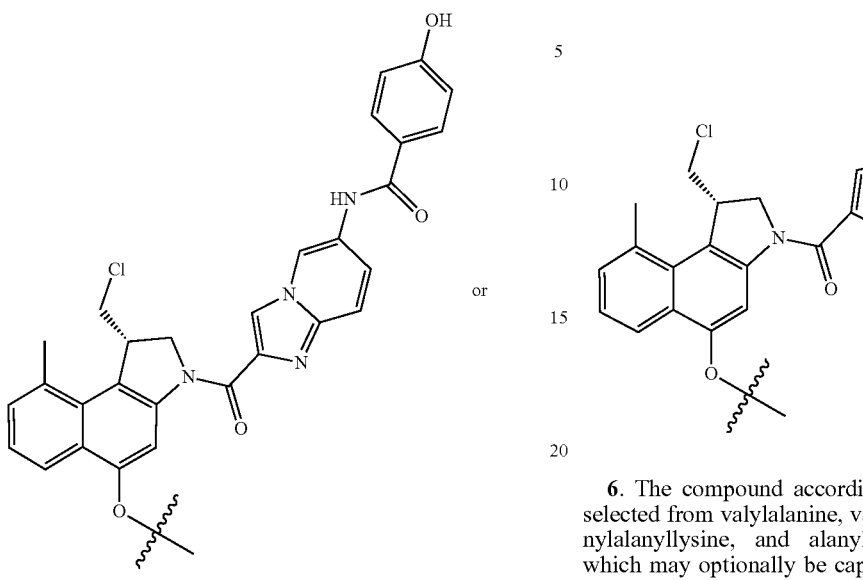
or
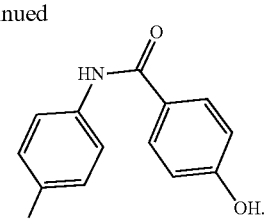
6. The compound according to claim 1, wherein V¹ is selected from valylalanine, valyllysine, valylcitrulline, phenylalanyllysine, and alanylphenylalanyllysine, each of which may optionally be capped.
7. The compound according to claim 1, selected from
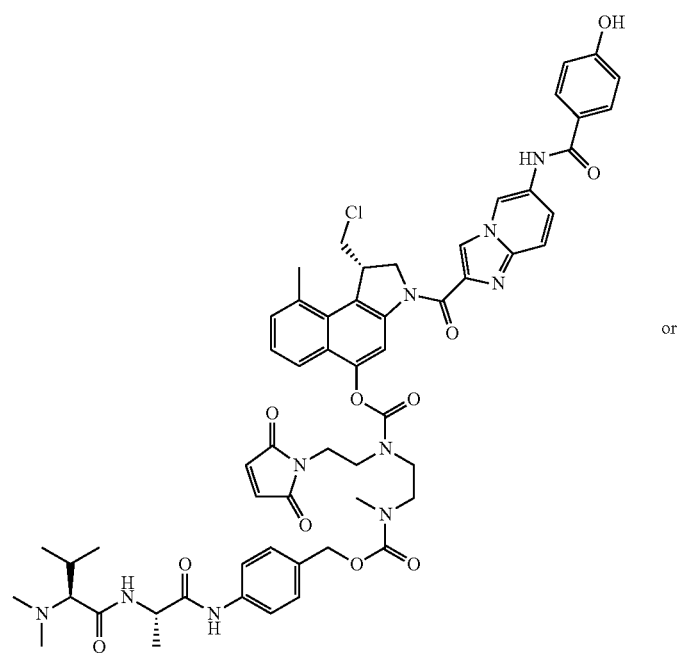
or -continued
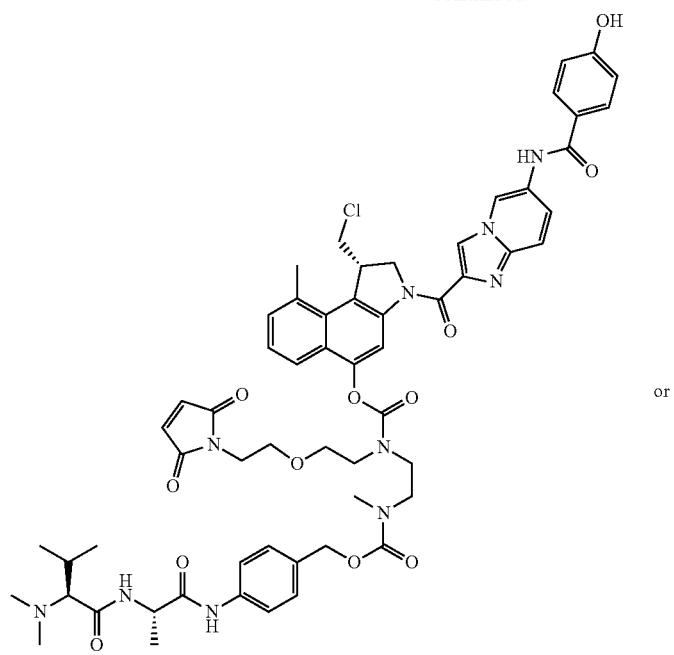
or
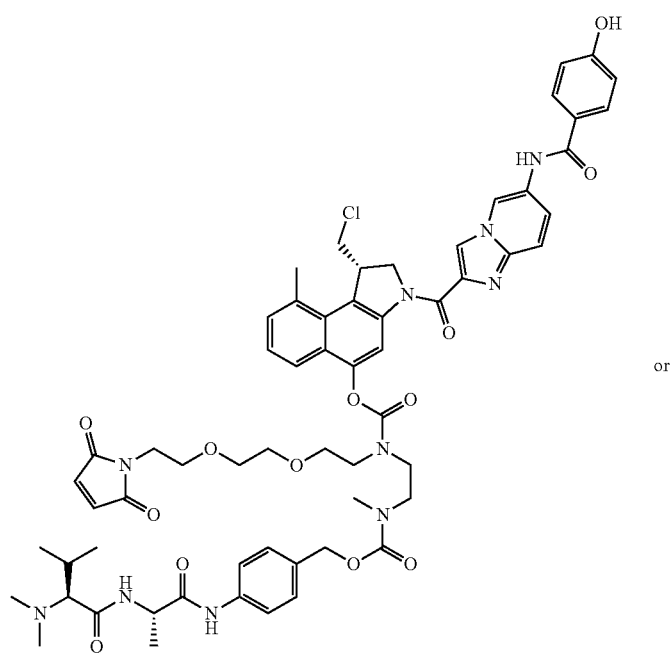
or

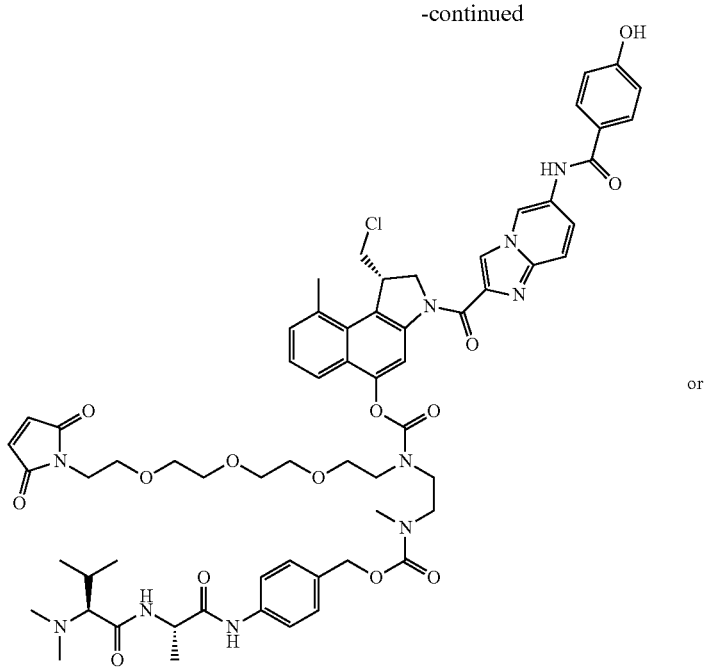
or
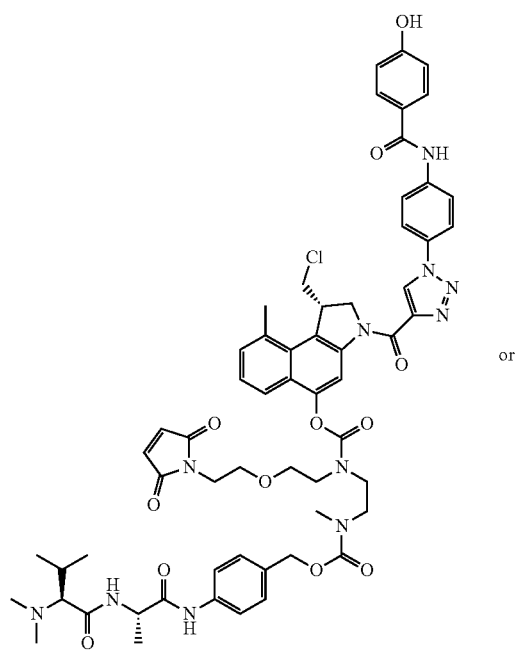
or

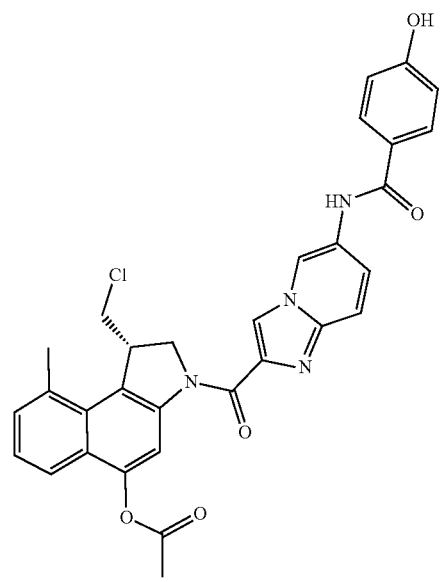
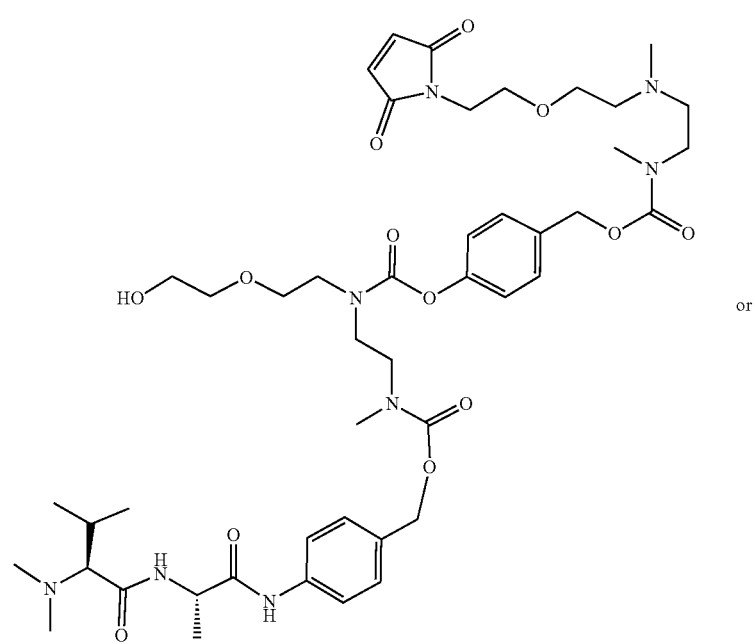 or

-continued

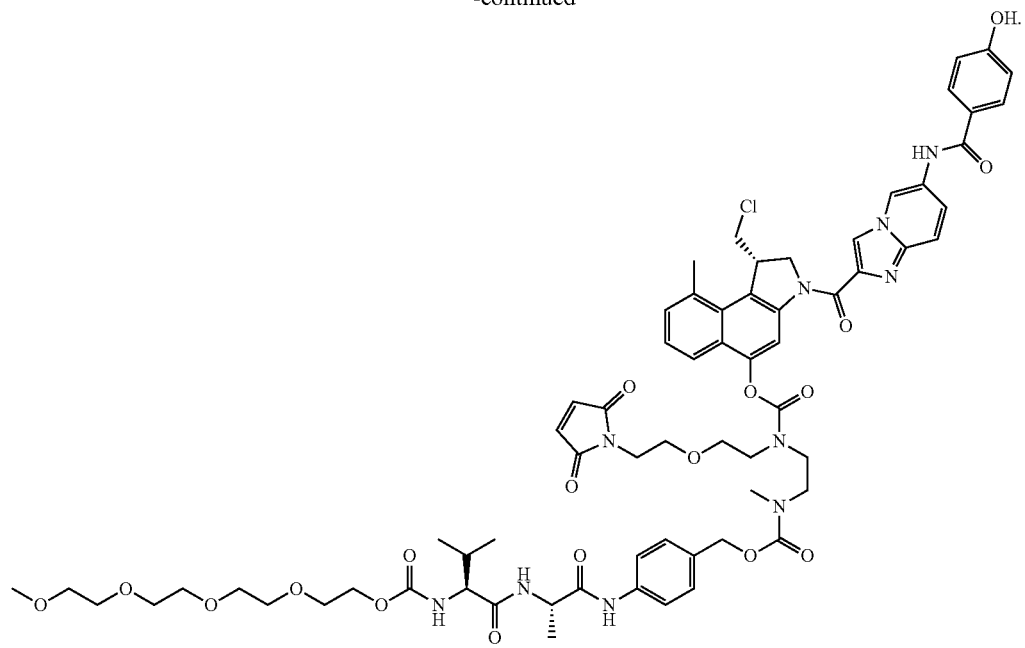

8. An antibody-drug conjugate comprising the compound according to claim 1 conjugated to an antibody or an antigen-binding fragment thereof through a cysteine residue of the antibody or the antigen-binding fragment.

9. The antibody-drug conjugate according to claim 8, wherein the compound is site-specifically conjugated to an antibody or antigen-binding fragment thereof through an engineered cysteine at one or more positions of said antibody or antigen-binding fragment selected from heavy chain 40, 41 and 89 (according to Kabat numbering);

heavy chain 152, 153, 155, 171, 247, 297, 339, 375 and 376 (according to Eu numbering); and light chain 40, 41, 165 and 168 (according to Kabat numbering).

10. The antibody-drug conjugate according to claim 9, wherein the compound is site-specifically conjugated to an antibody or antigen-binding fragment thereof through an engineered cysteine at one or more positions of said antibody or antigen-binding fragment selected from heavy chain 40, 41 and 89 (according to Kabat numbering); and light chain 40 and 41 (according to Kabat numbering).

11. The antibody-drug conjugate according to claim 8, wherein said antibody-drug conjugate is a compound of formula (III)

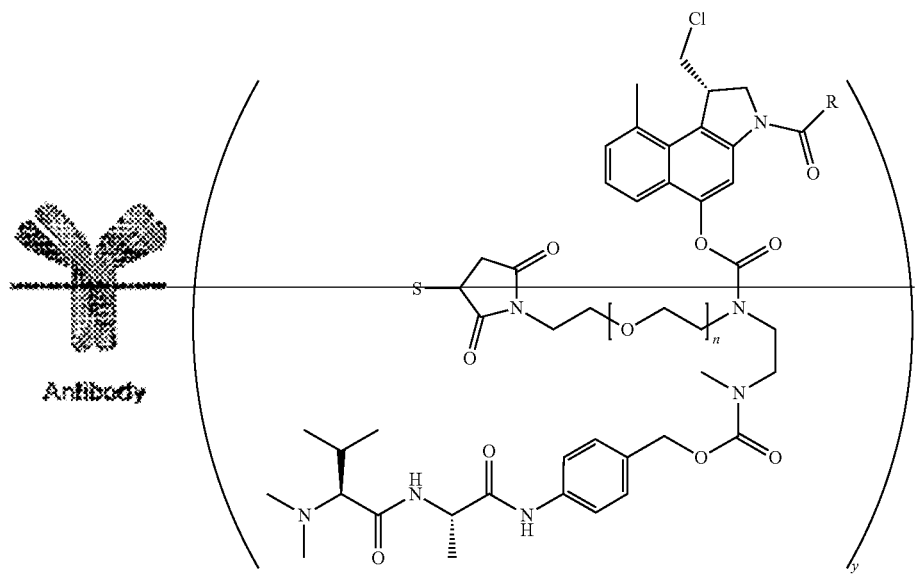

-continued

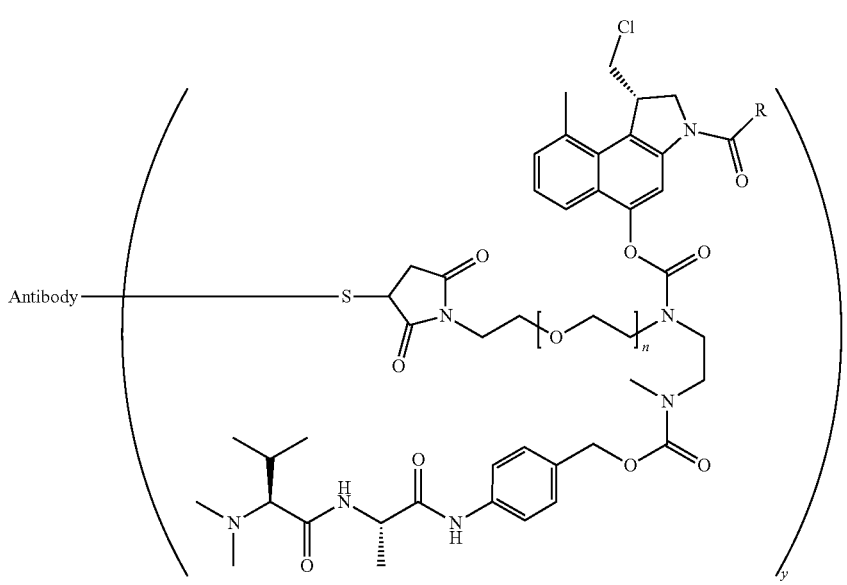

wherein Antibody is an antibody or antigen-binding fragment thereof;
n is 0, 1, 2 or 3;
y represents an average DAR of from 1 to 6; and
R is selected from

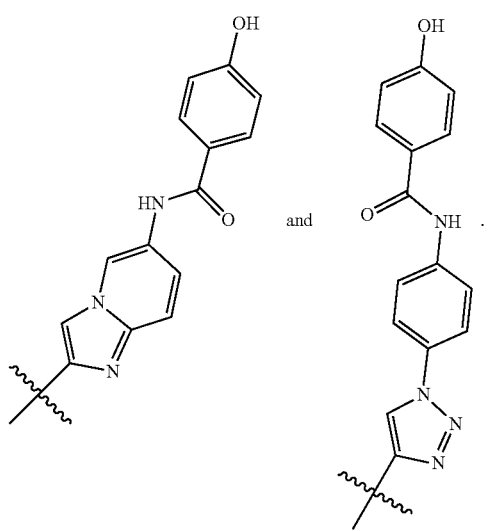 [SMILES: *c1cn2cc(NC(=O)c3ccc(O)cc3)ccc2n1 ; *c1cn(-c2ccc(NC(=O)c3ccc(O)cc3)cc2)nn1]

12. The antibody-drug conjugate according to claim 8, wherein the antibody or the antigen-binding fragment binds to an antigen target selected from the group consisting of annexin A1, CA242, CD19, CD22, CD30, CD33, CD37, CD38, CD44, CD47, CD56, CD70, CD74, CD79, CD115, CD123, CD138, CD203c, CD303, CD333, CEACAM, CLL-1, c-MET, Cripto, DLL3, EGFR, EPCAM, EphA2, EphB3, ETBR, FAP, FcRL5, FGFR3, FOLR1, GCC, GPNMB, HER2, HMW-MAA, integrin, Lewis A like carbohydrate, Lewis Y, LIV1, mesothelin, MN, MUC1, MUC16, NaPi2b, Nectin-4, PSMA, SLC44A4, STEAP-1, 5T4 antigen, Tag72, tissue factor, TF-Ag, TROP2, and VLA.

13. A pharmaceutical composition comprising the antibody-drug conjugate according to claim 8 and one or more pharmaceutically acceptable excipients.

14. The compound according to claim 1, wherein Z is a duocarmycin derivative or a CBI dimer derivative.

15. The compound according to claim 1, wherein Z is a duocarmycin derivative.

16. The compound according to claim 1, wherein $V^1$ comprises a di-, tri-, or tetra-peptide that is bonded to the linker via its C-terminal side, and optionally is capped on the N-terminal side by an amine blocking group or a water-soluble group.

17. The compound according to claim 2, wherein $V^1$ is selected from valylalanine, valyllysine, valylcitrulline, phenylalanyllysine, and alanylphenylalanyllysine, each of which may optionally be capped.

18. The compound according to claim 3, wherein $V^1$ is selected from valylalanine, valyllysine, valylcitrulline, phenylalanyllysine, and alanylphenylalanyllysine, each of which may optionally be capped.

19. The compound according to claim 5, wherein $V^1$ is selected from valylcitrulline and valylalanine, each of which may optionally be capped.

20. The antibody-drug conjugate according to claim 11, wherein the antibody or the antigen-binding fragment binds to an antigen target selected from the group consisting of annexin A1, CA242, CD19, CD22, CD30, CD33, CD37, CD38, CD44, CD47, CD56, CD70, CD74, CD79, CD115, CD123, CD138, CD203c, CD303, CD333, CEACAM, CLL-1, c-MET, Cripto, DLL3, EGFR, EPCAM, EphA2, EphB3, ETBR, FAP, FcRL5, FGFR3, FOLR1, GCC, GPNMB, HER2, HMW-MAA, integrin, Lewis A like carbohydrate, Lewis Y, LIV1, mesothelin, MN, MUC1, MUC16, NaPi2b, Nectin-4, PSMA, SLC44A4, STEAP-1, 5T4 antigen, Tag72, tissue factor, TF-Ag, TROP2, and VLA.

* * * * *